(12) United States Patent
Scrutton et al.

(10) Patent No.: US 11,174,474 B2
(45) Date of Patent: Nov. 16, 2021

(54) HYDROCARBON PRODUCTION

(71) Applicant: C3 BIOTECHNOLOGIES LIMITED, Lancaster (GB)

(72) Inventors: Nigel Scrutton, Manchester (GB); Helen Toogood, Manchester (GB); Robin Hoeven, Manchester (GB)

(73) Assignee: C3 BIOTECHNOLOGIES LIMITED, Lancaster (GB)

( * ) Notice: Subject to any disclaimer, the term of this patent is extended or adjusted under 35 U.S.C. 154(b) by 0 days.

(21) Appl. No.: 17/048,832

(22) PCT Filed: Apr. 17, 2019

(86) PCT No.: PCT/EP2019/060013
§ 371 (c)(1),
(2) Date: Oct. 19, 2020

(87) PCT Pub. No.: WO2019/202044
PCT Pub. Date: Oct. 24, 2019

(65) Prior Publication Data
US 2021/0163915 A1  Jun. 3, 2021

(30) Foreign Application Priority Data

Apr. 20, 2018 (GB) .................................... 1806483

(51) Int. Cl.
*C12N 9/88* (2006.01)
*C12P 5/02* (2006.01)
*C12P 7/24* (2006.01)

(52) U.S. Cl.
CPC .................. *C12N 9/88* (2013.01); *C12P 5/02* (2013.01); *C12P 7/24* (2013.01); *C12Y 401/99005* (2013.01)

(58) Field of Classification Search
CPC ............ C12Y 102/00; C12P 7/24; C12N 9/88
See application file for complete search history.

(56) References Cited

FOREIGN PATENT DOCUMENTS

EP   3246401 A1   11/2017

OTHER PUBLICATIONS

PCT International Search Report and Written Opinion for International Application No. PCT/EP2019/060013, dated Aug. 27, 2019, 15 pages.
Database UniProt, "Choline dehydrogenase," Raphidocelis subcapitata, https://www.uniprot.org/uniprot/A0A2V0NV1629/, Aug. 29, 2019, 3 pages.
Sorigue et al., "An algal photoenzyme converts fatty acids to hydrocarbons," Science 357, pp. 903-907, 2017.
Zhang et al., "Microbial synthesis of propane by engineering valine pathway and aldehydedeformylating oxygenase," Biotechnol Biofuels, 2016, 19 pages.
Khara et al., Production of propane and other short-chain alkanes by structure-based engineering of ligand specificity in aldehyde-deformylating oxygenase, ChemBioChem Communications, 2013, 14, 1204-1208.
Menon et al., "A microbial platform for renewable propane synthesis based on a fermentative butanol pathway," Biotechnology for Biofuels, 2015, 8:61, 12 pages.

*Primary Examiner* — Tekchand Saidha
(74) *Attorney, Agent, or Firm* — Hoffman Warnick, LLC

(57) ABSTRACT

A fatty acid decarboxylase is disclosed, the fatty acid decarboxylase comprising at least 40% sequence identity to SEQ ID NO:1 or 2, and an amino acid substitution at a position corresponding to G462 of SEQ ID NO:1.

19 Claims, 29 Drawing Sheets

Specification includes a Sequence Listing.

FIGURE 4

```
Vca       ----------------------------------MLLGQRPFGAPA-KGAMPCWKAA---
Cre-APS   ----------------------------------MMLGPKTVTRGATKGAAPRSMAA---
Gpe       ----------------------------------MMLGRKPVAPAKGASAARTVRPV---
Cva-APS   MASITSRASARASCSQANTR---AGRVALSG--GALLRPARPARSFVPARKQQQGAV---
Csu       -------------------------MMASQ--SVFLGTRPATRSPLPIGRAGHGSA---
Aan       ------------------------------------------------------------
Ptr       ------------------------------------------------------------
Csp       -----------------M---MRRLVYIC--AVATVTAAISSRSVPTSARRLIAL---
Ehu1      -----------------------MVALF--ALQLALSPPQARLGSGSARAALRL---
Ccr       ----------MASPCPAFATPIAVPRSTLTSLISSSSSCTPRPVRTPAPPTHRRLIHMA--
Cme       ---------------------MRSR-YCFLLSSTPCKYAGQRSPFPASALAGVCAGGR

Vca       ----RHGGVAGVARRPV------AVKAAASVGSEKFDYILVGGGTAGCVLANKLSANG--
Cre-APS   ----RR--VGGARRLSV------RAAAGP-AGSEKFDYVLVGGGTASCVLANKLSADG--
Gpe       ----RL--AGGRRQLVV------SAAAAPVDPAEKYDYILVGGGTAGCVLANKLSADG--
Cva-APS   ----RRGGALSARASAVEDIRKVLSDSSSPVAGQKYDYILVGGGTAACVLANRLSADG--
Csu       ----------GRRALR---VRA--IIKSDNPAADKYDFILVGGGTAGCVLANRLTADG--
Aan       --------------------MGRTLVLKVATTSYDYIIAGGGTAGCVLANRLSEDP--
Ptr       ------------------------------YDYIICGGGLAGCVLAERLSQDE--
Csp       -----RGGVA---------------AAEQLAEEPWDYIIVGGGAAGCVMAERLSAAE--
Ehu1      ------RGGSGVTG-------GSLGRGGGSPAIDGEFDYIIVGGGAAGCVLANRLSADP--
Ccr       ---------AP-AGTVA----STFRRTVPSSEAATTYDYIIVGGGAAGCVLANRLTEDP--
Cme       LRNVTRNLRPGLRTLR----ASAETEHSQGTRQAQYDFIIVGAGAAGCVLANRLSTAQFS
                                          :*:     *.*  *.**:*::*-

Vca       -----SKKVLVLEAGPTG--DAMEVAVPAGIARLFAHPVFDWGMSSLTQQQLV--AREIY
Cre-APS   -----NKKVLVLEAGPTG--DAMEVAVPAGITRLFAHPVMDWGMSSLTQKQLV--AREIY
Gpe       -----NKKVLVLEAGPSG--DSLEVAVPAGIARLFAHPVMDWGMSSLTQKQLV--AREIY
Cva-APS   -----SKRVLVLEAGPDN--TSRDVKIPAAITRLFRSP-LDWNLFSELQEQLA--ERQIY
Csu       -----SKKVLLLEAGGAN--KAREVRTPAGLPRLFKSA-LDWNLYSSLQQAAS--DRSIY
Aan       -----SKKVLVLEAGDRGP-NSPLVKIPVAILKLFKSA-YDWNFATRPSEAVA--DRSLY
Ptr       -----SKRVLVLEAGGSDY-KSLFIRIPAGVLRLFRSK-YDWQHETGGEKGCN--GRNVF
Csp       ------ARVLVLEAGTDAS-RDLRIRVPAGLIKVFKSE-RDWDFTTEAGQGTS--GRGIY
Ehu1      -----AHRVLLIEAGGDAS-RDKRAQVPWAFTKLLRSE-YDWDFHVEAEAAVN--QQEVY
Ccr       -----STRVLLLEAGK--PDDSFYLHVPLGFPYLLGSP-NDWAFVTEPEPNLA--NRRLY
Cme       NGDRRYPRVLLLEAGDALAEAPYFEHIPLGFPQLIGSR-LDYGFFSRENPTHLGGRGAVY
           **::***            *     ::     *:                   ::

Vca       LARGRLLGGSSGTNATLYHRGTPADYDSWGL----EGWTSKDLLDWFVKAECYG------
Cre-APS   LARGRMLGGSSGSNATLYHRGSAADYDAWGL----EGWSSKDVLDWFVKAECYA------
Gpe       LARGRLLGGSSGTNATLYHRGTSSDYDSWGL----EGWTSKDVLDWFVKAECYG------
Cva-APS   MARGRLLGGSSATNATLYHRGAAGDYDAWGV----EGWSSEDVLSCASLARRSP------
Csu       LARGKLLGGSSATNATLYHRGTAADYDAWGV----PGWTSQDALRWFIQAENNC--R---
Aan       VCRGKGLGGSSLTNVMLYNRGSANDYDAWAAACGDDSWGAEEMLGYFKKAEDCLVPA---
Ptr       LQRGKILGGSSCTNVCLHHRGSAEDYNSWNI----PGWTATDVLPFFKQSQKDE--T---
Csp       LCRGKALGGSSCTNVMLYNRGSPADYNSWVAA-GAEGWGPDSVLHYYRKSENY---V---
Ehu1      LCRGKALGGSSVTNVMLYHRGSPADYDAWEEA-GARGWGAKDVLPYYLRVEDY---G---
Ccr       FPRGKVLGGSHAISVMLYHRGHPADYTAWAES--APGWAPQDVLPYFLKSESQQSAV---
Cme       LPRGRGEGGSHAISVMLVHRGSRHDYETWVKDYEALGWGPDDVLPYFKRLESNERTAQRG
           **:  ***      *  **   **  *         *      *

Vca       ---DGPRAFHGQSGSMNVEQPRYQN-VLHDEFFRAAA-AAGLPANEDFNDWSRPQEGYGE
Cre-APS   ---DGPKPYHGTGGSMNTEQPRYEN-VLHDEFFKAAA-ATGLPANPDFNDWSHPQDGFGE
Gpe       ---DGPKPYHGNSGSMNVEQPRYQN-PLHEEFFRAAA-AAGIPANPDFNDWSRPQDGYGE
Cva-APS   ---AGPGAYHGSGGPMRVENPRYTNKQLHTAFFKAAE-EVGLTPNSDFNDWSHDHAGYGT
Csu       ---GIEDGVHGTGGLMRVENPRYNN-PLHEVFFQAAK-QAGLPENDNFNNWGRSQAGYGE
Aan       ---HRANHYHGVGGPYASSHVPYTN-EMSTAFVEAAV-EDGGVRNGDFNDWSTSQVGFGR
Ptr       ---GRDATFHGADGEWVMDEVRYQN-PLSKLFLEVGE-AAGLGTNDDFNNWSHPQDGVGR
Csp       ---GGASQYHGVDGPLSVSDVPYEN-ELSTAFLRAAG-ELGYRRVHDFNDWSAPQEGFGR
Ehu1      ---DGASQYHAVGGHVSVQEVPYQN-QLSATFLRAMG-QLGFRPNGDFNDWSSPQEGYGR
```

FIGURE 4 (cont.)

```
Ccr         ----PNQDAHGYEGPLAVSDLARLN-PMSKAFIKAAHNAAGLNHNPDFNDWATGQDGVGP
Cme         ADGEAATALHGSDGPLRVSDQRSPN-PLSLAFIEACL-ERGIRRNKDFNDWDHGQEGAGL
             *.  *    ..    *   :  *...    *        :**:*    :  *  *

Vca         FQVAQKNGERADTYRTYLKPA-MGRDNLKVMTGARTTKVHIEKSST---GPRARGVEYAT
Cre-APS     FQVSQKKGQRADTYRTYLKPA-MARGNLKVVIGARATKVNIEKGSS---GARTTGVEYAM
Gpe         FQVAQNKGQRADTYRTYLKPA-LSRGNLKVVTGARTTKVHIEKGSS---GPRARGVEFAT
Cva-APS     FQVMQDKGTRADMYRQYLKPV-LGRRNLQVLTGAAVTKVNIDQAAG---KAQALGVEFST
Csu         FQVTHSKGERADCFRMYLEPV-MGRSNLTVLTGAKTLKIETEKSGG---ATVSRGVTFQV
Aan         FAVSQRKGARVDAATAYLPRKVRRRANLDVVRGAALSGVTWNANK-------ATGVEFAF
Ptr         FQVSEVNGERCSGATAFLSKA-AKRSNVIVRTGTMVRRIDFDETKT------AKGITYDL
Csp         YKVTQRNGERCSAANAYLEGT-EGRSNLCVRTGVHATRVTLEGSGD---DLCAAGVEYI-
Ehu1        YKVTQRAGRRCTAADGYLAAA-RERANLVVVTGAQATRLALDSAYDGAGRLQVSGVEFAR
Ccr         FQVTQRDGSRESPATSYLRAA-KGRRNLTVMTGAVVERILFENPAG-SSTPVATAVSFID
Cme         FQVTQRDGRRESPATAYLQPV-RSRRNLHIETNALAEHLVWSKDGR-----RVEGIRFID
             : *  .  * *         :*       *  *:  :   ..    .           .:  :

Vca         Q-QFGERYTAELTPGGEVLMCTGAVHTPHLLMLSGIGPAPTLLEHGLDVISSLPGVGANL
Cre-APS     Q-QFGDRFTAELAPGGEVLMCSGAVHTPHLLMLSGVGPAATLKEHGIDVVSDLSGVGQNL
Gpe         Q-QFGDRYSAQLAPGGEVLMCTGAVHTPHLLMLSGVGPAAALREHGVDVVADLAGVGANL
Cva-APS     DGPT---GGAELAPGGEVIMCAGAVHTPFLLKHSGVGPSAELKEFGIPVVSNLAGVGQNL
Csu         NGQDGSKHSAELAAGGEVVLCAGSIHSPQILQLSGIGPQAELRSKDIPVVADLPGVGQNM
Aan         G-GV-----SGIACGGEVILSGGAVHSPQMLMLSGVGAKAQLEEFGIPVVADRPGVGKNL
Ptr         M-GDDTCTVPCLKEGGEVLVTGGAIASPQLLMCSGIGPGKHLRSLGIPVVHDNSAVGENL
Csp         G-ADGKPSRAQLAQGGEVLLSAGAVQSPQLLMLSGIGPRAHLEEVGIEVRKELDNVGVGL
Ehu1        G-DEREPCSVRLARGGEAVLCAGAVQTPHLLLLSGIGPAEHLREVGVPVRADLPGVGSGL
Ccr         SKG----TRVRMSASREILLCGGVYATPQLLMLSGVGPAEHLRSHGIEIVADVPAVGQNL
Cme         RHG----RRRAALAHCEVILAAGAINTPQLLMLSGLGPGAHLQDFGIPVVRDLPGVGQNL
                 *  ::  *    :*   :*   **:*      *  . .:  :   .   **  .:

Vca         QDHPAAVLAVRAKPEFEGLSVTSEIYDSK--CNIRLGAVMKYLFGRRGPLATTGCDHGAF
Cre-APS     QDHPAAVLAARAKPEFEKLSVTSEVYDDK--CNIKLGAVAQYLFQRRGPLATTGCDHGAF
Gpe         QDHPAAVVAVRAKPEFEKLSVTSEIYDEK--CNIKLGAVAQYLFNRRGPLATTGCDHGAF
Cva-APS     QDHPACLTAAPVKEKYDGIAISGERNSLL-------GQATIYLLGGRGGLTSTGCDRGAF
Csu         QDHPACLSAFYLKESAGPISVTDELLHTN--GRIRARAILKYLLFKKGPLATTGCDHGAF
Aan         QDHPACLVSWRGSAKAQGKSHSTQLRIPG-TTKTSPKALLQWLFLGRGPLASPGCDHGGF
Ptr         QDHPAAVSFKTPQKGV--SVTSKLRLFG---KTNPIPVFQWLFFKSGLLTSTGCDHGAF
Csp         ADHPAVVVSCGSK-KKV--SVTDEIRLWG-GSKTNPMALLRWLLWRRGPLTSVACEFGGF
Ehu1        QDHPAVVVSYESK-KAV--AATDDALLKGYASLVNPLAMLRWLLFGRGPLACAACDHGGF
Ccr         QDHAAAMVSFESQNPE-KDKANSSVYYTE-RTGKNIGTLLNYVFRGKGPLTSPMCEAGGF
Cme         QDHAAVMLSYYAPDPYGKDRDKKRIFYTE-RLGKDPLVLAEYFLLGRGPLTSPVCEAGAF
              *:  *   : :              .                       :..:    *  *:    *:  *.*

Vca         VRTSASH--SQPDLQMRFVPGCALDPDGVKSYIVF---GELKKQGRAWPGGITLQLLGIR
Cre-APS     VRTSSSL--SQPDLQMRFVPGCALDPDGVKSYIVF---GELKKQGRAWPGGITLQLLAIR
Gpe         VRTSGSH--SQPDLQMRFVPGCALDPDGVKSYIVF---GELKKQGRAWPGGITLQLLAIR
Cva-APS     VRTAG-Q--ALPDLQVRFVPGMALDPDGVSTYVRF------------ANGITMQLIACR
Csu         VKTAG-Q--SEPDLQIRFVPGLALDPDGIGSYTAF---GKMKD--QKWPSGITFQLLGVR
Aan         AKVGAGD--GDCDVQFRFLATKSITPDGMSTISDS---Y---EAAVDHPDGLTIQTIVAR
Ptr         VRTSDSL--EQPDLQIRFLAARALGPDGMTTYTKF-------RTMKTVEDGYSFQSVACR
Csp         FKTKPDL--KQADVQVRFVAARAMSPDGITTLQQL-------GAGAKFLSGYTTQIIACR
Ehu1        VRSSPDL--DQPDVQIRFVPARASSASGMNTLIEL-------GRRARFLPGFSTQVVACR
Ccr         AKTDPSM--DACDLQLRFIPFV-SEPDPYHSLADFATAGSYLQNRANRPTGFTIQSVAAR
Cme         VHTQAVIGEPSCDLQLRFVPFF-SDADPYKSLGEYRSGGHVLTNTSIRPAGFGLQAVAIR
              :        *:*.**:        .   :          *    *  :   *

Vca         AKS-RGSIGLKAADPFINPAININYFSDP--EDLATLKNGVRIAREIVAQEPLRKYLLEE
Cre-APS     AKS-KGSIGLKAADPFINPAININYFSDP--ADLATLVNAVKMARKIAAQEPLKKYLQEE
Gpe         AKS-KGSIGLKAADPFINPAININYFSDP--ADLATLKQGVRMARDIARQEPLRKYLQEE
Cva-APS     PQS-TGSVGLKSADPFAPPKLSPGYLTDKDGADLATLRKGIHWARDVARSSALSEYLDGE
```

FIGURE 4 (cont.)

```
Csu      PKS-RGSVGLRSDDPWDAPKLDIGFLTDKEGADLATLRSGIKLSREIAAEPAFGAYVGNE
Aan      PKSRAGEVKLASRDPAAKPVIENAYLSDE--ADVMTMVKALQKARSIASRAPLSAYAGHE
Ptr      AKS-KGRIRLSSSNSHVKPMIDGGYLSNQ--DDLATLRAGIKLGRMLGNRPEWGEYLGQE
Csp      PQS-TGLVRLRSSDPLAQPMLQDVHLSDD--ADVATLREGIKLGRQLLAAKSFDQYRDEE
Ehu1     PRS-EGRVRLRSADPFAKPIIEGIHLGAA--EDVASLRHGIRLGRQVCAAAAFDEYRGEE
Ccr      PKS-RGHVQLRSTDVRDSMSIHGNWISND--ADLKTLVHGVKLCRTIGNDDSMKEFRGRE
Cme      PRS-RGRIELATIDPRARPIIHTGWLEDK--RDLQTLLSGLKLGREILSGDSMRPYRGRE
             :*    *  : *  : :        :       :      *:  :: .::  * :         :   *

Vca      TFPGERANTDKDIEEYVRRTVHSGNALVGTCAMGTTPASGAVVSSADLKVFGVDGLRVVD
Cre-APS  TFPGERASSDKDLEEYIRRTVHSGNALVGTAAMGASPAAGAVVSSADLKVFGVEGLRVVD
Gpe      TFPGERASSDSDIEEYVRRTVHSGNALVGTCAMGTSPAKGAVVSSSDLKVFGVEGLRVVD
Cva-APS  LFPGSGVVSDDQIDEYIRRSIHSSNAITGTCKMGNAGDSSSVV-DNQLRVHGVEGLRVVD
Csu      LHPGAAASSDSAIDSFIRDTVHSGNANVGTCSMGVNGN--AVV-DPSLRVFGIRGLRVAD
Aan      EFPGEDVADERQLAAYVRNTAHTANAVVGTCKMGESSDALAVV-DNHLKVIGVSNLRVVD
Ptr      VYPGPDVQTDEEIDEYIRNSLHTANALTGTCKMGTG--RGAVV-GPDLRVIGVNGVRVAD
Csp      VYPGVAVQSDEDIDAYVRKTTHSANALVGSCRMGRVDDQAAVL-DPEMRVRGVGSLRVVD
Ehu1     VFPGAAVQSDEQIDEYIRSSVHSANALTSSCRMGDPSDPAAVL-DSHLRVRGVGGLRVAD
Ccr      LYPGGEKVSDADIEAYIRDTCHTANAMVGTCRMGIGEQ--AAV-DPALQVKGVARLRVVD
Cme      AFPET---LEDDLVTYIRRTCHTANAIVGTARMGTGRD--AVV-DPELRVHGVERLRVID
           .*         :    :    ::* : *:. **  ..:. **       :.:  .    ::* *:   :** *

Vca      ASVLPRIPGGQTGAATVMVAERAAAMLLGQATITSRREPAAV-------------------
Cre-APS  ASVLPRIPGGQTGAATVMVAERAAALLRGQATIAPSRQPVAV-------------------
Gpe      ASVLPQIPGGQTGAATVMVAERAAALLKGQTTMAPSRQPVAA-------------------
Cva-APS  ASVVPKIPGGQTGAPVVMIAERAAALLTGKATIGASAAAPAT----------VAA-------
Csu      ASVIPVIPGGQTGAATVMVAERAAEILLGSNQKQPAAAVPAA----------QPALA-----
Aan      ASVMPTLPGGQTAASTVALAEKAADLIKGG------------------------------
Ptr      SSVFPCIPGGQTATPTVMIADRAAVFVR--------------------------------
Csp      ASAMPHIIGGQTCGPTIMMAEKAADLVLRQRAEINAYMQQAQAYLAASAGAATPALSPAQAA
Ehu1     ASAMPRIIGGQTQAPTYMLAERAADILLHARLQAHEPATESVSQRLE---VAAAAL------
Ccr      SSVMPTLPGGQSGAPTMMIAEKGADLIRAAARQADAATVGAAA------------------
Cme      ASVMPKIIGGQTGVPTMMIAERGADLVKKTWKLV---------------------------
           :*..*  :  ***:         .  :*::.*  ::
```

FIGURE 15
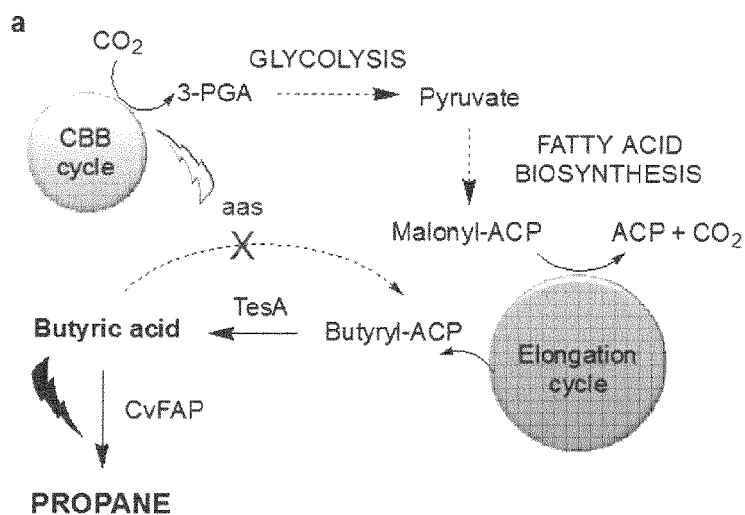
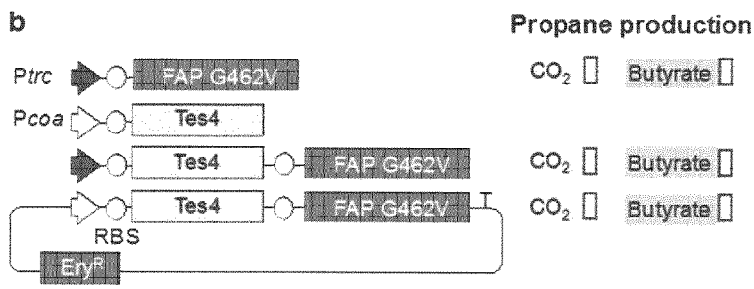
FIGURE 16
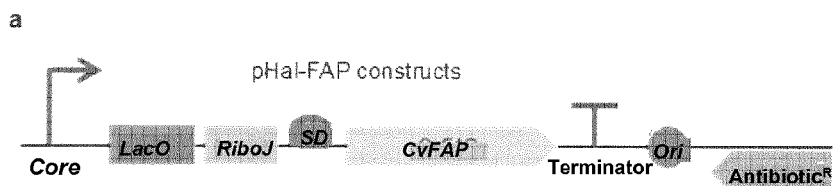
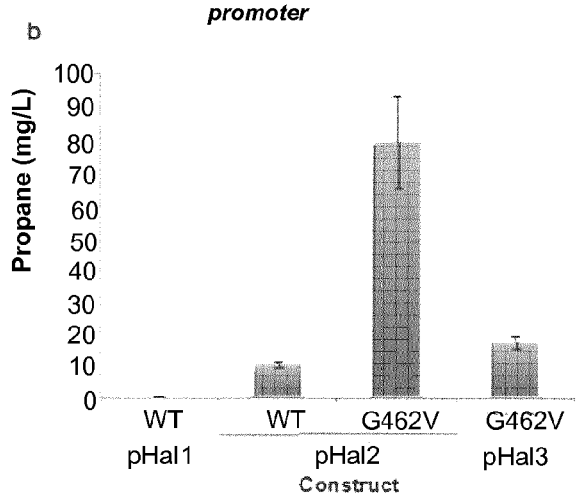
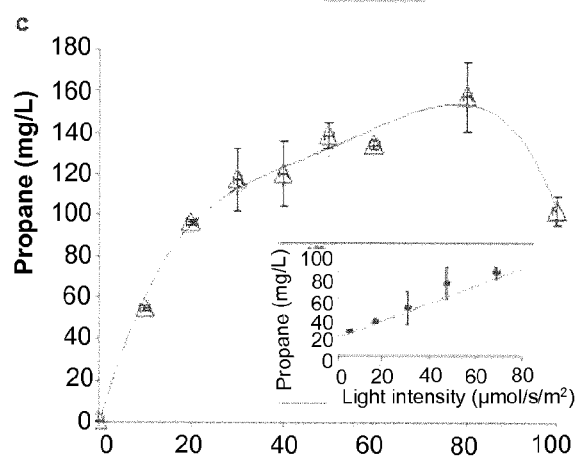

d

ATTAAAGCGGATAACAATTTCACACAGGAGGCCGCCTATTCTG*AAATGAGCTGATATTTGTG GCATTATAG*AATTGTGAGCGCTCACAATTAGCTGTCACCGGATGTGCTTTCCGGTCTGATGA GTCCGTGAGGACGAAACAGTTTCAGAATTCAAAAGATCTTTTAAGAAGGAGATATACCCATG

FIGURE 21

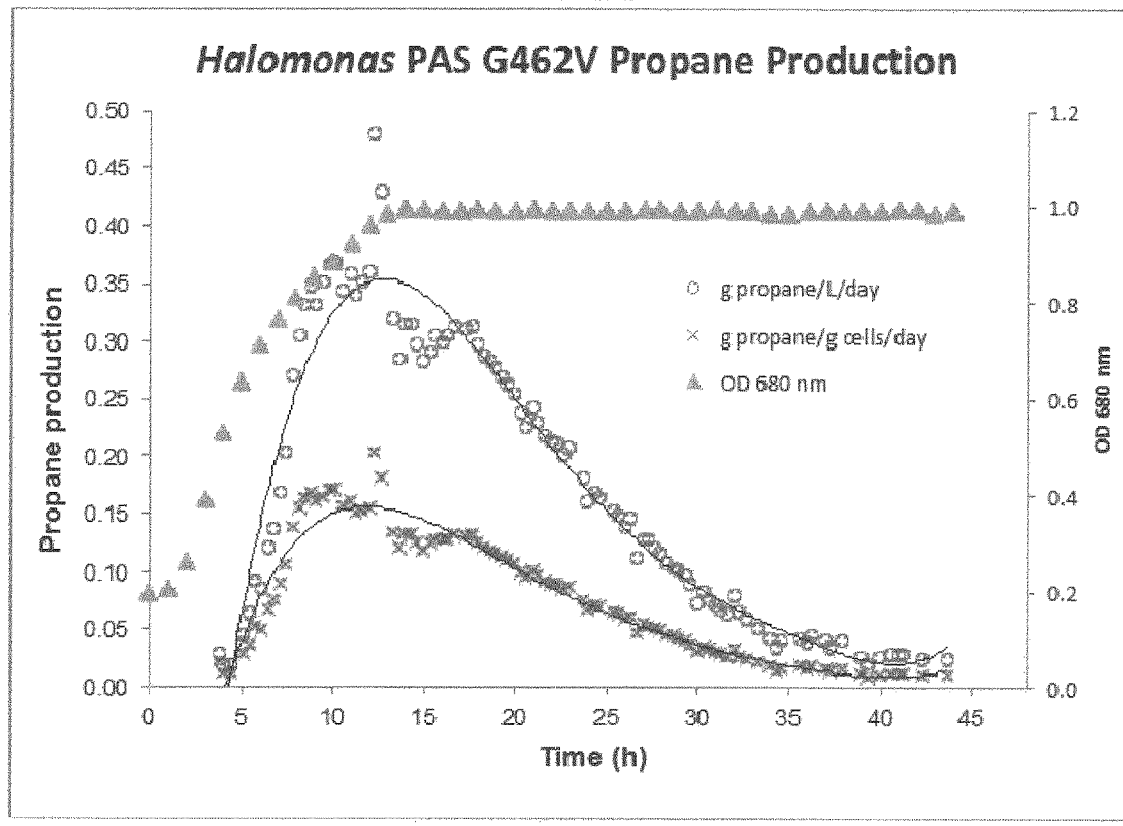

FIGURE 22
Table S1 Expression and activity of putative FAP homologues in *E. coli*.

| Homologue | Soluble expression | *In vitro* propane production |
|---|---|---|
| CvFAP | Very high | Yes |
| CrFAP | High | Yes |
| GpFAP | High | Yes |
| CcFAP | Low | No |
| ChFAP | Very low | No |
| CsFAP | Low | Yes |
| PtFAP | Very low | No |
| CmFAP | Low | No |

Cultures (5-20 mL) were grown in LB medium containing kanamycin (30 μg/mL) at 37 °C and 200 rpm until the $OD_{600\ nm}$ = 0.2. Recombinant protein expression was induced with IPTG (0.5 mM) and the cultures were incubated for 17 h at 17-25 °C. *In vitro* reactions (200 μL) were composed of cell-free lysate (180 μL) and butyric acid (400 μM) in sealed glass GC vials. The reactions were incubated at 30 °C for 24 h at 180 rpm in the presence or absence (control samples) of a blue LED (455 nm). Headspace gas was analysed for propane content using a Micro GC with an $Al_2O_3$/KCl column.

FIGURE 23

Table S2 Propane production of cell lysates of CvFAP$_{WT}$ and 28 variants expressed in E. coli.

| Variant | Propane production (mg/L lysate) | Relative activity[1] (mg/L lysate normalised) |
|---|---|---|
| WT | 0.67 ± 0.99 | 0.67 ± 0.99 |
| V453F | 0.95 ± 0.14 | 0.94 ± 0.14 |
| V453I | 1.81 ± 0.55 | 1.89 ± 0.57 |
| V453L | 0.33 ± 0.18 | 0.40 ± 0.22 |
| V453W | 1.25 ± 0.13 | 1.85 ± 0.20 |
| G455F | 0.29 ± 0.07 | 0.26 ± 0.06 |
| G455I | 0.08 ± 0.01 | 0.15 ± 0.02 |
| G455V | 0.05 ± 0.00 | 0.07 ± 0.00 |
| G455W | 0.25 ± 0.16 | 0.41 ± 0.27 |
| G455L | 0.08 ± 0.10 | 0.21 ± 0.26 |
| A457F | 0.02 ± 0.02 | 0.02 ± 0.03 |
| A457I | 0.03 ± 0.10 | - |
| A457L | 0.04 ± 0.08 | 0.05 ± 0.13 |
| A457V | 0.07 ± 0.15 | 0.07 ± 0.17 |
| G462A | 7.14 ± 1.09 | 16.87 ± 2.58 |
| G462C | 3.94 ± 2.38 | 5.91 ± 3.57 |
| G462F | 7.00 ± 0.38 | 9.34 ± 0.51 |
| G462H | 0.04 ± 0.02 | 0.04 ± 0.02 |
| G462I | 10.77 ± 1.19 | 14.77 ± 1.63 |
| G462L | 0.02 ± 0.01 | - |
| G462N | 0.53 ± 0.08 | 0.83 ± 0.12 |
| G462V | 5.07 ± 1.12 | 4.85 ± 1.07 |
| G462W | 0.61 ± 0.19 | 0.57 ± 0.18 |
| G462Y | 0.83 ± 0.46 | 1.75 ± 0.98 |
| Y466W | 0.23 ± 0.08 | 0.60 ± 0.19 |
| T484A | 0.03 ± 0.03 | 0.03 ± 0.02 |
| T484E | 0.01 ± 0.01 | 0.02 ± 0.02 |
| T484I | 0.00 ± 0.01 | 0.01 ± 0.01 |
| T484L | 0.03 ± 0.05 | 0.04 ± 0.07 |

Cultures (20 mL) were grown in LB medium containing kanamycin (30 µg/mL) at 37 °C until OD$_{600}$ ~ 0.6-0.8. Recombinant protein expression was induced with IPTG (0.1 mM) and cultures were supplemented with 10 mM butyric acid. Triplicate aliquots (1 mL) of cultures were sealed into 4 mL glass vials and incubated at 30 °C for 16-18 h at 200 rpm, illuminated with a blue LED panel. Headspace gas was analysed for gaseous hydrocarbon content using a Micro GC. Reactions were performed in triplicates of biological replicates. Normalised data was calculated by dividing the propane yields (mg/L lysate) by the relative protein concentration compared to wild type (WT) enzyme (Figure S1). [1]Lysates A457I and G462L did not show visible bands on SDS PAGE, so no relative activity data could be calculated.

FIGURE 24

Table S3 Molecular docking simulations of CvPAS wild-type and variants with butyrate and palmitate.

| Variant | -ΔG (kcal/mol) | | $K_b$ (kcal/mol) | |
|---|---|---|---|---|
| | Butyrate | Palmitate | Butyrate | Palmitate |
| WT | 1.00 | 1.00 | 1.00 | 1.00 |
| G462V | 1.05 | 0.70 | 1.40 | 0.03 |
| G462I | 1.05 | 0.73 | 1.40 | 0.03 |
| G462L | 1.05 | 1.00 | 1.40 | 1.00 |
| V453I | 1.02 | 0.97 | 1.18 | 0.72 |
| G455I | 1.05 | 1.05 | 1.40 | 1.96 |
| Y466W | 0.97 | 0.89 | 0.85 | 0.26 |
| T484I | 1.00 | 0.95 | 1.00 | 0.51 |
| A457V | 1.03 | 0.88 | 1.18 | 0.22 |

Molecular docking simulations were performed using Autodock Vina and the wild-type crystal structure of CvFAP.[2] Values of the predicted free energy of binding (-ΔG) and binding constant ($K_b$) are normalised against the values for WT.

FIGURE 25

Table S4 *In vivo* propane production by CvFAP$_{G462V}$ variant in *E. coli* BL21(DE3).

| Variable | Butyric acid (mM) | Additive | Propane (mg/L culture) |
|---|---|---|---|
| Cell leakiness | 1 | None | 0.67 ± 0.05 |
| | 1 | Triton X-100 | 1.07 ± 0.07 |
| | 1 | Sucrose | 0.94 ± 0.11 |
| | 1 | Triton X-100 and sucrose | 0.98 ± 0.31 |
| Butyric acid concentration | 0 | Triton X-100 | 0.04 ± 0.01 |
| | 1 | Triton X-100 | 0.36 ± 0.01 |
| | 5 | Triton X-100 | 2.03 ± 0.02 |
| | 10 | Triton X-100 | 7.53 ± 0.29 |
| | 15 | Triton X-100 | 6.20 ± 0.50 |
| | 20 | Triton X-100 | 4.80 ± 0.59 |
| | 25 | Triton X-100 | 2.20 ± 0.38 |
| Transporter stimulation | 10 | None | 9.53 ± 0.03 |
| | 10 | 0.1 mM EAA | 9.43 ± 0.78 |
| | 10 | 1 mM EAA | 14.86 ± 0.92 |
| | 10 | 10 mM EAA | 17.51 ± 0.98 |
| | 10 | 20 mM EAA | 15.75 ± 1.73 |
| | 10 | 30 mM EAA | 6.49 ± 0.17 |
| | 10 | 10 mM MAA | 26.91 ± 6.59 |

Cultures (20-100 mL) were grown in LB medium containing kanamycin (50 μg/mL) and an overnight starter culture (1% volume; same medium) for 6 h at 37 °C and 180 rpm. Recombinant protein expression was induced with IPTG (0.1 mM) and cultures were supplemented with butyric acid (1-25 mM) ± Triton X-100 (1%) and/or sucrose (1%). Triplicate aliquots (5 mL) of cultures were sealed into 20 mL glass vials and incubated at 30 °C for 16-18 h at 200 rpm, illuminated continuously with a blue LED panel. Headspace gas was analysed for propane content using a Micro GC (100 ms injection) with an Al$_2$O$_3$/KCl column. EAA = ethyl acetoacetate; MAA = methyl acetoacetate.

FIGURE 26

Table S5 *In vivo* propane production by N-His$_6$-CvFAP$_{G462V}$ in pET21b expressed in *E. coli*.

| Construct | Butyric acid (mM) | EAA (mM) | Propane (mg/L culture) |
|---|---|---|---|
| CvFAP$_{G462V}$ | 10 | 0 | 47.9 ± 11.8 |
| | 10 | 10 | 97.1 ± 10.3 |
| CvFAP$_{G462V}$/AtoE | 10 | 0 | 65.1 ± 3.2 |
| | 10 | 10 | 93.8 ± 8.1 |

Cultures (20 mL) were grown in LB medium containing ampicillin (100 μg/mL) and an overnight starter culture (1% volume; same medium) for 6 h at 37 °C and 180 rpm. Recombinant protein expression was induced with IPTG (0.1 mM) and cultures were supplemented with butyric acid (10 mM) ± ethyl acetoacetate (EAA; 10 mM). Triplicate aliquots (1 mL) of cultures were sealed into 5 mL glass vials and incubated at 30 °C for 16-18 h at 200 rpm, illuminated continuously with a blue LED panel. Headspace gas was analysed for propane content using a Micro GC (100 ms injection) with an Al$_2$O$_3$/KCl column. NA = not applicable.

FIGURE 27

Table S6 *In vivo* production of gaseous hydrocarbons by variant CvFAP in *E. coli* in the presence of short chain organic acids

| | Substrate acid | | | | |
|---|---|---|---|---|---|
| | Butyric | Isobutyric | Valeric | 2-MB | Isovaleric |
| | Propane | | Butane | | Isobutane |
| Variant | (mg/L culture) | | (mg/L culture) | | (mg/L culture) |
| WT | 7.0 ± 0.6 | 6.1 ± 2.4 | 17.7 ± 1.9 | 7.1 ± 1.4 | 5.6 ± 0.3 |
| G462A | 17.6 ± 0.7 | 5.0 ± 1.2 | 33.5 ± 6.5 | 50.0 ± 11.4 | 30.2 ± 3.9 |
| G462I | 43.8 ± 3.1 | 36.9 ± 5.4 | 47.1 ± 7.8 | 95.4 ± 5.8 | 86.8 ± 10.8 |
| G462F | 31.2 ± 0.7 | 31.4 ± 3.3 | 27.7 ± 0.8 | 38.5 ± 10.9 | 28.6 ± 4.0 |
| G462V | 24.5 ± 5.0 | 24.3 ± 1.6 | 21.9 ± 0.7 | 12.2 ± 2.1 | 17.4 ± 2.0 |

Cultures (20 mL) of FAP-pETM11 containing *E. coli* st. BL21(DE3)ΔyqhD/ΔyjgB were grown in LB medium containing kanamycin (50 μg/mL) at 37 °C until OD$_{600}$ = 0.6-0.8. Recombinant protein expression was induced with IPTG (0.1 mM) and cultures were supplemented with volatile fatty acid (10 mM). Triplicate aliquots (1 mL) of cultures were sealed into 4 mL glass vials and incubated at 30 °C for 16-18 h at 200 rpm, illuminated continuously with a blue LED panel. Headspace gas was analysed for propane content using a Micro GC (100 ms injection) with an Al$_2$O$_3$/KCl column. WT = wild type; 2-MB = 2-methylbutyric acid.

FIGURE 28

Table S7 Effect of butyric/valeric acid blends on gaseous hydrocarbon production by wild type CvFAP in *E. coli* st. BL21(DE3)ΔyqhD/ΔyjgB.

| Butyric Acid (%) | Valeric acid (%) | Propane (mg/L culture) | Butane (mg/L culture) |
| --- | --- | --- | --- |
| 0 | 0 | 0.6 ± 0.06 | 0.03 ± 0.00 |
| 0 | 100 | 0.21 ± 0.01 | 17.13 ± 0.31 |
| 20 | 80 | 3.62 ± 0.13 | 13.74 ± 0.42 |
| 30 | 70 | 5.76 ± 0.04 | 13.15 ± 0.03 |
| 35 | 65 | 6.43 ± 0.25 | 11.87 ± 0.5 |
| 40 | 60 | 7.39 ± 0.22 | 10.99 ± 0.07 |
| 50 | 50 | 8.75 ± 1.04 | 8.37 ± 0.91 |
| 60 | 40 | 11.67 ± 0.66 | 7.41 ± 0.29 |
| 70 | 30 | 11.96 ± 1.32 | 5.02 ± 0.59 |
| 80 | 20 | 14.04 ± 0.22 | 3.72 ± 0.05 |
| 90 | 10 | 17.29 ± 0.53 | 1.95 ± 0.04 |
| 92 | 8 | 17.56 ± 0.31 | 1.57 ± 0.05 |
| 95 | 5 | 17.10 ± 0.24 | 0.99 ± 0.02 |
| 100 | 0 | 19.32 ± 1.55 | 0.00 ± 0.00 |

Cultures (20 mL) were grown in LB medium containing kanamycin (50 µg/mL) at 37 °C until $OD_{600}$ ~ 0.6-0.8. Recombinant protein expression was induced with IPTG (0.1 mM) and cultures were supplemented with acid substrates (10 mM total). Triplicate aliquots (1 mL) of cultures were sealed into 4 mL glass vials and incubated at 30 °C for 16-18 h at 200 rpm, illuminated with a blue LED panel. Headspace gas was analysed for gaseous hydrocarbon content using a Micro GC.

FIGURE 29

Table S8 *In vivo* propane production by CvFAP$_{G462V}$ variant in *Halomonas* st. XV12.

| Variable | Butyric acid (mM) | Additive | Propane (mg/L culture) |
|---|---|---|---|
| Cell leakiness | 10 | None | 55.2 ± 13.2 |
|  | 10 | Triton X-100 | 55.5 ± 3.7 |
|  | 10 | Sucrose | 50.9 ± 9.1 |
|  | 25 | None | 127.8 ± 5.7 |
|  | 25 | Triton X-100 | 144.6 ± 6.1 |
|  | 25 | Sucrose | 121.4 ± 13.6 |
| Butyric acid concentration | 0 | None | 0.9 ± 0.1 |
|  | 10 | None | 54.9 ± 1.4 |
|  | 20 | None | 96.7 ± 1.6 |
|  | 30 | None | 117.2 ± 15.4 |
|  | 40 | None | 119.7 ± 15.3 |
|  | 50 | None | 138.4 ± 6.32 |
|  | 60 | None | 133.7 ± 2.25 |
|  | 80 | None | 157.1 ± 17.14 |
|  | 100 | None | 102.2 ± 7.0 |
| Transporter stimulation | 25 | None | 45.6 ± 1.1 |
|  | 25 | 10 mM EAA | 51.7 ± 0.5 |
|  | 25 | 10 mM MAA | 42.9 ± 1.6 |

Cultures (20-100 mL) were grown in LB medium containing kanamycin (50 µg/mL) and an overnight starter culture (1% volume; same medium) for 6 h at 37 °C and 180 rpm. Recombinant protein expression was induced with IPTG (0.1 mM) and cultures were supplemented with butyric acid (1-25 mM) ± Triton X-100 (1%) and/or sucrose (1%). Triplicate aliquots (5 mL) of cultures were sealed into 20 mL glass vials and incubated at 30 °C for 16-18 h at 200 rpm, illuminated continuously with a blue LED panel. Headspace gas was analysed for propane content using a Micro GC (100 ms injection) with an $Al_2O_3$/KCl column. EAA = ethyl acetoacetate; MAA = methyl acetoacetate.

FIGURE 30

Table S9 Oligonucleotide and other DNA sequences in *E. coli* and *Halomonas*.

| Protein | DNA sequence |
|---|---|
| OXB1 promoter[1] | AAGCTGTTGTGACCGCTTGCTCTAGCCAGCTATCGAGTTGTGAACCGATCCATCTAGCA ATTGGTCTCGATCTAGCGATAGGCTTCGATCTAGCTATGTAGAAACGCCGTGTGCTCGA TCGCCTGACGCTTTTTATCGCAACTCTCTACTGTTGCTTCAACAGAACATATTGACTAT CCGGTATTACCCGGC*CATGGTATATCTCCTTCTTAAAGTTAAACAAA* |

*Mutagenesis in E. coli*

| | |
|---|---|
| CvFAP$_{G462V}$ | 5'-GCACTGGATCCGGAT*GTT*GTTAGCACCTATGTG-3' |
| | 5'-CACATAGGTGCTAAC*AAC*ATCCGGATCCAGTGC-3' |
| CvFAP$_{G462I}$ | 5'-GATCCGGATATTGTTAGCACCTATG-3' |
| | 5'-CAGTGCCATACCAGGAACAAAAC-3' |
| CvFAP$_{G462F}$ | 5'-GATCCGGATTTTGTTAGCACC-3' |
| | 5'-CAGTGCCATACCAGGAACAAAAC-3' |
| CvFAP$_{G462A}$ | 5'-GCGGTTAGCACCTATGTGCGTTTTG-3' |
| | 5'-ATCCGGATCCAGTGCCATAC-3' |
| CvFAP$_{G462H}$ | 5'-CAGTGCCATACCAGGAACAAAACG-3' |
| | 5'-CAGTGCCATACCAGGAACAAAAC-3' |
| CvFAP$_{G462L}$ | 5'-GATCCGGATCACGTTAGCACCTATG-3' |
| | 5'-GATCCGGATCTGGTTAGCACCTATG-3' |
| CvFAP$_{G462C}$ | 5'-GATCCGGATTGTGTTAGCACCTATG-3' |
| | 5'-GATCCGGATTGGGTTAGCACCTATG-3' |
| CvFAP$_{G462W}$ | 5'-GATCCGGATTATGTTAGCACCTATG-3' |
| | 5'-GATCCGGATAACGTTAGCACCTATG-3' |
| CvFAP$_{G462Y}$ | 5'-GATCCGGATTATGTTAGCACCTATG-3' |
| | 5'-CAGTGCCATACCAGGAACAAAAC-3' |
| CvFAP$_{G462N}$ | 5'-GATCCGGATAACGTTAGCACCTATG-3' |
| | 5'-CAGTGCCATACCAGGAACAAAACG-3' |
| CvFAP$_{G455F}$ | 5'-GTTTTGTTCCTTTTATGGCACTGGATCC-3' |
| | 5'-GAACTTGCAGATCCGGCAG-3' |
| CvFAP$_{G455I}$ | 5'-GTTTTGTTCCTATTATGGCACTGGATCC-3' |
| | 5'-GAACTTGCAGATCCGGCAG-3' |
| CvFAP$_{G455V}$ | 5'-GTTTTGTTCCTGTTATGGCACTGGATCC-3' |
| | 5'-GAACTTGCAGATCCGGCAG-3' |
| CvFAP$_{G455W}$ | 5'-GTTTTGTTCCTTGGATGGCACTGGATC-3' |
| | 5'-GAACTTGCAGATCCGGCAG-3' |
| CvFAP$_{G455L}$ | 5'-TTTTGTTCCTCTGATGGCACTGGATCC-3' |
| | 5'-CGAACTTGCAGATCCGGC-3' |
| CvFAP$_{Y466W}$ | 5'-GTGTTAGCACCTGGGTGCGTTTTG-3' |
| | 5'-CATCCGGATCCAGTGCCATAC-3' |
| CvFAP$_{V453L}$ | 5'-CAAGTTCGTTTTCTGCCTGGTATGGCAC-3' |
| | 5'-CAGATCCGGCAGTGCCTG-3' |
| CvFAP$_{V453W}$ | 5'-CAAGTTCGTTTTTGGCCTGGTATGGCAC-3' |
| | 5'-CAGATCCGGCAGTGCCTG-3' |
| CvFAP$_{V453F}$ | 5'-CAAGTTCGTTTTTTTCCTGGTATGGCAC-3' |
| | 5'-CAGATCCGGCAGTGCCTG-3' |
| CvFAP$_{V453I}$ | 5'-CAAGTTCGTTTTATTCCTGGTATGGCAC-3' |

| | |
|---|---|
| CvFAP$_{T484I}$ | 5'-CAGATCCGGCAGTGCCTG-3'<br>5'-GCCTGAAATGGCCGAGCGGTATTDHMATGCAGCTGATTGCATGT-3'<br>5'-CCTGGCTCTGAAATTTGGCAAAACG-3' |
| CvFAP$_{T484L}$ | 5'-GCCTGAAATGGCCGAGCGGTATTDHMATGCAGCTGATTGCATGT-3'<br>5'-CCTGGCTCTGAAATTTGGCAAAACG-3' |
| CvFAP$_{T484E}$ | 5'-GCCTGAAATGGCCGAGCGGTATTDHMATGCAGCTGATTGCATGT-3'<br>5'-CCTGGCTCTGAAATTTGGCAAAACG-3' |
| CvFAP$_{T484A}$ | 5'-GCCTGAAATGGCCGAGCGGTATTDHMATGCAGCTGATTGCATGT-3'<br>5'-CCTGGCTCTGAAATTTGGCAAAACG-3' |
| CvFAP$_{A457L}$ | 5'-GTTCGTTTTGTTCCTGGTATGNTTCTGGATCCGGATGGTGTTAGC-3'<br>5'-GCTAACACCATCCGGATCCAGAANCATACCAGGAACAAAACGAAC-3' |
| CvFAP$_{A457V}$ | 5'-GTTCGTTTTGTTCCTGGTATGNTTCTGGATCCGGATGGTGTTAGC-3'<br>5'-GCTAACACCATCCGGATCCAGAANCATACCAGGAACAAAACGAAC-3' |
| CvFAP$_{A457I}$ | 5'-GTTCGTTTTGTTCCTGGTATGNTTCTGGATCCGGATGGTGTTAGC-3'<br>5'-GCTAACACCATCCGGATCCAGAANCATACCAGGAACAAAACGAAC-3' |
| CvFAP$_{A457F}$ | 5'-GTTCGTTTTGTTCCTGGTATGNTTCTGGATCCGGATGGTGTTAGC-3'<br>5'-GCTAACACCATCCGGATCCAGAANCATACCAGGAACAAAACGAAC-3' |
| *Assembly of FAPGV-OXB1-atoE construct in pET21b* | |
| Vector opening | 5'-CGACATCACCGATGGGGAAGA-3'<br>5'-CCATCGGTGATGTCGGTCCGGCGTAGAGGATCGAG-3' |
| Insert generation | 5'-CG

FIGURE 31

Table S11 Prefix and suffix used for DNA assembly.

| Assembly | Prefix linker | Plasmid | Suffix linker |
|---|---|---|---|
| Plasmid: pIY918 or pJET-Ptrc-Tes4-CvFAPG462V | | | |
| | LRBS1-4P | pIY840 | LRBS2-4S |
| 1 | LRBS2-4P | pIY882 | 1S |
| | 1P | pIY345[3] | LRBS1-4S |
| Plasmid: pIY906 or pJET-Pcoa-Tes4-CvFAPG462V | | | |
| | LRBS1-4P | pIY840 | LRBS2-4S |
| 2 | LRBS2-4P | pIY882 | 1S |
| | 1P | pIY417[3] | LRBS1-4S |
| Plasmid: pIY894 or pJET-Ptrc-CvFAPG462V | | | |
| 3 | LRBS1-4P | pIY882 | 1S |
| | 1P | pIY345 | LRBS1-4S |
| Plasmid: pIY845 or pJET-Pcoa-Tes4 | | | |
| 4 | LRBS1-4P | pIY840 | 1S |
| | 1P | pIY417[3] | LRBS1-4S |
| Plasmids pIY345 and pIY417 are described in Yunus, I. S. and Jones, P. R. (2018).[3] | | | |

FIGURE 32

Table S12 Prefix and suffix linkers

| Adapter | | Linker | | P linker |
|---|---|---|---|---|
| Name | Sequence (5' to 3') | Name | Sequence (5' to 3') | |
| Prefix linkers | | | | |
| 1P-A | TTTATTGAACTA | 1P-L | GGACTAGTTCAATAAATACCCTCTGACTGTCTCGGAG | 1P |
| LRBS1-4P-A | ATCACAAGGAGGTA | LRBS1-4P-L | GGACTACCTCCTTGTGATTTACAACTGATACTTACCTGA | LRBS1-4P |
| LRBS2-4P-A | ATCACAAGGAGGTA | LRBS2-4P-L | GGACTACCTCCTTGTGATTTTCTGCTACCCTTATCTCAG | LRBS2-4P |
| Suffix linkers | | | | S linker |
| 1S-A | TGTCGTAAGTAA | 1S-L | CTCGTTACTTACGACACTCCGAGACAGTCAGAGGGTA | 1S |
| LRBS1-4S-A | GACGGTGTTCAA | LRBS1-4S-L | CTCGTTGAACACCGTCTCAGGTAAGTATCAGTTGTAA | LRBS1-4S |
| LRBS2-4S-A | CCAATAGTAACA | LRBS2-4S-L | CTCGTGTTACTATTGGCTGAGATAAGGGTAGCAGAAA | LRBS2-4S |
| P linker = mixed prefix linker; S linker = mixed suffix linker. | | | | |

SEQUENCE LISTING

```
<160> NUMBER OF SEQ ID NOS: 126

<210> SEQ ID NO 1
<211> LENGTH: 654
<212> TYPE: PRT
<213> ORGANISM: Chlorella variabilis

<400> SEQUENCE: 1

Met Ala Ser Ile Thr Ser Arg Ala Ser Ala Arg Ala Ser Cys Ser Gln
1               5                   10                  15

Ala Asn Thr Arg Ala Gly Arg Val Ala Leu Ser Gly Gly Ala Leu Leu
            20                  25                  30

Arg Pro Ala Arg Pro Ala Arg Ser Phe Val Pro Ala Arg Lys Gln Gln
        35                  40                  45

Gln Gly Ala Val Arg Arg Gly Gly Ala Leu Ser Ala Arg Ala Ser Ala
    50                  55                  60

Val Glu Asp Ile Arg Lys Val Leu Ser Asp Ser Ser Ser Pro Val Ala
65                  70                  75                  80
```

```
Gly Gln Lys Tyr Asp Tyr Ile Leu Val Gly Gly Thr Ala Ala Cys
                85                  90                  95

Val Leu Ala Asn Arg Leu Ser Ala Asp Gly Ser Lys Arg Val Leu Val
            100                 105                 110

Leu Glu Ala Gly Pro Asp Asn Thr Ser Arg Asp Val Lys Ile Pro Ala
        115                 120                 125

Ala Ile Thr Arg Leu Phe Arg Ser Pro Leu Asp Trp Asn Leu Phe Ser
130                 135                 140

Glu Leu Gln Glu Gln Leu Ala Glu Arg Gln Ile Tyr Met Ala Arg Gly
145                 150                 155                 160

Arg Leu Leu Gly Gly Ser Ser Ala Thr Asn Ala Thr Leu Tyr His Arg
                165                 170                 175

Gly Ala Ala Gly Asp Tyr Asp Ala Trp Gly Val Glu Gly Trp Ser Ser
            180                 185                 190

Glu Asp Val Leu Ser Trp Phe Val Gln Ala Glu Thr Asn Ala Asp Phe
        195                 200                 205

Gly Pro Gly Ala Tyr His Gly Ser Gly Gly Pro Met Arg Val Glu Asn
    210                 215                 220

Pro Arg Tyr Thr Asn Lys Gln Leu His Thr Ala Phe Phe Lys Ala Ala
225                 230                 235                 240

Glu Glu Val Gly Leu Thr Pro Asn Ser Asp Phe Asn Asp Trp Ser His
                245                 250                 255

Asp His Ala Gly Tyr Gly Thr Phe Gln Val Met Gln Asp Lys Gly Thr
            260                 265                 270

Arg Ala Asp Met Tyr Arg Gln Tyr Leu Lys Pro Val Leu Gly Arg Arg
        275                 280                 285

Asn Leu Gln Val Leu Thr Gly Ala Ala Val Thr Lys Val Asn Ile Asp
290                 295                 300

Gln Ala Ala Gly Lys Ala Gln Ala Leu Gly Val Glu Phe Ser Thr Asp
305                 310                 315                 320

Gly Pro Thr Gly Glu Arg Leu Ser Ala Glu Leu Ala Pro Gly Gly Glu
                325                 330                 335

Val Ile Met Cys Ala Gly Ala Val His Thr Pro Phe Leu Leu Lys His
            340                 345                 350

Ser Gly Val Gly Pro Ser Ala Glu Leu Lys Glu Phe Gly Ile Pro Val
        355                 360                 365

Val Ser Asn Leu Ala Gly Val Gly Gln Asn Leu Gln Asp Gln Pro Ala
    370                 375                 380

Cys Leu Thr Ala Ala Pro Val Lys Glu Lys Tyr Asp Gly Ile Ala Ile
385                 390                 395                 400

Ser Asp His Ile Tyr Asn Glu Lys Gly Gln Ile Arg Lys Arg Ala Ile
                405                 410                 415

Ala Ser Tyr Leu Leu Gly Gly Arg Gly Gly Leu Thr Ser Thr Gly Cys
            420                 425                 430

Asp Arg Gly Ala Phe Val Arg Thr Ala Gly Gln Ala Leu Pro Asp Leu
        435                 440                 445

Gln Val Arg Phe Val Pro Gly Met Ala Leu Asp Pro Asp Gly Val Ser
    450                 455                 460

Thr Tyr Val Arg Phe Ala Lys Phe Gln Ser Gln Gly Leu Lys Trp Pro
465                 470                 475                 480

Ser Gly Ile Thr Met Gln Leu Ile Ala Cys Arg Pro Gln Ser Thr Gly
                485                 490                 495
```

-continued

```
Ser Val Gly Leu Lys Ser Ala Asp Pro Phe Ala Pro Lys Leu Ser
            500                 505                 510

Pro Gly Tyr Leu Thr Asp Lys Asp Gly Ala Asp Leu Ala Thr Leu Arg
        515                 520                 525

Lys Gly Ile His Trp Ala Arg Asp Val Ala Arg Ser Ser Ala Leu Ser
        530                 535                 540

Glu Tyr Leu Asp Gly Glu Leu Phe Pro Gly Ser Gly Val Val Ser Asp
545                 550                 555                 560

Asp Gln Ile Asp Glu Tyr Ile Arg Arg Ser Ile His Ser Ser Asn Ala
                565                 570                 575

Ile Thr Gly Thr Cys Lys Met Gly Asn Ala Gly Asp Ser Ser Ser Val
            580                 585                 590

Val Asp Asn Gln Leu Arg Val His Gly Val Glu Gly Leu Arg Val Val
        595                 600                 605

Asp Ala Ser Val Val Pro Lys Ile Pro Gly Gly Gln Thr Gly Ala Pro
        610                 615                 620

Val Val Met Ile Ala Glu Arg Ala Ala Ala Leu Leu Thr Gly Lys Ala
625                 630                 635                 640

Thr Ile Gly Ala Ser Ala Ala Ala Pro Ala Thr Val Ala Ala
                645                 650

<210> SEQ ID NO 2
<211> LENGTH: 594
<212> TYPE: PRT
<213> ORGANISM: Chlorella variabilis

<400> SEQUENCE: 2

Met Ala Ser Ala Val Glu Asp Ile Arg Lys Val Leu Ser Asp Ser Ser
1               5                   10                  15

Ser Pro Val Ala Gly Gln Lys Tyr Asp Tyr Ile Leu Val Gly Gly Gly
            20                  25                  30

Thr Ala Ala Cys Val Leu Ala Asn Arg Leu Ser Ala Asp Gly Ser Lys
        35                  40                  45

Arg Val Leu Val Leu Glu Ala Gly Pro Asp Asn Thr Ser Arg Asp Val
    50                  55                  60

Lys Ile Pro Ala Ala Ile Thr Arg Leu Phe Arg Ser Pro Leu Asp Trp
65                  70                  75                  80

Asn Leu Phe Ser Glu Leu Gln Glu Gln Leu Ala Glu Arg Gln Ile Tyr
                85                  90                  95

Met Ala Arg Gly Arg Leu Leu Gly Gly Ser Ser Ala Thr Asn Ala Thr
            100                 105                 110

Leu Tyr His Arg Gly Ala Ala Gly Asp Tyr Asp Ala Trp Gly Val Glu
        115                 120                 125

Gly Trp Ser Ser Glu Asp Val Leu Ser Trp Phe Val Gln Ala Glu Thr
    130                 135                 140

Asn Ala Asp Phe Gly Pro Gly Ala Tyr His Gly Ser Gly Gly Pro Met
145                 150                 155                 160

Arg Val Glu Asn Pro Arg Tyr Thr Asn Lys Gln Leu His Thr Ala Phe
                165                 170                 175

Phe Lys Ala Ala Glu Glu Val Gly Leu Thr Pro Asn Ser Asp Phe Asn
            180                 185                 190

Asp Trp Ser His Asp His Ala Gly Tyr Gly Thr Phe Gln Val Met Gln
        195                 200                 205

Asp Lys Gly Thr Arg Ala Asp Met Tyr Arg Gln Tyr Leu Lys Pro Val
    210                 215                 220
```

Leu Gly Arg Arg Asn Leu Gln Val Leu Thr Gly Ala Ala Val Thr Lys
225                 230                 235                 240

Val Asn Ile Asp Gln Ala Ala Gly Lys Ala Gln Ala Leu Gly Val Glu
            245                 250                 255

Phe Ser Thr Asp Gly Pro Thr Gly Glu Arg Leu Ser Ala Glu Leu Ala
            260                 265                 270

Pro Gly Gly Glu Val Ile Met Cys Ala Gly Ala Val His Thr Pro Phe
            275                 280                 285

Leu Leu Lys His Ser Gly Val Gly Pro Ser Ala Glu Leu Lys Glu Phe
            290                 295                 300

Gly Ile Pro Val Val Ser Asn Leu Ala Gly Val Gly Gln Asn Leu Gln
305                 310                 315                 320

Asp Gln Pro Ala Cys Leu Thr Ala Ala Pro Val Lys Glu Lys Tyr Asp
                325                 330                 335

Gly Ile Ala Ile Ser Asp His Ile Tyr Asn Glu Lys Gly Gln Ile Arg
                340                 345                 350

Lys Arg Ala Ile Ala Ser Tyr Leu Leu Gly Gly Arg Gly Gly Leu Thr
                355                 360                 365

Ser Thr Gly Cys Asp Arg Gly Ala Phe Val Arg Thr Ala Gly Gln Ala
370                 375                 380

Leu Pro Asp Leu Gln Val Arg Phe Val Pro Gly Met Ala Leu Asp Pro
385                 390                 395                 400

Asp Gly Val Ser Thr Tyr Val Arg Phe Ala Lys Phe Gln Ser Gln Gly
                405                 410                 415

Leu Lys Trp Pro Ser Gly Ile Thr Met Gln Leu Ile Ala Cys Arg Pro
            420                 425                 430

Gln Ser Thr Gly Ser Val Gly Leu Lys Ser Ala Asp Pro Phe Ala Pro
            435                 440                 445

Pro Lys Leu Ser Pro Gly Tyr Leu Thr Asp Lys Asp Gly Ala Asp Leu
        450                 455                 460

Ala Thr Leu Arg Lys Gly Ile His Trp Ala Arg Asp Val Ala Arg Ser
465                 470                 475                 480

Ser Ala Leu Ser Glu Tyr Leu Asp Gly Glu Leu Phe Pro Gly Ser Gly
                485                 490                 495

Val Val Ser Asp Asp Gln Ile Asp Glu Tyr Ile Arg Arg Ser Ile His
            500                 505                 510

Ser Ser Asn Ala Ile Thr Gly Thr Cys Lys Met Gly Asn Ala Gly Asp
        515                 520                 525

Ser Ser Ser Val Val Asp Asn Gln Leu Arg Val His Gly Val Glu Gly
        530                 535                 540

Leu Arg Val Val Asp Ala Ser Val Val Pro Lys Ile Pro Gly Gly Gln
545                 550                 555                 560

Thr Gly Ala Pro Val Val Met Ile Ala Glu Arg Ala Ala Ala Leu Leu
                565                 570                 575

Thr Gly Lys Ala Thr Ile Gly Ala Ser Ala Ala Pro Ala Thr Val
            580                 585                 590

Ala Ala

<210> SEQ ID NO 3
<211> LENGTH: 15
<212> TYPE: PRT
<213> ORGANISM: Artificial Sequence
<220> FEATURE:
<223> OTHER INFORMATION: Fatty acid decarboxylase consensus sequence

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa = D or E
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa = A or G
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: Xaa = K or R

<400> SEQUENCE: 3

Gly Xaa Leu Xaa Xaa Xaa Xaa Cys Xaa Xaa Gly Xaa Phe Xaa Xaa
 1               5                  10                  15

<210> SEQ ID NO 4
<211> LENGTH: 185
<212> TYPE: PRT
<213> ORGANISM: Artificial Sequence
<220> FEATURE:
<223> OTHER INFORMATION: Fatty acid decarboxylase active site
<220> FEATURE:
<221> NAME/KEY: misc_feature
<222> LOCATION: (1)..(1)
<223> OTHER INFORMATION: Xaa = I, L, K or D
<220> FEATURE:
<221> NAME/KEY: misc_feature
<222> LOCATION: (2)..(29)
<223> OTHER INFORMATION: Xaa can be any naturally occurring amino acid
<220> FEATURE:
<221> NAME/KEY: misc_feature
<222> LOCATION: (30)..(36)
<223> OTHER INFORMATION: Xaa = absent or any naturally occurring amino
      acid
<220> FEATURE:
<221> NAME/KEY: misc_feature
<222> LOCATION: (38)..(55)
<223> OTHER INFORMATION: Xaa can be any naturally occurring amino
      acid
<220> FEATURE:
<221> NAME/KEY: misc_feature
<222> LOCATION: (56)..(57)
<223> OTHER INFORMATION: Xaa = absent or any naturally occurring amino
      acid
<220> FEATURE:
<221> NAME/KEY: misc_feature
<222> LOCATION: (59)..(67)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa = absent or any naturally occurring amino
      acid
<220> FEATURE:
<221> NAME/KEY: misc_feature
<222> LOCATION: (70)..(72)
<223> OTHER INFORMATION: Xaa can be any naturally occurring amino acid
<220> FEATURE:
<221> NAME/KEY: misc_feature
```

```
<222> LOCATION: (73)..(73)
<223> OTHER INFORMATION: Xaa = Y, I or L
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa = F, S, L or Y
<220> FEATURE:
<221> NAME/KEY: misc_feature
<222> LOCATION: (77)..(80)
<223> OTHER INFORMATION: Xaa can be any naturally occurring amino acid
<220> FEATURE:
<221> NAME/KEY: misc_feature
<222> LOCATION: (81)..(93)
<223> OTHER INFORMATION: Xaa = absent or any naturally occurring amino
      acid
<220> FEATURE:
<221> NAME/KEY: misc_feature
<222> LOCATION: (94)..(94)
<223> OTHER INFORMATION: Xaa = T, S or G
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(178)
<223> OTHER INFORMATION: Xaa can be any naturally occurring amino acid
<220> FEATURE:
<221> NAME/KEY: misc_feature
<222> LOCATION: (179)..(181)
<223> OTHER INFORMATION: Xaa = absent or any naturally occurring amino
      acid
<220> FEATURE:
<221> NAME/KEY: misc_feature
<222> LOCATION: (183)..(184)
<223> OTHER INFORMATION: Xaa can be any naturally occurring amino acid

<400> SEQUENCE: 4

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Cys Xaa Xaa Xaa Xaa Xaa Xaa Xaa Xaa Xaa Xaa
        35                  40                  45

Xaa Xaa Xaa Xaa Xaa Xaa Xaa Xaa Arg Xaa Xaa Xaa Xaa Xaa Xaa
    50                  55                  60

Xaa Xaa Xaa Xaa Glx Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Gln
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa His Xaa Xaa Asn
            180                 185
```

```
<210> SEQ ID NO 5
<211> LENGTH: 185
<212> TYPE: PRT
<213> ORGANISM: Artificial Sequence
<220> FEATURE:
<223> OTHER INFORMATION: Fatty acid decarboxylase active site
<220> FEATURE:
<221> NAME/KEY: misc_feature
<222> LOCATION: (1)..(1)
<223> OTHER INFORMATION: Xaa = I or L
<220> FEATURE:
<221> NAME/KEY: misc_feature
<222> LOCATION: (2)..(29)
<223> OTHER INFORMATION: Xaa can be any naturally occurring amino acid
<220> FEATURE:
<221> NAME/KEY: misc_feature
<222> LOCATION: (30)..(36)
<223> OTHER INFORMATION: Xaa = absent or any naturally occurring amino
      acid
<220> FEATURE:
<221> NAME/KEY: misc_feature
<222> LOCATION: (38)..(55)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa = absent or any naturally occurring amino
      acid
<220> FEATURE:
<221> NAME/KEY: misc_feature
<222> LOCATION: (59)..(67)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa = absent or any naturally occurring amino
      acid
<220> FEATURE:
<221> NAME/KEY: misc_feature
<222> LOCATION: (70)..(72)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa = Y, I or L
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa = F or L
<220> FEATURE:
<221> NAME/KEY: misc_feature
<222> LOCATION: (77)..(80)
<223> OTHER INFORMATION: Xaa can be any naturally occurring amino acid
<220> FEATURE:
<221> NAME/KEY: misc_feature
<222> LOCATION: (81)..(93)
<223> OTHER INFORMATION: Xaa = absent or any naturally occurring amino
      acid
<220> FEATURE:
<221> NAME/KEY: misc_feature
<222> LOCATION: (94)..(94)
<223> OTHER INFORMATION: Xaa = T, S or G
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(178)
<223> OTHER INFORMATION: Xaa can be any naturally occurring amino acid
<220> FEATURE:
<221> NAME/KEY: misc_feature
<222> LOCATION: (179)..(181)
<223> OTHER INFORMATION: Xaa = absent or any naturally occurring amino
``` acid
<220> FEATURE:
<221> NAME/KEY: misc_feature
<222> LOCATION: (183)..(184)
<223> OTHER INFORMATION: Xaa can be any naturally occurring amino acid

<400> SEQUENCE: 5

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Cys Xaa Xaa Xaa Xaa Xaa Xaa Xaa Xaa Xaa
        35                  40                  45

Xaa Xaa Xaa Xaa Xaa Xaa Xaa Xaa Arg Xaa Xaa Xaa Xaa Xaa
    50                  55                  60

Xaa Xaa Xaa Xaa Glx Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Gln
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa
                165                 170                 175

Xaa Xaa Xaa Xaa Xaa His Xaa Xaa Asn
            180                 185
```

<210> SEQ ID NO 6
<211> LENGTH: 185
<212> TYPE: PRT
<213> ORGANISM: Artificial Sequence
<220> FEATURE:
<223> OTHER INFORMATION: Fatty acid decarboxylase active site
<220> FEATURE:
<221> NAME/KEY: misc_feature
<222> LOCATION: (2)..(29)
<223> OTHER INFORMATION: Xaa can be any naturally occurring amino acid
<220> FEATURE:
<221> NAME/KEY: misc_feature
<222> LOCATION: (30)..(36)
<223> OTHER INFORMATION: Xaa = absent or any naturally occurring amino acid
<220> FEATURE:
<221> NAME/KEY: misc_feature
<222> LOCATION: (38)..(55)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa = absent or any naturally occurring amino acid
<220> FEATURE:
<221> NAME/KEY: misc_feature
<222> LOCATION: (59)..(67)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa = absent or any naturally occurring amino acid
<220> FEATURE:

-continued

```
<221> NAME/KEY: misc_feature
<222> LOCATION: (70)..(72)
<223> OTHER INFORMATION: Xaa can be any naturally occurring amino acid
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (77)..(80)
<223> OTHER INFORMATION: Xaa can be any naturally occurring amino acid
<220> FEATURE:
<221> NAME/KEY: misc_feature
<222> LOCATION: (81)..(93)
<223> OTHER INFORMATION: Xaa = absent or any naturally occurring amino
      acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(178)
<223> OTHER INFORMATION: Xaa can be any naturally occurring amino acid
<220> FEATURE:
<221> NAME/KEY: misc_feature
<222> LOCATION: (179)..(181)
<223> OTHER INFORMATION: Xaa = absent or any naturally occurring amino
      acid
<220> FEATURE:
<221> NAME/KEY: misc_feature
<222> LOCATION: (183)..(184)
<223> OTHER INFORMATION: Xaa can be any naturally occurring amino acid

<400> SEQUENCE: 6

Ile Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Cys Xaa Xaa Xaa Xaa Xaa Xaa Xaa Xaa Xaa Xaa
        35                  40                  45

Xaa Xaa Xaa Xaa Xaa Xaa Xaa Xaa Arg Xaa Xaa Xaa Xaa Xaa Xaa
    50                  55                  60

Xaa Xaa Xaa Xaa Glx Xaa Xaa Xaa Tyr Xaa Xaa Phe Xaa Xaa Xaa Xaa
65                  70                  75                  80

Xaa Xaa Xaa Xaa Xaa Xaa Xaa Xaa Xaa Xaa Xaa Xaa Thr Xaa Gln
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa His Xaa Xaa Asn
        180                 185

<210> SEQ ID NO 7
<211> LENGTH: 178
<212> TYPE: PRT
<213> ORGANISM: Artificial Sequence
<220> FEATURE:
<223> OTHER INFORMATION: Fatty acid decarboxylase active site
```

<400> SEQUENCE: 7

Ile Ala Ile Ser Asp His Ile Tyr Asn Glu Lys Gly Gln Ile Arg Lys
1               5                   10                  15

Arg Ala Ile Ala Ser Tyr Leu Leu Gly Gly Arg Gly Gly Leu Thr Ser
            20                  25                  30

Thr Gly Cys Asp Arg Gly Ala Phe Val Arg Thr Ala Gly Gln Ala Leu
        35                  40                  45

Pro Asp Leu Gln Val Arg Phe Val Pro Gly Met Ala Leu Asp Pro Asp
    50                  55                  60

Glx Val Ser Thr Tyr Val Arg Phe Ala Lys Phe Gln Ser Gln Gly Leu
65                  70                  75                  80

Lys Trp Pro Ser Gly Ile Thr Met Gln Leu Ile Ala Cys Arg Pro Gln
                85                  90                  95

Ser Thr Gly Ser Val Gly Leu Lys Ser Ala Asp Pro Phe Ala Pro Pro
            100                 105                 110

Lys Leu Ser Pro Gly Tyr Leu Thr Asp Lys Asp Gly Ala Asp Leu Ala
        115                 120                 125

Thr Leu Arg Lys Gly Ile His Trp Ala Arg Asp Val Ala Arg Ser Ser
    130                 135                 140

Ala Leu Ser Glu Tyr Leu Asp Gly Glu Leu Phe Pro Gly Ser Gly Val
145                 150                 155                 160

Val Ser Asp Asp Gln Ile Asp Glu Tyr Ile Arg Arg Ser Ile His Ser
                165                 170                 175

Ser Asn

<210> SEQ ID NO 8
<211> LENGTH: 564
<212> TYPE: PRT
<213> ORGANISM: Aureococcus anophagefferens

<400> SEQUENCE: 8

Met Gly Arg Thr Leu Val Leu Lys Val Ala Thr Thr Ser Tyr Asp Tyr
1               5                   10                  15

Ile Ile Ala Gly Gly Thr Ala Gly Cys Val Leu Ala Asn Arg Leu
            20                  25                  30

Ser Glu Asp Pro Ser Lys Lys Val Leu Val Leu Glu Ala Gly Asp Arg
        35                  40                  45

Gly Pro Asn Ser Pro Leu Val Lys Ile Pro Val Ala Ile Leu Lys Leu
    50                  55                  60

Phe Lys Ser Ala Tyr Asp Trp Asn Phe Ala Thr Arg Pro Ser Glu Ala
65                  70                  75                  80

Val Ala Asp Arg Ser Leu Tyr Val Cys Arg Gly Lys Gly Leu Gly Gly
                85                  90                  95

Ser Ser Leu Thr Asn Val Met Leu Tyr Asn Arg Gly Ser Ala Asn Asp
            100                 105                 110

Tyr Asp Ala Trp Ala Ala Ala Cys Gly Asp Ser Trp Gly Ala Glu
        115                 120                 125

Glu Met Leu Gly Tyr Phe Lys Lys Ala Glu Asp Cys Leu Val Pro Ala
    130                 135                 140

His Arg Ala Asn His Tyr His Gly Val Gly Gly Pro Tyr Ala Ser Ser
145                 150                 155                 160

His Val Pro Tyr Thr Asn Glu Met Ser Thr Ala Phe Val Glu Ala Ala
                165                 170                 175

Val Glu Asp Gly Gly Val Arg Asn Gly Asp Phe Asn Asp Trp Ser Thr
            180                 185                 190

Ser Gln Val Gly Phe Gly Arg Phe Ala Val Ser Gln Arg Lys Gly Ala
            195                 200                 205

Arg Val Asp Ala Ala Thr Ala Tyr Leu Pro Arg Lys Val Arg Arg Arg
            210                 215                 220

Ala Asn Leu Asp Val Val Arg Gly Ala Ala Leu Ser Gly Val Thr Trp
225                 230                 235                 240

Asn Ala Asn Lys Ala Thr Gly Val Glu Phe Ala Phe Gly Gly Val Ser
            245                 250                 255

Gly Ile Ala Cys Gly Gly Glu Val Ile Leu Ser Gly Gly Ala Val His
            260                 265                 270

Ser Pro Gln Met Leu Met Leu Ser Gly Val Gly Ala Lys Ala Gln Leu
            275                 280                 285

Glu Glu Phe Gly Ile Pro Val Val Ala Asp Arg Pro Gly Val Gly Lys
            290                 295                 300

Asn Leu Gln Asp His Pro Ala Cys Leu Val Ser Trp Arg Gly Ser Ala
305                 310                 315                 320

Lys Ala Gln Gly Lys Ser His Ser Thr Gln Leu Arg Ile Pro Gly Thr
            325                 330                 335

Thr Lys Thr Ser Pro Lys Ala Leu Leu Gln Trp Leu Phe Leu Gly Arg
            340                 345                 350

Gly Pro Leu Ala Ser Pro Gly Cys Asp His Gly Gly Phe Ala Lys Val
            355                 360                 365

Gly Ala Gly Asp Gly Asp Cys Asp Val Gln Phe Arg Phe Leu Ala Thr
            370                 375                 380

Lys Ser Ile Thr Pro Asp Gly Met Ser Thr Ile Ser Asp Ser Tyr Glu
385                 390                 395                 400

Ala Ala Val Asp His Pro Asp Gly Leu Thr Ile Gln Thr Ile Val Ala
            405                 410                 415

Arg Pro Lys Ser Arg Ala Gly Glu Val Lys Leu Ala Ser Arg Asp Pro
            420                 425                 430

Ala Ala Lys Pro Val Ile Glu Asn Ala Tyr Leu Ser Asp Glu Ala Asp
            435                 440                 445

Val Met Thr Met Val Lys Ala Leu Gln Lys Ala Arg Ser Ile Ala Ser
450                 455                 460

Arg Ala Pro Leu Ser Ala Tyr Ala Gly His Glu Glu Phe Pro Gly Glu
465                 470                 475                 480

Asp Val Ala Asp Glu Arg Gln Leu Ala Ala Tyr Val Arg Asn Thr Ala
            485                 490                 495

His Thr Ala Asn Ala Val Val Gly Thr Cys Lys Met Gly Glu Ser Ser
            500                 505                 510

Asp Ala Leu Ala Val Val Asp Asn His Leu Lys Val Ile Gly Val Ser
            515                 520                 525

Asn Leu Arg Val Val Asp Ala Ser Val Met Pro Thr Leu Pro Gly Gly
            530                 535                 540

Gln Thr Ala Ala Ser Thr Val Ala Leu Ala Glu Lys Ala Ala Asp Leu
545                 550                 555                 560

Ile Lys Gly Gly

<210> SEQ ID NO 9
<211> LENGTH: 640
<212> TYPE: PRT
<213> ORGANISM: Chondrus crispus

<400> SEQUENCE: 9

Met Ala Ser Pro Cys Pro Ala Phe Ala Thr Pro Ile Ala Val Pro Arg
1               5                   10                  15

Ser Thr Leu Thr Ser Leu Ile Ser Ser Ser Ser Cys Thr Pro Arg
            20                  25                  30

Pro Val Arg Thr Pro Ala Pro Pro Thr His Arg Arg Leu Ile His Met
        35                  40                  45

Ala Ala Pro Ala Gly Thr Val Ala Ser Thr Phe Arg Arg Thr Val Pro
    50                  55                  60

Ser Ser Glu Ala Ala Thr Thr Tyr Asp Tyr Ile Ile Val Gly Gly Gly
65                  70                  75                  80

Ala Ala Gly Cys Val Leu Ala Asn Arg Leu Thr Glu Asp Pro Ser Thr
            85                  90                  95

Arg Val Leu Leu Leu Glu Ala Gly Lys Pro Asp Asp Ser Phe Tyr Leu
            100                 105                 110

His Val Pro Leu Gly Phe Pro Tyr Leu Leu Gly Ser Pro Asn Asp Trp
        115                 120                 125

Ala Phe Val Thr Glu Pro Glu Pro Asn Leu Ala Asn Arg Arg Leu Tyr
    130                 135                 140

Phe Pro Arg Gly Lys Val Leu Gly Gly Ser His Ala Ile Ser Val Met
145                 150                 155                 160

Leu Tyr His Arg Gly His Pro Ala Asp Tyr Thr Ala Trp Ala Glu Ser
            165                 170                 175

Ala Pro Gly Trp Ala Pro Gln Asp Val Leu Pro Tyr Phe Leu Lys Ser
        180                 185                 190

Glu Ser Gln Gln Ser Ala Val Pro Asn Gln Asp Ala His Gly Tyr Glu
    195                 200                 205

Gly Pro Leu Ala Val Ser Asp Leu Ala Arg Leu Asn Pro Met Ser Lys
210                 215                 220

Ala Phe Ile Lys Ala Ala His Asn Ala Ala Gly Leu Asn His Asn Pro
225                 230                 235                 240

Asp Phe Asn Asp Trp Ala Thr Gly Gln Asp Gly Val Gly Pro Phe Gln
            245                 250                 255

Val Thr Gln Arg Asp Gly Ser Arg Glu Ser Pro Ala Thr Ser Tyr Leu
        260                 265                 270

Arg Ala Ala Lys Gly Arg Arg Asn Leu Thr Val Met Thr Gly Ala Val
    275                 280                 285

Val Glu Arg Ile Leu Phe Glu Asn Pro Ala Gly Ser Ser Thr Pro Val
290                 295                 300

Ala Thr Ala Val Ser Phe Ile Asp Ser Lys Gly Thr Arg Val Arg Met
305                 310                 315                 320

Ser Ala Ser Arg Glu Ile Leu Leu Cys Gly Gly Val Tyr Ala Thr Pro
            325                 330                 335

Gln Leu Leu Met Leu Ser Gly Val Gly Pro Ala Glu His Leu Arg Ser
        340                 345                 350

His Gly Ile Glu Ile Val Ala Asp Val Pro Ala Val Gly Gln Asn Leu
    355                 360                 365

Gln Asp His Ala Ala Ala Met Val Ser Phe Glu Ser Gln Asn Pro Glu
    370                 375                 380

Lys Asp Lys Ala Asn Ser Ser Val Tyr Tyr Thr Glu Arg Thr Gly Lys
385                 390                 395                 400

Asn Ile Gly Thr Leu Leu Asn Tyr Val Phe Arg Gly Lys Gly Pro Leu

```
                        405                 410                 415
Thr Ser Pro Met Cys Glu Ala Gly Gly Phe Ala Lys Thr Asp Pro Ser
                420                 425                 430

Met Asp Ala Cys Asp Leu Gln Leu Arg Phe Ile Pro Phe Val Ser Glu
                435                 440                 445

Pro Asp Pro Tyr His Ser Leu Ala Asp Phe Ala Thr Ala Gly Ser Tyr
                450                 455                 460

Leu Gln Asn Arg Ala Asn Arg Pro Thr Gly Phe Thr Ile Gln Ser Val
465                 470                 475                 480

Ala Ala Arg Pro Lys Ser Arg Gly His Val Gln Leu Arg Ser Thr Asp
                485                 490                 495

Val Arg Asp Ser Met Ser Ile His Gly Asn Trp Ile Ser Asn Asp Ala
                500                 505                 510

Asp Leu Lys Thr Leu Val His Gly Val Lys Leu Cys Arg Thr Ile Gly
                515                 520                 525

Asn Asp Asp Ser Met Lys Glu Phe Arg Gly Arg Glu Leu Tyr Pro Gly
                530                 535                 540

Gly Glu Lys Val Ser Asp Ala Asp Ile Glu Ala Tyr Ile Arg Asp Thr
545                 550                 555                 560

Cys His Thr Ala Asn Ala Met Val Gly Thr Cys Arg Met Gly Ile Gly
                565                 570                 575

Glu Gln Ala Ala Val Asp Pro Ala Leu Gln Val Lys Gly Val Ala Arg
                580                 585                 590

Leu Arg Val Val Asp Ser Ser Val Met Pro Thr Leu Pro Gly Gly Gln
                595                 600                 605

Ser Gly Ala Pro Thr Met Met Ile Ala Glu Lys Gly Ala Asp Leu Ile
                610                 615                 620

Arg Ala Ala Ala Arg Gln Ala Asp Ala Ala Thr Val Gly Ala Ala Ala
625                 630                 635                 640

<210> SEQ ID NO 10
<211> LENGTH: 627
<212> TYPE: PRT
<213> ORGANISM: Chrysochromulina sp.

<400> SEQUENCE: 10

Met Met Arg Arg Leu Val Tyr Ile Cys Ala Val Ala Thr Val Thr Ala
1               5                   10                  15

Ala Ile Ser Ser Arg Ser Val Pro Thr Ser Ala Arg Arg Leu Ile Ala
                20                  25                  30

Leu Arg Gly Gly Val Ala Ala Glu Gln Leu Ala Glu Pro Trp
            35                  40                  45

Asp Tyr Ile Ile Val Gly Gly Gly Ala Gly Cys Val Met Ala Glu
        50                  55                  60

Arg Leu Ser Ala Ala Glu Ala Arg Val Leu Val Leu Glu Ala Gly Thr
65                  70                  75                  80

Asp Ala Ser Arg Asp Leu Arg Ile Arg Val Pro Ala Gly Leu Ile Lys
                85                  90                  95

Val Phe Lys Ser Glu Arg Asp Trp Asp Phe Thr Thr Glu Ala Gly Gln
                100                 105                 110

Gly Thr Ser Gly Arg Gly Ile Tyr Leu Cys Arg Gly Lys Ala Leu Gly
                115                 120                 125

Gly Ser Ser Cys Thr Asn Val Met Leu Tyr Asn Arg Gly Ser Pro Ala
                130                 135                 140
```

-continued

```
Asp Tyr Asn Ser Trp Val Ala Gly Ala Glu Gly Trp Gly Pro Asp
145                 150                 155                 160

Ser Val Leu His Tyr Tyr Arg Lys Ser Glu Asn Tyr Val Gly Gly Ala
            165                 170                 175

Ser Gln Tyr His Gly Val Asp Gly Pro Leu Ser Val Ser Asp Val Pro
            180                 185                 190

Tyr Glu Asn Glu Leu Ser Thr Ala Phe Leu Arg Ala Ala Gly Glu Leu
        195                 200                 205

Gly Tyr Arg Arg Val His Asp Phe Asn Asp Trp Ser Ala Pro Gln Glu
    210                 215                 220

Gly Phe Gly Arg Tyr Lys Val Thr Gln Arg Asn Gly Glu Arg Cys Ser
225                 230                 235                 240

Ala Ala Asn Ala Tyr Leu Glu Gly Thr Glu Gly Arg Ser Asn Leu Cys
                245                 250                 255

Val Arg Thr Gly Val His Ala Thr Arg Val Thr Leu Glu Gly Ser Gly
            260                 265                 270

Asp Asp Leu Cys Ala Ala Gly Val Glu Tyr Ile Gly Ala Asp Gly Lys
        275                 280                 285

Pro Ser Arg Ala Gln Leu Ala Gln Gly Gly Glu Val Leu Leu Ser Ala
    290                 295                 300

Gly Ala Val Gln Ser Pro Gln Leu Leu Met Leu Ser Gly Ile Gly Pro
305                 310                 315                 320

Arg Ala His Leu Glu Glu Val Gly Ile Glu Val Arg Lys Glu Leu Asp
                325                 330                 335

Asn Val Gly Val Gly Leu Ala Asp His Pro Ala Val Val Ser Cys
            340                 345                 350

Gly Ser Lys Lys Lys Val Ser Val Thr Asp Glu Ile Arg Leu Trp Gly
        355                 360                 365

Gly Ser Lys Thr Asn Pro Met Ala Leu Leu Arg Trp Leu Leu Trp Arg
    370                 375                 380

Arg Gly Pro Leu Thr Ser Val Ala Cys Glu Phe Gly Gly Phe Phe Lys
385                 390                 395                 400

Thr Lys Pro Asp Leu Lys Gln Ala Asp Val Gln Val Arg Phe Val Ala
                405                 410                 415

Ala Arg Ala Met Ser Pro Asp Gly Ile Thr Thr Leu Gln Gln Leu Gly
            420                 425                 430

Ala Gly Ala Lys Phe Leu Ser Gly Tyr Thr Thr Gln Ile Ile Ala Cys
        435                 440                 445

Arg Pro Gln Ser Thr Gly Leu Val Arg Leu Arg Ser Ser Asp Pro Leu
    450                 455                 460

Ala Gln Pro Met Leu Gln Asp Val His Leu Ser Asp Asp Ala Asp Val
465                 470                 475                 480

Ala Thr Leu Arg Glu Gly Ile Lys Leu Gly Arg Gln Leu Leu Ala Ala
                485                 490                 495

Lys Ser Phe Asp Gln Tyr Arg Asp Glu Glu Val Tyr Pro Gly Val Ala
            500                 505                 510

Val Gln Ser Asp Glu Asp Ile Asp Ala Tyr Val Arg Lys Thr Thr His
        515                 520                 525

Ser Ala Asn Ala Leu Val Gly Ser Cys Arg Met Gly Arg Val Asp Asp
    530                 535                 540

Gln Ala Ala Val Leu Asp Pro Glu Met Arg Val Arg Gly Val Gly Ser
545                 550                 555                 560

Leu Arg Val Val Asp Ala Ser Ala Met Pro His Ile Ile Gly Gly Gln
```

```
            565                 570                 575
Thr Cys Gly Pro Thr Ile Met Met Ala Glu Lys Ala Ala Asp Leu Val
            580                 585                 590

Leu Arg Gln Arg Ala Glu Ile Asn Ala Tyr Met Gln Gln Ala Gln Ala
        595                 600                 605

Tyr Leu Ala Ala Ser Ala Gly Ala Ala Thr Pro Ala Leu Ser Pro Ala
    610                 615                 620

Gln Ala Ala
625

<210> SEQ ID NO 11
<211> LENGTH: 642
<212> TYPE: PRT
<213> ORGANISM: Cyanidioschyzon merolae

<400> SEQUENCE: 11

Met Arg Ser Arg Tyr Cys Phe Leu Leu Ser Ser Thr Pro Cys Lys Tyr
1               5                   10                  15

Ala Gly Gln Arg Ser Pro Phe Pro Ala Ser Ala Leu Ala Gly Val Cys
            20                  25                  30

Ala Gly Gly Arg Leu Arg Asn Val Thr Arg Asn Leu Arg Pro Gly Leu
        35                  40                  45

Arg Thr Leu Arg Ala Ser Ala Glu Thr Glu His Ser Gln Gly Thr Arg
    50                  55                  60

Gln Ala Gln Tyr Asp Phe Ile Ile Val Gly Ala Gly Ala Ala Gly Cys
65                  70                  75                  80

Val Leu Ala Asn Arg Leu Ser Thr Ala Gln Phe Ser Asn Gly Asp Arg
                85                  90                  95

Arg Tyr Pro Arg Val Leu Leu Leu Glu Ala Gly Asp Ala Leu Ala Glu
            100                 105                 110

Ala Pro Tyr Phe Glu His Ile Pro Leu Gly Phe Pro Gln Leu Ile Gly
        115                 120                 125

Ser Arg Leu Asp Tyr Gly Phe Phe Ser Arg Glu Asn Pro Thr His Leu
    130                 135                 140

Gly Gly Arg Gly Ala Val Tyr Leu Pro Arg Gly Arg Gly Glu Gly Gly
145                 150                 155                 160

Ser His Ala Ile Ser Val Met Leu Val His Arg Gly Ser Arg His Asp
                165                 170                 175

Tyr Glu Thr Trp Val Lys Asp Tyr Glu Ala Leu Gly Trp Gly Pro Asp
            180                 185                 190

Asp Val Leu Pro Tyr Phe Lys Arg Leu Glu Ser Asn Glu Arg Thr Ala
        195                 200                 205

Gln Arg Gly Ala Asp Gly Glu Ala Ala Thr Ala Leu His Gly Ser Asp
    210                 215                 220

Gly Pro Leu Arg Val Ser Asp Gln Arg Ser Pro Asn Pro Leu Ser Leu
225                 230                 235                 240

Ala Phe Ile Glu Ala Cys Leu Glu Arg Gly Ile Arg Arg Asn Lys Asp
                245                 250                 255

Phe Asn Asp Trp Asp His Gly Gln Glu Gly Ala Gly Leu Phe Gln Val
            260                 265                 270

Thr Gln Arg Asp Gly Arg Arg Glu Ser Pro Ala Thr Ala Tyr Leu Gln
        275                 280                 285

Pro Val Arg Ser Arg Arg Asn Leu His Ile Glu Thr Asn Ala Leu Ala
    290                 295                 300
```

```
Glu His Leu Val Trp Ser Lys Asp Gly Arg Arg Val Glu Gly Ile Arg
305                 310                 315                 320

Phe Ile Asp Arg His Gly Arg Arg Ala Ala Leu Ala His Cys Glu
                325                 330                 335

Val Ile Leu Ala Ala Gly Ala Ile Asn Thr Pro Gln Leu Leu Met Leu
                340                 345                 350

Ser Gly Leu Gly Pro Gly Ala His Leu Gln Asp Phe Gly Ile Pro Val
                355                 360                 365

Val Arg Asp Leu Pro Gly Val Gly Gln Asn Leu Gln Asp His Ala Ala
                370                 375                 380

Val Met Leu Ser Tyr Tyr Ala Pro Asp Pro Tyr Gly Lys Asp Arg Asp
385                 390                 395                 400

Lys Lys Arg Ile Phe Tyr Thr Glu Arg Leu Gly Lys Asp Pro Leu Val
                405                 410                 415

Leu Ala Glu Tyr Phe Leu Leu Gly Arg Gly Pro Leu Thr Ser Pro Val
                420                 425                 430

Cys Glu Ala Gly Ala Phe Val His Thr Gln Ala Val Ile Gly Glu Pro
                435                 440                 445

Ser Cys Asp Leu Gln Leu Arg Phe Val Pro Phe Phe Ser Asp Ala Asp
                450                 455                 460

Pro Tyr Lys Ser Leu Gly Glu Tyr Arg Ser Gly His Val Leu Thr
465                 470                 475                 480

Asn Thr Ser Ile Arg Pro Ala Gly Phe Gly Leu Gln Ala Val Ala Ile
                485                 490                 495

Arg Pro Arg Ser Arg Gly Arg Ile Glu Leu Ala Thr Ile Asp Pro Arg
                500                 505                 510

Ala Arg Pro Ile Ile His Thr Gly Trp Leu Glu Asp Lys Arg Asp Leu
                515                 520                 525

Gln Thr Leu Leu Ser Gly Leu Lys Leu Gly Arg Glu Ile Leu Ser Gly
                530                 535                 540

Asp Ser Met Arg Pro Tyr Arg Gly Arg Glu Ala Phe Pro Glu Thr Leu
545                 550                 555                 560

Glu Asp Asp Leu Val Thr Tyr Ile Arg Arg Thr Cys His Thr Ala Asn
                565                 570                 575

Ala Ile Val Gly Thr Ala Arg Met Gly Thr Gly Arg Asp Ala Val Val
                580                 585                 590

Asp Pro Glu Leu Arg Val His Gly Val Glu Arg Leu Arg Val Ile Asp
                595                 600                 605

Ala Ser Val Met Pro Lys Ile Ile Gly Gly Gln Thr Gly Val Pro Thr
                610                 615                 620

Met Met Ile Ala Glu Arg Gly Ala Asp Leu Val Lys Lys Thr Trp Lys
625                 630                 635                 640

Leu Val

<210> SEQ ID NO 12
<211> LENGTH: 611
<212> TYPE: PRT
<213> ORGANISM: Chlamydomonas reinhardtii

<400> SEQUENCE: 12

Met Met Leu Gly Pro Lys Thr Val Thr Arg Gly Ala Thr Lys Gly Ala
1               5                   10                  15

Ala Pro Arg Ser Met Ala Ala Arg Val Gly Gly Ala Arg Arg Leu
            20                  25                  30
```

-continued

```
Ser Val Arg Ala Ala Ala Gly Pro Ala Gly Ser Glu Lys Phe Asp Tyr
         35                  40                  45
Val Leu Val Gly Gly Thr Ala Ser Cys Val Leu Ala Asn Lys Leu
 50                  55                  60
Ser Ala Asp Gly Asn Lys Lys Val Leu Val Leu Glu Ala Gly Pro Thr
 65                  70                  75                  80
Gly Asp Ala Met Glu Val Ala Val Pro Ala Gly Ile Thr Arg Leu Phe
             85                  90                  95
Ala His Pro Val Met Asp Trp Gly Met Ser Ser Leu Thr Gln Lys Gln
                100                 105                 110
Leu Val Ala Arg Glu Ile Tyr Leu Ala Arg Gly Arg Met Leu Gly Gly
             115                 120                 125
Ser Ser Gly Ser Asn Ala Thr Leu Tyr His Arg Gly Ser Ala Ala Asp
    130                 135                 140
Tyr Asp Ala Trp Gly Leu Glu Gly Trp Ser Ser Lys Asp Val Leu Asp
145                 150                 155                 160
Trp Phe Val Lys Ala Glu Cys Tyr Ala Asp Gly Pro Lys Pro Tyr His
                165                 170                 175
Gly Thr Gly Gly Ser Met Asn Thr Glu Gln Pro Arg Tyr Glu Asn Val
            180                 185                 190
Leu His Asp Glu Phe Phe Lys Ala Ala Ala Thr Gly Leu Pro Ala
    195                 200                 205
Asn Pro Asp Phe Asn Asp Trp Ser His Pro Gln Asp Gly Phe Gly Glu
    210                 215                 220
Phe Gln Val Ser Gln Lys Lys Gly Gln Arg Ala Asp Thr Tyr Arg Thr
225                 230                 235                 240
Tyr Leu Lys Pro Ala Met Ala Arg Gly Asn Leu Lys Val Val Ile Gly
                245                 250                 255
Ala Arg Ala Thr Lys Val Asn Ile Glu Lys Gly Ser Ser Gly Ala Arg
            260                 265                 270
Thr Thr Gly Val Glu Tyr Ala Met Gln Gln Phe Gly Asp Arg Phe Thr
    275                 280                 285
Ala Glu Leu Ala Pro Gly Gly Glu Val Leu Met Cys Ser Gly Ala Val
    290                 295                 300
His Thr Pro His Leu Leu Met Leu Ser Gly Val Gly Pro Ala Ala Thr
305                 310                 315                 320
Leu Lys Glu His Gly Ile Asp Val Val Ser Asp Leu Ser Gly Val Gly
                325                 330                 335
Gln Asn Leu Gln Asp His Pro Ala Ala Val Leu Ala Arg Ala Lys
            340                 345                 350
Pro Glu Phe Glu Lys Leu Ser Val Thr Ser Glu Val Tyr Asp Asp Lys
    355                 360                 365
Cys Asn Ile Lys Leu Gly Ala Val Ala Gln Tyr Leu Phe Gln Arg Arg
    370                 375                 380
Gly Pro Leu Ala Thr Thr Gly Cys Asp His Gly Ala Phe Val Arg Thr
385                 390                 395                 400
Ser Ser Ser Leu Ser Gln Pro Asp Leu Gln Met Arg Phe Val Pro Gly
                405                 410                 415
Cys Ala Leu Asp Pro Asp Gly Val Lys Ser Tyr Ile Val Phe Gly Glu
            420                 425                 430
Leu Lys Lys Gln Gly Arg Ala Trp Pro Gly Gly Ile Thr Leu Gln Leu
    435                 440                 445
Leu Ala Ile Arg Ala Lys Ser Lys Gly Ser Ile Gly Leu Lys Ala Ala
```

```
                450               455               460
Asp Pro Phe Ile Asn Pro Ala Ile Asn Ile Asn Tyr Phe Ser Asp Pro
465                 470                 475                 480

Ala Asp Leu Ala Thr Leu Val Asn Ala Val Lys Met Ala Arg Lys Ile
                485                 490                 495

Ala Ala Gln Glu Pro Leu Lys Lys Tyr Leu Gln Glu Glu Thr Phe Pro
            500                 505                 510

Gly Glu Arg Ala Ser Ser Asp Lys Asp Leu Glu Glu Tyr Ile Arg Arg
            515                 520                 525

Thr Val His Ser Gly Asn Ala Leu Val Gly Thr Ala Ala Met Gly Ala
            530                 535                 540

Ser Pro Ala Ala Gly Ala Val Val Ser Ser Ala Asp Leu Lys Val Phe
545                 550                 555                 560

Gly Val Glu Gly Leu Arg Val Val Asp Ala Ser Val Leu Pro Arg Ile
                565                 570                 575

Pro Gly Gly Gln Thr Gly Ala Ala Thr Val Met Val Ala Glu Arg Ala
            580                 585                 590

Ala Ala Leu Leu Arg Gly Gln Ala Thr Ile Ala Pro Ser Arg Gln Pro
            595                 600                 605

Val Ala Val
    610

<210> SEQ ID NO 13
<211> LENGTH: 617
<212> TYPE: PRT
<213> ORGANISM: Coccomyxa subellipsoidea

<400> SEQUENCE: 13

Met Met Ala Ser Gln Ser Val Phe Leu Gly Thr Arg Pro Ala Thr Arg
1               5                   10                  15

Ser Pro Leu Pro Ile Gly Arg Ala Gly His Gly Ser Ala Gly Arg Arg
                20                  25                  30

Ala Leu Arg Val Arg Ala Ile Ile Lys Ser Asp Asn Pro Ala Ala Asp
            35                  40                  45

Lys Tyr Asp Phe Ile Leu Val Gly Gly Gly Thr Ala Gly Cys Val Leu
50                  55                  60

Ala Asn Arg Leu Thr Ala Asp Gly Ser Lys Lys Val Leu Leu Leu Glu
65                  70                  75                  80

Ala Gly Gly Ala Asn Lys Ala Arg Glu Val Arg Thr Pro Ala Gly Leu
                85                  90                  95

Pro Arg Leu Phe Lys Ser Ala Leu Asp Trp Asn Leu Tyr Ser Ser Leu
            100                 105                 110

Gln Gln Ala Ala Ser Asp Arg Ser Ile Tyr Leu Ala Arg Gly Lys Leu
            115                 120                 125

Leu Gly Gly Ser Ser Ala Thr Asn Ala Thr Leu Tyr His Arg Gly Thr
130                 135                 140

Ala Ala Asp Tyr Asp Ala Trp Gly Val Pro Gly Trp Thr Ser Gln Asp
145                 150                 155                 160

Ala Leu Arg Trp Phe Ile Gln Ala Glu Asn Asn Cys Arg Gly Ile Glu
                165                 170                 175

Asp Gly Val His Gly Thr Gly Gly Leu Met Arg Val Glu Asn Pro Arg
            180                 185                 190

Tyr Asn Asn Pro Leu His Glu Val Phe Phe Gln Ala Ala Lys Gln Ala
            195                 200                 205
```

```
Gly Leu Pro Glu Asn Asp Asn Phe Asn Asn Trp Gly Arg Ser Gln Ala
    210                 215                 220

Gly Tyr Gly Glu Phe Gln Val Thr His Ser Lys Gly Glu Arg Ala Asp
225                 230                 235                 240

Cys Phe Arg Met Tyr Leu Glu Pro Val Met Gly Arg Ser Asn Leu Thr
                245                 250                 255

Val Leu Thr Gly Ala Lys Thr Leu Lys Ile Glu Thr Glu Lys Ser Gly
            260                 265                 270

Gly Ala Thr Val Ser Arg Gly Val Thr Phe Gln Val Asn Gly Gln Asp
        275                 280                 285

Gly Ser Lys His Ser Ala Glu Leu Ala Ala Gly Gly Glu Val Val Leu
    290                 295                 300

Cys Ala Gly Ser Ile His Ser Pro Gln Ile Leu Gln Leu Ser Gly Ile
305                 310                 315                 320

Gly Pro Gln Ala Glu Leu Arg Ser Lys Asp Ile Pro Val Val Ala Asp
                325                 330                 335

Leu Pro Gly Val Gly Gln Asn Met Gln Asp His Pro Ala Cys Leu Ser
            340                 345                 350

Ala Phe Tyr Leu Lys Glu Ser Ala Gly Pro Ile Ser Val Thr Asp Glu
        355                 360                 365

Leu Leu His Thr Asn Gly Arg Ile Arg Ala Arg Ala Ile Leu Lys Tyr
    370                 375                 380

Leu Leu Phe Lys Lys Gly Pro Leu Ala Thr Thr Gly Cys Asp His Gly
385                 390                 395                 400

Ala Phe Val Lys Thr Ala Gly Gln Ser Glu Pro Asp Leu Gln Ile Arg
                405                 410                 415

Phe Val Pro Gly Leu Ala Leu Asp Pro Asp Gly Ile Gly Ser Tyr Thr
            420                 425                 430

Ala Phe Gly Lys Met Lys Asp Gln Lys Trp Pro Ser Gly Ile Thr Phe
        435                 440                 445

Gln Leu Leu Gly Val Arg Pro Lys Ser Arg Gly Ser Val Gly Leu Arg
    450                 455                 460

Ser Asp Pro Trp Asp Ala Pro Lys Leu Asp Ile Gly Phe Leu Thr
465                 470                 475                 480

Asp Lys Glu Gly Ala Asp Leu Ala Thr Leu Arg Ser Gly Ile Lys Leu
                485                 490                 495

Ser Arg Glu Ile Ala Ala Glu Pro Ala Phe Gly Ala Tyr Val Gly Asn
            500                 505                 510

Glu Leu His Pro Gly Ala Ala Ser Ser Asp Ser Ala Ile Asp Ser
        515                 520                 525

Phe Ile Arg Asp Thr Val His Ser Gly Asn Ala Asn Val Gly Thr Cys
    530                 535                 540

Ser Met Gly Val Asn Gly Asn Ala Val Val Asp Pro Ser Leu Arg Val
545                 550                 555                 560

Phe Gly Ile Arg Gly Leu Arg Val Ala Asp Ala Ser Val Ile Pro Val
                565                 570                 575

Ile Pro Gly Gly Gln Thr Gly Ala Ala Thr Val Met Val Ala Glu Arg
            580                 585                 590

Ala Ala Glu Ile Leu Leu Gly Ser Asn Gln Lys Gln Pro Ala Ala Ala
        595                 600                 605

Val Pro Ala Ala Gln Pro Ala Leu Ala
    610                 615
```

```
<210> SEQ ID NO 14
<211> LENGTH: 612
<212> TYPE: PRT
<213> ORGANISM: Gonium pectorale

<400> SEQUENCE: 14

Met Met Leu Gly Arg Lys Pro Val Ala Pro Ala Lys Gly Ala Ser Ala
1               5                   10                  15

Ala Arg Thr Val Arg Pro Val Arg Leu Ala Gly Gly Arg Arg Gln Leu
            20                  25                  30

Val Val Ser Ala Ala Ala Pro Val Asp Pro Ala Glu Lys Tyr Asp
        35                  40                  45

Tyr Ile Leu Val Gly Gly Thr Ala Gly Cys Val Leu Ala Asn Lys
    50                  55                  60

Leu Ser Ala Asp Gly Asn Lys Lys Val Leu Val Leu Glu Ala Gly Pro
65                  70                  75                  80

Ser Gly Asp Ser Leu Glu Val Ala Val Pro Ala Gly Ile Ala Arg Leu
                85                  90                  95

Phe Ala His Pro Val Met Asp Trp Gly Met Ser Ser Leu Thr Gln Lys
                100                 105                 110

Gln Leu Val Ala Arg Glu Ile Tyr Leu Ala Arg Gly Arg Leu Leu Gly
            115                 120                 125

Gly Ser Ser Gly Thr Asn Ala Thr Leu Tyr His Arg Gly Thr Ser Ser
        130                 135                 140

Asp Tyr Asp Ser Trp Gly Leu Glu Gly Trp Thr Ser Lys Asp Val Leu
145                 150                 155                 160

Asp Trp Phe Val Lys Ala Glu Cys Tyr Gly Asp Gly Pro Lys Pro Tyr
                165                 170                 175

His Gly Asn Ser Gly Ser Met Asn Val Glu Gln Pro Arg Tyr Gln Asn
            180                 185                 190

Pro Leu His Glu Glu Phe Phe Arg Ala Ala Ala Ala Gly Ile Pro
        195                 200                 205

Ala Asn Pro Asp Phe Asn Asp Trp Ser Arg Pro Gln Asp Gly Tyr Gly
    210                 215                 220

Glu Phe Gln Val Ala Gln Asn Lys Gly Gln Arg Ala Asp Thr Tyr Arg
225                 230                 235                 240

Thr Tyr Leu Lys Pro Ala Leu Ser Arg Gly Asn Leu Lys Val Val Thr
                245                 250                 255

Gly Ala Arg Thr Thr Lys Val His Ile Glu Lys Gly Ser Ser Gly Pro
            260                 265                 270

Arg Ala Arg Gly Val Glu Phe Ala Thr Gln Gln Phe Gly Asp Arg Tyr
        275                 280                 285

Ser Ala Gln Leu Ala Pro Gly Gly Glu Val Leu Met Cys Thr Gly Ala
    290                 295                 300

Val His Thr Pro His Leu Leu Met Leu Ser Gly Val Gly Pro Ala Ala
305                 310                 315                 320

Ala Leu Arg Glu His Gly Val Asp Val Ala Asp Leu Ala Gly Val
                325                 330                 335

Gly Ala Asn Leu Gln Asp His Pro Ala Ala Val Val Ala Val Arg Ala
            340                 345                 350

Lys Pro Glu Phe Glu Lys Leu Ser Val Thr Ser Glu Ile Tyr Asp Glu
        355                 360                 365

Lys Cys Asn Ile Lys Leu Gly Ala Val Ala Gln Tyr Leu Phe Asn Arg
    370                 375                 380
```

```
Arg Gly Pro Leu Ala Thr Thr Gly Cys Asp His Gly Ala Phe Val Arg
385                 390                 395                 400

Thr Ser Gly Ser His Ser Gln Pro Asp Leu Gln Met Arg Phe Val Pro
            405                 410                 415

Gly Cys Ala Leu Asp Pro Asp Gly Val Lys Ser Tyr Ile Val Phe Gly
            420                 425                 430

Glu Leu Lys Lys Gln Gly Arg Ala Trp Pro Gly Gly Ile Thr Leu Gln
            435                 440                 445

Leu Leu Ala Ile Arg Ala Lys Ser Lys Gly Ser Ile Gly Leu Lys Ala
    450                 455                 460

Ala Asp Pro Phe Ile Asn Pro Ala Ile Asn Ile Asn Tyr Phe Ser Asp
465                 470                 475                 480

Pro Ala Asp Leu Ala Thr Leu Lys Gln Gly Val Arg Met Ala Arg Asp
                485                 490                 495

Ile Ala Arg Gln Glu Pro Leu Arg Lys Tyr Leu Gln Glu Glu Thr Phe
                500                 505                 510

Pro Gly Glu Arg Ala Ser Ser Asp Ser Asp Ile Glu Glu Tyr Val Arg
            515                 520                 525

Arg Thr Val His Ser Gly Asn Ala Leu Val Gly Thr Cys Ala Met Gly
            530                 535                 540

Thr Ser Pro Ala Lys Gly Ala Val Val Ser Ser Asp Leu Lys Val
545                 550                 555                 560

Phe Gly Val Glu Gly Leu Arg Val Val Asp Ala Ser Val Leu Pro Gln
                565                 570                 575

Ile Pro Gly Gly Gln Thr Gly Ala Ala Thr Val Met Val Ala Glu Arg
            580                 585                 590

Ala Ala Ala Leu Leu Lys Gly Gln Thr Thr Met Ala Pro Ser Arg Gln
            595                 600                 605

Pro Val Ala Ala
    610

<210> SEQ ID NO 15
<211> LENGTH: 541
<212> TYPE: PRT
<213> ORGANISM: Phaeodactylum tricornutum

<400> SEQUENCE: 15

Met Tyr Asp Tyr Ile Ile Cys Gly Gly Gly Leu Ala Gly Cys Val Leu
1               5                   10                  15

Ala Glu Arg Leu Ser Gln Asp Glu Ser Lys Arg Val Leu Val Leu Glu
            20                  25                  30

Ala Gly Gly Ser Asp Tyr Lys Ser Leu Phe Ile Arg Ile Pro Ala Gly
        35                  40                  45

Val Leu Arg Leu Phe Arg Ser Lys Tyr Asp Trp Gln His Glu Thr Gly
    50                  55                  60

Gly Glu Lys Gly Cys Asn Gly Arg Asn Val Phe Leu Gln Arg Gly Lys
65                  70                  75                  80

Ile Leu Gly Gly Ser Ser Cys Thr Asn Val Cys Leu His His Arg Gly
                85                  90                  95

Ser Ala Glu Asp Tyr Asn Ser Trp Asn Ile Pro Gly Trp Thr Ala Thr
            100                 105                 110

Asp Val Leu Pro Phe Phe Lys Gln Ser Gln Lys Asp Glu Thr Gly Arg
            115                 120                 125

Asp Ala Thr Phe His Gly Ala Asp Gly Glu Trp Val Met Asp Glu Val
            130                 135                 140
```

Arg Tyr Gln Asn Pro Leu Ser Lys Leu Phe Leu Glu Val Gly Glu Ala
145                 150                 155                 160

Ala Gly Leu Gly Thr Asn Asp Asp Phe Asn Asn Trp Ser His Pro Gln
            165                 170                 175

Asp Gly Val Gly Arg Phe Gln Val Ser Glu Val Asn Gly Glu Arg Cys
        180                 185                 190

Ser Gly Ala Thr Ala Phe Leu Ser Lys Ala Ala Lys Arg Ser Asn Val
    195                 200                 205

Ile Val Arg Thr Gly Thr Met Val Arg Arg Ile Asp Phe Asp Glu Thr
210                 215                 220

Lys Thr Ala Lys Gly Ile Thr Tyr Asp Leu Met Gly Asp Asp Thr Cys
225                 230                 235                 240

Thr Val Pro Cys Leu Lys Glu Gly Glu Val Leu Val Thr Gly Gly
                245                 250                 255

Ala Ile Ala Ser Pro Gln Leu Leu Met Cys Ser Gly Ile Gly Pro Gly
            260                 265                 270

Lys His Leu Arg Ser Leu Gly Ile Pro Val Val His Asp Asn Ser Ala
        275                 280                 285

Val Gly Glu Asn Leu Gln Asp His Pro Ala Ala Val Ser Phe Lys
290                 295                 300

Thr Pro Gln Lys Gly Val Ser Val Thr Ser Lys Leu Arg Leu Phe Gly
305                 310                 315                 320

Lys Thr Asn Pro Ile Pro Val Phe Gln Trp Leu Phe Phe Lys Ser Gly
            325                 330                 335

Leu Leu Thr Ser Thr Gly Cys Asp His Gly Ala Phe Val Arg Thr Ser
        340                 345                 350

Asp Ser Leu Glu Gln Pro Asp Leu Gln Ile Arg Phe Leu Ala Ala Arg
    355                 360                 365

Ala Leu Gly Pro Asp Gly Met Thr Thr Tyr Thr Lys Phe Arg Thr Met
370                 375                 380

Lys Thr Val Glu Asp Gly Tyr Ser Phe Gln Ser Val Ala Cys Arg Ala
385                 390                 395                 400

Lys Ser Lys Gly Arg Ile Arg Leu Ser Ser Asn Ser His Val Lys
            405                 410                 415

Pro Met Ile Asp Gly Gly Tyr Leu Ser Asn Gln Asp Asp Leu Ala Thr
        420                 425                 430

Leu Arg Ala Gly Ile Lys Leu Gly Arg Met Leu Gly Asn Arg Pro Glu
    435                 440                 445

Trp Gly Glu Tyr Leu Gly Gln Glu Val Tyr Pro Gly Pro Asp Val Gln
450                 455                 460

Thr Asp Glu Glu Ile Asp Glu Tyr Ile Arg Asn Ser Leu His Thr Ala
465                 470                 475                 480

Asn Ala Leu Thr Gly Thr Cys Lys Met Gly Thr Gly Arg Gly Ala Val
            485                 490                 495

Val Gly Pro Asp Leu Arg Val Ile Gly Val Asn Gly Val Arg Val Ala
        500                 505                 510

Asp Ser Ser Val Phe Pro Cys Ile Pro Gly Gly Gln Thr Ala Thr Pro
    515                 520                 525

Thr Val Met Ile Ala Asp Arg Ala Ala Val Phe Val Arg
530                 535                 540

<210> SEQ ID NO 16
<211> LENGTH: 629

<212> TYPE: PRT
<213> ORGANISM: Emiliania huxleyi

<400> SEQUENCE: 16

```
Met Val Ala Leu Phe Ala Leu Gln Leu Ala Leu Ser Pro Pro Gln Ala
1               5                   10                  15

Arg Leu Gly Ser Gly Ser Ala Arg Ala Leu Arg Leu Arg Gly Gly
            20                  25                  30

Ser Gly Val Thr Gly Gly Ser Leu Gly Arg Gly Gly Gly Ser Pro Ala
            35                  40                  45

Ile Asp Gly Glu Phe Asp Tyr Ile Ile Val Gly Gly Gly Ala Ala Gly
        50                  55                  60

Cys Val Leu Ala Asn Arg Leu Ser Ala Asp Pro Ala His Arg Val Leu
65                  70                  75                  80

Leu Ile Glu Ala Gly Gly Asp Ala Ser Arg Asp Lys Arg Ala Gln Val
                85                  90                  95

Pro Trp Ala Phe Thr Lys Leu Leu Arg Ser Glu Tyr Asp Trp Asp Phe
            100                 105                 110

His Val Glu Ala Glu Ala Val Asn Gln Gln Glu Val Tyr Leu Cys
        115                 120                 125

Arg Gly Lys Ala Leu Gly Gly Ser Ser Val Thr Asn Val Met Leu Tyr
    130                 135                 140

His Arg Gly Ser Pro Ala Asp Tyr Asp Ala Trp Glu Glu Ala Gly Ala
145                 150                 155                 160

Arg Gly Trp Gly Ala Lys Asp Val Leu Pro Tyr Tyr Leu Arg Val Glu
                165                 170                 175

Asp Tyr Gly Asp Gly Ala Ser Gln Tyr His Ala Val Gly Gly His Val
            180                 185                 190

Ser Val Gln Glu Val Pro Tyr Gln Asn Gln Leu Ser Ala Thr Phe Leu
        195                 200                 205

Arg Ala Met Gly Gln Leu Gly Phe Arg Pro Asn Gly Asp Phe Asn Asp
    210                 215                 220

Trp Ser Ser Pro Gln Glu Gly Tyr Gly Arg Tyr Lys Val Thr Gln Arg
225                 230                 235                 240

Ala Gly Arg Arg Cys Thr Ala Ala Asp Gly Tyr Leu Ala Ala Arg
                245                 250                 255

Glu Arg Ala Asn Leu Val Val Val Thr Gly Ala Gln Ala Thr Arg Leu
            260                 265                 270

Ala Leu Asp Ser Ala Tyr Asp Gly Ala Gly Arg Leu Gln Val Ser Gly
        275                 280                 285

Val Glu Phe Ala Arg Gly Asp Glu Arg Glu Pro Cys Ser Val Arg Leu
    290                 295                 300

Ala Arg Gly Gly Glu Ala Val Leu Cys Ala Gly Ala Val Gln Thr Pro
305                 310                 315                 320

His Leu Leu Leu Leu Ser Gly Ile Gly Pro Ala Glu His Leu Arg Glu
                325                 330                 335

Val Gly Val Pro Val Arg Ala Asp Leu Pro Gly Val Gly Ser Gly Leu
            340                 345                 350

Gln Asp His Pro Ala Val Val Ser Tyr Glu Ser Lys Lys Ala Val
        355                 360                 365

Ala Ala Thr Asp Asp Ala Leu Leu Lys Gly Tyr Ala Ser Leu Val Asn
    370                 375                 380

Pro Leu Ala Met Leu Arg Trp Leu Leu Phe Gly Arg Gly Pro Leu Ala
385                 390                 395                 400
```

```
Cys Ala Ala Cys Asp His Gly Gly Phe Val Arg Ser Ser Pro Asp Leu
                405                 410                 415

Asp Gln Pro Asp Val Gln Ile Arg Phe Val Pro Ala Arg Ala Ser Ser
            420                 425                 430

Ala Ser Gly Met Asn Thr Leu Ile Glu Leu Gly Arg Arg Ala Arg Phe
        435                 440                 445

Leu Pro Gly Phe Ser Thr Gln Val Val Ala Cys Arg Pro Arg Ser Glu
    450                 455                 460

Gly Arg Val Arg Leu Arg Ser Ala Asp Pro Phe Ala Lys Pro Ile Ile
465                 470                 475                 480

Glu Gly Ile His Leu Gly Ala Ala Glu Asp Val Ala Ser Leu Arg His
                485                 490                 495

Gly Ile Arg Leu Gly Arg Gln Val Cys Ala Ala Ala Phe Asp Glu
            500                 505                 510

Tyr Arg Gly Glu Glu Val Phe Pro Gly Ala Ala Val Gln Ser Asp Glu
        515                 520                 525

Gln Ile Asp Glu Tyr Ile Arg Ser Ser Val His Ser Ala Asn Ala Leu
    530                 535                 540

Thr Ser Ser Cys Arg Met Gly Asp Pro Ser Asp Pro Ala Ala Val Leu
545                 550                 555                 560

Asp Ser His Leu Arg Val Arg Gly Val Gly Gly Leu Arg Val Ala Asp
                565                 570                 575

Ala Ser Ala Met Pro Arg Ile Ile Gly Gly Gln Thr Gln Ala Pro Thr
            580                 585                 590

Tyr Met Leu Ala Glu Arg Ala Ala Asp Ile Leu Leu His Ala Arg Leu
        595                 600                 605

Gln Ala His Glu Pro Ala Thr Glu Ser Val Ser Gln Arg Leu Glu Val
    610                 615                 620

Ala Ala Ala Ala Leu
625

<210> SEQ ID NO 17
<211> LENGTH: 640
<212> TYPE: PRT
<213> ORGANISM: Emiliania huxleyi

<400> SEQUENCE: 17

Met Ser Ala Arg Trp Leu Leu Leu Leu Ala Thr His Cys Ser Ala Ala
1               5                   10                  15

Leu Arg Asn Pro Phe Arg Ala Ala Pro Thr His Phe Asp Tyr Ile Ile
            20                  25                  30

Val Gly Gly Gly Thr Ala Gly Cys Val Leu Ala Asp Arg Leu Ser Ala
        35                  40                  45

Ala Ser Lys Gln Val Leu Val Leu Glu Pro Gly Pro Ser Pro Ala Ala
    50                  55                  60

Glu Leu Lys Ile Ala Ala Pro Val Ala Leu Thr Lys Leu Phe Gly Ser
65                  70                  75                  80

Glu Tyr Asp Trp Gly Phe Arg Ser Ala Pro Ala Pro Gly Thr Ala Gly
                85                  90                  95

Arg Glu Val His Leu Cys Arg Gly Lys Cys Leu Gly Gly Ser Ser Ala
            100                 105                 110

Thr Asn Ala Leu Leu Tyr Leu Arg Gly Thr Ala Ala Asp Phe Asp Gly
        115                 120                 125

Trp Gly Leu Asp Gly Trp Gly Ser Glu Ala Met Leu Ala Ser Phe Leu
```

```
              130                 135                 140
Ala Val Glu Ala Gln Arg Asp Ala Ala Phe Arg Thr Asp Ala Leu His
145                 150                 155                 160

His Gly Ser Gly Gly Ala Val Pro Ala Glu Thr Pro Arg Tyr Ala Asn
                165                 170                 175

Pro Leu Ser Glu Arg Phe Leu Glu Ala Ala Gln Ala Gly His Pro
            180                 185                 190

Ser Asn Ala Asp Phe Asn Asp Trp Ser Arg Pro Gln Ala Gly Val Gly
            195                 200                 205

Arg Phe Gln Leu Thr Thr Arg Gly Arg Arg Ala His Ser Ala Ala
    210                 215                 220

Thr His Leu Arg Arg Ala Ala Arg Arg Pro Asn Leu His Val Arg Cys
225                 230                 235                 240

Gly Cys Ala Ala Thr Arg Leu Leu Leu Glu Ala Glu Gly Gly Gly
                245                 250                 255

Gly Gly Gly Gly Gly Gly Lys Thr Arg Pro Trp Thr Gly Pro Ala Val
                260                 265                 270

Thr Gly Gln Ala Gly Arg Arg Ala Val Gly Val Glu Tyr Ile Asp Ala
            275                 280                 285

Ala Gly Val Gln Arg Thr Ala Ser Val Ser Gly Gly Gly Gly Gly
    290                 295                 300

Gly Gly Glu Val Leu Leu Cys Ala Gly Ala Val Ser Pro His Leu
305                 310                 315                 320

Leu Leu Leu Ser Gly Ile Gly Ser Pro Asp Glu Leu Ala Ala His Gly
                325                 330                 335

Ile Gly Ala Glu Val Cys Leu Pro Gly Val Gly Arg Asn Leu Ile Asp
            340                 345                 350

Gln Pro Ala Val Val Thr Gly Tyr Thr Val Thr Ser Pro Leu Ser Ile
            355                 360                 365

Thr Asp Glu Met Phe Trp Arg Arg Ser Gly Ala Leu Ser Pro Arg Arg
370                 375                 380

Val Gly Glu Trp Leu Leu Arg Gly Ser Gly Pro Leu Ala Ser Ser Gly
385                 390                 395                 400

Cys Asp Phe Gly Gly Phe Phe Ser Ser Arg Pro Gly Leu Ala Gln Pro
                405                 410                 415

Asp Leu Gln Leu Arg Phe Val Pro Gly Leu Gly Thr Ser Pro Asp Gly
            420                 425                 430

Val Ser Ser Tyr Arg Asp Ile Gly Arg Ala Gly Lys Thr Pro Ser Gly
            435                 440                 445

Leu Thr Leu Gln Ser Ile Ala Val Arg Pro Thr Ala Arg Gly Ser Val
450                 455                 460

Ser Leu Ser Ser Ala Asp Pro Ser Ala Pro Arg Ile Glu Thr Gly
465                 470                 475                 480

Tyr Gly Thr Ser Glu Ala Asp Leu Ala Thr Leu Arg Gln Gly Leu Arg
                485                 490                 495

Leu Ser Arg Glu Leu Val Ala Gln Pro Ala Phe Asp Gly Val Arg Gly
            500                 505                 510

Glu Glu Ala Trp Pro Arg Ala Ala Cys Arg Leu Arg Arg Pro Gly Asp
            515                 520                 525

Asp Ala Ala Leu Asp Glu Tyr Ile Arg Ser Thr Ala His Ser Ala Asn
            530                 535                 540

Ala Leu Gly Gly Ser Cys Arg Met Gly Arg Ala Thr Ser Pro Ala Arg
545                 550                 555                 560
```

```
Leu Val Glu Gly Ser Asp Pro Leu Ala Val Asp Pro Ala Leu Arg
            565                 570                 575

Val Arg Gly Ala Ser Gly Leu Arg Val Val Asp Ala Ser Val Leu Pro
            580                 585                 590

Thr Leu Pro Gly Gly Gln Leu Gly Ala Thr Thr Phe Ala Leu Ala Glu
            595                 600                 605

Arg Ala Ala Arg Ile Ile Leu Gly Glu Arg Ala Ala Gly Glu Ala Glu
            610                 615                 620

Ala Pro Ala Glu Arg Arg Gln Glu His Ala His Ala Leu Gly Ala Ala
625                 630                 635                 640

<210> SEQ ID NO 18
<211> LENGTH: 1265
<212> TYPE: PRT
<213> ORGANISM: Nannochloropsis gaditana

<400> SEQUENCE: 18

Met Ser Ser Asn Gly Tyr Leu Arg Ala Tyr His Leu Leu Ile Ala Leu
1               5                   10                  15

Leu Ile Ser Ala Asn Ala Phe Leu Ile Thr Pro Pro Arg Leu Ser Lys
            20                  25                  30

Thr Thr Ile Gly Leu Gln Ser Phe Val Thr Ala Asn Tyr Gly Val Arg
        35                  40                  45

Arg Ala Ile Ser Leu Arg Gly Gly Leu Gln Ser Val Ser Met Lys Ala
    50                  55                  60

Pro Ala Ala Val Ala Ser Ser Thr Tyr Asp Tyr Ile Ile Val Gly Gly
65                  70                  75                  80

Gly Ile Gly Gly Cys Val Leu Ala Asn Arg Leu Thr Glu Ser Gly Arg
                85                  90                  95

Phe Lys Val Leu Leu Leu Glu Ala Gly Lys Ser Ala Glu Arg Asn Pro
            100                 105                 110

Tyr Val Asn Ile Pro Ala Gly Val Val Arg Leu Phe Lys Ser Ala Leu
        115                 120                 125

Asp Trp Gln Phe Glu Ser Ala Pro Glu Arg His Leu Asp Gly Lys Glu
    130                 135                 140

Val Tyr Leu Val Arg Gly Lys Ala Met Gly Gly Ser Ser Ala Val Asn
145                 150                 155                 160

Val Met Leu Val His Arg Gly Ser Ala Ser Asp Tyr Ala Lys Trp Glu
                165                 170                 175

Ala Glu Gly Ala Gln Gly Trp Gly Pro Glu Glu Ala Leu Arg Tyr Phe
            180                 185                 190

Lys Lys Met Glu Asp Asn Leu Val Gly Gly Glu Gly Arg Trp His Gly
        195                 200                 205

Gln Gly Gly Met Tyr Pro Val Asp Asp Val Lys Tyr Gln Asn Pro Leu
    210                 215                 220

Ser Lys Arg Phe Leu Gln Ala Cys Glu Glu Tyr Gly Trp Arg Ala Asn
225                 230                 235                 240

Pro Asp Phe Asn Asp Trp Ser His Pro Gln Asp Gly Tyr Gly Ser Phe
                245                 250                 255

Lys Val Ala Gln Lys His Gly Lys Arg Val Thr Ala Ala Ser Gly Tyr
            260                 265                 270

Leu Asn Lys Ala Val Arg Arg Pro Asn Leu Asp Ile Leu Ser Glu
        275                 280                 285

Ala Leu Val Thr Arg Val Leu Leu Glu Gly Glu Gly Asp Val Lys Ala
```

```
            290                 295                 300
Val Gly Val Glu Phe Thr Gly Lys Asp Gly Lys Thr His Gln Val Arg
305                 310                 315                 320

Thr Thr Gly Lys Ala Gly Glu Val Leu Leu Ala Gly Gly Ala Val Asn
                325                 330                 335

Ser Pro Gln Leu Leu Met Leu Ser Gly Ile Gly Pro Glu Ala Asp Leu
                340                 345                 350

Gln Ala Val Gly Ile Ala Thr Lys Val Asn Arg Pro Gly Val Gly Glu
                355                 360                 365

Asn Leu Gln Asp His Pro Ala Val Thr Ile Ala His Asn Ile Thr Arg
370                 375                 380

Pro Ile Ser Leu Cys Asp Asp Leu Phe Leu Phe His Thr Pro Val Pro
385                 390                 395                 400

Lys Pro His Gln Val Leu Arg Trp Thr Leu Thr Gly Ser Gly Pro Leu
                405                 410                 415

Thr Thr Pro Gly Cys Asp His Gly Ala Phe Leu Lys Thr Arg Glu Asp
                420                 425                 430

Leu Gln Glu Pro Asn Val Gln Phe Arg Phe Ile Ala Gly Arg Gly Ser
                435                 440                 445

Asp Pro Asp Gly Val Arg Ser Tyr Ile Met Gly Gly Ser Ala Arg Pro
                450                 455                 460

Leu Ser Gly Leu Thr Leu Gln Val Val Asn Ile Arg Pro Lys Ser Lys
465                 470                 475                 480

Gly Lys Leu Thr Leu Ala Ser Lys Asp Pro Leu Lys Lys Pro Arg Ile
                485                 490                 495

Glu Val Arg Tyr Leu Ser Ala Ala Glu Asp Leu Gln Ala Leu Arg Thr
                500                 505                 510

Gly Met Arg Ile Gly Arg Asp Leu Ile Lys Gln Arg Ala Phe Ala Asp
                515                 520                 525

Ile Leu Asp Glu Glu Val Phe Pro Gly Pro Ala Ala Gln Thr Asp Glu
                530                 535                 540

Glu Leu Asp Ala Tyr Ile Arg Asp Ser Leu His Thr Ala Asn Ala Leu
545                 550                 555                 560

Val Gly Thr Cys Lys Met Gly Ser Val Glu Asp Arg Asn Ala Val Val
                565                 570                 575

Asp Pro Glu Cys Arg Val Ile Gly Val Gly Gly Leu Arg Val Val Asp
                580                 585                 590

Ala Ser Val Met Pro Val Ile Pro Gly Gly Gln Thr Gly Ser Gly Thr
                595                 600                 605

Thr Met Leu Ala Glu Lys Ala Ala Asp Leu Val Arg Ala His Ala Gly
610                 615                 620

Asp Leu Val Glu Met Gly Val Gln Asp Glu Arg Lys Gly Gly Trp
625                 630                 635                 640

Phe Asn Gly Leu Leu Gly Arg Lys Gln Lys Val Ala Thr Glu Lys Glu
                645                 650                 655

Arg Gly Glu Arg Gly Lys Ser Glu Arg Phe Val Ser Glu Val Ile Arg
                660                 665                 670

His Met Gly Arg Val Phe Val Gln Val Ser Arg Ala Arg Arg Ala Gln
                675                 680                 685

Thr Cys Met Arg Val Gly Lys Gly Leu Asp Arg Glu Arg Gln Leu Glu
                690                 695                 700

Cys Ala Met Arg Lys Glu Leu Thr Ile Ala Leu Phe Tyr Ala Met Leu
705                 710                 715                 720
```

```
Phe Thr Met Arg His Ser Gly Phe Leu Ser Thr Thr Gly Arg Ala Ser
                725                 730                 735

Tyr Lys Asp Leu Gly Tyr Leu Thr Gly Ser Cys Arg Ala His Pro Cys
            740                 745                 750

Thr Ser Pro Ser Ser Leu Cys Leu Phe Pro Glu Lys Pro Phe Met Lys
            755                 760             765

Leu Ser Pro Ala Leu Ala Val Val Gly Phe Cys Phe Asn Ser Ile Asn
770                 775                 780

Val Gln Gly Phe Leu Leu Ser Asn Leu Ala Gly Arg Ser Leu Lys His
785                 790                 795                 800

Pro Val Pro Gln Lys Gly Leu Tyr Ser Arg Ile Glu Tyr Asp Ala Arg
                805                 810                 815

Glu Pro Arg Leu Asp Glu Phe Gly Leu Pro Leu Asp Pro Ala Asp Leu
            820                 825                 830

Met Glu Lys Pro Arg Val Pro Leu Lys Asp Arg Val Tyr His Ile Ile
            835                 840                 845

Asp Met Thr Asn Asp Trp Val Asp Ala Val Ser Arg Gly Arg Arg Glu
    850                 855                 860

Glu Glu Thr Arg Arg Ile Ile Gln Arg Arg Ala Ala Ala Lys Ala
865                 870                 875                 880

Met Ala Ile Lys Asp Lys Val Leu Ile Ser Leu Asp Tyr Val Phe His
                885                 890                 895

Pro Val Lys Ala Trp Arg Thr Phe Val Ala Asp Pro Leu Glu Ala Arg
                900                 905                 910

His Gln Arg Gln Leu Arg Gln Gln Ala Glu Lys Arg Ala Arg Leu Glu
                915                 920                 925

Arg Tyr Leu Gln Arg Tyr Asn Thr Val Lys Asn Arg Phe His Asp Thr
    930                 935                 940

Leu Asp Leu Leu Glu Ser Thr Thr Arg Thr Ser Val Lys Val Ala Lys
945                 950                 955                 960

Ser Val Ser Ser Ala Val Val Gly Ala Pro Gly Thr Val Thr Arg Thr
                965                 970                 975

Val Lys Glu Val Lys Ser Gln Ala Gln Gly Thr Ala Glu Ala Val Ala
                980                 985                 990

Lys Val Ser Ser Ser Val Ser Ser  Val Val Ser Lys Ile  Thr Ser Val
                995                 1000                 1005

Ile Arg  Lys Glu Asp Gly Ala  Leu Ala Gly Ala Lys  Gly Lys Lys
    1010                1015                1020

Asp Pro  Arg Ser Glu Asp Glu  Gly Lys Ala Asp Pro  Val Lys Val
    1025                1030                1035

Arg Glu  Ile Trp Glu Thr Lys  Glu Gln Thr Ala Ile  Arg Thr Ile
    1040                1045                1050

Trp Glu  Ala Asp Glu Leu Val  Thr Pro Val Thr Pro  Pro Ala Thr
    1055                1060                1065

Ala Met  Ala Ser Thr Val Ser  Val Ser Glu Pro Gln  Asp Glu Asn
    1070                1075                1080

Glu Ala  Ser Ile Ser Gln Gly  Ala Ala Pro Ser Pro  Ser Thr Ser
    1085                1090                1095

Ser Pro  Ser Ser Pro Glu Pro  Val Thr Arg Leu Ser  Phe Arg Ala
    1100                1105                1110

Arg Val  Glu Ala Asp Glu Lys  Glu Arg Phe Gly Ser  Arg Arg Leu
    1115                1120                1125
```

```
Lys Ile Ser Gly Asn Val Pro Pro Thr Ala Ser Pro Thr Arg Gly
    1130                1135                1140

Ala Ser Ser Leu Pro Leu Asp Thr Leu Ser Ser Ser Ala Thr Gln
    1145                1150                1155

Thr Phe Glu Arg Ser Lys Val Gly Pro Pro Ile Arg Thr Ser Lys
    1160                1165                1170

Ala Arg Cys Ile Gly Lys Cys Val His Asn Gly Trp Lys Gly Ile
    1175                1180                1185

Cys Glu Glu Trp Phe Val His Ile Ser Phe Pro Thr Tyr Ala Val
    1190                1195                1200

Ser Ile Val Arg Pro Pro Met His Val His Asn Phe Lys Val Ile
    1205                1210                1215

Cys Cys Val Leu Ala Val Arg His Ala Arg Arg Lys Lys Glu Met
    1220                1225                1230

Ser Thr Ala Leu Ser Thr His Leu Ile Tyr Leu Leu Leu Lys Thr
    1235                1240                1245

Val Lys Met Leu Gln Asp Leu Pro Gln Leu Arg Arg Lys Gly Lys
    1250                1255                1260

Thr Asn
    1265

<210> SEQ ID NO 19
<211> LENGTH: 613
<212> TYPE: PRT
<213> ORGANISM: Volvox carteri f. nagariensis

<400> SEQUENCE: 19

Met Leu Leu Gly Gln Arg Pro Phe Gly Ala Pro Ala Lys Gly Ala Met
1               5                   10                  15

Pro Cys Trp Lys Ala Ala Arg His Gly Gly Val Ala Gly Val Ala Arg
                20                  25                  30

Arg Pro Val Ala Val Lys Ala Ala Ser Val Gly Ser Glu Lys Phe
            35                  40                  45

Asp Tyr Ile Leu Val Gly Gly Thr Ala Gly Cys Val Leu Ala Asn
        50                  55                  60

Lys Leu Ser Ala Asn Gly Ser Lys Lys Val Leu Val Leu Glu Ala Gly
65                  70                  75                  80

Pro Thr Gly Asp Ala Met Glu Val Ala Val Pro Ala Gly Ile Ala Arg
                85                  90                  95

Leu Phe Ala His Pro Val Phe Asp Trp Gly Met Ser Ser Leu Thr Gln
                100                 105                 110

Gln Gln Leu Val Ala Arg Glu Ile Tyr Leu Ala Arg Gly Arg Leu Leu
            115                 120                 125

Gly Gly Ser Ser Gly Thr Asn Ala Thr Leu Tyr His Arg Gly Thr Pro
        130                 135                 140

Ala Asp Tyr Asp Ser Trp Gly Leu Glu Gly Trp Thr Ser Lys Asp Leu
145                 150                 155                 160

Leu Asp Trp Phe Val Lys Ala Glu Cys Tyr Gly Asp Gly Pro Arg Ala
                165                 170                 175

Phe His Gly Gln Ser Gly Ser Met Asn Val Glu Gln Pro Arg Tyr Gln
                180                 185                 190

Asn Val Leu His Asp Glu Phe Phe Arg Ala Ala Ala Ala Gly Leu
            195                 200                 205

Pro Ala Asn Glu Asp Phe Asn Asp Trp Ser Arg Pro Gln Glu Gly Tyr
        210                 215                 220
```

Gly Glu Phe Gln Val Ala Gln Lys Asn Gly Glu Arg Ala Asp Thr Tyr
225                 230                 235                 240

Arg Thr Tyr Leu Lys Pro Ala Met Gly Arg Asp Asn Leu Lys Val Met
            245                 250                 255

Thr Gly Ala Arg Thr Thr Lys Val His Ile Glu Lys Ser Ser Thr Gly
        260                 265                 270

Pro Arg Ala Arg Gly Val Glu Tyr Ala Thr Gln Gln Phe Gly Glu Arg
        275                 280                 285

Tyr Thr Ala Glu Leu Thr Pro Gly Gly Glu Val Leu Met Cys Thr Gly
    290                 295                 300

Ala Val His Thr Pro His Leu Leu Met Leu Ser Gly Ile Gly Pro Ala
305                 310                 315                 320

Pro Thr Leu Leu Glu His Gly Leu Asp Val Ile Ser Ser Leu Pro Gly
            325                 330                 335

Val Gly Ala Asn Leu Gln Asp His Pro Ala Ala Val Leu Ala Val Arg
        340                 345                 350

Ala Lys Pro Glu Phe Glu Gly Leu Ser Val Thr Ser Glu Ile Tyr Asp
        355                 360                 365

Ser Lys Cys Asn Ile Arg Leu Gly Ala Val Met Lys Tyr Leu Phe Gly
    370                 375                 380

Arg Arg Gly Pro Leu Ala Thr Thr Gly Cys Asp His Gly Ala Phe Val
385                 390                 395                 400

Arg Thr Ser Ala Ser His Ser Gln Pro Asp Leu Gln Met Arg Phe Val
            405                 410                 415

Pro Gly Cys Ala Leu Asp Pro Asp Gly Val Lys Ser Tyr Ile Val Phe
        420                 425                 430

Gly Glu Leu Lys Lys Gln Gly Arg Ala Trp Pro Gly Gly Ile Thr Leu
        435                 440                 445

Gln Leu Leu Gly Ile Arg Ala Lys Ser Arg Gly Ser Ile Gly Leu Lys
    450                 455                 460

Ala Ala Asp Pro Phe Ile Asn Pro Ala Ile Asn Ile Asn Tyr Phe Ser
465                 470                 475                 480

Asp Pro Glu Asp Leu Ala Thr Leu Lys Asn Gly Val Arg Ile Ala Arg
            485                 490                 495

Glu Ile Val Ala Gln Glu Pro Leu Arg Lys Tyr Leu Leu Glu Glu Thr
        500                 505                 510

Phe Pro Gly Glu Arg Ala Asn Thr Asp Lys Asp Ile Glu Glu Tyr Val
        515                 520                 525

Arg Arg Thr Val His Ser Gly Asn Ala Leu Val Gly Thr Cys Ala Met
    530                 535                 540

Gly Thr Thr Pro Ala Ser Gly Ala Val Val Ser Ser Ala Asp Leu Lys
545                 550                 555                 560

Val Phe Gly Val Asp Gly Leu Arg Val Val Asp Ala Ser Val Leu Pro
            565                 570                 575

Arg Ile Pro Gly Gly Gln Thr Gly Ala Ala Thr Val Met Val Ala Glu
        580                 585                 590

Arg Ala Ala Ala Met Leu Leu Gly Gln Ala Thr Ile Thr Ser Arg Arg
        595                 600                 605

Glu Pro Ala Ala Val
    610

<210> SEQ ID NO 20
<211> LENGTH: 476

```
<212> TYPE: PRT
<213> ORGANISM: Clostridium beijerinckii

<400> SEQUENCE: 20

Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400
```

-continued

Tyr Ile Tyr Ser Lys Asn Ile Asp Asn Leu Asn Arg Phe Glu Arg Glu
            405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Phe Thr Ile Ala Gly Ser Thr
            435                 440                 445

Gly Glu Gly Ile Thr Ser Ala Arg Asn Phe Thr Arg Gln Arg Cys
    450                 455                 460

Val Leu Ala Gly Leu Glu His His His His His His
465                 470                 475

<210> SEQ ID NO 21
<211> LENGTH: 243
<212> TYPE: PRT
<213> ORGANISM: Prochlorococcus marinus

<400> SEQUENCE: 21

Met Pro Thr Leu Glu Met Pro Val Ala Ala Val Leu Asp Ser Thr Val
1               5                   10                  15

Gly Ser Ser Glu Ala Leu Pro Asp Phe Thr Ser Asp Arg Tyr Lys Asp
            20                  25                  30

Ala Tyr Ser Arg Ile Asn Ala Ile Val Ile Glu Gly Glu Gln Glu Ala
        35                  40                  45

His Asp Asn Tyr Ile Ala Ile Gly Thr Leu Leu Pro Asp His Val Glu
    50                  55                  60

Glu Leu Lys Arg Leu Ala Lys Met Glu Met Arg His Lys Lys Gly Phe
65                  70                  75                  80

Thr Ala Cys Gly Lys Asn Leu Gly Val Glu Ala Asp Met Asp Phe Ala
                85                  90                  95

Arg Glu Phe Phe Ala Pro Leu Arg Asp Asn Phe Gln Thr Ala Leu Gly
            100                 105                 110

Gln Gly Lys Thr Pro Thr Cys Leu Leu Ile Gln Ala Leu Leu Ile Glu
        115                 120                 125

Ala Phe Ala Ile Ser Ala Tyr His Thr Tyr Ile Pro Val Ser Asp Pro
130                 135                 140

Phe Ala Arg Lys Ile Thr Glu Gly Val Val Lys Asp Glu Tyr Thr His
145                 150                 155                 160

Leu Asn Tyr Gly Glu Ala Trp Leu Lys Ala Asn Leu Glu Ser Cys Arg
                165                 170                 175

Glu Glu Leu Leu Glu Ala Asn Arg Glu Asn Leu Pro Leu Ile Arg Arg
            180                 185                 190

Met Leu Asp Gln Val Ala Gly Asp Ala Ala Val Leu Gln Met Asp Lys
        195                 200                 205

Glu Asp Leu Ile Glu Asp Phe Leu Ile Ala Tyr Gln Glu Ser Leu Thr
    210                 215                 220

Glu Ile Gly Phe Asn Thr Arg Glu Ile Thr Arg Met Ala Ala Ala Ala
225                 230                 235                 240

Leu Val Ser

<210> SEQ ID NO 22
<211> LENGTH: 218
<212> TYPE: PRT
<213> ORGANISM: Clostridium acetobutylicum

<400> SEQUENCE: 22

```
Met Asn Ser Lys Ile Ile Arg Phe Glu Asn Leu Arg Ser Phe Phe Lys
1               5                   10                  15

Asp Gly Met Thr Ile Met Ile Gly Gly Phe Leu Asn Cys Gly Thr Pro
            20                  25                  30

Thr Lys Leu Ile Asp Phe Leu Val Asn Leu Asn Ile Lys Asn Leu Thr
        35                  40                  45

Ile Ile Ser Asn Asp Thr Cys Tyr Pro Asn Thr Gly Ile Gly Lys Leu
50                  55                  60

Ile Ser Asn Asn Gln Val Lys Lys Leu Ile Ala Ser Tyr Ile Gly Ser
65                  70                  75                  80

Asn Pro Asp Thr Gly Lys Lys Leu Phe Asn Asn Glu Leu Glu Val Glu
                85                  90                  95

Leu Ser Pro Gln Gly Thr Leu Val Glu Arg Ile Arg Ala Gly Gly Ser
            100                 105                 110

Gly Leu Gly Gly Val Leu Thr Lys Thr Gly Leu Gly Thr Leu Ile Glu
        115                 120                 125

Lys Gly Lys Lys Lys Ile Ser Ile Asn Gly Thr Glu Tyr Leu Leu Glu
    130                 135                 140

Leu Pro Leu Thr Ala Asp Val Ala Leu Ile Lys Gly Ser Ile Val Asp
145                 150                 155                 160

Glu Ala Gly Asn Thr Phe Tyr Lys Gly Thr Thr Lys Asn Phe Asn Pro
                165                 170                 175

Tyr Met Ala Met Ala Ala Lys Thr Val Ile Val Glu Ala Glu Asn Leu
            180                 185                 190

Val Ser Cys Glu Lys Leu Glu Lys Glu Lys Ala Met Thr Pro Gly Val
        195                 200                 205

Leu Ile Asn Tyr Ile Val Lys Glu Pro Ala
    210                 215

<210> SEQ ID NO 23
<211> LENGTH: 154
<212> TYPE: PRT
<213> ORGANISM: Haemophilus influenza

<400> SEQUENCE: 23

Met Ser Ala Asn Phe Thr Asp Lys Asn Gly Arg Gln Ser Lys Gly Val
1               5                   10                  15

Leu Leu Leu Arg Thr Leu Ala Met Pro Ser Asp Thr Asn Ala Asn Gly
            20                  25                  30

Asp Ile Phe Gly Gly Trp Ile Met Ser Gln Met Asp Met Gly Gly Ala
        35                  40                  45

Ile Leu Ala Lys Glu Ile Ala His Gly Arg Val Val Thr Val Ala Val
50                  55                  60

Glu Ser Met Asn Phe Ile Lys Pro Ile Ser Val Gly Asp Val Val Cys
65                  70                  75                  80

Cys Tyr Gly Gln Cys Leu Lys Val Gly Arg Ser Ser Ile Lys Ile Lys
                85                  90                  95

Val Glu Val Trp Val Lys Lys Val Ala Ser Glu Pro Ile Gly Glu Arg
            100                 105                 110

Tyr Cys Val Thr Asp Ala Val Phe Thr Phe Val Ala Val Asp Asn Asn
        115                 120                 125

Gly Arg Ser Arg Thr Ile Pro Arg Glu Asn Asn Gln Glu Leu Glu Lys
    130                 135                 140

Ala Leu Ala Leu Ile Ser Glu Gln Pro Leu
145                 150
```

<210> SEQ ID NO 24
<211> LENGTH: 329
<212> TYPE: PRT
<213> ORGANISM: Streptomyces sp.

<400> SEQUENCE: 24

| Met | Thr | Asp | Val | Arg | Phe | Arg | Ile | Ile | Gly | Thr | Gly | Ala | Tyr | Val | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Glu Arg Ile Val Ser Asn Asp Glu Val Gly Ala Pro Ala Gly Val Asp
            20                  25                  30

Asp Asp Trp Ile Thr Arg Lys Thr Gly Ile Arg Gln Arg Arg Trp Ala
        35                  40                  45

Ala Asp Asp Gln Ala Thr Ser Asp Leu Ala Thr Ala Ala Gly Arg Ala
    50                  55                  60

Ala Leu Lys Ala Ala Gly Ile Thr Pro Glu Gln Leu Thr Val Ile Ala
65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Ala Phe Asp Val Asn
            100                 105                 110

Ala Val Cys Ser Gly Thr Val Phe Ala Leu Ser Ser Val Ala Gly Thr
        115                 120                 125

Leu Val Tyr Arg Gly Gly Tyr Ala Leu Val Ile Gly Ala Asp Leu Tyr
    130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
            180                 185                 190

Leu Ile Arg Val Pro Ala Gly Gly Ser Arg Gln Pro Leu Asp Thr Asp
        195                 200                 205

Gly Leu Asp Ala Gly Leu Gln Tyr Phe Ala Met Asp Gly Arg Glu Val
    210                 215                 220

Arg Arg Phe Val Thr Glu His Leu Pro Gln Leu Ile Lys Gly Phe Leu
225                 230                 235                 240

His Glu Ala Gly Val Asp Ala Ala Asp Ile Ser His Phe Val Pro His
                245                 250                 255

Gln Ala Asn Gly Val Met Leu Asp Glu Val Phe Gly Glu Leu His Leu
            260                 265                 270

Pro Arg Ala Thr Met His Arg Thr Val Glu Thr Tyr Gly Asn Thr Gly
        275                 280                 285

Ala Ala Ser Ile Pro Ile Thr Met Asp Ala Val Arg Ala Gly Ser
    290                 295                 300

Phe Arg Pro Gly Glu Leu Val Leu Leu Ala Gly Phe Gly Gly Met
305                 310                 315                 320

Ala Ala Ser Phe Ala Leu Ile Glu Trp
                325

<210> SEQ ID NO 25
<211> LENGTH: 165
<212> TYPE: PRT
<213> ORGANISM: Bacillus subtilis

<400> SEQUENCE: 25

-continued

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
                20                  25                  30

Arg Arg Phe Tyr His Lys Glu Asp Ala His Arg Thr Leu Leu Gly Asp
            35                  40                  45

Val Leu Val Arg Ser Val Ile Ser Arg Gln Tyr Gln Leu Asp Lys Ser
        50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Cys Ala Phe Asp Ser Gln Pro Ile Gly Ile Asp Ile Glu Lys Thr Lys
                100                 105                 110

Pro Ile Ser Leu Glu Met Pro Lys Arg Phe Phe Ser Lys Thr Glu Tyr
            115                 120                 125

Ser Asp Leu Leu Ala Lys Asp Lys Asp Glu Gln Thr Asp Tyr Phe Tyr
130                 135                 140

His Leu Trp Ser Met Lys Glu Ser Phe Ile Lys Gln Gly Arg Gln Arg
145                 150                 155                 160

Leu Ile Ala Ser Ala
                165

<210> SEQ ID NO 26
<211> LENGTH: 97
<212> TYPE: PRT
<213> ORGANISM: Synechocystis sp

<400> SEQUENCE: 26

Met Ala Ser Tyr Thr Val Lys Leu Ile Thr Pro Asp Gly Glu Ser Ser
1               5                   10                  15

Ile Glu Cys Ser Asp Asp Thr Tyr Ile Leu Asp Ala Ala Glu Glu Ala
                20                  25                  30

Gly Leu Asp Leu Pro Tyr Ser Cys Arg Ala Gly Ala Cys Ser Thr Cys
            35                  40                  45

Ala Gly Lys Ile Thr Ala Gly Ser Val Asp Gln Ser Asp Gln Ser Phe
        50                  55                  60

Leu Asp Asp Asp Gln Ile Glu Ala Gly Tyr Val Leu Thr Cys Val Ala
65                  70                  75                  80

Tyr Pro Thr Ser Asp Cys Thr Ile Glu Thr His Lys Glu Glu Asp Leu
                85                  90                  95

Tyr

<210> SEQ ID NO 27
<211> LENGTH: 61
<212> TYPE: PRT
<213> ORGANISM: unknown
<220> FEATURE:
<223> OTHER INFORMATION: CvPAS chloroplast targeting sequence (length =
    61 amino acid)

<400> SEQUENCE: 27

Met Ala Ser Ile Thr Ser Arg Ala Ser Arg Ala Ser Cys Ser Gln
1               5                   10                  15

Ala Asn Thr Arg Ala Gly Arg Val Ala Leu Ser Gly Gly Ala Leu Leu
                20                  25                  30

Arg Pro Ala Arg Pro Ala Arg Ser Phe Val Pro Ala Arg Lys Gln Gln
                35                  40                  45

Gln Gly Ala Val Arg Arg Gly Gly Ala Leu Ser Ala Arg
 50                  55                  60

<210> SEQ ID NO 28
<211> LENGTH: 394
<212> TYPE: PRT
<213> ORGANISM: Escherichia coli

<400> SEQUENCE: 28

Met Lys Asn Cys Val Ile Val Ser Ala Val Arg Thr Ala Ile Gly Ser
 1               5                  10                  15

Phe Asn Gly Ser Leu Ala Ser Thr Ser Ala Ile Asp Leu Gly Ala Thr
                20                  25                  30

Val Ile Lys Ala Ala Ile Glu Arg Ala Lys Ile Asp Ser Gln His Val
            35                  40                  45

Asp Glu Val Ile Met Gly Asn Val Leu Gln Ala Gly Leu Gly Gln Asn
 50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
    130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ala Ile Glu
            180                 185                 190

Ser Gly Ala Phe Thr Ala Glu Ile Val Pro Val Asn Val Val Thr Arg
        195                 200                 205

Lys Lys Thr Phe Val Phe Ser Gln Asp Glu Phe Pro Lys Ala Asn Ser
    210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Leu Ala Ala Gly Leu Thr Pro
            260                 265                 270

Leu Ala Arg Ile Lys Ser Tyr Ala Ser Gly Gly Val Pro Pro Ala Leu
        275                 280                 285

Met Gly Met Gly Pro Val Pro Ala Thr Gln Lys Ala Leu Gln Leu Ala
    290                 295                 300

Gly Leu Gln Leu Ala Asp Ile Asp Leu Ile Glu Ala Asn Glu Ala Phe
305                 310                 315                 320

Ala Ala Gln Phe Leu Ala Val Gly Lys Asn Leu Gly Phe Asp Ser Glu
                325                 330                 335

Lys Val Asn Val Asn Gly Gly Ala Ile Ala Leu Gly His Pro Ile Gly
            340                 345                 350

```
Ala Ser Gly Ala Arg Ile Leu Val Thr Leu Leu His Ala Met Gln Ala
        355                 360                 365

Arg Asp Lys Thr Leu Gly Leu Ala Thr Leu Cys Ile Gly Gly Gly Gln
    370                 375                 380

Gly Ile Ala Met Val Ile Glu Arg Leu Asn
385                 390

<210> SEQ ID NO 29
<211> LENGTH: 282
<212> TYPE: PRT
<213> ORGANISM: Clostridium acetobutylicum

<400> SEQUENCE: 29

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280

<210> SEQ ID NO 30
<211> LENGTH: 261
<212> TYPE: PRT
<213> ORGANISM: Clostridium acetobutylicum

<400> SEQUENCE: 30
```

```
Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
            115                 120                 125

Arg Phe Gly Gln Pro Glu Val Gly Leu Gly Ile Thr Pro Gly Phe Gly
130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
            195                 200                 205

Leu Ser Lys Gln Ala Ile Asn Arg Gly Met Gln Cys Asp Ile Asp Thr
210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
                260

<210> SEQ ID NO 31
<211> LENGTH: 397
<212> TYPE: PRT
<213> ORGANISM: Treponema denticola

<400> SEQUENCE: 31

Met Ile Val Lys Pro Met Val Arg Asn Asn Ile Cys Leu Asn Ala His
1               5                   10                  15

Pro Gln Gly Cys Lys Lys Gly Val Glu Asp Gln Ile Glu Tyr Thr Lys
            20                  25                  30

Lys Arg Ile Thr Ala Glu Val Lys Ala Gly Ala Lys Ala Pro Lys Asn
        35                  40                  45

Val Leu Val Leu Gly Cys Ser Asn Gly Tyr Gly Leu Ala Ser Arg Ile
    50                  55                  60

Thr Ala Ala Phe Gly Tyr Gly Ala Ala Thr Ile Gly Val Ser Phe Glu
65                  70                  75                  80

Lys Ala Gly Ser Glu Thr Lys Tyr Gly Thr Pro Gly Trp Tyr Asn Asn
                85                  90                  95

Leu Ala Phe Asp Glu Ala Ala Lys Arg Glu Gly Leu Tyr Ser Val Thr
```

```
            100             105             110
Ile Asp Gly Asp Ala Phe Ser Asp Glu Ile Lys Ala Gln Val Ile Glu
            115             120             125

Glu Ala Lys Lys Lys Gly Ile Lys Phe Asp Leu Ile Val Tyr Ser Leu
            130             135             140

Ala Ser Pro Val Arg Thr Asp Pro Asp Thr Gly Ile Met His Lys Ser
145             150             155             160

Val Leu Lys Pro Phe Gly Lys Thr Phe Thr Gly Lys Thr Val Asp Pro
            165             170             175

Phe Thr Gly Glu Leu Lys Glu Ile Ser Ala Glu Pro Ala Asn Asp Glu
            180             185             190

Glu Ala Ala Thr Val Lys Val Met Gly Gly Glu Asp Trp Glu Arg
            195             200             205

Trp Ile Lys Gln Leu Ser Lys Glu Gly Leu Leu Glu Glu Gly Cys Ile
            210             215             220

Thr Leu Ala Tyr Ser Tyr Ile Gly Pro Glu Ala Thr Gln Ala Leu Tyr
225             230             235             240

Arg Lys Gly Thr Ile Gly Lys Ala Lys Glu His Leu Glu Ala Thr Ala
            245             250             255

His Arg Leu Asn Lys Glu Asn Pro Ser Ile Arg Ala Phe Val Ser Val
            260             265             270

Asn Lys Gly Leu Val Thr Arg Ala Ser Ala Val Ile Pro Val Ile Pro
            275             280             285

Leu Tyr Leu Ala Ser Leu Phe Lys Val Met Lys Glu Lys Gly Asn His
            290             295             300

Glu Gly Cys Ile Glu Gln Ile Thr Arg Leu Tyr Ala Glu Arg Leu Tyr
305             310             315             320

Arg Lys Asp Gly Thr Ile Pro Val Asp Glu Glu Asn Arg Ile Arg Ile
            325             330             335

Asp Asp Trp Glu Leu Glu Glu Asp Val Gln Lys Ala Val Ser Ala Leu
            340             345             350

Met Glu Lys Val Thr Gly Glu Asn Ala Glu Ser Leu Thr Asp Leu Ala
            355             360             365

Gly Tyr Arg His Asp Phe Leu Ala Ser Asn Gly Phe Asp Val Glu Gly
            370             375             380

Ile Asn Tyr Glu Ala Glu Val Glu Arg Phe Asp Arg Ile
385             390             395

<210> SEQ ID NO 32
<211> LENGTH: 464
<212> TYPE: PRT
<213> ORGANISM: Salmonella typhimurium

<400> SEQUENCE: 32

Met Asn Thr Ser Glu Leu Glu Thr Leu Ile Arg Thr Ile Leu Ser Glu
1               5               10              15

Gln Leu Thr Thr Pro Ala Gln Thr Pro Val Gln Pro Gly Lys Gly
            20              25              30

Ile Phe Gln Ser Val Ser Glu Ala Ile Asp Ala His Gln Ala Phe
            35              40              45

Leu Arg Tyr Gln Gln Cys Pro Leu Lys Thr Arg Ser Ala Ile Ile Ser
    50              55              60

Ala Met Arg Gln Glu Leu Thr Pro Leu Leu Ala Pro Leu Ala Glu Glu
65              70              75              80
```

Ser Ala Asn Glu Thr Gly Met Gly Asn Lys Glu Asp Lys Phe Leu Lys
            85                  90                  95

Asn Lys Ala Ala Leu Asp Asn Thr Pro Gly Val Glu Asp Leu Thr Thr
        100                 105                 110

Thr Ala Leu Thr Gly Asp Gly Gly Met Val Leu Phe Glu Tyr Ser Pro
        115                 120                 125

Phe Gly Val Ile Gly Ser Val Ala Pro Ser Thr Asn Pro Thr Glu Thr
        130                 135                 140

Ile Ile Asn Asn Ser Ile Ser Met Leu Ala Ala Gly Asn Ser Ile Tyr
145                 150                 155                 160

Phe Ser Pro His Pro Gly Ala Lys Lys Val Ser Leu Lys Leu Ile Ser
                165                 170                 175

Leu Ile Glu Glu Ile Ala Phe Arg Cys Cys Gly Ile Arg Asn Leu Val
            180                 185                 190

Val Thr Val Ala Glu Pro Thr Phe Glu Ala Thr Gln Gln Met Met Ala
        195                 200                 205

His Pro Arg Ile Ala Val Leu Ala Ile Thr Gly Pro Gly Ile Val
        210                 215                 220

Ala Met Gly Met Lys Ser Gly Lys Lys Val Ile Gly Ala Gly Ala Gly
225                 230                 235                 240

Asn Pro Pro Cys Ile Val Asp Glu Thr Ala Asp Leu Val Lys Ala Ala
                245                 250                 255

Glu Asp Ile Ile Asn Gly Ala Ser Phe Asp Tyr Asn Leu Pro Cys Ile
            260                 265                 270

Ala Glu Lys Ser Leu Ile Val Val Glu Ser Val Ala Glu Arg Leu Val
        275                 280                 285

Gln Gln Met Gln Thr Phe Gly Ala Leu Leu Ser Pro Ala Asp Thr
        290                 295                 300

Asp Lys Leu Arg Ala Val Cys Leu Pro Glu Gly Gln Ala Asn Lys Lys
305                 310                 315                 320

Leu Val Gly Lys Ser Pro Ser Ala Met Leu Glu Ala Ala Gly Ile Ala
                325                 330                 335

Val Pro Ala Lys Ala Pro Arg Leu Leu Ile Ala Leu Val Asn Ala Asp
            340                 345                 350

Asp Pro Trp Val Thr Ser Glu Gln Leu Met Pro Met Leu Pro Val Val
        355                 360                 365

Lys Val Ser Asp Phe Asp Ser Ala Leu Ala Leu Ala Leu Lys Val Glu
        370                 375                 380

Glu Gly Leu His His Thr Ala Ile Met His Ser Gln Asn Val Ser Arg
385                 390                 395                 400

Leu Asn Leu Ala Ala Arg Thr Leu Gln Thr Ser Ile Phe Val Lys Asn
                405                 410                 415

Gly Pro Ser Tyr Ala Gly Ile Gly Val Gly Gly Glu Gly Phe Thr Thr
            420                 425                 430

Phe Thr Ile Ala Thr Pro Thr Gly Glu Gly Thr Thr Ser Ala Arg Thr
        435                 440                 445

Phe Ala Arg Ser Arg Arg Cys Val Leu Thr Asn Gly Phe Ser Ile Arg
450                 455                 460

<210> SEQ ID NO 33
<211> LENGTH: 521
<212> TYPE: PRT
<213> ORGANISM: Aeromonas hydrophila subsp. hydrophila

<400> SEQUENCE: 33

```
Met Leu Ser Arg Gln Asn Ala Arg Glu Leu Val Arg Asn Ala Lys Gln
1               5                   10                  15

Ala Gln Val Ile Met Ala Thr Phe Ser Gln Gln Lys Ile Asp Ala Ile
            20                  25                  30

Val Lys Asn Val Ala Glu Glu Ala Ala Arg His Ala Glu Thr Leu Ala
        35                  40                  45

Lys Met Ala Ala Glu Glu Thr Gly Phe Gly Asn Trp Gln Asp Lys Val
    50                  55                  60

Leu Lys Asn Arg Phe Ala Ser Leu His Val Tyr Asp Ala Ile Lys Glu
65                  70                  75                  80

Met Lys Thr Val Gly Ile Ile His Asp Asp Gln Ala Lys Lys Val Met
                85                  90                  95

Asp Val Gly Val Pro Leu Gly Val Ile Cys Ala Leu Val Pro Ser Thr
            100                 105                 110

Asn Pro Thr Ser Thr Ile Phe Tyr Lys Thr Leu Ile Ala Leu Lys Ala
        115                 120                 125

Gly Asn Ala Ile Ile Phe Ser Pro His Pro Gly Ala Arg Gln Cys Ser
    130                 135                 140

Trp Lys Ala Ile Glu Ile Val Lys Arg Ala Ala Glu Ala Ala Gly Ala
145                 150                 155                 160

Pro Ala Gly Ile Val Asp Gly Val Thr Gln Leu Thr Leu Glu Ala Thr
                165                 170                 175

Ser Glu Leu Met His Ser Lys Asp Val Ser Leu Ile Leu Ala Thr Gly
            180                 185                 190

Gly Glu Gly Met Val Arg Ala Ala Tyr Ala Ser Gly Thr Pro Thr Ile
        195                 200                 205

Ser Gly Gly Pro Gly Asn Gly Pro Ala Phe Ile Glu Arg Ser Ala Asp
    210                 215                 220

Ile His Gln Ala Val Lys Asp Ile Ile Thr Ser Lys Thr Phe Asp Asn
225                 230                 235                 240

Gly Val Ile Cys Ala Ser Glu Gln Ser Ile Ile Val Glu Arg Cys Ile
                245                 250                 255

Tyr Asp Glu Val His Arg Glu Leu Ala Ala Gln Gly Ala Tyr Phe Met
            260                 265                 270

Asn Glu Asp Glu Ala Ala Arg Met Ala Ala Leu Leu Leu Arg Pro Asn
        275                 280                 285

Gly Thr Ile Asn Pro Lys Val Val Gly Lys Thr Ala Leu His Leu Ser
    290                 295                 300

Gln Leu Ala Gly Phe Ser Val Pro Pro Ser Thr Arg Val Leu Val Ala
305                 310                 315                 320

Glu Gln Thr Thr Val Ser His Ser Asn Pro Tyr Ser Arg Glu Lys Leu
                325                 330                 335

Cys Pro Val Leu Gly Leu Tyr Val Glu Glu Trp Arg Ala Ala Cys
            340                 345                 350

His Arg Val Val Glu Leu Leu Thr Asn Glu Gly Leu Gly His Thr Leu
        355                 360                 365

Val Ile His Thr Arg Asn Gln Asp Val Ile Arg Gln Phe Ser Leu Glu
    370                 375                 380

Lys Pro Val Asn Arg Ile Leu Ile Asn Thr Pro Ala Ala Leu Gly Gly
385                 390                 395                 400

Ile Gly Ala Thr Thr Asn Leu Thr Pro Ala Leu Thr Leu Gly Cys Gly
                405                 410                 415
```

Ala Val Gly Gly Gly Ser Ser Asp Asn Val Gly Pro Met Asn Leu
            420             425             430

Leu Asn Ile Arg Lys Val Gly Tyr Gly Val Arg Thr Ile Glu Glu Leu
        435             440             445

Arg Ala Pro Ile Gln Pro Val Ala Val Gln Pro Ala Ser Ala Ala Pro
    450             455             460

Thr Ala Pro Gln Pro Cys Ser Ile Leu Asp Asp Ala Arg Phe Ser Ala
465             470             475             480

Pro Ala Pro Ala Cys His Ser Ala Asp Asp Arg Phe Ala Gly Ala Ser
            485             490             495

Ala Glu Val Gly Gly Glu Ile Ser Glu Gln Asn Val Glu Arg Val Ile
        500             505             510

Arg Gln Val Leu Glu Arg Leu Gly Lys
    515             520

<210> SEQ ID NO 34
<211> LENGTH: 462
<212> TYPE: PRT
<213> ORGANISM: Klebsiella pneumoniae subsp. rhinoscleromatis

<400> SEQUENCE: 34

Met Asn Thr Ala Glu Leu Glu Thr Leu Ile Arg Thr Ile Leu Ser Glu
1               5                   10                  15

Lys Leu Ala Pro Thr Pro Pro Ala Pro Gln Gln Glu Gln Gly Ile Phe
            20                  25                  30

Cys Asp Val Gly Ser Ala Ile Asp Ala Ala His Gln Ala Phe Leu Arg
        35                  40                  45

Tyr Gln Gln Cys Pro Leu Lys Thr Arg Ser Ala Ile Ile Ser Ala Leu
    50                  55                  60

Arg Glu Thr Leu Ala Pro Glu Leu Ala Thr Leu Ala Glu Glu Ser Ala
65                  70                  75                  80

Thr Glu Thr Gly Met Gly Asn Lys Glu Asp Lys Tyr Leu Lys Asn Lys
                85                  90                  95

Ala Ala Leu Glu Asn Thr Pro Gly Ile Glu Asp Leu Thr Thr Ser Ala
            100                 105                 110

Leu Thr Gly Asp Gly Gly Met Val Leu Phe Glu Tyr Ser Pro Phe Gly
        115                 120                 125

Val Ile Gly Ala Val Ala Pro Ser Thr Asn Pro Thr Glu Thr Ile Ile
    130                 135                 140

Asn Asn Ser Ile Ser Met Leu Ala Ala Gly Asn Ser Val Tyr Phe Ser
145                 150                 155                 160

Pro His Pro Gly Ala Lys Lys Val Ser Leu Lys Leu Ile Ala Arg Ile
                165                 170                 175

Glu Glu Ile Ala Tyr Arg Cys Ser Gly Ile Arg Asn Leu Val Val Thr
            180                 185                 190

Val Ala Glu Pro Thr Phe Glu Ala Thr Gln Gln Met Met Ser His Pro
        195                 200                 205

Leu Ile Ala Val Leu Ala Ile Thr Gly Gly Pro Gly Ile Val Ala Met
    210                 215                 220

Gly Met Lys Ser Gly Lys Lys Val Ile Gly Ala Gly Ala Gly Asn Pro
225                 230                 235                 240

Pro Cys Ile Val Asp Glu Thr Ala Asp Leu Val Lys Ala Ala Glu Asp
                245                 250                 255

Ile Ile Ser Gly Ala Ala Phe Asp Tyr Asn Leu Pro Cys Ile Ala Glu
            260                 265                 270

```
Lys Ser Leu Ile Val Ala Ser Val Ala Asp Arg Leu Ile Gln Gln
            275                 280                 285

Met Gln Asp Phe Asp Ala Leu Leu Ser Arg Gln Glu Ala Asp Thr
    290                 295                 300

Leu Arg Ala Val Cys Leu Pro Asp Gly Ala Ala Asn Lys Lys Leu Val
305                 310                 315                 320

Gly Lys Ser Pro Ala Ala Leu Leu Ala Ala Gly Leu Ala Val Pro
                325                 330                 335

Pro Arg Pro Pro Arg Leu Leu Ile Ala Glu Val Glu Ala Asn Asp Pro
                340                 345                 350

Trp Val Thr Cys Glu Gln Leu Met Pro Val Leu Pro Ile Val Arg Val
                355                 360                 365

Ala Asp Phe Asp Ser Ala Leu Ala Leu Ala Leu Arg Val Glu Glu Gly
    370                 375                 380

Leu His His Thr Ala Ile Met His Ser Gln Asn Val Ser Arg Leu Asn
385                 390                 395                 400

Leu Ala Ala Arg Thr Leu Gln Thr Ser Ile Phe Val Lys Asn Gly Pro
                405                 410                 415

Ser Tyr Ala Gly Ile Gly Val Gly Gly Glu Gly Phe Thr Thr Phe Thr
                420                 425                 430

Ile Ala Thr Pro Thr Gly Glu Gly Thr Thr Ser Ala Arg Thr Phe Ala
                435                 440                 445

Arg Leu Arg Arg Cys Val Leu Thr Asn Gly Phe Ser Ile Arg
                450                 455                 460

<210> SEQ ID NO 35
<211> LENGTH: 477
<212> TYPE: PRT
<213> ORGANISM: Lactobacillus brevis

<400> SEQUENCE: 35

Met Asn Thr Glu Asn Ile Glu Gln Ala Ile Arg Lys Ile Leu Ser Glu
1               5                   10                  15

Glu Leu Ser Asn Pro Gln Ser Ser Thr Ala Thr Asn Thr Thr Val Pro
                20                  25                  30

Gly Lys Asn Gly Ile Phe Lys Thr Val Asn Glu Ala Ile Ala Ala Thr
                35                  40                  45

Lys Ala Ala Gln Glu Asn Tyr Ala Asp Gln Pro Ile Ser Val Arg Asn
        50                  55                  60

Lys Val Ile Asp Ala Ile Arg Glu Gly Phe Arg Pro Tyr Ile Glu Asp
65              70                  75                  80

Met Ala Lys Arg Ile His Asp Glu Thr Gly Met Gly Thr Val Ser Ala
                85                  90                  95

Lys Ile Ala Lys Leu Asn Asn Ala Leu Tyr Asn Thr Pro Gly Pro Glu
                100                 105                 110

Ile Leu Gln Pro Glu Ala Glu Thr Gly Asp Gly Gly Leu Val Met Tyr
            115                 120                 125

Glu Tyr Ala Pro Phe Gly Val Ile Gly Ala Val Gly Pro Ser Thr Asn
    130                 135                 140

Pro Ser Glu Thr Val Ile Ala Asn Ala Ile Met Met Leu Ala Gly Gly
145                 150                 155                 160

Asn Thr Leu Phe Phe Gly Ala His Pro Gly Ala Lys Asn Ile Thr Arg
                165                 170                 175

Trp Thr Ile Glu Lys Leu Asn Glu Leu Val Ala Asp Ala Thr Gly Leu
```

180                 185                 190
His Asn Leu Val Val Ser Leu Glu Thr Pro Ser Ile Glu Ser Val Gln
            195                 200                 205

Glu Val Met Gln His Pro Asp Val Ala Met Leu Ser Ile Thr Gly Gly
            210                 215                 220

Pro Ala Val Val His Gln Ala Leu Ile Ser Gly Lys Lys Ala Val Gly
225                 230                 235                 240

Ala Gly Ala Gly Asn Pro Pro Ala Met Val Asp Ala Thr Ala Asn Ile
            245                 250                 255

Ala Leu Ala Ala His Asn Ile Val Asp Ser Ala Ala Phe Asp Asn Asn
            260                 265                 270

Ile Leu Cys Thr Ala Glu Lys Glu Val Val Glu Ala Ala Val Lys
            275                 280                 285

Asp Glu Leu Ile Met Arg Met Gln Gln Glu Gly Ala Phe Leu Val Thr
            290                 295                 300

Asp Ser Ala Asp Ile Glu Lys Leu Ala Gln Met Thr Ile Gly Pro Lys
305                 310                 315                 320

Gly Ala Pro Asp Arg Lys Phe Val Gly Lys Asp Ala Thr Tyr Ile Leu
                325                 330                 335

Asp Gln Ala Gly Ile Ser Tyr Thr Gly Thr Pro Thr Leu Ile Ile Leu
            340                 345                 350

Glu Ala Ala Lys Asp His Pro Leu Val Thr Thr Glu Met Leu Met Pro
            355                 360                 365

Ile Leu Pro Val Val Cys Cys Pro Asp Phe Asp Ser Val Leu Ala Thr
370                 375                 380

Ala Thr Glu Val Glu Gly Gly Leu His His Thr Ala Ser Ile His Ser
385                 390                 395                 400

Glu Asn Leu Pro His Ile Asn Lys Ala Ala His Arg Leu Asn Thr Ser
                405                 410                 415

Ile Phe Val Val Asn Gly Pro Thr Tyr Cys Gly Thr Gly Val Ala Thr
                420                 425                 430

Asn Gly Ala His Ser Gly Ala Ser Ala Leu Thr Ile Ala Thr Pro Thr
            435                 440                 445

Gly Glu Gly Thr Ala Thr Ser Lys Thr Tyr Thr Arg Arg Arg Leu
            450                 455                 460

Asn Ser Pro Glu Gly Phe Ser Leu Arg Thr Trp Glu Ala
465                 470                 475

<210> SEQ ID NO 36
<211> LENGTH: 469
<212> TYPE: PRT
<213> ORGANISM: Listeria monocytogenes

<400> SEQUENCE: 36

Met Glu Ser Leu Glu Leu Glu Lys Leu Val Lys Val Leu Leu Glu
1               5                   10                  15

Lys Leu Ala Glu Gln Lys Gly Ile Pro Val Lys Thr Met Thr Lys Gly
            20                  25                  30

Ala Lys Ser Gly Val Phe Asp Thr Val Asp Glu Ala Val Gln Ala Ala
            35                  40                  45

Val Ile Ala Gln Asn Ser Tyr Lys Glu Lys Ser Leu Glu Glu Arg Arg
            50                  55                  60

Asn Val Val Lys Ala Ile Arg Glu Ala Leu Tyr Pro Glu Ile Glu Ser
65                  70                  75                  80

-continued

```
Ile Ala Ala Arg Ala Val Ala Glu Thr Gly Met Gly Asn Val Ala Asp
                85                  90                  95
Lys Ile Leu Lys Asn Thr Leu Ala Ile Glu Lys Thr Pro Gly Val Glu
            100                 105                 110
Asp Leu Tyr Thr Glu Val Ala Thr Gly Asp Asn Gly Met Thr Leu Tyr
        115                 120                 125
Glu Leu Ser Pro Tyr Gly Val Ile Gly Ala Val Ala Pro Ser Thr Asn
    130                 135                 140
Pro Thr Glu Thr Leu Ile Cys Asn Thr Ile Gly Met Leu Ala Ala Gly
145                 150                 155                 160
Asn Ala Val Phe Tyr Ser Pro His Pro Gly Ala Lys Asn Ile Ser Leu
                165                 170                 175
Trp Leu Ile Glu Lys Leu Asn Thr Ile Val Arg Glu Ser Cys Gly Val
            180                 185                 190
Asp Asn Leu Val Val Thr Val Glu Lys Pro Ser Ile Gln Ala Ala Gln
        195                 200                 205
Glu Met Met Asn His Pro Lys Val Pro Leu Leu Val Ile Thr Gly Gly
    210                 215                 220
Pro Gly Val Val Leu Gln Ala Met Gln Ser Gly Lys Lys Val Ile Gly
225                 230                 235                 240
Ala Gly Ala Gly Asn Pro Pro Ser Ile Val Asp Glu Thr Ala Asn Ile
                245                 250                 255
Glu Lys Ala Ala Ala Asp Ile Val Asp Gly Ala Ser Phe Asp His Asn
            260                 265                 270
Ile Leu Cys Ile Ala Glu Lys Ser Val Val Ala Val Asp Ser Ile Ala
        275                 280                 285
Asp Phe Leu Met Phe Gln Met Glu Lys Asn Gly Ala Leu His Val Thr
    290                 295                 300
Asn Pro Ser Asp Ile Gln Lys Leu Glu Lys Val Ala Val Thr Asp Lys
305                 310                 315                 320
Gly Val Thr Asn Lys Lys Leu Val Gly Lys Ser Ala Ser Glu Ile Leu
                325                 330                 335
Lys Glu Ala Gly Ile Ala Cys Asp Phe Ser Pro Arg Leu Ile Ile Val
            340                 345                 350
Glu Thr Glu Lys Thr His Pro Phe Ala Thr Val Glu Leu Leu Met Pro
        355                 360                 365
Ile Val Pro Val Val Arg Val Pro Asn Phe Glu Glu Ala Leu Glu Val
    370                 375                 380
Ala Ile Glu Leu Glu Gln Gly Leu His His Thr Ala Thr Met His Ser
385                 390                 395                 400
Gln Asn Ile Ser Arg Leu Asn Lys Ala Ala Arg Asp Met Gln Thr Ser
                405                 410                 415
Ile Phe Val Lys Asn Gly Pro Ser Phe Ala Gly Leu Gly Phe Arg Gly
            420                 425                 430
Glu Gly Ser Thr Thr Phe Thr Ile Ala Thr Pro Thr Gly Glu Gly Thr
        435                 440                 445
Thr Thr Ala Arg His Phe Ala Arg Arg Arg Cys Val Leu Thr Asp
    450                 455                 460
Gly Phe Ser Ile Arg
465
```

<210> SEQ ID NO 37
<211> LENGTH: 451
<212> TYPE: PRT

<213> ORGANISM: Porphyromonas gingivalis

<400> SEQUENCE: 37

```
Met Glu Ile Lys Glu Met Val Ser Leu Ala Arg Lys Ala Gln Lys Glu
1               5                   10                  15

Tyr Gln Ala Thr His Asn Gln Glu Ala Val Asp Asn Ile Cys Arg Ala
            20                  25                  30

Ala Ala Lys Val Ile Tyr Glu Asn Ala Ala Ile Leu Ala Arg Glu Ala
        35                  40                  45

Val Asp Glu Thr Gly Met Gly Val Tyr Glu His Lys Val Ala Lys Asn
50                  55                  60

Gln Gly Lys Ser Lys Gly Val Trp Tyr Asn Leu His Asn Lys Lys Ser
65                  70                  75                  80

Val Gly Ile Leu Asn Ile Asp Glu Arg Thr Gly Met Ile Glu Ile Ala
                85                  90                  95

Lys Pro Ile Gly Val Val Gly Ala Val Thr Pro Thr Thr Asn Pro Ile
            100                 105                 110

Val Thr Pro Met Ser Asn Ile Ile Phe Ala Leu Lys Thr Cys Asn Ala
        115                 120                 125

Ile Ile Ile Ala Pro His Pro Arg Ser Lys Lys Cys Ser Ala His Ala
130                 135                 140

Val Arg Leu Ile Lys Glu Ala Ile Ala Pro Phe Asn Val Pro Glu Gly
145                 150                 155                 160

Met Val Gln Ile Ile Glu Glu Pro Ser Ile Glu Lys Thr Gln Glu Leu
                165                 170                 175

Met Gly Ala Val Asp Val Val Ala Thr Gly Gly Met Gly Met Val
            180                 185                 190

Lys Ser Ala Tyr Ser Ser Gly Lys Pro Ser Phe Gly Val Gly Ala Gly
        195                 200                 205

Asn Val Gln Val Ile Val Asp Ser Asn Ile Asp Phe Glu Ala Ala Ala
210                 215                 220

Glu Lys Ile Ile Thr Gly Arg Ala Phe Asp Asn Gly Ile Ile Cys Ser
225                 230                 235                 240

Gly Glu Gln Ser Ile Ile Tyr Asn Glu Ala Asp Lys Glu Ala Val Phe
                245                 250                 255

Thr Ala Phe Arg Asn His Gly Ala Tyr Phe Cys Asp Glu Ala Glu Gly
            260                 265                 270

Asp Arg Ala Arg Ala Ala Ile Phe Glu Asn Gly Ala Ile Ala Lys Asp
        275                 280                 285

Val Val Gly Gln Ser Val Ala Phe Ile Ala Lys Lys Ala Asn Ile Asn
290                 295                 300

Ile Pro Glu Gly Thr Arg Ile Leu Val Val Glu Ala Arg Gly Val Gly
305                 310                 315                 320

Ala Glu Asp Val Ile Cys Lys Glu Lys Met Cys Pro Val Met Cys Ala
                325                 330                 335

Leu Ser Tyr Lys His Phe Glu Glu Gly Val Glu Ile Ala Arg Thr Asn
            340                 345                 350

Leu Ala Asn Glu Gly Asn Gly His Thr Cys Ala Ile His Ser Asn Asn
        355                 360                 365

Gln Ala His Ile Ile Leu Ala Gly Ser Glu Leu Thr Val Ser Arg Ile
370                 375                 380

Val Val Asn Ala Pro Ser Ala Thr Thr Ala Gly Gly His Ile Gln Asn
385                 390                 395                 400
```

-continued

```
Gly Leu Ala Val Thr Asn Thr Leu Gly Cys Gly Ser Trp Gly Asn Asn
            405                 410                 415

Ser Ile Ser Glu Asn Phe Thr Tyr Lys His Leu Leu Asn Ile Ser Arg
        420                 425                 430

Ile Ala Pro Leu Asn Ser Ser Ile His Ile Pro Asp Asp Lys Glu Ile
    435                 440                 445

Trp Glu Leu
    450

<210> SEQ ID NO 38
<211> LENGTH: 90
<212> TYPE: DNA
<213> ORGANISM: Artificial Sequence
<220> FEATURE:
<223> OTHER INFORMATION: MmP1_high expression level (Ih)

<400> SEQUENCE: 38
atatttgtgg cattatagaa ttgtgagcgc tcacaattag ctgtcaccgg atgtgctttc    60
cggtctgatg agtccgtgag gacgaaacag                                    90

<210> SEQ ID NO 39
<211> LENGTH: 90
<212> TYPE: DNA
<213> ORGANISM: Artificial Sequence
<220> FEATURE:
<223> OTHER INFORMATION: MmP1_medium expression level (Im)

<400> SEQUENCE: 39
atatttgtgg cattagggaa ttgtgagcgc tcacaattag ctgtcaccgg atgtgctttc    60
cggtctgatg agtccgtgag gacgaaacag                                    90

<210> SEQ ID NO 40
<211> LENGTH: 90
<212> TYPE: DNA
<213> ORGANISM: Artificial Sequence
<220> FEATURE:
<223> OTHER INFORMATION: MmP1_low expression level (Il)

<400> SEQUENCE: 40
atatttgtgg catacttgaa ttgtgagcgc tcacaattag ctgtcaccgg atgtgctttc    60
cggtctgatg agtccgtgag gacgaaacag                                    90

<210> SEQ ID NO 41
<211> LENGTH: 44
<212> TYPE: DNA
<213> ORGANISM: Artificial Sequence
<220> FEATURE:
<223> OTHER INFORMATION: P40-1_low expression level (Cl)

<400> SEQUENCE: 41
tttttctatt gcgtccgtgt attcttttgt atagagtttg agac                    44

<210> SEQ ID NO 42
<211> LENGTH: 44
<212> TYPE: DNA
<213> ORGANISM: Artificial Sequence
<220> FEATURE:
<223> OTHER INFORMATION: P40-1_medium expression level (Cm)

<400> SEQUENCE: 42
tttttctatt gcgttcactg gaatcccagt atagagtttg agac                    44
```

<210> SEQ ID NO 43
<211> LENGTH: 44
<212> TYPE: DNA
<213> ORGANISM: Artificial Sequence
<220> FEATURE:
<223> OTHER INFORMATION: P40-1 high expression level (Ch)

<400> SEQUENCE: 43
tttttctatt gcgtgaaaac aaggatttgt atagagtttg agac        44

<210> SEQ ID NO 44
<211> LENGTH: 44
<212> TYPE: DNA
<213> ORGANISM: Artificial Sequence
<220> FEATURE:
<223> OTHER INFORMATION: >P40-1 very high expression level (Cvh)

<400> SEQUENCE: 44
tttttctatt gcgtcaaaac atttatttgt atagagtttg agac        44

<210> SEQ ID NO 45
<211> LENGTH: 26
<212> TYPE: PRT
<213> ORGANISM: Artificial Sequence
<220> FEATURE:
<223> OTHER INFORMATION: TEV protease cleavable 78 bp N-His6-tag

<400> SEQUENCE: 45

Met Lys His His His His His His Pro Met Ser Asp Tyr Asp Ile Pro
1               5                   10                  15

Thr Thr Glu Asn Leu Tyr Phe Gln Gly Ala
            20                  25

<210> SEQ ID NO 46
<211> LENGTH: 185
<212> TYPE: DNA
<213> ORGANISM: Artificial Sequence
<220> FEATURE:
<223> OTHER INFORMATION: promoter region of the insert used to construct
    pHal3-FAPG462V

<400> SEQUENCE: 46
attaaagcgg ataacaattt cacacaggag gcgcctattc tgaaatgagc tgatatttgt    60
ggcattatag aattgtgagc gctcacaatt agctgtcacc ggatgtgctt tccggtctga   120
tgagtccgtg aggacgaaac agtttcagaa ttcaaaagat cttttaagaa ggagatatac   180
ccatg                                                              185

<210> SEQ ID NO 47
<211> LENGTH: 224
<212> TYPE: DNA
<213> ORGANISM: Artificial Sequence
<220> FEATURE:
<223> OTHER INFORMATION: OXB1 promoter1

<400> SEQUENCE: 47
aagctgttgt gaccgcttgc tctagccagc tatcgagttg tgaaccgatc catctagcaa    60
ttggtctcga tctagcgata ggcttcgatc tagctatgta gaaacgccgt gtgctcgatc   120
gcctgacgct ttttatcgca actctctact gttgcttcaa cagaacatat tgactatccg   180
gtattacccg gccatggtat atctccttct taaagttaaa caaa                   224

<210> SEQ ID NO 48
<211> LENGTH: 33

<212> TYPE: DNA
<213> ORGANISM: Artificial Sequence
<220> FEATURE:
<223> OTHER INFORMATION: CvFAPG462V

<400> SEQUENCE: 48
gcactggatc cggatgttgt tagcacctat gtg                                33

<210> SEQ ID NO 49
<211> LENGTH: 33
<212> TYPE: DNA
<213> ORGANISM: Artificial Sequence
<220> FEATURE:
<223> OTHER INFORMATION: CvFAPG462V

<400> SEQUENCE: 49
cacataggtg ctaacaacat ccggatccag tgc                                33

<210> SEQ ID NO 50
<211> LENGTH: 25
<212> TYPE: DNA
<213> ORGANISM: Artificial Sequence
<220> FEATURE:
<223> OTHER INFORMATION: CvFAPG462I

<400> SEQUENCE: 50
gatccggata ttgttagcac ctatg                                         25

<210> SEQ ID NO 51
<211> LENGTH: 23
<212> TYPE: DNA
<213> ORGANISM: Artificial Sequence
<220> FEATURE:
<223> OTHER INFORMATION: CvFAPG462I

<400> SEQUENCE: 51
cagtgccata ccaggaacaa aac                                           23

<210> SEQ ID NO 52
<211> LENGTH: 21
<212> TYPE: DNA
<213> ORGANISM: Artificial Sequence
<220> FEATURE:
<223> OTHER INFORMATION: CvFAPG462F

<400> SEQUENCE: 52
gatccggatt tgttagcac c                                              21

<210> SEQ ID NO 53
<211> LENGTH: 23
<212> TYPE: DNA
<213> ORGANISM: Artificial Sequence
<220> FEATURE:
<223> OTHER INFORMATION: CvFAPG462F

<400> SEQUENCE: 53
cagtgccata ccaggaacaa aac                                           23

<210> SEQ ID NO 54
<211> LENGTH: 25
<212> TYPE: DNA
<213> ORGANISM: Artificial Sequence
<220> FEATURE:
<223> OTHER INFORMATION: CvFAPG462A

<400> SEQUENCE: 54

```
gcggttagca cctatgtgcg ttttg                                              25

<210> SEQ ID NO 55
<211> LENGTH: 20
<212> TYPE: DNA
<213> ORGANISM: Artificial Sequence
<220> FEATURE:
<223> OTHER INFORMATION: CvFAPG462A

<400> SEQUENCE: 55
atccggatcc agtgccatac                                                    20

<210> SEQ ID NO 56
<211> LENGTH: 24
<212> TYPE: DNA
<213> ORGANISM: Artificial Sequence
<220> FEATURE:
<223> OTHER INFORMATION: CvFAPG462H

<400> SEQUENCE: 56
cagtgccata ccaggaacaa aacg                                               24

<210> SEQ ID NO 57
<211> LENGTH: 23
<212> TYPE: DNA
<213> ORGANISM: Artificial Sequence
<220> FEATURE:
<223> OTHER INFORMATION: CvFAPG462H

<400> SEQUENCE: 57
cagtgccata ccaggaacaa aac                                                23

<210> SEQ ID NO 58
<211> LENGTH: 25
<212> TYPE: DNA
<213> ORGANISM: Artificial Sequence
<220> FEATURE:
<223> OTHER INFORMATION: CvFAPG462L

<400> SEQUENCE: 58
gatccggatc acgttagcac ctatg                                              25

<210> SEQ ID NO 59
<211> LENGTH: 25
<212> TYPE: DNA
<213> ORGANISM: Artificial Sequence
<220> FEATURE:
<223> OTHER INFORMATION: CvFAPG462L

<400> SEQUENCE: 59
gatccggatc tggttagcac ctatg                                              25

<210> SEQ ID NO 60
<211> LENGTH: 25
<212> TYPE: DNA
<213> ORGANISM: Artificial Sequence
<220> FEATURE:
<223> OTHER INFORMATION: CvFAPG462C

<400> SEQUENCE: 60
gatccggatt gtgttagcac ctatg                                              25

<210> SEQ ID NO 61
<211> LENGTH: 25
<212> TYPE: DNA
<213> ORGANISM: Artificial Sequence
```

```
<220> FEATURE:
<223> OTHER INFORMATION: CvFAPG462C

<400> SEQUENCE: 61
gatccggatt gggttagcac ctatg                                              25

<210> SEQ ID NO 62
<211> LENGTH: 25
<212> TYPE: DNA
<213> ORGANISM: Artificial Sequence
<220> FEATURE:
<223> OTHER INFORMATION: CvFAPG462W

<400> SEQUENCE: 62
gatccggatt atgttagcac ctatg                                              25

<210> SEQ ID NO 63
<211> LENGTH: 25
<212> TYPE: DNA
<213> ORGANISM: Artificial Sequence
<220> FEATURE:
<223> OTHER INFORMATION: CvFAPG462W

<400> SEQUENCE: 63
gatccggata acgttagcac ctatg                                              25

<210> SEQ ID NO 64
<211> LENGTH: 25
<212> TYPE: DNA
<213> ORGANISM: Artificial Sequence
<220> FEATURE:
<223> OTHER INFORMATION: CvFAPG462Y

<400> SEQUENCE: 64
gatccggatt atgttagcac ctatg                                              25

<210> SEQ ID NO 65
<211> LENGTH: 23
<212> TYPE: DNA
<213> ORGANISM: Artificial Sequence
<220> FEATURE:
<223> OTHER INFORMATION: CvFAPG462Y

<400> SEQUENCE: 65
cagtgccata ccaggaacaa aac                                                23

<210> SEQ ID NO 66
<211> LENGTH: 25
<212> TYPE: DNA
<213> ORGANISM: Artificial Sequence
<220> FEATURE:
<223> OTHER INFORMATION: CvFAPG462N

<400> SEQUENCE: 66
gatccggata acgttagcac ctatg                                              25

<210> SEQ ID NO 67
<211> LENGTH: 24
<212> TYPE: DNA
<213> ORGANISM: Artificial Sequence
<220> FEATURE:
<223> OTHER INFORMATION: CvFAPG462N

<400> SEQUENCE: 67
cagtgccata ccaggaacaa aacg                                               24
```

```
<210> SEQ ID NO 68
<211> LENGTH: 28
<212> TYPE: DNA
<213> ORGANISM: Artificial Sequence
<220> FEATURE:
<223> OTHER INFORMATION: CvFAPG455F

<400> SEQUENCE: 68
gttttgttcc ttttatggca ctggatcc                                     28

<210> SEQ ID NO 69
<211> LENGTH: 19
<212> TYPE: DNA
<213> ORGANISM: Artificial Sequence
<220> FEATURE:
<223> OTHER INFORMATION: CvFAPG455F

<400> SEQUENCE: 69
gaacttgcag atccggcag                                               19

<210> SEQ ID NO 70
<211> LENGTH: 28
<212> TYPE: DNA
<213> ORGANISM: Artificial Sequence
<220> FEATURE:
<223> OTHER INFORMATION: CvFAPG455I

<400> SEQUENCE: 70
gttttgttcc tattatggca ctggatcc                                     28

<210> SEQ ID NO 71
<211> LENGTH: 19
<212> TYPE: DNA
<213> ORGANISM: Artificial Sequence
<220> FEATURE:
<223> OTHER INFORMATION: CvFAPG455I

<400> SEQUENCE: 71
gaacttgcag atccggcag                                               19

<210> SEQ ID NO 72
<211> LENGTH: 28
<212> TYPE: DNA
<213> ORGANISM: Artificial Sequence
<220> FEATURE:
<223> OTHER INFORMATION: CvFAPG455V

<400> SEQUENCE: 72
gttttgttcc tgttatggca ctggatcc                                     28

<210> SEQ ID NO 73
<211> LENGTH: 19
<212> TYPE: DNA
<213> ORGANISM: Artificial Sequence
<220> FEATURE:
<223> OTHER INFORMATION: CvFAPG455V

<400> SEQUENCE: 73
gaacttgcag atccggcag                                               19

<210> SEQ ID NO 74
<211> LENGTH: 27
<212> TYPE: DNA
<213> ORGANISM: Artificial Sequence
<220> FEATURE:
<223> OTHER INFORMATION: CvFAPG455W
```

<400> SEQUENCE: 74
gttttgttcc ttggatggca ctggatc     27

<210> SEQ ID NO 75
<211> LENGTH: 19
<212> TYPE: DNA
<213> ORGANISM: Artificial Sequence
<220> FEATURE:
<223> OTHER INFORMATION: CvFAPG455W

<400> SEQUENCE: 75
gaacttgcag atccggcag     19

<210> SEQ ID NO 76
<211> LENGTH: 27
<212> TYPE: DNA
<213> ORGANISM: Artificial Sequence
<220> FEATURE:
<223> OTHER INFORMATION: CvFAPG455L

<400> SEQUENCE: 76
ttttgttcct ctgatggcac tggatcc     27

<210> SEQ ID NO 77
<211> LENGTH: 18
<212> TYPE: DNA
<213> ORGANISM: Artificial Sequence
<220> FEATURE:
<223> OTHER INFORMATION: CvFAPG455L

<400> SEQUENCE: 77
cgaacttgca gatccggc     18

<210> SEQ ID NO 78
<211> LENGTH: 24
<212> TYPE: DNA
<213> ORGANISM: Artificial Sequence
<220> FEATURE:
<223> OTHER INFORMATION: CvFAPY466W

<400> SEQUENCE: 78
gtgttagcac ctgggtgcgt tttg     24

<210> SEQ ID NO 79
<211> LENGTH: 21
<212> TYPE: DNA
<213> ORGANISM: Artificial Sequence
<220> FEATURE:
<223> OTHER INFORMATION: CvFAPY466W

<400> SEQUENCE: 79
catccggatc cagtgccata c     21

<210> SEQ ID NO 80
<211> LENGTH: 28
<212> TYPE: DNA
<213> ORGANISM: Artificial Sequence
<220> FEATURE:
<223> OTHER INFORMATION: CvFAPV453L

<400> SEQUENCE: 80
caagttcgtt ttctgcctgg tatggcac     28

<210> SEQ ID NO 81

```
<211> LENGTH: 18
<212> TYPE: DNA
<213> ORGANISM: Artificial Sequence
<220> FEATURE:
<223> OTHER INFORMATION: CvFAPV453L

<400> SEQUENCE: 81
cagatccggc agtgcctg                                                 18

<210> SEQ ID NO 82
<211> LENGTH: 28
<212> TYPE: DNA
<213> ORGANISM: Artificial Sequence
<220> FEATURE:
<223> OTHER INFORMATION: CvFAPV453W

<400> SEQUENCE: 82
caagttcgtt tttggcctgg tatggcac                                      28

<210> SEQ ID NO 83
<211> LENGTH: 18
<212> TYPE: DNA
<213> ORGANISM: Artificial Sequence
<220> FEATURE:
<223> OTHER INFORMATION: CvFAPV453W

<400> SEQUENCE: 83
cagatccggc agtgcctg                                                 18

<210> SEQ ID NO 84
<211> LENGTH: 28
<212> TYPE: DNA
<213> ORGANISM: Artificial Sequence
<220> FEATURE:
<223> OTHER INFORMATION: CvFAPV453F

<400> SEQUENCE: 84
caagttcgtt tttttcctgg tatggcac                                      28

<210> SEQ ID NO 85
<211> LENGTH: 18
<212> TYPE: DNA
<213> ORGANISM: Artificial Sequence
<220> FEATURE:
<223> OTHER INFORMATION: CvFAPV453F

<400> SEQUENCE: 85
cagatccggc agtgcctg                                                 18

<210> SEQ ID NO 86
<211> LENGTH: 28
<212> TYPE: DNA
<213> ORGANISM: Artificial Sequence
<220> FEATURE:
<223> OTHER INFORMATION: CvFAPV453I

<400> SEQUENCE: 86
caagttcgtt ttattcctgg tatggcac                                      28

<210> SEQ ID NO 87
<211> LENGTH: 18
<212> TYPE: DNA
<213> ORGANISM: Artificial Sequence
<220> FEATURE:
<223> OTHER INFORMATION: CvFAPV453I

<400> SEQUENCE: 87
```

-continued

```
cagatccggc agtgcctg                                                18

<210> SEQ ID NO 88
<211> LENGTH: 44
<212> TYPE: DNA
<213> ORGANISM: Artificial Sequence
<220> FEATURE:
<223> OTHER INFORMATION: CvFAPT484I

<400> SEQUENCE: 88
gcctgaaatg gccgagcggt attdhmatgc agctgattgc atgt                   44

<210> SEQ ID NO 89
<211> LENGTH: 25
<212> TYPE: DNA
<213> ORGANISM: Artificial Sequence
<220> FEATURE:
<223> OTHER INFORMATION: CvFAPT484I

<400> SEQUENCE: 89
cctggctctg aaatttggca aaacg                                        25

<210> SEQ ID NO 90
<211> LENGTH: 44
<212> TYPE: DNA
<213> ORGANISM: Artificial Sequence
<220> FEATURE:
<223> OTHER INFORMATION: CvFAPT484L

<400> SEQUENCE: 90
gcctgaaatg gccgagcggt attdhmatgc agctgattgc atgt                   44

<210> SEQ ID NO 91
<211> LENGTH: 25
<212> TYPE: DNA
<213> ORGANISM: Artificial Sequence
<220> FEATURE:
<223> OTHER INFORMATION: CvFAPT484L

<400> SEQUENCE: 91
cctggctctg aaatttggca aaacg                                        25

<210> SEQ ID NO 92
<211> LENGTH: 44
<212> TYPE: DNA
<213> ORGANISM: Artificial Sequence
<220> FEATURE:
<223> OTHER INFORMATION: CvFAPT484E

<400> SEQUENCE: 92
gcctgaaatg gccgagcggt attdhmatgc agctgattgc atgt                   44

<210> SEQ ID NO 93
<211> LENGTH: 25
<212> TYPE: DNA
<213> ORGANISM: Artificial Sequence
<220> FEATURE:
<223> OTHER INFORMATION: CvFAPT484E

<400> SEQUENCE: 93
cctggctctg aaatttggca aaacg                                        25

<210> SEQ ID NO 94
<211> LENGTH: 44
<212> TYPE: DNA
```

```
<213> ORGANISM: Artificial Sequence
<220> FEATURE:
<223> OTHER INFORMATION: CvFAPT484A

<400> SEQUENCE: 94
gcctgaaatg gccgagcggt attdhmatgc agctgattgc atgt         44

<210> SEQ ID NO 95
<211> LENGTH: 25
<212> TYPE: DNA
<213> ORGANISM: Artificial Sequence
<220> FEATURE:
<223> OTHER INFORMATION: CvFAPT484A

<400> SEQUENCE: 95
cctggctctg aaatttggca aaacg                              25

<210> SEQ ID NO 96
<211> LENGTH: 45
<212> TYPE: DNA
<213> ORGANISM: Artificial Sequence
<220> FEATURE:
<223> OTHER INFORMATION: CvFAPA457L
<220> FEATURE:
<221> NAME/KEY: misc_feature
<222> LOCATION: (22)..(22)
<223> OTHER INFORMATION: n is a, c, g, or t

<400> SEQUENCE: 96
gttcgttttg ttcctggtat gnttctggat ccggatggtg ttagc        45

<210> SEQ ID NO 97
<211> LENGTH: 45
<212> TYPE: DNA
<213> ORGANISM: Artificial Sequence
<220> FEATURE:
<223> OTHER INFORMATION: CvFAPA457L
<220> FEATURE:
<221> NAME/KEY: misc_feature
<222> LOCATION: (24)..(24)
<223> OTHER INFORMATION: n is a, c, g, or t

<400> SEQUENCE: 97
gctaacacca tccggatcca gaancatacc aggaacaaaa cgaac        45

<210> SEQ ID NO 98
<211> LENGTH: 45
<212> TYPE: DNA
<213> ORGANISM: Artificial Sequence
<220> FEATURE:
<223> OTHER INFORMATION: CvFAPA457V
<220> FEATURE:
<221> NAME/KEY: misc_feature
<222> LOCATION: (22)..(22)
<223> OTHER INFORMATION: n is a, c, g, or t

<400> SEQUENCE: 98
gttcgttttg ttcctggtat gnttctggat ccggatggtg ttagc        45

<210> SEQ ID NO 99
<211> LENGTH: 45
<212> TYPE: DNA
<213> ORGANISM: Artificial Sequence
<220> FEATURE:
<223> OTHER INFORMATION: CvFAPA457V
<220> FEATURE:
<221> NAME/KEY: misc_feature
<222> LOCATION: (24)..(24)
<223> OTHER INFORMATION: n is a, c, g, or t
```

<400> SEQUENCE: 99
gctaacacca tccggatcca gaancatacc aggaacaaaa cgaac            45

<210> SEQ ID NO 100
<211> LENGTH: 45
<212> TYPE: DNA
<213> ORGANISM: Artificial Sequence
<220> FEATURE:
<223> OTHER INFORMATION: CvFAPA457I
<220> FEATURE:
<221> NAME/KEY: misc_feature
<222> LOCATION: (22)..(22)
<223> OTHER INFORMATION: n is a, c, g, or t

<400> SEQUENCE: 100
gttcgttttg ttcctggtat gnttctggat ccggatggtg ttagc            45

<210> SEQ ID NO 101
<211> LENGTH: 45
<212> TYPE: DNA
<213> ORGANISM: Artificial Sequence
<220> FEATURE:
<223> OTHER INFORMATION: CvFAPA457I
<220> FEATURE:
<221> NAME/KEY: misc_feature
<222> LOCATION: (24)..(24)
<223> OTHER INFORMATION: n is a, c, g, or t

<400> SEQUENCE: 101
gctaacacca tccggatcca gaancatacc aggaacaaaa cgaac            45

<210> SEQ ID NO 102
<211> LENGTH: 45
<212> TYPE: DNA
<213> ORGANISM: Artificial Sequence
<220> FEATURE:
<223> OTHER INFORMATION: CvFAPA457F
<220> FEATURE:
<221> NAME/KEY: misc_feature
<222> LOCATION: (22)..(22)
<223> OTHER INFORMATION: n is a, c, g, or t

<400> SEQUENCE: 102
gttcgttttg ttcctggtat gnttctggat ccggatggtg ttagc            45

<210> SEQ ID NO 103
<211> LENGTH: 45
<212> TYPE: DNA
<213> ORGANISM: Artificial Sequence
<220> FEATURE:
<223> OTHER INFORMATION: CvFAPA457F
<220> FEATURE:
<221> NAME/KEY: misc_feature
<222> LOCATION: (24)..(24)
<223> OTHER INFORMATION: n is a, c, g, or t

<400> SEQUENCE: 103
gctaacacca tccggatcca gaancatacc aggaacaaaa cgaac            45

<210> SEQ ID NO 104
<211> LENGTH: 21
<212> TYPE: DNA
<213> ORGANISM: Artificial Sequence
<220> FEATURE:
<223> OTHER INFORMATION: Assembly of FAPGV-OXB1-atoE construct in pET21b
      Vector Opening

<400> SEQUENCE: 104
cgacatcacc gatggggaag a                                                  21

<210> SEQ ID NO 105
<211> LENGTH: 35
<212> TYPE: DNA
<213> ORGANISM: Artificial Sequence
<220> FEATURE:
<223> OTHER INFORMATION: Assembly of FAPGV-OXB1-atoE construct in pET21b
      Vector Opening

<400> SEQUENCE: 105
ccatcggtga tgtcggtccg gcgtagagga tcgag                                   35

<210> SEQ ID NO 106
<211> LENGTH: 39
<212> TYPE: DNA
<213> ORGANISM: Artificial Sequence
<220> FEATURE:
<223> OTHER INFORMATION: Assembly of FAPGV-OXB1-atoE construct in pET21b
      Insert generation

<400> SEQUENCE: 106
cggttgctgg cgcctatatc taatgcgccg ctacagggc                               39

<210> SEQ ID NO 107
<211> LENGTH: 20
<212> TYPE: DNA
<213> ORGANISM: Artificial Sequence
<220> FEATURE:
<223> OTHER INFORMATION: Assembly of FAPGV-OXB1-atoE construct in pET21b
      Insert generation

<400> SEQUENCE: 107
gatataggcg ccagcaaccg                                                    20

<210> SEQ ID NO 108
<211> LENGTH: 21
<212> TYPE: DNA
<213> ORGANISM: Artificial Sequence
<220> FEATURE:
<223> OTHER INFORMATION: Assembly of pHal1-FAPWT vector opening

<400> SEQUENCE: 108
tgccaccgct gagcaataaa a                                                  21

<210> SEQ ID NO 109
<211> LENGTH: 29
<212> TYPE: DNA
<213> ORGANISM: Artificial Sequence
<220> FEATURE:
<223> OTHER INFORMATION: Assembly of pHal1-FAPWT vector opening

<400> SEQUENCE: 109
catctagtat ttctcctctt tctctagta                                          29

<210> SEQ ID NO 110
<211> LENGTH: 36
<212> TYPE: DNA
<213> ORGANISM: Artificial Sequence
<220> FEATURE:
<223> OTHER INFORMATION: Assembly of pHal1-FAPWT insert generation

<400> SEQUENCE: 110
gagaaatact agatggccag cgcagttgaa gatatt                                  36

<210> SEQ ID NO 111
<211> LENGTH: 35
<212> TYPE: DNA
<213> ORGANISM: Artificial Sequence
<220> FEATURE:
<223> OTHER INFORMATION: Assembly of pHal1-FAPWT insert generation

<400> SEQUENCE: 111
tgctcagcgg tggcattatg ctgcaacggt tgccg                                35

<210> SEQ ID NO 112
<211> LENGTH: 27
<212> TYPE: DNA
<213> ORGANISM: Artificial Sequence
<220> FEATURE:
<223> OTHER INFORMATION: Generation of FAPG462V in pET21b vector opening

<400> SEQUENCE: 112
ctgaaaggag gaactatatc cggattg                                        27

<210> SEQ ID NO 113
<211> LENGTH: 35
<212> TYPE: DNA
<213> ORGANISM: Artificial Sequence
<220> FEATURE:
<223> OTHER INFORMATION: Generation of FAPG462V in pET21b vector opening

<400> SEQUENCE: 113
agttcctcct ttcagctcta cgccggacgc atcgt                               35

<210> SEQ ID NO 114
<211> LENGTH: 12
<212> TYPE: DNA
<213> ORGANISM: Artificial Sequence
<220> FEATURE:
<223> OTHER INFORMATION: 1P-A adapter

<400> SEQUENCE: 114
tttattgaac ta                                                        12

<210> SEQ ID NO 115
<211> LENGTH: 37
<212> TYPE: DNA
<213> ORGANISM: Artificial Sequence
<220> FEATURE:
<223> OTHER INFORMATION: 1P-A linker

<400> SEQUENCE: 115
ggactagttc aataaatacc ctctgactgt ctcggag                             37

<210> SEQ ID NO 116
<211> LENGTH: 14
<212> TYPE: DNA
<213> ORGANISM: Artificial Sequence
<220> FEATURE:
<223> OTHER INFORMATION: LRBS1-4P-A adapter

<400> SEQUENCE: 116
atcacaagga ggta                                                      14

<210> SEQ ID NO 117
<211> LENGTH: 39
<212> TYPE: DNA
<213> ORGANISM: Artificial Sequence
<220> FEATURE:
<223> OTHER INFORMATION: LRBS1-4P-A linker

<400> SEQUENCE: 117
ggactacctc cttgtgattt acaactgata cttacctga                           39

<210> SEQ ID NO 118
<211> LENGTH: 14
<212> TYPE: DNA
<213> ORGANISM: Artificial Sequence
<220> FEATURE:
<223> OTHER INFORMATION: LRBS2-4P-A adapter

<400> SEQUENCE: 118
atcacaagga ggta                                                      14

<210> SEQ ID NO 119
<211> LENGTH: 39
<212> TYPE: DNA
<213> ORGANISM: Artificial Sequence
<220> FEATURE:
<223> OTHER INFORMATION: LRBS2-4P-A linker

<400> SEQUENCE: 119
ggactacctc cttgtgattt tctgctaccc ttatctcag                           39

<210> SEQ ID NO 120
<211> LENGTH: 12
<212> TYPE: DNA
<213> ORGANISM: Artificial Sequence
<220> FEATURE:
<223> OTHER INFORMATION: 1S-A adapter

<400> SEQUENCE: 120
tgtcgtaagt aa                                                        12

<210> SEQ ID NO 121
<211> LENGTH: 37
<212> TYPE: DNA
<213> ORGANISM: Artificial Sequence
<220> FEATURE:
<223> OTHER INFORMATION: 1S-A linker

<400> SEQUENCE: 121
ctcgttactt acgacactcc gagacagtca gagggta                             37

<210> SEQ ID NO 122
<211> LENGTH: 12
<212> TYPE: DNA
<213> ORGANISM: Artificial Sequence
<220> FEATURE:
<223> OTHER INFORMATION: LRBS1-4S-A adapter

<400> SEQUENCE: 122
gacggtgttc aa                                                        12

<210> SEQ ID NO 123
<211> LENGTH: 37
<212> TYPE: DNA
<213> ORGANISM: Artificial Sequence
<220> FEATURE:
<223> OTHER INFORMATION: LRBS1-4S-L linker

<400> SEQUENCE: 123
ctcgttgaac accgtctcag gtaagtatca gttgtaa                             37

<210> SEQ ID NO 124
<211> LENGTH: 12

```
<212> TYPE: DNA
<213> ORGANISM: Artificial Sequence
<220> FEATURE:
<223> OTHER INFORMATION: LRBS2-4S-A

<400> SEQUENCE: 124
ccaatagtaa ca                                                          12

<210> SEQ ID NO 125
<211> LENGTH: 37
<212> TYPE: DNA
<213> ORGANISM: Artificial Sequence
<220> FEATURE:
<223> OTHER INFORMATION: LRBS2-4S-L linker

<400> SEQUENCE: 125
ctcgtgttac tattggctga gataagggta gcagaaa                               37

<210> SEQ ID NO 126
<211> LENGTH: 33
<212> TYPE: DNA
<213> ORGANISM: Artificial Sequence
<220> FEATURE:
<223> OTHER INFORMATION: start codon

<400> SEQUENCE: 126
tttgtttaac tttaagaagg agatatacca tgg                                   33
```

HYDROCARBON PRODUCTION

This application claims priority from GB 1806483.2 filed 20 Apr. 2018, the contents and elements of which are herein incorporated by reference for all purposes.

SEQUENCE LISTINGS

The sequence listings contained in the electronic file titled "007735525-final_ST25.txt," with a creation date of 17 Feb. 2021, comprising 164 kB, hereby incorporated herein, are substantively identical to the sequence listings disclosed and described herein.

FIELD OF THE INVENTION

The present invention relates to enzymatic production of hydrocarbons and to enzymes, constructs and cells suitable for use in this process. In particular, the invention relates to materials and methods the enzymatic production of light alkanes, such as butane, propane and isobutane, from biomass feedstocks.

BACKGROUND

Intensive research into the development of economically viable microbial biofuels is a reflection of global concerns of reducing carbon emissions, dwindling fossil fuel supply and the necessity to develop alternative strategies that are renewable and sustainable [1,2]. Concerns over energy security and climate change have led to governmental policies restricting greenhouse gas emissions, increasing waste biomaterial recycling and a drive towards a more bio-based economy [3,4]. This has led to a wide range of recent studies into biofuel production, such as bio-alcohols, utilising a wide range of microorganism hosts [5].

Current transportation fossil fuels (e.g. unleaded petrol) are composed of more than 30 aliphatic and aromatic hydrocarbons, predominantly pentane, propane and nonane [6]. Combustion of fossil fuels is a major source of pollution, contributing to greenhouse gas emissions, acid rain and ultimately climate change. In contrast, propane is a highly efficient and clean-burning fuel with a low carbon footprint and significant reduction in carbon monoxide and hydrocarbon emissions than crude oil. It is a major constituent of liquefied petroleum gas (LPG), and is sourced from either natural gas or petroleum refining [7]. It is used globally as the third most widely used transportation fuel (20 million tons per annum), and is a popular source for domestic heat, energy and environmentally friendly refrigerant and aerosol propellants [7,8]. It has advantages over alternative gaseous fuels due to its easy separation from contaminating hydrocarbons and lower energy requirements for liquefaction and storage [8].

Routes to microbial sourced propane are limited by the absence of any known natural metabolic pathways to its production. However the discovery of the cyanobacterial aldehyde deformylating enzyme (ADO) from *Procholorococcus marinus* st. MIT9313 showed microbial routes to hydrocarbons were possible [9]. This enzyme catalyses the ferredoxin and oxygen-dependent decarbonylation of primarily long chain fatty aldehydes into alkane hydrocarbons and formate (FIG. 1A) [9]. Structure-based engineering of the substrate access channel of ADO generated the variant A134F with enhanced propane production [10]. Synthetic biology approaches to microbial propane production in *E. coli* employing ADO have been described, where the generation of the precursor butyraldehyde is via the fatty acid biosynthesis [11], reverse β-oxidation [6], valine biosynthesis (isobutyraldehyde precursor) [7] or the clostridial butanol production pathways [8]. However each pathway suffers from the bottleneck of extremely low turnover numbers of ADO (~3-5 h$^{-1}$), with a k$_{cat}$ value of only ~1 min$^{-1}$ reported with heptanal [12]. Therefore reported microbial biopropane yields were only up to 32 mg/L [6,8,11]. Considerable improvements in the catalytic rate of ADO with butyraldehyde are needed before this route to biopropane is commercially feasible.

Recently a new class of photoenzyme has been described, that catalyses the blue light dependent decarboxylation of free fatty acids to n-alkanes or alkenes [13]. This fatty acid photodecarboxylase, or photoalkane synthase (PAS or FAP), from *Chlorella variabilis* NC64A is a member of the glucose-methanol-choline oxidoreductase family, and contains a bound photoexcitable FAD cofactor with a quantum yield of >80% (0.86±0.13 s$^{-1}$) [13]. This discovery opens up the field of biocatalytically generated hydrocarbon fuels as it bypasses the need for the catalytically slow ADO enzyme. While long chain fatty acids are the preferred substrates of PAS, engineering the enzyme to increase performance with butyric acid could provide biosynthetic routes to propane.

Described herein is the development of in vivo biopropane production biofactories, employing the fatty acid decarboxylase from *C. variabilis* (CvPAS or CvFAP). We performed site directed mutagenesis in the substrate access channel to generate variant G462V (G402V mature sequence) with improved performance towards butyric acid. Studies were performed within a halophilic *Halomonas* strain, a known robust low cost production host for the production of polyhydroxyalkanoate bioplastics [14,15]. This organism is capable of growth at both high pH and high salt concentrations under non-sterile conditions without significant microbial contamination [14]. To our knowledge this is the first reported instance of the use of *Halomonas* as a gaseous biofuel production host, and combined with an enhanced propane-producing CvPAS variant is a key development in the realisation of commercially viable biopropane production.

SUMMARY OF THE INVENTION

In a first aspect disclosed herein is a fatty acid decarboxylase comprising at least 40% sequence identity to a reference sequence selected from SEQ ID NO:1 or 2, and an amino acid substitution at a position corresponding to G462 of SEQ ID NO:1.

In some embodiments, the fatty acid decarboxylase comprises an amino acid substitution selected from G462V, G462F, G462I, G462L, G462A, G462Y, G462C, G462H, G462N, G462Q, and G462W. Optionally, the substitution may be G462V or G462I.

In some embodiments disclosed herein the fatty acid decarboxylase further comprises an amino acid substitution at a position corresponding to at least one of: V453 of SEQ ID NO:1, G455 of SEQ ID NO:1, A457 of SEQ ID NO:1, Y466 of SEQ ID NO:1, or T484 of SEQ ID NO:1.

In some embodiments the fatty acid decarboxylase comprises an amino acid substitution selected from V453F, V453I, V453L, V453W, V453E, V453A. The substitution may preferably be one of V453F, V453I, V453L, V453W. Optionally, the substitution may be V453I.

In some embodiments the fatty acid decarboxylase comprises an amino acid substitution selected from G455F, G455I, G455V, G455W, G455L, G455E, G455A. The substitution may preferably be one of G455F, G455I, G455V, G455W, G455L.

In some embodiments the fatty acid decarboxylase comprises an amino acid substitution selected from A457F, A457I, A457L, A457V, A457W, A457E. The substitution may preferably be one of A457F, A457I, A457L, A457V.

In some embodiments the fatty acid decarboxylase comprises an amino acid substitution selected from Y466W, Y466F, Y466I, Y466V, Y466L, Y466E, Y466A. The substitution may preferably be Y466W.

In some embodiments the fatty acid decarboxylase comprises an amino acid substitution selected from one or more of T484A, T484E, T484I, T484L, T484F, T484V, T484W. The substitution may preferably be one of T484A, T484E, T484I, T484L.

In one embodiment the fatty acid decarboxylase comprises amino acid substitutions G462V and V453I.

In one embodiment the fatty acid decarboxylase comprises amino acid substitutions G462I and V453I.

In some embodiments, the fatty acid decarboxylase comprises an amino acid consensus sequence at a position corresponding to residues 425-429 of SEQ ID NO:1, wherein the consensus sequence comprises at least 70% sequence identity to SEQ ID NO:3.

In some embodiments, the fatty acid decarboxylase comprises amino acid sequence having an active site at a position corresponding to residues 398-575 of SEQ ID NO:1, wherein the active site comprises at least 70% identity to one or more sequence selected from SEQ ID NOs: 4 to 7.

In some embodiments, the fatty acid decarboxylase comprises an amino acid sequence having at least 70% sequence identity to SEQ ID NO:1 or 2.

In some embodiments, the fatty acid decarboxylase accepts as a substrate a fatty acid having a chain length of 8 carbons or less. Preferably, the fatty acid decarboxylase accepts as a substrate a fatty acid having a chain length of 2-5 carbons.

In some embodiments, the amino acid substitution at a position corresponding to G462 of SEQ ID NO:1 sterically impedes fatty acids with a chain length equal to or greater than 8 carbons from binding to the fatty acid decarboxylase.

In some embodiments, the fatty acid decarboxylase gives a higher yield of a $C_n$ alkane compared to the yield of the same $C_n$ alkane obtained using a fatty acid decarboxylase lacking the substitution at a position corresponding to G462 of SEQ ID NO:1 using a $C_{n+1}$ fatty acid as a substrate, where $n \leq 5$.

In some embodiments, the fatty acid decarboxylase has an improved butyric acid to propane decarboxylase activity compared to a fatty acid decarboxylase comprising SEQ ID NO:1.

In some embodiments, the fatty acid decarboxylase has light-dependent decarboxylase activity. In some embodiments, the fatty acid decarboxylase has blue light-dependent decarboxylase activity. In some embodiments, the activity is dependent of light with a wavelength of 400-520 nm.

In another aspect disclosed herein is a fatty acid decarboxylase comprising at least 40% sequence identity to a reference sequence selected from SEQ ID NO:1 or 2, and an amino acid substitution at a position corresponding to at least one of: V453 of SEQ ID NO:1, G455 of SEQ ID NO:1, A457 of SEQ ID NO:1, Y466 of SEQ ID NO:1, or T484 of SEQ ID NO:1.

In some embodiments the fatty acid decarboxylase comprises an amino acid substitution selected from V453F, V453I, V453L, V453W, V453E, V453A. The substitution may preferably be one of V453F, V453I, V453L, V453W. Optionally, the substitution may be V453I.

In some embodiments the fatty acid decarboxylase comprises an amino acid substitution selected from G455F, G455I, G455V, G455W, G455L, G455E, G455A. The substitution may preferably be one of G455F, G455I, G455V, G455W, G455L.

In some embodiments the fatty acid decarboxylase comprises an amino acid substitution selected from A457F, A457I, A457L, A457V, A457W, A457E. The substitution may preferably be one of A457F, A457I, A457L, A457V.

In some embodiments the fatty acid decarboxylase comprises an amino acid substitution selected from Y466W, Y466F, Y466I, Y466V, Y466L, Y466E, Y466A. The substitution may preferably be Y466W.

In some embodiments the fatty acid decarboxylase comprises an amino acid substitution selected from one or more of T484A, T484E, T484I, T484L, T484F, T484V, T484W. The substitution may preferably be one of T484A, T484E, T484I, T484L.

The present disclosure also provides a cell comprising a fatty acid decarboxylase described herein. In some embodiments, the cell is a bacterial cell. In a preferred embodiment, the cell is a *Halomonas* cell.

Also provided herein is a method comprising catalysis of the conversion of a $C_{n+1}$ fatty acid to a $C_n$ alkane/alkene, or the conversion of a mixture of $C_{n+1}$ fatty acids to a mixture of $C_n$ alkanes/alkenes, using a fatty acid decarboxylase, wherein $n \leq 5$.

In some embodiments, the $C_{n+1}$ fatty acid is or includes butyric acid, and the $C_n$ alkane/alkene is or includes propane. In some embodiments, the $C_{n+1}$ fatty acid is or includes valeric acid, and the $C_n$ alkane/alkene is or includes butane. In some embodiments, the $C_{n+1}$ fatty acid is or includes isovaleric acid, and the $C_n$ alkane/alkene is or includes isobutane.

In some embodiments, the fatty acid decarboxylase is a fatty acid decarboxylase described herein, or a fragment, variant, or homologue thereof. In some embodiments, the fatty acid decarboxylase is comprised within a cell according to claim 11. In some embodiments, the method comprises contacting the $C_{n+1}$ fatty acid with a cell according to claim 11.

In some embodiments, the method comprises the step of recovering propane.

Also provided herein is a method of producing a $C_n$ alkane/alkene, or a mixture of $C_n$ alkanes/alkenes, comprising the step of catalysis of the conversion of a $C_{n+1}$ fatty acid to a $C_n$ alkane using a fatty acid decarboxylase, wherein $n \leq 5$.

In some embodiments, the $C_{n+1}$ fatty acid is or includes butyric acid, and the $C_n$ alkane/alkene is or includes propane. In some embodiments, the $C_{n+1}$ fatty acid is or includes valeric acid, and the $C_n$ alkane/alkene is or includes butane. In some embodiments, the $C_{n+1}$ fatty acid is or includes isovaleric acid, and the $C_n$ alkane/alkene is or includes isobutane.

In some embodiments, the method of producing a $C_n$ alkane/alkene comprises the steps of catalysis of the conversion of a $C_{n+1}$ acyl-CoA to a $C_{n+1}$ fatty acid using an acyl-CoA thioester hydrolase prior to the step of conversion of a $C_{n+1}$ fatty acid to a $C_n$ alkane using a fatty acid decarboxylase. Preferably, the $C_{n+1}$ acyl is butyryl-CoA, the $C_{n+1}$ fatty acid is butyric acid, and the $C_n$ alkane is propane.

In some embodiments, the fatty acid decarboxylase is a fatty acid decarboxylase described herein, or a fragment, variant, or homologue thereof. In some embodiments, the fatty acid decarboxylase is comprised within a cell comprising a nucleic acid encoding a fatty acid decarboxylase as described herein. In some embodiments, the method comprises contacting the $C_{n+1}$ fatty acid, or a composition comprising a $C_{n+1}$ fatty acid, with a cell comprising a nucleic acid encoding a fatty acid decarboxylase as described herein.

In some embodiments, the methods comprise the step of recovering the alkane/alkene.

Also provided is the use of a fatty acid decarboxylase in a method of producing an alkane/alkene as described herein.

In a further aspect, the disclosure provides a method comprising:
catalysis of the conversion of butyryl-CoA to butyraldehyde using an aldehyde dehydrogenase.

Also provided is a method comprising:
catalysis of the conversion of butyraldehyde to propane using an aldehyde deformylating oxygenase.

The disclosure also provides a method comprising:
catalysis of the conversion of butyryl-CoA to butyraldehyde using an aldehyde dehydrogenase, followed by catalysis of the conversion of butyraldehyde to propane using an aldehyde deformylating oxygenase.

Also provided is method of producing propane, comprising the step of catalysis of the conversion of butyryl-CoA to butyraldehyde using an aldehyde dehydrogenase.

Also provided is method of producing propane, comprising the steps of:
a. catalysis of the conversion of butyryl-CoA to butyraldehyde using an aldehyde dehydrogenase, and
b. catalysis of the conversion of butyraldehyde to propane using an aldehyde deformylating oxygenase.

In some embodiments, the method comprises the step of recovering propane.

In some embodiments, the aldehyde dehydrogenase is aldehyde dehydrogenase from *Clostridium beijerinckii*, or a fragment, variant, or homologue thereof.

In some embodiments, the aldehyde dehydrogenase comprises an amino acid sequence having at least 70% sequence identity to SEQ ID NO:20.

In some embodiments, the aldehyde deformylating oxygenase comprises an amino acid sequence having at least 70% sequence identity to SEQ ID NO:21

In some embodiments, the method comprises the step of the catalytic conversion of butyric acid to butyryl-CoA using a butyrate-acetoacetate CoA transferase prior to the catalysis of the conversion of butyryl-CoA to butyraldehyde using an aldehyde dehydrogenase.

In some embodiments, the butyrate-acetoacetate CoA transferase comprises an amino acid sequence having at least 70% sequence identity to SEQ ID NO:22.

Also provided herein is a polynucleotide sequence comprising a nucleic acid sequence encoding an aldehyde dehydrogenase and an aldehyde deformylating oxygenase.

Also provided herein is a cell comprising a nucleic acid encoding a heterologous aldehyde dehydrogenase. In some embodiments, the cell comprises a nucleic acid encoding an aldehyde deformylating oxygenase.

In some embodiments, a cell comprises a nucleic acid encoding an aldehyde dehydrogenase and an aldehyde deformylating oxygenase. In some embodiments, a cell comprises an expression vector (as defined herein) comprising a nucleic acid encoding an aldehyde dehydrogenase and a nucleic acid encoding an aldehyde deformylating oxygenase. In some embodiments, the expression comprises one or more promoters operably linked to the nucleic acid encoding an aldehyde dehydrogenase and/or to the nucleic acid encoding an aldehyde deformylating oxygenase.

In some embodiments, the aldehyde dehydrogenase comprises an amino acid sequence having at least 70% sequence identity to SEQ ID NO:20.

In some embodiments, the aldehyde deformylating oxygenase comprises an amino acid sequence having at least 70% sequence identity to SEQ ID NO:21.

In some embodiments, the methods comprise the step of contacting butyryl-CoA, or a composition containing butyryl-CoA, with a cell comprising a nucleic acid encoding a heterologous aldehyde dehydrogenase, or a cell comprising a nucleic acid encoding a heterologous aldehyde dehydrogenase and an aldehyde deformylating oxygenase, as described herein.

Also provided is the use of an aldehyde dehydrogenase in a method of producing butane as described herein.

The invention includes the combination of the aspects and preferred features described except where such a combination is clearly impermissible or expressly avoided.

Sequences

| SEQ ID NO: | Description | |
|---|---|---|
| SEQ ID NO: 1. | CvPAS / CvFAP (*Chlorella variabilis* NC64A), Genbank ID: A0A248QE08 654 amino acid wild type sequence, comprising 61 amino acid N-terminal chloroplast targeting sequence | MASITSRASARASCSQANTRAGRVALSGGALLRPARPARSF VPARKQQQGAVRRGGALSARASAVEDIRKVLSDSSSPVAG QKYDYILVGGGTAACVLANRLSADGSKRVLVLEAGPDNTSR DVKIPAAITRLFRSPLDWNLFSELQEQLAERQIYMARGRLLG GSSATNATLYHRGAAGDYDAWGVEGWSSEDVLSWFVQAE TNADFGPGAYHGSGGPMRVENPRYTNKQLHTAFFKAAEEV GLTPNSDFNDWSHDHAGYGTFQVMQDKGTRADMYRQYLK PVLGRRNLQVLTGAAVTKVNIDQAAGKAQALGVEFSTDGPT GERLSAELAPGGEVIMCAGAVHTPFLLKHSGVGPSAELKEF GIPVVSNLAGVGQNLQDQPACLTAAPVKEKYDGIAISDHIYN EKGQIRKRAIASYLLGGRGGLTSTGCDRGAFVRTAGGQALPD LQVRFVPGMALDPDGVSTYVRFAKFQSQGLKWPSGITMQLI ACRPQSTGSVGLKSADPFAPPKLSPGYLTDKDGADLATLRK GIHWARDVARSSALSEYLDGELFPGSGVVSDDQIDEYIRRSI HSSNAITGTCKMGNAGDSSSVVDNQLRVHGVEGLRVVDAS VVPKIPGGQTGAPVVMIAERAAALLTGKATIGASAAAPATVA A |
| SEQ ID NO: 2. | CvPAS / CvFAP 594 amino acid wild type sequence, with 61 amino acid N- | MASAVEDIRKVLSDSSSPVAGQKYDYILVGGGTAACVLANRL SADGSKRVLVLEAGPDNTSRDVKIPAAITRLFRSPLDWNLFS ELQEQLAERQIYMARGRLLGGSSATNATLYHRGAAGDYDA WGVEGWSSEDVLSWFVQAETNADFGPGAYHGSGGPMRVE NPRYTNKQLHTAFFKAAEEVGLTPNSDFNDWSHDHAGYGT |

| SEQ ID NO: | Description | Sequences |
|---|---|---|
| | terminal chloroplast targeting sequence removed and an N-terminal methionine added | FQVMQDKGTRADMYRQYLKPVLGRRNLQVLTGAAVTKVNID QAAGKAQALGVEFSTDGPTGERLSAELAPGGEVIMCAGAVH TPFLLKHSGVGPSAELKEFGIPVVSNLAGVGQNLQDQPACLT AAPVKEKYDGIAISDHIYNEKGQIRKRAIASYLLGGRGGLTST GCDRGAFVRTAGQALPDLQVRFVPGMALDPDGVSTYVRFA KFQSQGLKWPSGITMQLIACRPQSTGSVGLKSADPFAPPKL SPGYLTDKDGADLATLRKGIHWARDVARSSALSEYLDGELF PGSGVVSDDQIDEYIRRSIHSSNAITGTCKMGNAGDSSSVVD NQLRVHGVEGLRVVDASVVPKIPGGQTGAPVVMIAERAAAL LTGKATIGASAAAPATVAA |
| SEQ ID NO: 3. | Fatty acid decarboxylase consensus sequence | GXLXXXXC[D/E]XG[A/G]FX[K/R] |
| SEQ ID NO: 4. | Fatty acid decarboxylase active site | [I/L/K/D]$X_{28-35}$C$X_{18-20}$R$X_{9-10}$[Z]$X_3$[Y/I/L]XX[F/S/L/Y]$X_{4-17}$ [T/S/G]XQX$_{82-85}$HXXN |
| SEQ ID NO: 5. | Fatty acid decarboxylase active site | [I/L]$X_{28-35}$C$X_{18-20}$R$X_{9-10}$[Z]$X_3$[Y/I/L]XX[F/L]$X_{4-17}$[T/S/G] XQ$_{X82-85}$HXXN |
| SEQ ID NO: 6. | Fatty acid decarboxylase active site | I$X_{28-35}$C$X_{18-20}$R$X_{9-10}$[Z]$X_3$YXXF$X_{4-17}$TXQ$_{X82-85}$HXXN |
| SEQ ID NO: 7. | Fatty acid decarboxylase active site | IAISDHIYNEKGQIRKRAIASYLLGGRGGLTSTGCDRGAFVRT AGQALPDLQVRFVPGMALDPD[Z]VSTYVRFAKFQSQGLKW PSGITMQLIACRPQSTGSVGLKSADPFAPPKLSPGYLTDKDG ADLATLRKGIHWARDVARSSALSEYLDGELFPGSGVVSDDQI DEYIRRSIHSSN |
| SEQ ID NO: 8. | AaPAS (*Aureococcus anophagefferens*) UniProt ID: F0YAB1 | MGRTLVLKVATTSYDYIIAGGGTAGCVLANRLSEDPSKKVLV LEAGDRGPNSPLVKIPVAILKLFKSAYDWNFATRPSEAVADR SLYVCRGKGLGGSSLTNVMLYNRGSANDYDAWAAACGDDS WGAEEMLGYFKKAEDCLVPAHRANHYHGVGGPYASSHVPY TNEMSTAFVEAAVEDGGVRNGDFNDWSTSQVGFGRFAVS QRKGARVDAATAYLPRKVRRRANLDVVRGAALSGVTWNAN KATGVEFAFGGVSGIACGGEVILSGGAVHSPQMLMLSGVGA KAQLEEFGIPVVADRPVGKNLQDHPACLVSWRGSAKAQG KSHSTQLRIPGTTKTSPKALLQWLFLGRGPLASPGCDHGGF AKVGAGDGDCDVQFRFLATKSITPDGMSTISDSYEAAVDHP DGLTIQTIVARPKSRAGEVKLASRDPAAKPVIENAYLSDEADV MTMVKALQKARSIASRAPLSAYAGHEEFPGEDVADERQLAA YVRNTAHTANAVVGTCKMGESSDALAVVDNHLKVIGVSNLR VVDASVMPTLPGGQTAASTVALAEKAADLIKGG |
| SEQ ID NO: 9. | CcPAS (*Chondrus crispus*) UniProt ID: R7Q9C0 | MASPCPAFATPIAVPRSTLTSLISSSSSCTPRPVRTPAPPTHR RLIHMAAPAGTVASTFRRTVPSSEAATTYDYIIVGGGAAGCV LANRLTEDPSTRVLLLEAGKPDDSFYLHVPLGFPYLLGSPND WAFVTEPEPNLANRRLYFPRGKVLGGSHAISVMLYHRGHPA DYTAWAESAPGWAPQDVLPYFLKSESQQSAVPNQDAHGYE GPLAVSDLARLNPMSKAFIKAAHNAAGLNHNPDFNDWATGQ DGVGPFQVTQRDGSRESPATSYLRAAKGRRNLTVMTGAVV ERILFENPAGSSTPVATAVSFIDSKGTRVRMSASREILLCGGV YATPQLLMLSGVGPAEHLRSHGIEIVADVPAVGQNLQDHAA AMVSFESQNPEKDKANSSVYYTERTGKNIGTLLNYVFRGKG PLTSPMCEAGGFAKTDPSMDACDLQLRFIPFVSEPDPYHSL ADFATAGSYLQNRANRPTGFTIQSVAARPKSRGHVQLRSTD VRDSMSIHGNWISNDADLKTLVHGVKLCRTIGNDDSMKEFR GRELYPGGEKVSDADIEAYIRDTCHTANAMVGTCRMGIGEQ AAVDPALQVKGVARLVVDSSVMPTLPGGQSGAPTMMIAEK GADLIRAAARQADAATVGAAA |
| SEQ ID NO: 10. | ChPAS (*Chrysochromulina* sp. CCMP291) UniProt ID: A0A0M0JFC3 | MMRRLVYICAVATVTAAISSRSVPTSARRLIALRGGVAAAEQ LAEEPWDYIIVGGGAAGCVMAERLSAAEARVLVLEAGTDAS RDLRIRVPAGLIKVFKSERDWDFTTEAGQGTSGRGIYLCRGK ALGGSSCTNVMLYNRGSPADYNSWVAAGAEGWGPDSVLH YYRKSENYVGGASQYHGVDGPLSVSDVPYENELSTAFLRAA GELGYRRVHDFNDWSAPQEGFGRYKVTQRNGERCSAANA YLEGTEGRSNLCVRTGVHATRVTLEGSGDDLCAAGVEYIGA DGKPSRAQLAQGGEVLLSAGAVQSPQLLMLSGIGPRAHLEE VGIEVRKELDNVGVGLADHPAVVVSCGSKKKVSVTDEIRLW |

| SEQ ID NO: | Description | Sequences |
|---|---|---|
| | | GGSKTNPMALLRWLLWRRGPLTSVACEFGGFFKTKPDLKQ ADVQVRFVAARAMSPDGITTLQQLGAGAKFLSGYTTQIIACR PQSTGLVRLRSSDPLAQPMLQDVHLSDDADVATLREGIKLG RQLLAAKSFDQYRDEEVYPGVAVQSDEDIDAYVRKTTHSAN ALVGSCRMGRVDDQAAVLDPEMRVRGVGSLRVVDASAMP HIIGGQTCGPTIMMAEKAADLVLRQRAEINAYMQQAQAYLAA SAGAATPALSPAQAA |
| SEQ ID NO: 11. | CmPAS (Cyanidioschyzon merolae) UniProt ID: M1VK13 | MRSRYCFLLSSTPCKYAGQRSPFPASALAGVCAGGRLRNVT RNLRPGLRTLRASAETEHSQGTRQAQYDFIIVGAGAAGCVL ANRLSTAQFSNGDRRYPRVLLLEAGDALAEAPYFEHIPLGFP QLIGSRLDYGFFSRENPTHLGGRGAVYLPRGRGEGGSHAIS VMLVHRGSRHDYETWVKDYEALGWGPDDVLPYFKRLESNE RTAQRGADGEAATALHGSDGPLRVSDQRSPNPLSLAFIEAC LERGIRRNKDFNDWDHGQEGAGLFQVTQRDGRRESPATAY LQPVRSRRNLHIETNALAEHLVWSKDGRRVEGIRFIDRHGRR RAALAHCEVILAAGAINTPQLLMLSGLGPGAHLQDFGIPVVR DLPGVGQNLQDHAAVMLSYYAPDPYGKDRDKKRIFYTERLG KDPLVLAEYFLLGRGPLTSPVCEAGAFVHTQAVIGEPSCDLQ LRFVPFFSDADPYKSLGEYRSGGHVLTNTSIRPAGFGLQAVA IRPRSRGRIELATIDPRARPIIHTGWLEDKRDLQTLLSGLKLG REILSGDSMRPYRGREAFPETLEDDLVTYIRRTCHTANAIVG TARMGTGRDAVVDPELRVHGVERLRVIDASVMPKIIGGQTG VPTMMIAERGADLVKKTWKLV |
| SEQ ID NO: 12. | CrPAS (Chlamydomonas reinhardtii) UniProt ID: A8JHB7 | MMLGPKTVTRGATKGAAPRSMAARRVGGARRLSVRAAAGP AGSEKFDYVLVGGGTASCVLANKLSADGNKKVLVLEAGPTG DAMEVAVPAGITRLFAHPVMDWGMSSLTQKQLVAREIYLAR GRMLGGSSGSNATLYHRGSAADYDAWGLEGWSSKDVLDW FVKAECYADGPKPYHGTGGSMNTEQPRYENVLHDEFFKAA AATGLPANPDFNDWSHPQDGFGEFQVSQKKGQRADTYRTY LKPAMARGNLKVVIGARATKVNIEKGSSGARTTGVEYAMQQ FGDRFTAELAPGGEVLMCSGAVHTPHLLMLSGVGPAATLKE HGIDVVSDLSGVGQNLQDHPAAVLAARAKPEFEKLSVTSEV YDDKCNIKLGAVAQYLFQRRGPLATTGCDHGAFVRTSSSLS QPDLQMRFVPGCALDPDGVKSYIVFGELKKQGRAWPGGITL QLLAIRAKSKGSIGLKAADPFINPAININYFSDPADLATLVNAV KMARKIAAQEPLKKYLQEETFPGERASSDKDLEEYIRRTVHS GNALVGTAAMGASPAAGAVVSSADLKVFGVEGLRVVDASVL PRIPGGQTGAATVMVAERAAALLRGQATIAPSRQPVAV |
| SEQ ID NO: 13. | CsPAS (Coccomyxa subellipsoidea) UniProt ID: I0YJ13 | MMASQSVFLGTRPATRSPLPIGRAGHGSAGRRALRVRAIIKS DNPAADKYDFILVGGGTAGCVLANRLTADGSKKVLLLEAGG ANKAREVRTPAGLPRLFKSALDWNLYSSLQQAASDRSIYLA RGKLLGGSSATNATLYHRGTAADYDAWGVPGWTSQDALR WFIQAENNCRGIEDGVHGTGGLMRVENPRYNNPLHEVFFQ AAKQAGLPENDNFNNWGRSQAGYGEFQVTHSKGERADCF RMYLEPVMGRSNLTVLTGAKTLKIETEKSGGATVSRGVTFQ VNGQDGSKHSAELAAGGEVVLCAGSIHSPQILQLSGIGPQAE LRSKDIPVVADLPGVGQNMQDHPACLSAFYLKESAGPISVTD ELLHTNGRIRARAILKYLLFKKGPLATTGCDHGAFVKTAGQS EPDLQIRFVPGLALDPDGIGSYTAFGKMKDQKWPSGITFQLL GVRPKSRGSVGLRSDDPWDAPKLDIGFLTDKEGADLATLRS GIKLSREIAAEPAFGAYVGNELHPGAAASSDSAIDSFIRDTVH SGNANVGTCSMGVNGNAVVDPSLRVFGIRGLRVADASVIPVI PGGQTGAATVMVAERAAEILLGSNQKPAAAVPAAQPALA |
| SEQ ID NO: 14. | GpPAS (Gonium pectorale) UniProt ID: A0A150GC51 | MMLGRKPVAPAKGASAARTVRPVRLAGGRRQLVVSAAAAP VDPAEKYDYILVGGGTAGCVLANKLSADGNKKVLVLEAGPS GDSLEVAVPAGIARLFAHPVMDWGMSSLTQKQLVAREIYLA RGRLLGGSSGTNATLYHRGTSSDYDSWGLEGWTSKDVLD WFVKAECYGDGPKPYHGNSGSMNVEQPRYQNPLHEEFFR AAAAAGIPANPDFNDWSRPQDGYGEFQVAQNKGQRADTYR TYLKPALSRGNLKVVTGARTTKVHIEKGSSGPRARGVEFAT QQFGDRYSAQLAPGGEVLMCTGAVHTPHLLMLSGVGPAAA LREHGVDVVADLAGVGANLQDHPAAVVAVRAKPEFEKLSVT SEIYDEKCNIKLGAVAQYLFNRRGPLATTGCDHGAFVRTSGS HSQPDLQMRFVPGCALDPDGVKSYIVFGELKKQGRAWPGG ITLQLLAIRAKSKGSIGLKAADPFINPAININYFSDPADLATLKQ GVRMARDIARQEPLRKYLQEETFPGERASSDSDIEEYVRRT VHSGNALVGTCAMGTSPAKGAVVSSSDLKVFGVEGLRVVD ASVLPQIPGGQTGAATVMVAERAAALLKGQTTMAPSRQPVA A |

| SEQ ID NO: | Description | Sequences |
|---|---|---|
| SEQ ID NO: 15. | PtPAS (*Phaeodactylum tricomutum*) UniProt ID: B7FSU6 | MYDYIICGGGLAGCVLAERLSQDESKRVLVLEAGGSDYKSLF IRIPAGVLRLFRSKYDWQHETGGEKGCNGRNVFLQRGKILG GSSCTNVCLHHRGSAEDYNSWNIPGWTATDVLPFFKQSQK DETGRDATFHGADGEWVMDEVRYQNPLSKLFLEVGEAAGL GTNDDFNNWSHPQDGVGRFQVSEVNGERCSGATAFLSKA AKRSNVIVRTGTMVRRIDFDETKTAKGITYDLMGDDTCTVPC LKEGGEVLVTGGAIASPQLLMCSGIGPGKHLRSLGIPVVHDN SAVGENLQDHPAAVVSFKTPQKGVSVTSKLRLFGKTNPIPVF QWLFFKSGLLTSTGCDHGAFVRTSDSLEQPDLQIRFLAARAL GPDGMTTYTKFRTMKTVEDGYSFQSVACRAKSKGRIRLSSS NSHVKPMIDGGYLSNQDDLATLRAGIKLGRMLGNRPEWGEY LGQEVYPGPDVQTDEEIDEYIRNSLHTANALTGTCKMGTGR GAVVGPDLRVIGVNGVRVADSSVFPCIPGGQTATPTVMIADR AAVFVR |
| SEQ ID NO: 16. | EhPAS (*Emiliania huxlep*) UniProt ID: R1FBM9 | MVALFALQLALSPPQARLGSGSARAALRLRGGSGVTGGSLG RGGGSPAIDGEFDYIIVGGGAAGCVLANRLSADPAHRVLLIE AGGDASRDKRAQVPWAFTKLLRSEYDWDFHVEAEAAVNQQ EVYLCRGKALGGSSVTNVMLYHRGSPADYDAWEEAGARG WGAKDVLPYYLRVEDYGDGASQYHAVGGHVSVQEVPYQN QLSATFLRAMGQLGFRPNGDFNDWSSPQEGYGRYKVTQR AGRRCTAADGYLAAARERANLVVVTGAQATRLALDSAYDGA GRLQVSGVEFARGDEREPCSVRLARGGEAVLCAGAVQTPH LLLLSGIGPAEHLREVGVPVRADLPGVGSGLQDHPAVVVSY ESKKAVAATDDALLKGYASLVNPLAMLRWLLFGRGPLACAA CDHGGFVRSSPDLDQPDVQIRFVPARASSASGMNTLIELGR RARFLPGFSTQVVACRPRSEGRVRLRSADPFAKPIIEGIHLG AAEDVASLRHGIRLGRQVCAAAAFDEYRGEEVFPGAAVQSD EQIDEYIRSSVHSANALTSSCRMGDPSDPAAVLDSHLRVRG VGGLRVADASAMPRIIGGQTQAPTYMLAERAADILLHARLQA HEPATESVSQRLEVAAAAL |
| SEQ ID NO: 17. | EhPAS2 (*Emiliania huxlep*) UniProt ID: R1E6L1 | MSARWLLLLATHCSAALRNPFRAAPTHFDYIIVGGGTAGCVL ADRLSAASKQVLVLEPGPSPAAELKIAAPVALTKLFGSEYDW GFRSAPAPGTAGREVHLCRGKCLGGSSATNALLYLRGTAAD FDGWGLDGWGSEAMLASFLAVEAQRDAAFRTDALHHGSG GAVPAETPRYANPLSERFLEAAAQAGHPSNADFNDWSRPQ AGVGRFQLTTRRGRRAHSAATHLRRAARRPNLHVRCGCAA TRLLLEAEGGGGGGGGGKTRPWTGPAVTGQAGRRAVGV EYIDAAGVQRTASVSGGGGGGGGEVLLCAGAVSSPHLLLLS GIGSPDELAAHGIGAEVCLPGVGRNLIDQPAVVTGYTVTSPL SITDEMFWRRSGALSPRRVGEWLLRGSGPLASSGCDFGGF FSSRPGLAQPDLQLRFVPGLGTSPDGVSSYRDIGRAGKTPS GLTLQSIAVRPTARGSVSLSSADPSAPPRIETGYGTSEADLA TLRQGLRLSRELVAQPAFDGVRGEEAWPRAACRLRRPGDD AALDEYIRSTAHSANALGGSCRMGRATSPARLVEGSDPLAV VDPALRVRGASGLRVVDASVLPTLPGGQLGATTFALAERAA RIILGERAAGEAEAPAERRQEHAHALGAA |
| SEQ ID NO: 18. | NgPAS (*Nannochloropsis gaditana*) UniProt ID: W7TN63 | MSSNGYLRAYHLLIALLISANAFLITPPRLSKTTIGLQSFVTAN YGVRRAISLRGGLQSVSMKAPAAVASSTYDYIIVGGGIGGCV LANRLTESGRPKVLLLEAGKSAERNPYVNIPAGVVRLFKSAL DWQFESAPERHLDGKEVYLVRGKAMGGSSAVNVMLVHRG SASDYAKWEAEGAQGWGPEEALRYFKKMEDNLVGGEGRN HGQGGMYPVDDVKYQNPLSKRFLQACEEYGWRANPDFND WSHPQDGYGSFKVAQKHGKRVTAASGYLNKAVRRRPNLDI LSEALVTRVLLEGEGDVKAVGVEFTGKDGKTHQVRTTGKAG EVLLAGGAVNSPQLLMLSGIGPEADLQAVGIATKVNRPGVGE NLQDHPAVTIAHNITRPISLCDDLFLFHTPVPKPHQVLRWTLT GSGPLTTPGCDHGAFLKTREDLQEPNVQFRFIAGRGSDPDG VRSYIMGGSARPLSGLTLQVVNIRPKSKGKLTLASKDPLKKP RIEVRYLSAAEDLQALRTGMRIGRDLIKQRAFADILDEEVFPG PAAQTDEELDAYIRDSLHTANALVGTCKMGSVEDRNAVVDP ECRVIGVGGLRVVDASVMPVIPGGQTGSGTTMLAEKAADLV RAHAGDLVEMGVQDEERKGGWFNGLLGRKQKVATEKERG ERGKSERFVSEVIRHMGRVFVQVSRARRAQTCMRVGKGLD RERQLECAMRKELTIALFYAMLFTMRHSGFLSTTGRASYKDL GYLTGSCRAHPCTSPSSLCLFPEKPFMKLSPALAVVGFCFN SINVQGFLLSNLAGRSLKHPVPQKGLYSRIEYDAREPRLDEF GLPLDPADLMEKPRVPLKDRVYHIIDMTNDWVDAVSRGRRE EETRRIIQRRRAAAKAMAIKDKVLISLDYVFHPVKAWRTFVAD PLEARHQRQLRQQAEKRARLERYLQRYNTVKNRFHDTLDLL ESTTRTSVKVAKSVSSAVVGAPGTVTRTVKEVKSQAQGTAE AVAKVSSSVSSVVSKITSVIRKEDGALAGAKGKKDPRSEDEG |

| SEQ ID NO: | Description | Sequences |
|---|---|---|
| | | KADPVKVREIWETKEQTAIRTIWEADELVTPVTPPATAMAST VSVSEPQDENEASISQGAAPSPSTSSPSSPEPVTRLSFRAR VEADEKERFGSRRLKISGNVPPTASPTRGASSLPLDTLSSSA TQTFERSKVGPPIRTSKARCIGKCVHNGWKGICEEWFVHISF PTYAVSIVRPPMHVHNFKVICCVLAVRHARRKKEMSTALSTH LIYLLLKTVKMLQDLPQLRRKGKTN |
| SEQ ID NO: 19. | VcPAS (*Volvox carteri f. nagariensis*) UniProt ID: D8TNQ4 | MLLGQRPFGAPAKGAMPCWKAARHGGVAGVARRPVAVKA AASVGSEKFDYILVGGGTAGCVLANKLSANGSKKVLVLEAG PTGDAMEVAVPAGIARLFAHPVFDWGMSSLTQQQLVAREIY LARGRLLGGSSGTNATLYHRGTPADYDSWGLEGWTSKDLL DWFVKAECYGDGPRAFHGQSGSMNVEQPRYQNVLHDEFF RAAAAAGLPANEDFNDWSRPQEGYGEFQVAQKNGERADT YRTYLKPAMGRDNLKVMTGARTTKVHIEKSSTGPRARGVEY ATQQFGERYTAELTPGGEVLMCTGAVHTPHLLMLSGIGPAP TLLEHGLDVISSLPGVGANLQDHPAAVLAVRAKPEFEGLSVT SEIYDSKCNIRLGAVMKYLFGRRGPLATTGCDHGAFVRTSAS HSQPDLQMRFVPGCALDPDGVKSYIVFGELKKQGRAWPGG ITLQLLGIRAKSRGSIGLKAADPFINPAININYFSDPEDLATLKN GVRIAREIVAQEPLRKYLLEETFPGERANTDKDIEEYVRRTVH SGNALVGTCAMGTTPASGAVVSSADLKVFGVDGLRVVDAS VLPRIPGGQTGAATVMVAERAAAMLLGQATITSRREPAAV |
| SEQ ID NO: 20. | BALDH (*Clostridium beijerinckii*) UniProt ID: Q716S8 | MNKDTLIPTTKDLKVKTNGENINLKNYKDNSSCFGVFENVEN AISSAVHAQKILSLHYTKEQREKIITEIRKAALQNKEVLATMILE ETHMGRYEDKILKHELVAKYTPGTEDLTTTAWSGDNGLTVV EMSPYGVIGAITPSTNPTETVICNSIGMIAAGNAVVFNGHPCA KKCVAFAVEMINKAIISCGGPENLVTTIKNPTMESLDAIIKHPSI KLLCGTGGPGMVKTLLNSGKKAIGAGAGNPPVIVDDTADIEK AGRSIIEGCSFDNNLPCIAEKEVFVFENVADDLISNMLKNNAV IINEDQVSKLIDLVLQKNNETQEYFINKKWVGKDAKLFLDEIDV ESPSNVKCIICEVNANHPFVMTELMMPILPIVRVKDIDEAIKYA KIAEQNRKHSAYIYSKNIDNLRFEREIDTTIFVKNAKSFAGV GYEAEGFTTFTIAGSTGEGITSARNFTRQRRCVLAGLEHHHH HH |
| SEQ ID NO: 21. | ADO (*Prochlorococcus marinus* MIT9313), UniProt ID: Q7V6D4 | MPTLEMPVAAVLDSTVGSSEALPDFTSDRYKDAYSRINAIVIE GEQEAHDNYIAIGTLLPDHVEELKRLAKMEMRHKKGFTACG KNLGVEADMDFAREFFAPLRDNFQTALGQGKTPTCLLIQALL IEAFAISAYHTYIPVSDPFARKITEGVVKDEYTHLNYGEAWLK ANLESCREELLEANRENLPLIRRMLDQVAGDAAVLQMDKED LIEDFLIAYQESLTEIGFNTREITRMAAAALVS |
| SEQ ID NO: 22. | CoAT (*C. acetobutylicum*), Genbank ID: P33752/P23673 | MNSKIIRFENLRSFFKDGMTIMIGGFLNCGTPTKLIDFLVNLNI KNLTIISNDTCYPNTGIGKLISNNQVKKLIASYIGSNPDTGKKL FNNELEVELSPQGTLVERIRAGGSGLGGVLTKTGLGTLIEKG KKKISINGTEYLLELPLTADVALIKGSIVDEAGNTFYKGTTKNF NPYMAMAAKTVIVEAENLVSCEKLEKEKAMTPGVLINYIVKEP A |
| SEQ ID NO: 23. | YciA (*Haemophilus influenza*), Genbank ID: AAC22485 | MSANFTDKNGRQSKGVLLLRTLAMPSDTNANGDIFGGWIMS QMDMGGAILAKEIAHGRVVTVAVESMNFIKPISVGDVVCCYG QCLKVGRSSIKIKVEVWVKKVASEPIGERYCVTDAVFTFVAV DNNGRSRTIPRENNQELEKALALISEQPL |
| SEQ ID NO: 24. | NphT7 (*Streptomyces* sp. st. CL190) UniProt ID: D7URV0-1 | MTDVRFRIIGTGAYVPERIVSNDEVGAPAGVDDDWITRKTGI RQRRWAADDQATSDLATAAGRAALKAAGITPEQLTVIAVATS TPDRPQPPTAAYVQHHLGATGTAAFDVNAVCSGTVFALSSV AGTLVYRGGYALVIGADLYSRILNPADRKTVVLFGDGAGAMV LGPTSTGTGPIVRRVALHTFGGLTDLIRVPAGGSRQPLDTDG LDAGLQYFAMDGREVRRFVTEHLPQLIKGFLHEAGVDAADIS HFVPHQANGVMLDEVFGELHLPRATMHRTVETYGNTGAASI PITMDAAVRAGSFRPGELVLLAGFGGGMAASFALIEW |
| SEQ ID NO: 25. | SFP (*Bacillus subtilis*), Genbank ID: X65610 | MKIYGIYMDRPLSQEENERFMSFISPEKREKCRRFYHKEDAH RTLLGDVLVRSVISRQYQLDKSDIRFSTQEYGKPCIPDLPDA HFNISHSGRWVICAFDSQPIGIDIEKTKPISLEMPKRFFSKTEY SDLLAKDKDEQTDYFYHLWSMKESFIKQGRQRLIASA |
| SEQ ID NO: 26. | Ferr (*Synechocystis* sp PCC 6803), Genbank ID: WP_010873424 | MASYTVKLITPDGESSIECSDDTYILDAAEEAGLDLPYSCRAG ACSTCAGKITAGSVDQSDQSFLDDDQIEAGYVLTCVAYPTSD CTIETHKEEDLY |

| SEQ ID NO: | Description | Sequences |
|---|---|---|
| SEQ ID NO: 27. | CvPAS chloroplast targeting sequence (length = 61 amino acid) | MASITSRASARASCSQANTRAGRVALSGGALLRPARPARSF VPARKQQQGAVRRGGALSAR |
| SEQ ID NO: 28. | AtoB (*E. coli*), Genbank ID: P76461 | MKNCVIVSAVRTAIGSFNGSLASTSAIDLGATVIKAAIERAKID SQHVDEVIMGNVLQAGLGQNPARQALLKSGLAETVCGFTVN KVCGSGLKSVALAAQAIQAGQAQSIVAGGMENMSLAPYLLD AKARSGYRLGDGQVYDVILRDGLMCATHGYHMGITAENVAK EYGITREMQDELALHSQRKAAAAIESGAFTAEIVPVNVVTRK KTFVFSQDEFPKANSTAEALGALRPAFDKAGTVTAGNASGIN DGAAALVIMEESAALAAGLTPLARIKSYASGGVPPALMGMGP VPATQKALQLAGLQLADIDLIEANEAFAAQFLAVGKNLGFDS EKVNVNGGAIALGHPIGASGARILVTLLHAMQARDKTLGLATL CIGGGQGIAMVIERLN |
| SEQ ID NO: 29. | Hbd (*Clostridium acetobutylicum* ATCC 824), Genbank ID: P52041 | MKKVCVIGAGTMGSGIAQAFAAKGFEVVLRDIKDEFVDRGLD FINKNLSKLVKKGKIEEATKVEILTRISGTVDLNMAADCDLVIE AAVERMDIKKQIFADLDNICKPETILASNTSSLSITEVASATKR PDKVIGMHFFNPAPVMKLVEVIRGIATSQETFDAVKETSIAIG KDPVEVAEAPGFVVNRILIPMINEAVGILAEGIASVEDIDKAMK LGANHPMGPLELGDFIGLDICLAIMDVLYSETGDSKYRPHTLL KKYVRAGWLGRKSGKGFYDYSK |
| SEQ ID NO: 30. | Crt (*C. acetobutylicum* ATCC 824), Genbank ID: P52046 | MELNNVILEKEGKVAVVTINRPKALNALNSDTLKEMDYVIGEI ENDSEVLAVILTGAGEKSFVAGADISEMKEMNTIEGRKFGILG NKVFRRLELLEKPVIAAVNGFALGGGCEIAMSCDIRIASSNAR FGQPEVGLGITPGFGGTQRLSRLVGMGMAKQLIFTAQNIKA DEALRIGLVNKVVEPSELMNTAKEIANKIVSNAPVAVKLSKQA INRGMQCDIDTALAFESEAFGECFSTEDQKDAMTAFIEKRKIE GFKNR |
| SEQ ID NO: 31. | Ter (*Treponema denticola* ATCC 35405), Genbank ID: Q73Q47 | MIVKPMVRNNICLNAHPQGCKKGVEDQIEYTKKRITAEVKAG AKAPKNVLVLGCSNGYGLASRITAAFGYGAATIGVSFEKAGS ETKYGTPGWYNNLAFDEAAKREGLYSVTIDGDAFSDEIKAQ VIEEAKKKGIKFDLIVYSLASPVRTDPDTGIMHKSVLKPFGKTF TGKTVDPFTGELKEISAEPANDEEAAATVKVMGGEDWERWI KQLSKEGLLEEGCITLAYSYIGPEATQALYRKGTIGKAKEHLE ATAHRLNKENPSIRAFVSVNKGLVTRASAVIPVIPLYLASLFKV MKEKGNHEGCIEQITRLYAERLYRKDGTIPVDEENRIRIDDW ELEEDVQKAVSALMEKVTGENAESLTDLAGYRHDFLASNGF DVEGINYEAEVERFDRI |
| SEQ ID NO: 32. | PduP (*Salmonella typhimurium*) UniProt ID: H9L4I6 | MNTSELETLIRTILSEQLTTPAQTPVQPQGKGIFQSVSEAIDA AHQAFLRYQQCPLKTRSAIISAMRQELTPLLAPLAEESANET GMGNKEDKFLKNKAALDNTPGVEDLTTTALTGDGGMVLFEY SPFGVIGSVAPSTNPTETIINNSISMLAAGNSIYFSPHPGAKKV SLKLISLIEEIAFRCCGIRNLVVTVAEPTFEATQQMMAHPRIAV LAITGGPGIVAMGMKSGKKVIGAGAGNPPCIVDETADLVKAA EDIINGASFDYNLPCIAEKSLIVVESVAERLVQQMQTFGALLL SPADTDKLRAVCLPEGQANKKLVGKSPSAMLEAAGIAVPAK APRLLIALVNADDPWVTSEQLMPMLPVVKVSDFDSALALALK VEEGLHHTAIMHSQNVSRLNLAARTLQTSIFVKNGPSYAGIG VGGEGFTTFTIATPTGEGTTSARTFARSRRCVLTNGFSIR |
| SEQ ID NO: 33. | Acetaldehyde dehydrogenase (Acetylating) (*Aeromonas hydrophila* subsp. *hydrophila*) UniProt ID: A0KHX2 | MLSRQNARELVRNAKQAQVIMATFSQQKIDAIVKNVAEEAAR HAETLAKMAAEETGFGNWQDKVLKNRFASLHVYDAIKEMKT VGIIHDDQAKKVMDVGVPLGVICALVPSTNPTSTIFYKTLIALK AGNAIIFSPHPGARQCSWKAIEIVKRAAEEAAGAPAGIVDGVT QLTLEATSELMHSKDVSLILATGGEGMVRAAYASGTPTISGG PGNGPAFIERSADIHQAVKDIITSKTFDNGVICASEQSIIVERCI YDEVHRELAAQGAYFMNEDEAARMAALLLRPNGTINPKVVG KTALHLSQLAGFSVPPSTRVLVAEQTTVSHSNPYSREKLCPV LGLYVEEEWRAACHRVVELLTNEGLGHTLVIHTRNQDVIRQF SLEKPVNRILINTPAALGGIGATTNLTPALTLGCGAVGGGSSS DNVGPMNLLNIRKVGYGVRTIEELRAPIQPVAVQPASAAPTA PQPCSILDDARFSAPACHSADDRFAGASAEVGGEISEQN VERVIRQVLERLGK |
| SEQ ID NO: 34. | Aldehyde dehydrogenase (NAD) family protein (*Klebsiella* | MNTAELETLIRTILSEKLAPTPPAPQQEQGIFCDVGSAIDAAH QAFLRYQQCPLKTRSAIISALRETLAPELATLAEESATETGMG NKEDKYLKNKAALENTPGIEDLTTSALTGDGGMVLFEYSPFG VIGAVAPSTNPTETIINNSISMLAAGNSVYFSPHPGAKKVSLK |

| SEQ ID NO: | Description | Sequences |
|---|---|---|
| | pneumoniae subsp. rhinoscleromatis ATCC 13884) UniProt ID: C8SXL7 | LIARIEEIAYRCSGIRNLVVTVAEPTFEATQQMMSHPLIAVLAI TGGPGIVAMGMKSGKKVIGAGAGNPPCIVDETADLVKAAEDI ISGAAFDYNLPCIAEKSLIVVASVADRLIQQMQDFDALLLSRQ EADTLRAVGLPDGAANKKLVGKSPAALLAAAGLAVPPRPPRL LIAEVEANDPWVTCEQLMPVLPIVRVADFDSALALALRVEEG LHHTAIMHSQNVSRLNLAARTLQTSIFVKNGPSYAGIGVGGE GFTTFTIATPTGEGTTSARTFARLRRCVLTNGFSIR |
| SEQ ID NO: 35. | PduP_L.bre aldehyde dehydrogenase EutE (Lactobacillus brevis) UniProt ID: Q03Q42 | MNTENIEQAIRKILSEELSNPQSSTATNTTVPGKNGIFKTVNE AIAATKAAQENYADQPISVRNKVIDAIREGFRPYIEDMAKRIH DETGMGTVSAKIAKLNNALYNTPGPEILQPEAETGDGGLVM YEYAPFGVIGAVGPSTNPSETVIANAIMMLAGGNTLFFGAHP GAKNITRWTIEKLNELVADATGLHNLVVSLETPSIESVQEVM QHPDVAMLSITGGPAVVHQALISGKKAVGAGAGNPPAMVDA TANIALAAHNIVDSAAFDNNILCTAEKEVVVEAAVKDELIMRM QQEGAFLVTDSADIEKLAQMTIGPKGAPDRKFVGKDATYILD QAGISYTGTPTLIILEAAKDHPLVTTEMLMPILPVVCCPDFDSV LATATEVEGGLHHTASIHSENLPHINKAAHRLNTSIFVVNGPT YCGTGVATNGAHSGASALTIATPTGEGTATSKTYTRRRRLN SPEGFSLRTWEA |
| SEQ ID NO: 36. | EutE ethanolamine utilization protein (Listeria monocytogenes EGD-e) UniProt ID: Q8Y7V4 | MESLELEKLVKKVLLEKLAEQKGIPVKTMTKGAKSGVFDTVD EAVQAAVIAQNSYKEKSLEERRNVVKAIREALYPEIESIAARA VAETGMGNVADKILKNTLAIEKTPGVEDLYTEVATGDNGMTL YELSPYGVIGAVAPSTNPTETLICNTIGMLAAGNAVFYSPHPG AKNISLWLIEKLNTIVRESCGVDNLVVTVEKPSIQAAQEMN HPKVPLLVITGGPGVVLQAMQSGKKVIGAGAGNPPSIVDETA NIEKAAADIVDGASFDHNILCIAEKSVVAVDSIADFLMFQMEK NGALHVTNPSDIQKLEKVAVTDKGVTNKKLVGKSASEILKEA GIACDFSPRLIIVETEKTHPFATVELLMPIVPVVRVPNFEEALE VAIELEQGLHHTATMHSQNISRLNKAARDMQTSIFVKNGPSF AGLGFRGEGSTTFTIATPTGEGTTTARHFARRRCVLTDGF SIR |
| SEQ ID NO: 37. | Succinate-semialdehyde dehyd rogenase (Porphyromonas gingivalis) Genbank ID: WP_012457729 | MEIKEMVSLARKAQKEYQATHNQEAVDNICRAAAKVIYENAA ILAREAVDETGMGVYEHKVAKNQGKSKGVWYNLHNKKSVGI LNIDERTGMIEIAKPIGVVGAVTPTTNPIVTPMSNIIFALKTCNA IIIAPHPRSKKCSAHAVRLIKEAIAPFNVPEGMVQIIEEPSIEKT QELMGAVDVVVATGGMGMVKSAYSSGKPSFGVGAGNVQVI VDSNIDFEAAAEKIITGRAFDNGIICSGEQSIIYNEADKEAVFT AFRNHGAYFCDEAEGDRARAAIFENGAIAKDVVGQSVAFIAK KANINIPEGTRILVVEARGVGAEDVICKEKMCPVMCALSYKH FEEGVEIARTNLANEGNGHTCAIHSNNQAHIILAGSELTVSRI VVNAPSATTAGGHIQNGLAVTNTLGCGSWGNNSISENFTYK HLLNISRIAPLNSSIHIPDDKEIWEL |
| SEQ ID NO: 38. | MmP1_high expression level (Ih) | ATATTTGTGGCATTATAGAATTGTGAGCGCTCACAATTAGC TGTCACCGGATGTGCTTTCCGGTCTGATGAGTCCGTGAGg acgaaacag |
| SEQ ID NO: 39. | MmP1_medium expression level (Im) | ATATTTGTGGCATTAGGGAATTGTGAGCGCTCACAATTAG CTGTCACCGGATGTGCTTTCCGGTCTGATGAGTCCGTGA Ggacgaaacag |
| SEQ ID NO: 40. | MmP1_low expression level (Il) | ATATTTGTGGCATACTTGAATTGTGAGCGCTCACAATTAGC TGTCACCGGATGTGCTTTCCGGTCTGATGAGTCCGTGAG GACGAAACAG |
| SEQ ID NO: 41. | P40-1_low expression level (Cl) | TTTTTCTATTGCGTCCGTGTATTCTTTTGTATAGAGTTTGA GAC |
| SEQ ID NO: 42. | P40-1_medium expression level (Cm) | TTTTTCTATTGCGTTCACTGGAATCCCAGTATAGAGTTTGA GAC |
| SEQ ID NO: 43. | P40-1 high expression level (Ch) | TTTTTCTATTGCGTGAAAACAAGGATTTGTATAGAGTTTGA GAC |
| SEQ ID NO: 44. | >P40-1 very high expression level (Cvh) | TTTTTCTATTGCGTCAAAACATTTATTTGTATAGAGTTTGAG AC |

SUMMARY OF THE FIGURES

Embodiments and experiments illustrating the principles of the invention will now be discussed with reference to the accompanying figures in which:

FIG. 4. Clustal alignment of fatty acid decarboxylases from various species: (top to bottom) *Volvox carteri* f. *nagariensis* (SEQ ID NO:19), *Chlamydomonas reinhardtii* (SEQ ID N0:12), *Gonium pectorale* (SEQ ID NO:14), *Chlorella variabilis* (Cva-APS; SEQ ID NO:1), *Coccomyxa subellipsoidea* (SEQ ID NO:13), *Aureococcus anophageffrens* (SEQ ID NO:8), *Phaeodactylum tricornutum* (SEQ ID NO:15), *Chrysochromulina* spp. (SEQ ID NO:10), *Emiliania huxleyi* (SEQ ID NO:16), *Chondrus crispus* (SEQ ID NO:9), *Cyanidioschyzon merolae* (SEQ ID NO:11). Positions corresponding to G462 of SEQ ID NO:1 are indicated in bold and underline. Positions corresponding to V453 of SEQ ID NO:1 are indicated in underline. Positions corresponding to G455 of SEQ ID NO:1 are indicated in double underline. Positions corresponding to A457 of SEQ ID NO:1 are indicated in dash-dot underline. Positions corresponding to Y466 of SEQ ID NO:1 are indicated in bold and dotted underline. Positions corresponding to T484 of SEQ ID NO:1 are indicated in bold and double underline. Positions corresponding to consensus sequence SEQ ID NO:3 are dotted underlined. Positions corresponding to active site sequence SEQ ID NO:4 are highlighted in bold.

FIGS. 15A and B. Diagrammatic illustration of metabolic engineering enabling the conversion of $CO_2$ to propane via the up-regulation of butyric acid production in vivo. a) Engineering scheme and b) propane production from plasmid constructs of *Synechocystis* Aaas from $CO_2$ or butyrate feeding. CBB cycle=Calvin-Benson-Bassham cycle; 3-PGA=3-phosphoglycerate; ACP=acyl carrier protein; aas=acyl-acyl carrier protein synthase; Tes4=acyl-ACP thioesterase; Ery$^R$=erythromycin resistance gene.

FIG. 16A to C. Propane production by Halomonas st. XV12 expressing CvFAP constructs. a) Schematic of gene expression construct. b) Chart showing propane production of Halomonas constructs. c) Chart showing effect of butyric acid concentration on propane production by pHal2$_{G462V}$. Inset=effect of light intensity on propane production by the same construct. Constructs (all non-Hiss-tagged) were generated in the following modified plasmids: pSEVA321 (pHal1-FAP$_{WT}$ and pHal3-FAP$_{G462V}$ and pSEVA441 (pHal2-FAP$_{WT}$ and pHal2-FAP$_{G462V}$). Cultures were grown in phosphate buffered YTN6 medium spectinomycin (pHal2-FAPG462V; 50 µg/mL) or chloramphenicol (pHal1- and pHal3 constructs; 34 µg/mL) for 5 h at 37° C. and 180 rpm. Recombinant protein expression was induced with IPTG (0.1 mM) at an OD$_{600}$~1.6), and cultures were supplemented with butyric acid (0-100 mM). Triplicate aliquots (1 mL) of cultures were sealed into 4 mL glass vials and incubated at 30° C. for 16-18 h at 200 rpm, illuminated with a blue LED panel. Headspace gas was analysed for gaseous hydrocarbon content using a Micro GC.

FIG. 21. Chart showing fermentation of Halomonas expressing pHal2-FAP. G462V in a flat bed photobioreactor showing the culture growth (OD 680 nm) and propane production. Cultures were grown in high salt glycerol medium at pH 6.8 (5 g/L yeast extract, 1 g/L glycerol, 60 g/L NaCl, 50 µg/mL spectinomycin and 0.2 mL/L antifoam; 400 mL) at 30° C. with maximal stirring and 1 L/min aeration. For crude medium, seawater with supplemental NaCl and biodiesel waste glycerol were used in place of laboratory grade reagents. FAP$_{G462V}$ expression was induced with IPTG (0.1 mM) at mid-log phase (indicated by an asterisk), followed by the addition of sodium butyrate (60 mM pH ~6.8) and blue light exposure (1625 µmol/s/m$^2$ photons) for up to 48 h. Culture growth was maintained at OD 680 of 1.0 by automated feed addition. Propane production was monitored every 20 minutes by automated headspace sampling using a Micro GC.

FIG. 22. Table S1: Expression and activity of putative FAP homologues in E. coli.

FIG. 23. Table S2: Propane production of cell lysates of CvFAP$_{WT}$ and 28 variants expressed in E. coli.

FIG. 24. Table S3: Molecular docking simulations of CvPAS wild-type and variants with butyrate and palmitate.

FIG. 25. Table S4: In vivo propane production by CvFAP$_{G462V}$ variant in E. coli BL21(DE3).

FIG. 26. Table S5: In vivo propane production by N-His6-CvFAP$_{G462V}$ in pET21b expressed in E. coli.

FIG. 27. Table S6: In vivo production of gaseous hydrocarbons by variant CvFAP in E. coli in the presence of short chain organic acids FIG. 28. Table S7: Effect of butyric/valeric acid blends on gaseous hydrocarbon production by wild type CvFAP in E. colist. BL21(DE3)ΔyqhD/ΔyjgB.

FIG. 29. Table S8: In vivo propane production by CvFAP$_{G462V}$ variant in Halomonas st. XV12.

FIG. 30. Table S9: Oligonucleotide and other DNA sequences in E. coli and Halomonas.

FIG. 31. Table S11: Prefix and suffix used for DNA assembly.

FIG. 32. Table S12: Prefix and suffix linkers.

DETAILED DESCRIPTION OF THE INVENTION

Figure 1:
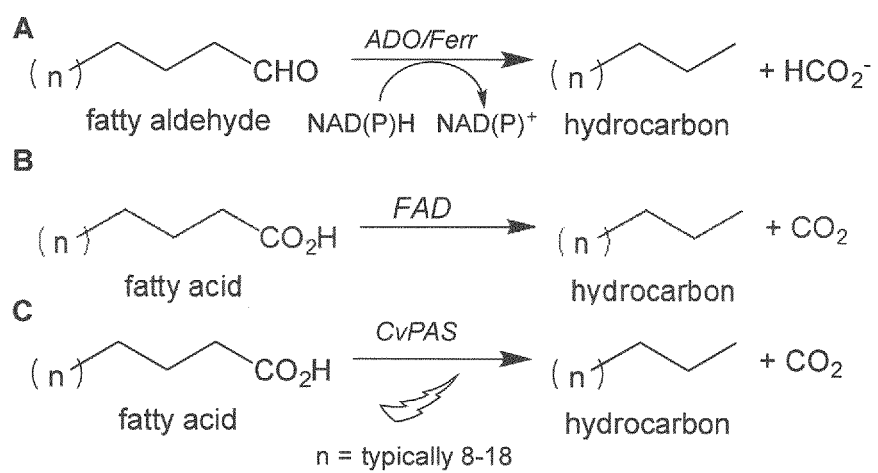
FIG. 1. Enzymatic routes to alkane formation. (A) NAD(P)H-dependent decarboxylation of fatty aldehydes by aldehyde deformylating enzyme (ADO) from *P. marinus* st. MIT9313. (B) General scheme of decarboxylation of fatty acids by fatty acid decarboxylases (FAD) (C) Decarboxylation of fatty acids by the light-dependent fatty acid decarboxylase photoalkane synthase (CvPAS) from *C. variabilis* NC64A.

Aspects and embodiments of the present invention will now be discussed with reference to the accompanying figures. Further aspects and embodiments will be apparent to those skilled in the art. All documents mentioned in this text are incorporated herein by reference.

The present invention is based on the identification by the inventors of enzymes capable of producing short chain hydrocarbons, such as butane, isobutane and propane, from short-chain fatty acids and coenzyme A activated fatty acids. As short chain fatty acids are commonly produced during the microbial breakdown of biomass, this provides a means of generating short chain hydrocarbons useful as biofuels from a readily accessible feedstock.

General Definitions

As used herein, a "fragment", "variant" or "homologue" of a protein may optionally be characterised as having at least 50%, preferably one of 60%, 70%, 75%, 80%, 85%, 90%, 91%, 92%, 93%, 94%, 95%, 96%, 97%, 98%, 99% or 100% amino acid sequence identity to the amino acid sequence of the reference protein. Fragments, variants, isoforms and homologues of a reference protein may be characterised by the ability to perform a function performed by the reference protein.

Pairwise and multiple sequence alignment for the purpose of determining percent identity between two or more amino acid or nucleic acid sequences can be achieved in various ways known to a person of skill in the art, for instance, using publicly available computer software such as ClustalOmega (Soding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

A "fragment" generally refers to a fraction of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by the same species as the species of the reference protein. A "homologue" generally refers to a variant of the reference protein produced by a different species as compared to the species of the reference protein.

A "fragment" of a reference protein may be of any length (by number of amino acids), although may optionally be at least 25% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein.

A fragment of a polypeptide may have a minimum length of one of 10, 20, 30, 40, 50, 60, 70, 80, 90 or 100 amino acids, and may have a maximum length of one of 15, 20, 25, 30, 40, 50, 100, 110, 120 or 130 amino acids.

As used herein, "hydrocarbons" are organic compounds comprising a backbone consisting of hydrogen and carbon. Hydrocarbons include alkanes, alkenes, arenes, cycloalkanes and alkynes. An alkane is a saturated hydrocarbon of the general formula Alkanes herein include straight chained (i.e. unbranched) and branched alkanes. An alkene is an unsaturated hydrocarbon with at least one carbon-carbon double bond. Preferred are isobutane, butane and propane, or a blend thereof commonly referred to as "liquid petroleum gas".

As used herein, a "CX" hydrocarbon or fatty acid is one having a total carbon number of X. For example, butane and isobutane are both a C4 hydrocarbons. The "CX" carbon is the carbon at the $X^h$ position. For example, the C5 carbon of stearic acid is the carbon at the $5^{th}$ position.

As used herein, "chain length" refers to the number of carbons in the longest continuous chain. For example, n-pentane has a chain length of 5, n-butane has a chain length of 4, whilst isobutane and propane have a chain length of 3.

As used herein, "fatty acid" refers to molecules a carboxylic acid (—COOH) with an aliphatic hydrocarbon chain. "Fatty acids" include salts and ions of fatty acids. For example, the fatty acid "butyric acid" includes the free acid butyric acid as well as butyrate, etc. "Short-chain" fatty acid as used herein, unless otherwise stated, refers to fatty acids having a 2-8 carbon chain length. Short-chain fatty acids may be 2, 3, 4, 5, 6, 7, or 8 carbons in chain length, for example 2-7, 2-6, 2-5, 2-4, 2-3 or 2 carbons in length. "Long-chain" fatty acids refers to those fatty acids which have longer chains than short-chain fatty acids. For example, long-chain fatty acids may refer to those a chain length of 13 or greater, preferably a chain length of 13-21, 13-20, 13-19, 13-18, 13-17, 13-16, 13-15, 13-14, 14-21, 14-20, 14-19, 14-18, 14-17, 14-16, 14-15, 14, 15-21, 15-20, 15-19, 15-18, 15-17, 15-16, 15, 16-21, 16-20, 16-19, 16-18, 16-17, 16, 17-21, 17-20, 17-19, 17-18, 17, 18-21, 18-20, 18-19, 18, 19-21, 19-20, 19, 20-21, 20, or 21 carbons.

Fatty Acid Decarboxylase

"Fatty acid decarboxylase", as used herein, refers to an enzyme with fatty acid decarboxylase activity, i.e. being capable of catalysing the removal of the carboxylic acid group from an n-fatty acid to produce an n-alkane or -alkene, in particular the direct removal without an aldehyde intermediate and without introducing a terminal unsaturation. This reaction scheme is depicted in FIG. 1C. Fatty acid decarboxylase activity can be measured by any method available to the skilled person.

Exemplary fatty acid decarboxylases are encoded by a polypeptide having the amino acid sequence of one of SEQ ID NOs:1, 2, and 8-19. In particular, SEQ ID NO:1 encodes photoalkane synthase from *Chlorella variabilis* NC64A (CvPAS), which is capable of blue light dependent decarboxylation of free fatty acids to n-alkanes or alkenes (FIG. 1C) [13]. CvPAS is a member of the glucose-methanol-choline oxidoreductase family, contains a bound photoexcitable FAD cofactor with a quantum yield of >80% (0.86±0.13 s$^{-1}$), and shows a preference for long chain fatty acids, particularly palmitic acid (C16) [13].

The 654 amino acid SEQ ID NO:1 corresponds to the full length polypeptide sequence for CvPAS (UniProt: A0A248QE08). This sequence is shown below:

SEQ ID NO: 1

MASITSRASARASCSQANTRAGRVALSGGALLRPARPARSFVPARKQQQGAVRRGGALSARASAVEDIR

KVLSDSSSPVAGQKYDYILVGGGTAACVLANRLSADGSKRVLVLEAGPDNTSRDVKIPAAITRLFRSPLD

WNLFSELQEQLAERQIYMARGRLLGGSSATNATLYHRGAAGDYDAWGVEGWSSEDVLSWFVQAETNA

DFGPGAYHGSGGPMRVENPRYTNKQLHTAFFKAAEEVGLTPNSDFNDWSHDHAGYGTFQVMQDKGTR

ADMYRQYLKPVLGRRNLQVLTGAAVTKVNIDQAAGKAQALGVEFSTDGPTGERLSAELAPGGEVIMCAG

AVHTPFLLKHSGVGPSAELKEFGIPVVSNLAGVGQNLQDQPACLTAAPVKEKYDGIAISDHIYNEKGQIRK

-continued
```
RAIASYLLGGRGGLTSTGCDRGAFVRTAGOALPDLQVRFVPGMALDPDGVSTYVRFAKFQSQGLKWPS

GITMQLIACRPOSTGSVGLKSADPFAPPKLSPGYLTDKDGADLATLRKGIHWARDVARSSALSEYLDGEL

FPGSGVVSDDQIDEYIRRSIHSSNAITGTCKMGNAGDSSSVVDNQLRVHGVEGLRVVDASVVPKIPGGQT

GAPVVMIAERAAALLTGKATIGASAAAPATVAA
```

The position G462 of SEQ ID NO:1 is highlighted in bold and solid underlined.

The native sequence comprises a 61 amino acid chloroplast targeting sequence at the N terminus (dotted underline), which is excised during trafficking. This sequence is removed and replaced by a methionine residue in the 594 amino acid SEQ ID NO:2:

```
                                                  SEQ ID NO: 2
MASAVEDIRKVLSDSSSPVAGQKYDYILVGGGTAACVLANRLSADGSKRV

LVLEAGPDNTSRDVKIPAAITRLFRSPLDWNLFSELQEQLAERQIYMARG

RLLGGSSATNATLYHRGAAGDYDAWGVEGWSSEDVLSWFVQAETNADFGP

GAYHGSGGPMRVENPRYTNKQLHTAFFKAAEEVGLTPNSDFNDWSHDHAG

YGTFQVMQDKGTRADMYRQYLKPVLGRRNLQVLTGAAVTKVNIDQAAGKA

QALGVEFSTDGPTGERLSAELAPGGEVIMCAGAVHTPFLLKHSGVGPSAE

LKEFGIPVVSNLAGVGQNLQDQPACLTAAPVKEKYDGIAISDHIYNEKGQ

IRKRAIASYLLGGRGGLTSTGCDRGAFVRTAGQALPDLQVRFVPGMALDP

DGVSTYVRFAKFQSQGLKWPSGITMQLIACRPQSTGSVGLKSADPFAPPK

LSPGYLTDKDGADLATLRKGIHWARDVARSSALSEYLDGELFPGSGVVSD

DQIDEYIRRSIHSSNAITGTCKMGNAGDSSSVVDNQLRVHGVEGLRVVDA

SVVPKIPGGQTGAPVVMIAERAAALLTGKATIGASAAAPATVAA
```

Position G402 of SEQ ID NO:2, corresponding to position G462 of SEQ ID NO:1, is highlighted in bold and solid underlined.

In this specification, "position G462 of SEQ ID NO:1" also refers to "position G402 of SEQ ID NO:2". "Position G462 of SEQ ID NO:1" shall be taken as equivalent to and interchangeable with "position G402 of SEQ ID NO:2".

Similarly, positions V453, G455, A457, Y466, T484 of SEQ ID NO:1 may be interchangeably described as positions V393, G395, A397, Y406 and T424 of SEQ ID NO:2.

SEQ ID NOs: 8 to 19 are homologues to SEQ ID NO:1 found in Aureococcus anophagefferens (SEQ ID NO:8), Chondrus crispus (SEQ ID NO:9), Chrysochromulina spp. (SEQ ID NO:10), Cyanidioschyzon merolae (SEQ ID NO:11), Chlamydomonas reinhardtii (SEQ ID NO:12), Coccomyxa subellipsoidea (SEQ ID NO:13), Gonium pectorale (SEQ ID NO:14), Phaeodactylum tricornutum (SEQ ID NO:15), Emiliania huxleyi (SEQ ID NOs:16 and 17), Nannochloropsis gaditana (SEQ ID NO:18, and Volvox carteri f. nagariensis (SEQ ID NO:19). The skilled person will appreciate how to perform sequence alignment to determine which residues are equivalent to G462 of SEQ ID NO:1. These residues are highlighted in FIG. 4.

In this specification "fatty acid decarboxylase" refers to a fatty acid decarboxylase from any species and includes isoforms, fragments, variants or homologues of fatty acid decarboxylase from any species. Homologues include orthologues. In some embodiments, the fatty acid decarboxylase is a prokaryotic fatty acid decarboxylase, e.g. a bacterial fatty acid decarboxylase. In some embodiments, the fatty acid decarboxylase is from, or is derived from, a microalgae, for example in a species within the genus Volvox, Chlamydomonas, Gonium, Chlorella, Coccomyxa, Aureococcus, Phaeodactylum, Chrysochromulina, Emiliania, Chondrus, or Cyanidioschyzon. Exemplary fatty acid decarboxylases are those found in Volvox carteri f. nagariensis, Chlamydomonas reinhardtii, Gonium pectorale, Chlorella variabilis, Coccomyxa subellipsoidea, Aureococcus anophagefferens, Phaeodactylum tricornutum, Chrysochromulina spp., Emiliania huxleyi, Chondrus crispus, or Cyanidioschyzon merolae.

The fatty acid decarboxylases provided herein are intended to be variants of a wild type that are not identical in terms of amino acid sequence to a naturally occurring wild type enzyme. As such, they may be described as "mutant", "non-naturally occurring" or "modified". Any amino acid substitutions that may have the effect of modifying the subject enzyme (e.g. the sequence of SEQ ID NO:1 or SEQ ID NO:2) so as to create a wild type sequence of a different enzyme, e.g. a homologue such as one of SEQ ID NOs 8-19 (or the mature amino acid sequence thereof lacking the chloroplast targeting sequence) is optionally excluded from the disclosure and may optionally be disclaimed from the invention claimed.

Fragments, variants, isoforms and homologues of a fatty acid decarboxylase may optionally be characterised by ability to catalyse conversion of a fatty acid into an alkane or alkene, in particular of a short-chain fatty acid to a short-chain alkene or alkane.

The fatty acid decarboxylases of the various aspects of the invention may be described in terms of similarity to a reference fatty acid decarboxylase. For example, the fatty acid decarboxylases may comprise at least 40% sequence identity to a reference sequence. The fatty acid decarboxylases of the various aspects of the invention may comprise at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% sequence identity to a reference sequence. The reference sequence may be any fatty acid decarboxylase, and may comprise an amino acid sequence corresponding to SEQ ID NO:1, SEQ ID NO:2, or any one of SEQ ID NOs:8 to 19. In preferred embodiments, the reference sequence is selected from SEQ ID NO:1 or 2. The fatty acid decarboxylases of the invention may have improved decarboxylase activity and/or give a higher yield compared to a reference fatty acid decarboxylase.

In some embodiments, the fatty acid decarboxylase comprises one or more amino acid substitutions relative to the amino acid sequence of a reference fatty acid decarboxylase (e.g. the fatty acid decarboxylase having the amino acid sequence of SEQ ID NO:1 or 2). In some embodiments, the fatty acid decarboxylase comprises e.g. 1, 2, 3, 4, 5, 6, 7, 8, 9, 10, 11, 12, 13, 14, 15, 16, 17, 18, 19, 20 or more amino acid substitutions relative to the amino acid sequence of the reference fatty acid decarboxylase. In some embodiments, the fatty acid decarboxylase comprises e.g. 1-3, 1-5, 1-10, 1-15 or 1-20 amino acid substitutions relative to the amino acid sequence of the reference fatty acid decarboxylase.

Figure 2:
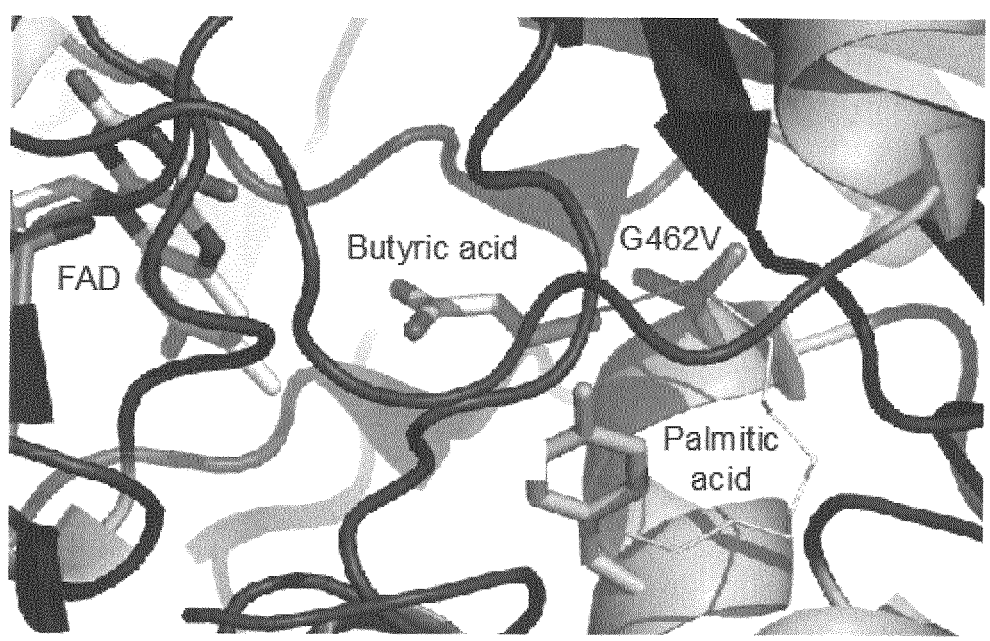
FIG. 2. Active site of palmitic acid-bound $CvPAS_{WT}$, showing the location of the variant G462V residue and modelled butyric acid. The overall structure (PDB: 5NCC) is shown as a cartoon with secondary structure colouring. The FAD and palmitic acid are shown as atom sticks and lines, respectively. A model of the butyric acid and G462V variant residue are shown as atom sticks. In this model, V462 clashes with the C5 atom of palmitic acid, but allows and stabilises butyric acid binding.

The higher preference of wild type fatty acid decarboxylases for palmitic acid (C16) is thought to be due to stabilisation of short hydrophobic chains as it wraps around the curved narrow solvent-exposed substrate-binding channel, (FIG. 2). Consequently, a preference for short-chain fatty acids can be engineered by introducing a substitution at a position equivalent to G462 to sterically block access to the solvent exposed substrate-binding channel.

As such, the fatty acid decarboxylases of the present invention comprise an amino acid substitution at a position corresponding to G462 of SEQ ID NO:1. A steric block may be introduced by substituting relatively small glycine side chain of G462 with a larger side chain. The amino acid substitution at the position corresponding to G462 of SEQ ID NO:1 may be made with any other amino acid not found at that position in the wild type sequence. Included in the disclosure is a method of substituting the amino acid at the position corresponding to G462 of SEQ ID NO:1 with any other amino acid not found at that position in the wild type sequence as specified herein.

Preferably, the substitution replaces the amino acid at the position corresponding to G462 of SEQ ID NO:1 with an amino acid the side chain of which sterically blocks access to the solvent exposed substrate-binding channel, e.g. so as to physically obstruct the channel so as to prevent binding of a long-chained fatty acid as defined herein. A steric block may be introduced by substituting an amino acid for one with a large, bulky, non-charged and/or non-polar side-chain. For example, a steric block may be introduced by substituting relatively small glycine side chain (H) of G462 of SEQ ID NO:1 with a larger, bulkier, non-charged and/or non-polar side chain.

In some embodiments, the amino acid at a position corresponding to G462 of SEQ ID NO:1 is substituted for a bulky residue selected from V, F, I, L, A, Y, C, H, N, Q, and W. In some embodiments, the amino acid at a position corresponding to G462 of SEQ ID NO:1 is substituted for a non-charged residue selected from V, F, I, L, A, Y, C, N, Q, and W. In some embodiments, the amino acid at a position corresponding to G462 of SEQ ID NO:1 is substituted for a non-polar residue selected from V, F, I, L, A, and W.

In some embodiments, the amino acid substitution at a position corresponding to G462 of SEQ ID NO:1 is G462V. In some embodiments, the amino acid substitution is G462F. In some embodiments, the amino acid substitution is G462I. In some embodiments, the amino acid substitution is G462L. In some embodiments, the amino acid substitution is G462A. In some embodiments, the amino acid substitution is and G462W. In some embodiments, the amino acid substitution is G462Y. In some embodiments, the amino acid substitution is G462C. In some embodiments, the amino acid substitution is G462H. In some embodiments, the amino acid substitution is G462N. In some embodiments, the amino acid substitution is G462Q.

The skilled person is well able to identify corresponding positions to the indicated positions in fatty acid decarboxylases other than that provided by reference sequence SEQ ID NO:1. Corresponding positions can be identified e.g. by alignment of the amino acid sequence of a given fatty acid decarboxylase to the amino acid sequence of SEQ ID NO:1. Sequence alignments for such purposes can be achieved in various ways known to a person of skill in the art, for instance, using publicly available computer software such as ClustalOmega (Soding, J. 2005, Bioinformatics 21, 951-960). By way of example, an alignment of the amino acid sequence of multiple fatty acid decarboxylases with SEQ ID NO:1 is shown in FIG. 4.

In some embodiments, the fatty acid decarboxylases further comprise the consensus sequence $$\text{(SEQ ID NO: 3)}$$
$$\text{G-X1-L-X2-X3-X4-X5-C-[D/E]-X6-G-[AG]-F-X7-[K/R]},$$

X being any amino acid.

Preferably, X1 can be selected from the group consisting of P, L and G. Preferably, X2 can be selected from the group consisting of T and A. Preferably, X3 can be selected from the group consisting of T, S and C. Preferably, X4 can be selected from the group consisting of P, T and A. Preferably, X5 can be selected from the group consisting of G and A. Preferably, X6 can be selected from the group consisting of H, N and R. Preferably, X7 can be a hydrophobic amino acid, especially selected from the group consisting of L, V A and F.

In some embodiments, the consensus sequence may have at least 50%, at least 55%, at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO:3. The consensus sequence may comprise 0, 1, 2, 3, 4, 5, 6, 7 or 8 substitutions, insertions or deletions relative to SEQ ID NO:3. In a preferred embodiment, the consensus sequence may comprise 0, 1, or 2 substitutions, insertions or deletions relative to SEQ ID NO:3.

The consensus sequence may be at a position corresponding to residues 425-429 of SEQ ID NO:1, or may be at a position within up to 20, up to 15, up to 10, up to 5, up to 3, up to 2 or up to 1 residues away from this position.

In some embodiments, the fatty acid decarboxylases of the invention comprise the active site sequence:

$$\text{(SEQ ID NO: 4)}$$
$$[I/L/K/D]X_{28-35}CX_{18-20}RX_{9-10}[Z]X_3[Y/I/L]XX[F/S/L/Y]X_{4-17}[T/S/G]XQX_{82-85}HXXN$$

wherein X is any amino acid, and [Z] is the amino acid substitution residue at a position corresponding to G462 of SEQ ID NO:1. In a preferred embodiment, the active site sequence comprises any of SEQ ID NO:5 or SEQ ID NO:6, wherein X is any amino acid and [Z] is the amino acid substitution residue at a position corresponding to G462 of SEQ ID NO:1. In a specific embodiment, the active site comprises the sequence:

(SEQ ID NO: 7)
IAISDHIYNEKGQIRKRAIASYLLGGRGGLTSTGCDRGAFVRTAGQALPD

LQVRFVPGMALDPD[Z]VSTYVRFAKFQSQGLKWPSGITMQLIACRPQST

GSVGLKSADPFAPPKLSPGYLTDKDGADLATLRKGIHWARDVARSSALSE

YLDGELFPGSGVVSDDQIDEYIRRSIHSSN wherein [Z] is the amino acid substitution residue at a position corresponding to G462 of SEQ ID NO:1.

The active site sequence may be at a position corresponding to residues 393-575 of SEQ ID NO:1, or may be at a position within up to 20, up to 15, up to 10, up to 5, up to 3, up to 2 or up to 1 residues away from this position.

The active site sequence may be further modified by an amino acid substitution at a position corresponding to one or more of V453, G455, A457, Y466, T484 of SEQ ID NO:1, as described herein.

In some embodiments, the fatty acid decarboxylases comprises an active site having a sequence which comprises at least 40% sequence identity, preferably at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% sequence identity to one or more consensus sequence selected from SEQ ID NOs:4 to 7.

Figure 3:
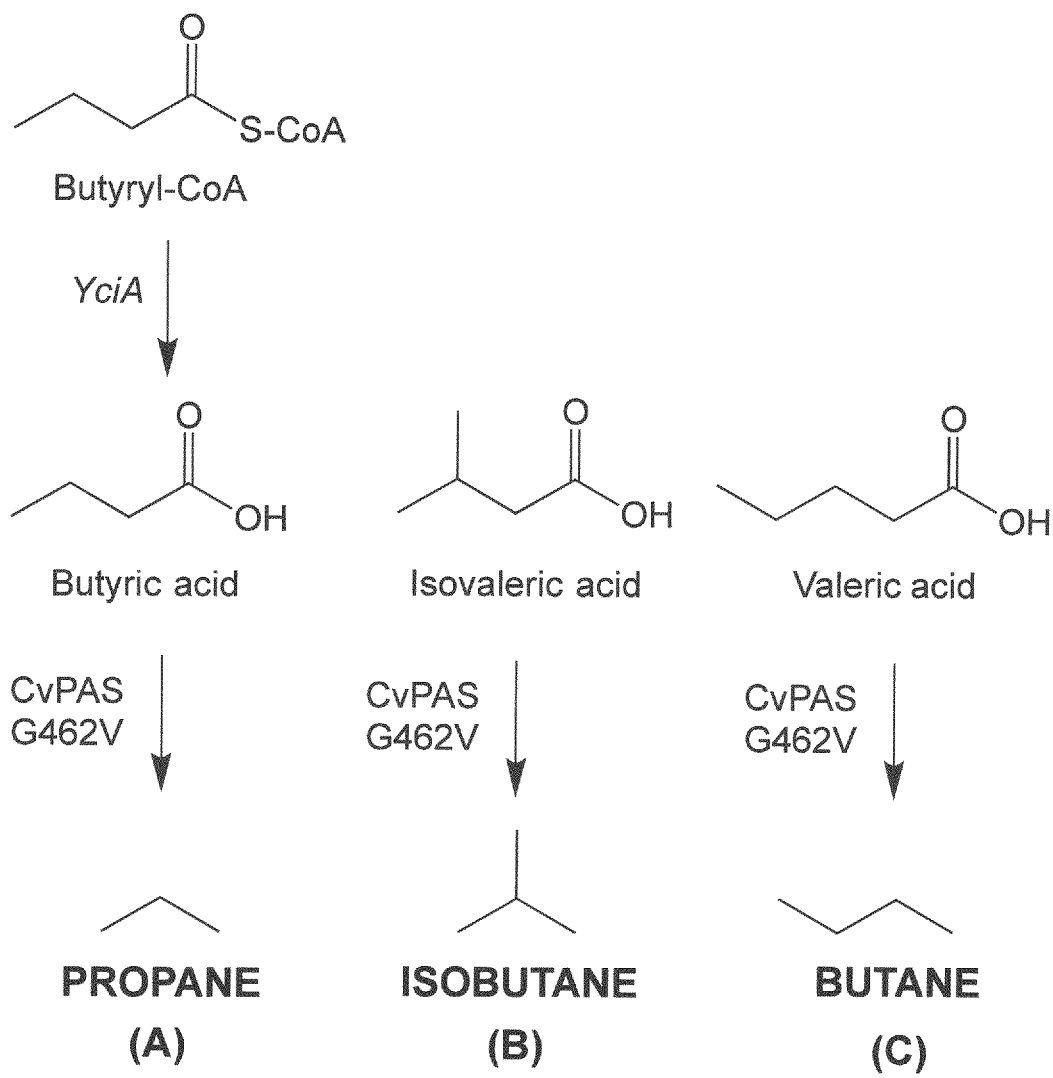
FIG. 3. Reaction pathways of exemplary fatty acid decarboxylase CvPAS G462V: (A) catalysis of the conversion of butyric acid to propane by CvPAS G462V; the pre-step of converting butyryl-CoA to butyric acid by YciA is optional. (B) catalysis of the conversion of valeric acid to butane by CvPAS G462V. (C) catalysis of the conversion of isovaleric acid to isobutane by CvPAS G462V.

The fatty acid decarboxylases described herein are capable of catalysing the conversion of a fatty acid into an alkane or alkene, in particular of a short-chain fatty acid to a short-chain alkene or alkane. For example, a fatty acid decarboxylase of the invention may be able to catalyse one, two, or all three of the conversion of butyric acid to propane (FIG. 3A), the conversion of valeric acid to butane (FIG. 3B) and/or the conversion of isovaleric acid to isobutane (FIG. 3B). In some embodiments, a fatty acid decarboxylase of the invention may be able to catalyse the conversion of butyric acid to propane and the conversion of valeric acid to butane. In a preferred embodiment, a fatty acid decarboxylase of the invention is able to catalyse the conversion of butyric acid to propane.

The fatty acid decarboxylases of the invention accept fatty acids as a substrate. A fatty acid accepted as a substrate is one capable of being bound and catalytically converted into a hydrocarbon by the fatty acid decarboxylase. Moreover, the fatty acid decarboxylases of the invention are engineered for the use of short-chain fatty acids as a substrate. This preferentially results in the generation of short-chain alkenes/alkanes, including as volatile alkenes/alkanes such as butane, isobutane and propane.

In some embodiments, the fatty acid decarboxylases accept short-chain fatty acids as a substrate, such as C2, C3, C4, C5, C6, C7, and/or C8 fatty acids. In some embodiments, the fatty acid decarboxylases accept C3 to C5 fatty acids. In some embodiments, the fatty acid decarboxylases accept C3 and/or C4 fatty acids. In some embodiments, the fatty acid decarboxylases may accept as a substrate fatty acids having a chain length of 10 carbons or less, 9 or less, 8 or less, 7 or less, 6 or less, 5 or less, 4 or less, 3 or less, or 2 or less. In some embodiments, the fatty acid decarboxylases may be able to accept C1-C8, C1-C7, C1-C6, C1-C5, C1-C4, or C1-C3 fatty acids. In some embodiments, the fatty acid decarboxylases may be able to accept C2-C8, C2-C7, C2-C6, C2-C5, C2-C4, or C2-C3 fatty acids.

In some embodiments, the fatty acid decarboxylases may have a preference for short chain length fatty acids compared to long chain fatty acids. In some embodiments, the fatty acid decarboxylases may be mostly or totally unable to accept fatty acids as a substrate other than short-chain fatty acids. In some embodiments, the fatty acid decarboxylases may be mostly or totally unable to accept fatty acids as a substrate with a chain length above a certain threshold. This preference and/or inability may be a result of the amino acid substitution at a position corresponding to G462 of SEQ ID NO:1 sterically clashing with and impeding the binding of fatty acids with a chain length greater than 8 carbons.

For example, the fatty acid decarboxylases of the invention may be unable to accept longer-chain fatty acids as a substrate, such as those with a chain length and/or total carbon number of 5 or more, 6 or more, 7 or more, 8 or more, 9 or more, 10 or more, 11 or more, 12 or more, 12 or more, 13 or more, 14 or more, 15 or more, 16 or more, 17 or more, 18 or more, 19 or more, 20 or more, 21 or more, or 22 or more carbons.

Properties of the fatty acid decarboxylases of the invention may be described by reference to a reference fatty acid decarboxylase. A "reference fatty acid decarboxylase" as used herein may be any fatty acid decarboxylase which does not comprise an amino acid substitution at a position corresponding to G462 of SEQ ID NO:1. The reference fatty acid decarboxylase may be a wild-type fatty acid decarboxylase. The reference fatty acid decarboxylase may be an equivalent fatty acid decarboxylase lacking the substitution at a position corresponding to G462 of SEQ ID NO:1 that is otherwise identical to the fatty acid decarboxylase of the invention. Reference fatty acid decarboxylases include SEQ ID NOs:1, 2, and 8 to 19, and homologues, variants and/or active fragments thereof.

The fatty acid decarboxylases may give a higher yield of short-chain alkanes/alkenes from the decarboxylation of short-chain fatty acids. In some embodiments, a fatty acid decarboxylase comprising the substitution gives a higher yield of a short-chain alkane/alkene compared to the yield of the same alkane/alkene obtained using a reference fatty acid decarboxylase in a comparable assay of fatty acid decarboxylase activity using a short-chain fatty acid as a substrate. The yield of the short-chain alkane/alkene obtained by a fatty acid decarboxylase comprising the substitution may be 5 times, 4.5 times, 4 times, 3.5 times, 3 times, times, 2 times, 1.9 times, 1.8 times, 1.7 times, 1.6 times, 1.5 times, 1.4 times, 1.3 times, 1.2 times, or 1.1 times the yield of the same short-chain alkane/alkene obtained using the reference fatty acid decarboxylase in a comparable assay of fatty acid decarboxylase activity using a short-chain fatty acid as a substrate.

In some embodiments, the higher yield is of a $C_n$ alkane/alkene and the short-chain fatty acid substrate is a $C_{n+1}$ fatty acid, where n≤8. For example, n may be selected from 1, 2, 3, 4, 5, 6, 7 or 8. In some embodiments, the higher yield is of a $C_n$ alkane/alkene and the short-chain fatty acid substrate is a $C_{n+1}$ fatty acid, where n≤5. For example, n may be selected from 1, 2, 3, 4, or 5. In a preferred embodiment, n=3. In some embodiments, the fatty acid substrate is valeric acid and the higher yield is of butane. In some embodiments, the fatty acid substrate is isovaleric acid and the higher yield is of isobutane. In some embodiments, the fatty acid substrate is a combination of valeric, isovaleric acid and/or butyric acids, and the higher yield is of a respective mixture of butane, isobutane and/or propane. In a preferred embodiment, n=3, the fatty acid substrate is butyric acid and the higher yield is of is propane.

In some embodiments, the fatty acid decarboxylase of the invention has a substrate preference for short-chain fatty acids compared to long-chain fatty acids. In some embodiments, the fatty acid decarboxylase of the invention may have a higher substrate preference for short-chain fatty acids over long-chain fatty acids relative to the substrate preference of a reference fatty acid decarboxylase. Substrate preference may be described with reference to the specificity constant ($k_{cat}/K_M$). A short-chain fatty acid substrate preference may be at least a 1.5-fold, 2-fold, 3-fold, 4-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, or 1000-fold higher than the preference for long-chain fatty acids. A short-chain fatty acid substrate preference of an enzyme of the invention may be at least a 1.5-fold, 2-fold, 3-fold, 4-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, or 1000-fold higher than the preference of a reference fatty acid decarboxylase. In some embodiments, the fatty acid decarboxylase of the invention may have a higher affinity for short-chain fatty acids compared to long-chain fatty acids. Higher affinity may be described with reference to $K_M$ value. In some embodiments, the fatty acid decarboxylase of the invention may have a higher affinity for short-chain fatty acids and/or a lower affinity for long-chain fatty acids compared to a reference fatty acid decarboxylase as defined herein. A higher affinity may be at least a 1.5-fold, 2-fold, 3-fold, 4-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, or 1000-fold higher affinity. The skilled person will appreciate how to calculate enzyme kinetics, which are reviewed for example in "The Chemical Kinetics of Enzyme Action", K J Laidler and P S Bunting, Clarendon Press, 1973, which is herein incorporated by reference.

In some embodiments, the fatty acid decarboxylases of the invention may give a yield of an alkene/alkane which is than 1 times, e.g. more than 1.1 times, 1.2 times, 1.3 times, 1.4 times, 1.5 times, 1.6 times, 1.7 times, 1.8 times, 1.9 times, 2.0 times, 2.1 times, 2.2 times, 2.3 times, 2.4 times, 2.5 times, 2.6 times, 2.7 times, 2.8 times, 2.9 times, 3.0 times, 3.5 times, 4.0 times, 5.0 times, 6.0 times, 7.0 times, 8.0 times, 9.0 times, or more than 10.0 times the yield obtained using the equivalent fatty acid decarboxylase lacking the substitution.

In some embodiments, a fatty acid decarboxylase comprising the substitution(s) produces an increased amount of an alkene/alkane, per unit time, per unit enzyme as compared to the reference protein. In some embodiments a fatty acid decarboxylase has a specific activity for conversion fatty acid to alkene/alkane (expressed e.g. in nmol·min$^{-1}$·mg$^{-1}$) which is more than 1 times, e.g. more than 1.1 times, 1.2 times, 1.3 times, 1.4 times, 1.5 times, 1.6 times, 1.7 times, 1.8 times, 1.9 times, 2.0 times, 2.1 times, 2.2 times, 2.3 times, 2.4 times, 2.5 times, 2.6 times, 2.7 times, 2.8 times, 2.9 times, 3.0 times, 3.5 times, 4.0 times, 5.0 times, 6.0 times, 7.0 times, 8.0 times, 9.0 times, or more than 10.0 times the specific activity of the equivalent fatty acid decarboxylase lacking the substitution(s) in a comparable assay.

Suitable comparative assays include one or more assays selected from: the cell free assay described in Example 3, the *E. coli* expression assay described in Example 4, and/or the *Halomonas* assay described in Example 6.

In some embodiments, a fatty acid decarboxylase comprising the substitution(s) produces in an assay an alkene/alkane yield per litre of reaction, for example of culture of cells comprising a fatty decarboxylase of the invention, equivalent to 0.01 mg/L, 0.02 mg/L, 0.03 mg/L, 0.04 mg/L, 0.05 mg/L, 0.06 mg/L, 0.07 mg/L, 0.08 mg/L, 0.09 mg/L, 0.1 mg/L, 0.2 mg/L, 0.3 mg/L, 0.4 mg/L, 0.5 mg/L, 0.6 mg/L, 0.7 mg/L, 0.8 mg/L, 0.9 mg/L, 1 mg/L, 2 mg/L, 3 mg/L, 4 mg/L, 5 mg/L, 6 mg/L, 7 mg/L, 8 mg/L, 9 mg/L, 10 mg/L, 11 mg/L, 12 mg/L, 13 mg/L, 14 mg/L, 15 mg/L, 16 mg/L, 17 mg/L, 18 mg/L, 19 mg/L, 20 mg/L, or more. In some embodiments, the yield may be normalised against the total weight of the fatty acid decarboxylase or cells comprising the fatty acid decarboxylase. In some embodiments, the reaction is performed at optimal conditions (e.g. temperature, pH, salinity, and saturating concentrations of substrate, cofactor, light, etc.). In some embodiments, the assay is as described in examples 2-4 and/or 6-8.

Fatty acid decarboxylases may be light dependent i.e. require exposure to light for its activity. For example, the microalga *Chlorella variabilis* NC64A harbours a glucose-methanol-choline oxidoreductase which catalyses the decarboxylation of free fatty acids to n-alkanes or n-alkenes in response to blue light. The light may be of any wavelength and/or colour or combination thereof (e.g. white light), but in particular may be blue (400-520 nm) or red (620-750 nm wavelength) light, most preferably blue light. In a preferred embodiment, the light has a wavelength from 400 to 520 nm, preferably from 450 nm to 495 nm, especially about 450 nm or 470 nm. The amount of light provided can be for instance from 10 to 3000 µmole.photon.m$^{-2}$·s$^{-1}$, preferably about 2000 µmole.photon.m$^{-2}$·s$^{-1}$. Fatty acid decarboxylases may require one or more cofactors in order to function. Exemplary cofactors include FAD (flavin adenine dinucleotide), which may be provided to the enzyme or, in the case of cell expression systems, produced from a heterologous or homologous gene(s).

Methods according to the present invention may be performed such that the fatty acid decarboxylases or cells producing them are exposed to light of the appropriate wavelength.

Aldehyde Dehydrogenase

As used herein, "aldehyde dehydrogenase" refers to an enzyme capable of catalysing the conversion of acyl-CoA to aldehydes, for example the conversion of butyryl-CoA to butyraldehyde.

Some aldehyde dehydrogenases, such as the *C. acetobutylicum* ATCC 824 enzyme AdhE2 (aldehyde/alcohol dehydrogenase; GenBank ID: Q9ANR5), are bi-functional enzymes that, in addition to converting butyrl-CoA to butyric acid, also convert butyryl-CoA to butanol, which is a toxic and undesirable by-product. Consequently, in some embodiments, an aldehyde dehydrogenase as employed by the invention does not catalyse an alcohol-forming reaction.

An exemplary aldehyde dehydrogenase is that from *Clostridium beijerinckii* (BALDH), the amino acid sequence of which is provided by SEQ ID NO:20. Other aldehyde dehydrogenases comprise polypeptides comprising an amino acid sequence selected from SEQ ID NO:32-37. In some embodiments, the butyraldehyde dehydrogenase comprises, or consists of, the amino acid sequence of any one of SEQ ID NO:20 or 32-37, or an amino acid sequence having at least 30%, preferably one of at least 35%, 40%, 45%, 50%, 55%, 60%, 65%, 70%, 75%, 80%, 85%, 90%, 91%, 92%, 93%, 94%, 95%, 96%, 97%, 98%, 99% or 100% amino acid sequence identity to the amino acid sequence of any one of SEQ ID NOs:20 or 32-37.

Fragments, variants, isoforms and homologues of an aldehyde dehydrogenase may optionally be characterised by the ability to catalyse conversion of butyryl-CoA to butyraldehyde.

Aldehyde Deformylating Oxygenase

As used herein, "aldehyde deformylating oxygenase" refers to an enzyme capable of catalysing the deformylation of aliphatic aldehydes for alkane biosynthesis (FIG. 1A). In particular, the present usage refers to enzymes capable of catalysing the deformylation of butyraldehyde to propane.

An exemplary aldehyde deformylating oxygenase is that from *Procholorococcus marinus* st. MIT9313 (ADO), as described in Menon N, et al *Biotechnol Biofuels* 2015; 8:61-12, which is herein incorporated by reference in its entirety. This enzyme catalyses the ferredoxin and oxygen-dependent decarbonylation of primarily long chain (C17-C19) fatty aldehydes into alkane hydrocarbons (C15-C17) and formate [9]. Structure-based engineering of the substrate access channel of ADO generated the variants A134F and V41Y with enhanced propane production [10].

The amino acid sequence of ADO is provided in SEQ ID NO:21. In some embodiments, an aldehyde deformylating oxygenase comprises, or consists of, the amino acid sequence of SEQ ID NO:21, or an amino acid sequence having at least 70%, preferably one of 80%, 85%, 90%, 91%, 92%, 93%, 94%, 95%, 96%, 97%, 98%, 99% or 100% amino acid sequence identity to the amino acid sequence of SEQ ID NO:21. In some embodiments, an aldehyde deformylating oxygenase comprises an amino acid substitution at a position corresponding to position A134 of SEQ ID NO:21. In some embodiments, the amino acid substitution is A134F. In some embodiments, an aldehyde deformylating oxygenase comprises an amino acid substitution at a position corresponding to position V41 of SEQ ID NO:21. In some embodiments, the amino acid substitution is V41Y.

The aldehyde deformylating oxygenases may give a higher yield of propane from the deformylation of butyraldehyde. In some embodiments, an aldehyde deformylating oxygenase comprising the substitution gives a higher yield of propane compared to the yield of propane obtained using a polypeptide comprising SEQ ID NO:21 in a comparable assay of aldehyde deformylating oxygenase activity using butyraldehyde as a substrate. The yield of propane obtained by an aldehyde deformylating oxygenase comprising the substitution may be ≥5 times, ≥4.5 times, ≥4 times, ≥3.5 times, ≥3 times, times, ≥2 times, ≥1.9 times, ≥1.8 times, ≥1.7 times, ≥1.6 times, ≥1.5 times, ≥1.4 times, ≥1.3 times, ≥1.2 times, or ≥1.1 times the yield of propane obtained using a polypeptide comprising SEQ ID NO:21 in a comparable assay of aldehyde deformylating oxygenase activity using butyraldehyde as a substrate.

Fragments, variants, isoforms and homologues of an aldehyde deformylating oxygenase may optionally be characterised by the ability to catalyse conversion of butyraldehyde to butane.

In some embodiments, the aldehyde deformylating oxygenase may use an electron transfer partner protein, such as ferredoxin. In some embodiments, the aldehyde deformylating oxygenase may use a coenzyme, such as nicotinamide adenine dinucleotide ($NAD^+$/NADH) or nicotinamide adenine dinucleotide phosphate ($NADP^+$/NADPH).

Other Enzymes

As used herein, an "acetyl-CoA acetyltransferase" refers to an enzyme capable of catalysis of the conversion of acetyl CoA to acetylacetyl-CoA. In some embodiments, the acetyl-CoA acetyltransferase comprises, or consists of, the amino acid sequence of SEQ ID NO:28, or an amino acid sequence having at least 70%, preferably one of 80%, 85%, 90%, 91%, 92%, 93%, 94%, 95%, 96%, 97%, 98%, 99% or 100% amino acid sequence identity to the amino acid sequence of SEQ ID NO:28.

As used herein, an "acetoacetyl CoA synthase" refers to an enzyme capable of catalysis of the conversion of malonyl-CoA to acetylacetyl-CoA. In some embodiments, the acetoacetyl CoA synthase comprises, or consists of, the amino acid sequence of SEQ ID NO:24, or an amino acid sequence having at least 70%, preferably one of 80%, 85%, 90%, 91%, 92%, 93%, 94%, 95%, 96%, 97%, 98%, 99% or 100% amino acid sequence identity to the amino acid sequence of SEQ ID NO:24.

As used herein, a "clostridial 3-hydroxybutyryl-CoA dehydrogenase" refers to an enzyme capable of catalysis of the conversion of acetylacetyl-CoA to 3-hydroxybutryryl-CoA. In some embodiments, the clostridial 3-hydroxybutyryl-CoA dehydrogenase comprises, or consists of, the amino acid sequence of SEQ ID NO:29, or an amino acid sequence having at least 70%, preferably one of 80%, 85%, 90%, 91%, 92%, 93%, 94%, 95%, 96%, 97%, 98%, 99% or 100% amino acid sequence identity to the amino acid sequence of SEQ ID NO:29.

As used herein, a "3-hydroxybutyryl-CoA dehydratase" refers to an enzyme capable of catalysis of the conversion of 3-hydroxybutryryl-CoA to crotonyl-CoA. In some embodiments, the clostridial 3-hydroxybutyryl-CoA dehydrogenase comprises, or consists of, the amino acid sequence of SEQ ID NO:30, or an amino acid sequence having at least 70%, preferably one of 80%, 85%, 90%, 91%, 92%, 93%, 94%, 95%, 96%, 97%, 98%, 99% or 100% amino acid sequence identity to the amino acid sequence of SEQ ID NO:30.

As used herein, a "trans-enoyl-CoA reductase" refers to an enzyme capable of catalysis of the conversion of crotonyl-CoA to butyryl-CoA. In some embodiments, the clostridial 3-hydroxybutyryl-CoA dehydrogenase comprises, or consists of, the amino acid sequence of SEQ ID NO:31, or an amino acid sequence having at least 70%, preferably one of 80%, 85%, 90%, 91%, 92%, 93%, 94%, 95%, 96%, 97%, 98%, 99% or 100% amino acid sequence identity to the amino acid sequence of SEQ ID NO:31.

As used herein, an "acyl-CoA thioester hydrolase" refers to an enzyme capable of catalysis of the conversion of butyryl-coenzyme A to butyric acid. In some embodiments, the clostridial 3-hydroxybutyryl-CoA dehydrogenase comprises, or consists of, the amino acid sequence of SEQ ID NO:23, or an amino acid sequence having at least 70%, preferably one of 80%, 85%, 90%, 91%, 92%, 93%, 94%, 95%, 96%, 97%, 98%, 99% or 100% amino acid sequence identity to the amino acid sequence of SEQ ID NO:23.

Nucleic Acids

In addition to amino acid sequences encoding the enzymes described herein, the disclosure provides nucleic acids encoding said sequences.

In some embodiments the nucleic acid is DNA. In some embodiments the nucleic acid is RNA. The nucleic acid may be single-stranded or double-stranded. The nucleic acid may be provided in isolated/purified form, or within a host cell.

A nucleic acid encoding an enzyme as described herein may be operably linked to a heterologous regulatory sequence, such as a promoter, for example a constitutive, or inducible promoter.

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

A "promoter" refers to a natural, engineered or synthetic nucleotide sequence that directs the initiation and rate of transcription of a coding sequence. Many suitable promoters are known in the art and may be used in accordance with the invention. The promoter contains the site at which RNA polymerase binds and also contains sites for the binding of other regulatory elements (such as transcription factors). Typically, a promoter includes a minimal promoter that is a short DNA sequence comprised of a Pribnow box (TATAAT), and other sequences that serve to specify the site of transcription initiation, to which regulatory elements are added for control of expression.

The nucleic acid encoding the enzyme may be contained on a nucleic acid construct or vector, particularly an expression vector. A "vector" as used herein is an oligonucleotide molecule (DNA or RNA) used as a vehicle to transfer foreign genetic material into a cell. Vectors include, inter alia, any plasmid, cosmid, phage etc. in double or single stranded linear or circular form, which may or may not be self-transmissible or mobilisable, and which can transform a prokaryotic or eukaryotic host, in particular a bacterial host, either by integration into the cellular genome or exist extra-chromasomally (e.g. autonomous replicating plasmid with an origin of replication).

The vector may be an expression vector for expression of the foreign genetic material in the cell. Such vectors may include a promoter and/or a ribosome binding site (RBS) sequence operably linked to the nucleotide sequence encoding the sequence to be expressed. A vector may also include a termination codon and expression enhancers. Such expression vectors are routinely constructed in the art of molecular biology and may for example involve the use of plasmid DNA and appropriate initiators, promoters, RBS, enhancers and other elements, such as for example polyadenylation signals, which may be necessary and which are positioned in the correct orientation in order to allow for protein expression.

The vector may be used to replicate the nucleic acid in a compatible host cell. Therefore, nucleic acids according to the present invention can be produced by introducing a polynucleotide into a replicable vector, introducing the vector into a compatible host cell and growing the host cell under conditions that bring about replication of the vector.

Vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express the enzymes from a vector according to the invention. Suitable vectors include plasmids, binary vectors, viral vectors and artificial chromosomes (e.g. yeast artificial chromosomes).

A construct or vector comprising nucleic acid as described above need not include a promoter or other regulatory sequence, particularly if the vector is to be used to introduce the nucleic acid into cells for recombination into the genome.

Constructs and vectors may further comprise selectable genetic markers consisting of genes that confer selectable phenotypes such as resistance to antibiotics such as kanamycin, hygromycin, phosphinotricin, chlorsulfuron, methotrexate, gentamycin, spectinomycin, chloramphenicol, ampicillin, etc.

Those skilled in the art can construct vectors and design protocols for recombinant gene expression, for example in a microbial cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook et al, 2001, Cold Spring Harbor Laboratory Press and Protocols in Molecular Biology, Second Edition, Ausubel et al. eds. John Wiley & Sons, 1992.

Any suitable vectors, promoters, enhancers and termination codons known in the art may be used to express a polypeptide from a vector according to the invention. In some embodiments, the vector may be a plasmid, phage, MAC, virus, etc.

In some embodiments, the vector may be a eukaryotic expression vector. In some embodiments, the vector may be a eukaryotic expression vector, e.g. a vector comprising the elements necessary for expression of protein from the vector in a eukaryotic cell. In some embodiments, the vector may be a mammalian expression vector, e.g. comprising a cytomegalovirus (CMV) or SV40 promoter to drive protein expression.

Other suitable vectors would be apparent to persons skilled in the art. By way of further example in this regard we refer to Sambrook et al., 2001, Molecular Cloning: a laboratory manual, $3^{rd}$ edition, Cold Harbour Laboratory Press.

The term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. The resulting transcript may then be translated into a desired peptide or polypeptide. The promoter may be a T7 promoter.

In some embodiments, the vector may comprise element for facilitating translation of encoded protein from mRNA transcribed from the construct. For example, the construct may comprise a ribosomal binding site (RBS) such as a Shine-Delgarno (SD) sequence upstream of the start codon. In some embodiments, RBS sequences may be designed to provide for different levels of expression of the encoded proteins.

In some embodiments, the vector may encode one or more response elements for modulating expression of the encoded protein(s). In some embodiments, the response element is an element that causes upregulation of gene or protein expression in response to treatment with a particular agent. For example, the agent may induce transcription of DNA encoding the protein(s) from a vector including a response element for the agent. In some embodiments the agent may be isopropyl β-D-1-thiogalactopyranoside (IPTG), and the vector may comprise a lac operator. Other induction agent/response element combinations are known in the art.

In some embodiments, the vector may encode one or more response elements for constitutive expression of the encoded protein(s), such that no induction is necessary.

In some embodiments the vector may comprise a transcription terminator sequence downstream of the sequences encoding to the protein or proteins of interest. In some embodiments the terminator may be a T7 terminator sequence. In some embodiments the vector may comprise a sequence encoding a detectable marker in-frame with the sequence encoding the protein of interest to facilitate detection of expression of the protein, and/or purification or isolation of the protein (e.g. a His, (e.g. 6×His), Myc, GST, MBP, FLAG, HA, E, or Biotin tag, optionally at the N- or C-terminus).

The nucleic acids/expression vectors can be introduced into a cell by any suitable means, which are well known to the skilled person. In some embodiments the nucleic acids/expression vectors are introduced into a cell by transformation, transduction, conjugation, transfection or electroporation.

Especially preferred are the T7 and T7-like promoter systems. T7 RNA polymerase is well known in the art. It is a very active enzyme, synthesising RNA at a high rate several times that of *E. coli* RNA polymerase. Furthermore, it has a lower frequency of termination, and its transcription can circumnavigate a plasmid, resulting in RNA several times the plasmid length in size. T7 RNA polymerase is also highly selective for initiation at its own promoter sequences and is resistant to antibiotics such as rifampicin that inhibit *E. coli* RNA polymerase.

"T7-like" systems are IPTG-inducible system that work like the viral polymerase T7 (IPTG-inducible; found in pET system vectors) but is a compatible system in other bacterial species, e.g. *Halomonas*. The gene MmP1 is a T7-like promoter that enables the IPTG-inducible expression of recombinant proteins in *Halomonas* (Zhao H et a/2017 Novel T7-like expression systems used for *Halomonas*. Metabolic Engineering 39: p. 128-140 which is herein incorporated by reference in its entirety). Preferably, the *Halomonas* strain comprises the MmP1 gene, either chromosomally integrated or on a vector or plasmid.

In some embodiments, the inducible system may use T7-like MmP1 or similar system (e.g. K1F, VP4 or RiboJ), or constitutive systems based on proD.

The following are T7-like promoter sequences which may be used upstream of the nucleic acids encoding the enzyme polypeptides in *Halomonas*:

```
>MmP1_high (Ih)
                                    (SEQ ID NO: 38)
ATATTTGTGGCATTATAGAATTGTGAGCGCTCACAATTAGCTGTCACCGG

ATGTGCTTTCCGGTCTGATGAGTCCGTGAGGACGAAACAG

>MmP1_med (Im)
                                    (SEQ ID NO: 39)
ATATTTGTGGCATTAGGGAATTGTGAGCGCTCACAATTAGCTGTCACCGG

ATGTGCTTTCCGGTCTGATGAGTCCGTGAGGACGAAACAG

>MmP1_low (Il)
                                    (SEQ ID NO: 40)
ATATTTGTGGCATACTTGAATTGTGAGCGCTCACAATTAGCTGTCACCGG

ATGTGCTTTCCGGTCTGATGAGTCCGTGAGGACGAAACAG
```

These require MmP1 genes in the *Halomonas* strain, where the MmP1 genes are incorporated either chromosomally or in a vector or plasmid.

Promoters may also be constitutive. "Constitutive" means no induction is needed (specific chemical addition such as IPTG) to express the recombinant protein. The following promoter sequences may be used upstream of the nucleic acids encoding the enzyme polypeptides in *Halomonas*, and provide varying levels of expression.

```
>P40-1_low (Cl)
                                    (SEQ ID NO: 41)
TTTTTCTATTGCGTCCGTGTATTCTTTTGTATAGAGTTTGAGAC >P40_med (Cm)
                                    (SEQ ID NO: 42)
TTTTTCTATTGCGTTCACTGGAATCCCAGTATAGAGTTTGAGAC >P40-9_high (Ch)
                                    (SEQ ID NO: 43)
TTTTTCTATTGCGTGAAAACAAGGATTTGTATAGAGTTTGAGAC >P40-58_vhigh (Cvh)
                                    (SEQ ID NO: 44)
TTTTTCTATTGCGTCAAAACATTTATTTGTATAGAGTTTGAGAC
```

Cells

The present disclosure also relates to cells comprising nucleic acids encoding the enzymes described herein. The cells may express the enzymes described herein. The cells may produce, contain, or secrete the enzymes described herein.

Cells may be provided in isolated form and/or in culture. Cells may be provided in vitro.

A cell comprising an enzyme according to the present invention may do so through expression from a nucleic acid/expression vector according to the present invention that has been introduced into the cell.

Cells contemplated for use with the present invention include prokaryotic and eukaryotic cells. For example, the prokaryotic cell may be a bacteria or archaea, and the eukaryotic microorganism may be a fungi, protist, or microscopic animal or microscopic plant organism. In some embodiments, the cells are isolated cells from a multicellular organism.

In preferred aspects, the cells are of a bacterium. In some embodiments, the bacterium may be a Gram-positive bacterium. Gram-positive bacteria include bacteria from the genus *Bacillus*, bacteria from the genus *Listeria*, *Clostridium* (e.g. *C. difficile*), or coccus such as *Staphylococcus* (e.g. *S. aureus*), or

*Streptococcus*. In some embodiments the bacterium may be a Gram-negative bacterium. Gram-negative bacteria may be defined as a class of bacteria that do not retain the crystal violet stain used in the Gram staining method of bacterial differentiation, making positive identification possible. Gram-negative bacteria include proteobacteria or bacteria of the family Enterobacteriaceae, such as *Escherichia coli*, *Salmonella* sp, *Shigella* sp, or bacteria selected from the genus *Pseudomonas, Helicobacter, Neisseria, Legionella, Halomonas, Klebsiella* or *Yersinia* bacterium.

Any bacterium may be used, such as laboratory strains (such as *E. coli* or *Bacillus subtilis*), or field strains. Preferred bacteria will be those that are organotrophic, e.g. chemoheterotrophic bacteria, capable of using biomass or compounds derived therefrom as an energy source.

Preferred bacteria are robust bacteria, such as soil bacteria and/or extremophilic bacteria. Extremophilic bacteria include slight halophiles (able to grow in 1.7 to 4.8% NaCl), moderate halophiles (able to grow in 4.7 to 20% NaCl), extreme halophiles (able to grow in 20 to 30% NaCl), acidophiles (able to grow in conditions of low pH, such as below pH 5.0, e.g. pH 2 or below), alkaliphiles (able to grow in conditions of pH 8.5 or above), metallotolerant bacteria (able to survive in environments containing high concentrations of dissolved heavy metals), thermophiles (with an optimal growth temperature between about 41 and 122° C., e.g. strains of Caldicellulosiruptor, *Thermotoga, Thermoanaerobacterium, Pyrococcus*, and Aeropyrum), or polyextremophiles (bacterial possessing two or more extremophilic characteristics). Such bacteria may find particular utility in the culture of bacteria in biomass fermenters to produce hydrocarbons.

Especially preferred are halophilic bacteria. These are capable of growing in open non-sterile conditions. As these strains are salt tolerant, they will not be outcompeted so long as there is a high salt content. Furthermore, the addition of a high salt buffer (e.g. at least a 3% salt solution) can be used to control competing bacteria. Halophilic bacteria include those of the genus *Halomonas*. Exemplary species of *Halomonas* have been described, including *H. alimentaria, H. alkaliantarctica, H. alkaliphila, H. almeriensis, H. andesensis, H. anticariensis, H. aquamarina, H. arcis, H. axialensis, H. beimenensis, H. bluephagenesis, H. boliviensis, H. campaniensis, H. campisalis, H. caseinilytica, H. cerina, H. cibimaris, H. cupida, H. daqiaonensis, H. daqingensis, H.*

*denitrificans, H. desiderata, H. elongata, H. eurihalina, H. flava, H. fontilapidosi, H. garicola, H. gomseomensis, H. gudaonensis, H. halmophila, H. halocynthiae, H. halodenitrificans, halophila, H. hamiltonii, H. heilongjiangensis, H. huangheensis, H. hydrothermalis, H. ilicicola, H. janggokensis, H. jeotgali, H. johnsoniae, H. kenyensis, H. koreensis, H. korlensis, H. kribbensis, H. lutea, H. lutescence, H. magadiensis, H. maura, H. meridian, H. mongoliensis, H. muralis, H. nanhaiensis, H. neptunia, H. nitroreducens, H. olivaria, H. organivorans, H. pacifica, H. pantelleriensis, H. qiaohouensis, H. qijiaojingensis, H. ramblicola, H. rifensis, H. sabkhae, H. saccharevitans, H. salicampi, H. salifodinae, H. salina, H. sediminicola, H. shengliensis, H. sinaiensis, H. smyrnensis, H. songnenensis, H. stenophila, H. stevensii, H. subglaciescola, H. subterranean, H. sulfidaeris, H. taeanensis, H. titanicae, H. urumqiensis, H. variabilis, H. ventosae, H. venusta, H. vilamensis, H. xianhensis, H. xinjiangensis, H. zhangjiangensis,* and *H. zincidurans.*

Preferred *Halomonas* strains include *Halomonas* st. TQ10 and *Halomonas* st. TD01. Strain TQ10 is a genetically modified version of TD01 strain where the gene encoding MmP1 has been chromosomally integrated into the bacterium. The gene MmP1 is a T7-like promoter that enables the IPTG-inducible expression of recombinant proteins in *Halomonas* (Zhao H et al 2017 Novel T7-like expression systems used for *Halomonas*. Metabolic Engineering 39: p. 128-140 which is herein incorporated by reference in its entirety). Preferably, the *Halomonas* strain comprises the MmP1 gene, either chromosomally integrated or on a vector or plasmid.

Figure 9:
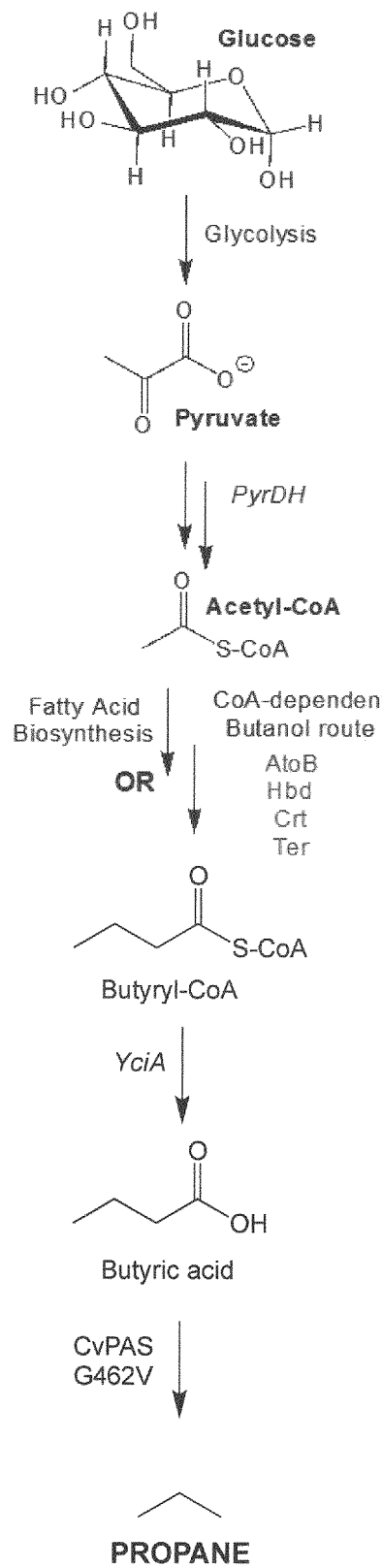
FIG. 9. Reaction pathway from glucose to propane via butyric acid through the action of CvPAS.

Bacteria for use in the invention may be able to produce fatty acids, for example short chain fatty acids like butyric acid, from biomass feedstocks. For example, bacteria may be able to convert glucose or cellulose to a fatty acid, and the fatty acid into hydrocarbon, as shown in FIG. 9. A bacterium may possess the endogenous genes required for the conversion of glucose or cellulose to a fatty acid, or this ability may be conferred by one or more heterologous genes. A bacteria capable of producing fatty acids may comprise a nucleotide sequence encoding any number of polypeptides according to SEQ ID NOs:23-31.

In particular embodiments, *Escherichia* bacteria such as *E. coli, Saccharomyces* yeast such as *S. cerevisiae* and cyanobacteria are contemplated for use in the present invention.

In some embodiments the polypeptides may be prepared by cell-free-protein synthesis (CFPS), e.g. using a system described in Zemella et al. Chembiochem (2015) 16(17): 2420-2431, which is hereby incorporated by reference in its entirety.

The present invention also provides a method for producing a composition according to the invention, comprising (i) culturing a cell according to the present invention under conditions suitable for expression of encoded protein(s). In some embodiments the method further comprises (ii) isolating said expressed protein(s). The invention also encompasses the compositions produced by such methods.

The present invention also provides compositions comprising the cells, nucleic acids, expression vectors, and enzymes/combinations of enzymes according to the present invention. The compositions find use e.g. in methods for hydrocarbon biosynthesis according to the present invention.

The present invention also provides a cell, such as a bacterial cell, comprising a heterologous fatty acid decarboxylase.

Recombinant Production of Polypeptides Encoding Enzymes

The polypeptides encoding enzymes according to the present disclosure may be prepared according to methods for recombinant protein production known to the skilled person. Molecular biology techniques suitable for recombinant production are well known in the art, such as those set out in Green and Sambrook, Molecular Cloning: A Laboratory Manual (4th Edition), Cold Spring Harbor Press, 2012, which is hereby incorporated by reference in its entirety.

Expression may be from a nucleic acid sequence and/or an expression vector, e.g. a nucleic acid sequence or expression vector according to the present invention. Any suitable vectors, promoters, enhancers and termination codons known in the art may be used to express a peptide or polypeptide from an expression vector according to the invention. Expression may be from a cell according to the present invention. Any cell suitable for the expression of polypeptides encoding enzymes may be used.

Production may involve culture or fermentation of cell modified to express the relevant polypeptide(s). The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted or expressed peptide or polypeptide. Culture, fermentation and separation techniques are well known to those of skill in the art, and are described, for example, in Green and Sambrook, Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, light wavelength and intensity, flow rates into and out of, and agitation within the vessel such that optimum conditions are provided for the cells being cultured.

Following culturing the cells that express the polypeptide(s) of interest may be isolated. Any suitable method for separating proteins from cells known in the art may be used. In order to isolate the polypeptide it may be necessary to separate the cells from nutrient medium.

If the polypeptide(s) are secreted from the cells, the cells may be separated from the culture media that contains the secreted polypeptide(s) of interest by centrifugation.

If the polypeptide(s) of interest collect within the cell, protein isolation may comprise centrifugation to separate cells from cell culture medium, treatment of the cell pellet with a lysis buffer, and cell disruption e.g. by sonification, rapid freeze-thaw or osmotic lysis.

It may then be desirable to isolate the polypeptide(s) of interest from the supernatant or nutrient medium, which may contain other protein and non-protein components.

One approach to separating protein components from a supernatant or culture medium is by precipitation. Proteins of different solubilities are precipitated at different concentrations of precipitating agent such as ammonium sulphate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulphate from the separated proteins. Other methods for separating protein components include ion exchange chromatography and size exclusion chromatography. These may be used as an alternative to precipitation, or may be performed subsequently to precipitation.

Once the polypeptide(s) of interest have been isolated from the culture it may be desired or necessary to concentrate the peptide or polypeptide. A number of methods for concentrating proteins are known in the art, such as ultrafiltration and lyophilisation.

It will be appreciated that the polypeptides encoding enzymes according to the present invention may be provided as components of larger polypeptides encoding enzymes or polypeptide complexes. For example, the polypeptides encoding enzymes described herein may be provided as fusion polypeptides encoding enzymes. In some embodiments the polypeptides encoding enzymes may comprise amino acid sequence(s) to facilitate expression, folding, trafficking, processing or purification, e.g. His, (e.g. 6×His), Myc GST, MBP, FLAG, HA, E, or Biotin tag, optionally at the N- or C-terminus.

Production of Hydrocarbons

The present disclosure also provides methods comprising the catalysis of the conversion of feed stocks into alkenes and/or alkanes using one or more enzymes. These methods may be methods of producing short-chain alkanes such as propane, butane and isobutane, which are useful as fuels.

In some embodiments, the methods comprise providing substrate for a conversion. The method may comprise adding the substrate or a metabolic precursor to a vessel containing the enzyme. In some embodiments the methods additionally comprise recovering the product of a conversion. In some embodiments the product may be recovered and used as the substrate in a conversion in accordance with a subsequent method step. In some embodiments the product is recovered as the final product of the method. Recovered product may be isolated/purified. Products of reactions can be analysed e.g. by gas chromatography, high performance liquid chromatography and/or mass spectrometry.

Any suitable substance containing the catalytic substrate may be used as a feedstock. In a preferred embodiment, the method uses biomass-derived feedstock, such as the products of microbial processing of biomass by microbial digestion/fermentation. Such feed stocks are typically rich in butyric acid, isovaleric acid, and/or valeric acid, as well as their precursors.

It will further be appreciated that "a method comprising catalysis of the conversion of substrate X into product Y using an enzyme Z" implicitly includes contacting substrate X with enzyme Z under conditions suitable for conversion of the substrate X to product Y. The method may include incubation steps.

In some embodiments the enzymes are provided sequentially. In some embodiments the enzymes are provided simultaneously (i.e. together). In some embodiments the enzymes are provided simultaneously by sequentially adding enzyme/enzymes (i.e. one after another).

Factors relevant to the conditions suitable for the relevant conversion or conversions in accordance with the methods of the present invention include the enzyme(s), the substrate(s), the activity of the enzyme(s), the concentration of the enzyme(s), the concentration of the substrate(s), enzyme co-factor concentration/availability, temperature, salinity, pH, agitation, carbon dioxide levels, oxygen levels, nutrient availability, reaction volume, presence of visible light (in particular blue light e.g. around 470 nm), etc.

Suitable conditions for a given conversion or combination of conversions in accordance with the methods of the present invention can be readily determined by the skilled person with reference e.g. to the experimental examples of the present application and the references identified herein, as appropriate to the desired reaction products.

In some embodiments, one or more co-factors or electron transfer partner may be provided to the reaction(s). In some embodiments, one or more sources of co-factors or electron transfer partner are provided. In some embodiments systems for producing/recycling one or more co-factors/electron transfer partner or sources of co-factors/electron transfer partner are provided. In some embodiments the co-factor or electron transfer partner is selected from NADH, $NAD^+$, NADPH, $NADP^+$, FAD, ferredoxin and/or di-iron or a manganese-iron prosthetic group. If the electron transfer partner is ferredoxin, the ferredoxin may contain an iron sulphur prosthetic group.

Methods according to the present invention may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo" refers to something present or taking place outside an organism, e.g. outside the human or animal body, which may be on tissue (e.g. whole organs) or cells taken from the organism.

Methods according to the present invention may be performed outside the human or animal body. For example, the methods may be performed in in a container, bioreactor, fermenter or similar apparatus. As such, methods according to the present invention may be performed, or products may be present, in vitro or ex vivo. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo" refers to something present or taking place outside an organism, e.g. outside the human or animal body, which may be on tissue (e.g. whole organs) or cells taken from the organism.

In some embodiments, the methods of the present invention are performed in vitro. In some embodiments, the methods of the present invention are performed using an isolated/purified enzyme(s). In some embodiments the enzyme(s) are obtained from a commercial source. In some embodiments the enzyme(s) may be, or may have been, expressed recombinantly and subsequently isolated/purified, e.g. as described herein. In some embodiments the enzyme(s) may be obtained from an organism (e.g. a microorganism) or cells, tissue or organs of a multicellular organism expressing the enzyme(s). In some embodiments, the enzyme(s) may be obtained from an organism or cells, tissue or organs of a multicellular organism expressing the enzyme(s) as a consequence of expression of nucleic acid endogenous to the organism. In some embodiments, the enzyme(s) may be obtained from an organism expressing the enzyme(s) as a consequence of expression of heterologous nucleic acid that is non-endogenous to the organism (e.g. a nucleic acid/expression vector according to the present invention). In some embodiments, the organism or cells, tissue or organs of a multicellular organism expressing the enzyme(s) may secrete the enzyme(s). In some embodiments, obtaining the enzyme(s) may comprise isolating/purifying the enzyme(s) from an organism (e.g. a microorganism) or cells, tissue or organs of a multicellular organism expressing the enzyme(s), or from secreted products thereof.

In some embodiments, the methods of the present invention are performed using an extract(s) of an organism (e.g. a microorganism) or cells, tissue or organs of a multicellular organism expressing the enzyme(s). Extracts are prepared such that the enzyme(s) retain the relevant activity. In some embodiments, the extract(s) may be prepared from organism or cells, tissue or organs of a multicellular organism expressing the enzyme(s) as a consequence of expression of nucleic acid endogenous to the organism. In some embodiments, the extract(s) may be prepared from organism or cells, tissue or organs of a multicellular organism expressing the enzyme(s) as a consequence of expression of heterologous nucleic acid that is non-endogenous to the organism (e.g. a nucleic acid/expression vector according to the present invention). Preparation of extracts may include one or more of: homogenising the organ/tissue/cells (e.g. via a cell disruptor or sonication), lysing the cells (e.g. with a lysis buffer), removing cell debris, etc.

In some embodiments the methods of the present invention are performed using live or whole cells (e.g. intact respiring cells). In some embodiments, the enzyme(s) and substrate(s) may contact one another inside a cell. In some embodiments the substrate may be produced by the cell. In some embodiments the substrate/a precursor thereof may diffuse into the cell. In some embodiments the substrate/a precursor thereof may be taken up by the cell, e.g. by active transport across the cell membrane. In some embodiments the enzyme(s) may be secreted from live cells, and the enzyme(s) and substrate(s) may contact one another outside of a cell. In some embodiments, the method is performed in non-sterile conditions.

In methods requiring multiple catalytic steps, it will be appreciated that compositions providing multiple enzymes are desirable. The disclosure therefore provides compositions comprising multiple enzymes, for example all the enzymes listed for a given method. Also provided herein are nucleic acids encoding multiple enzymes required for a given method. These encoded enzymes may be comprised as a single expression cassette, for example under unitary control of a promoter. Also provided herein are a plurality of nucleic acids encoding all the enzymes listed for the given method, wherein an or each individual nucleic acid may encode none, one, or multiple enzymes listed for the given method. In a preferred embodiment, cells are provided, such as bacterial cells, comprising nucleic acids encoding multiple enzymes listed for a given method. Also provided herein is a composition comprising a plurality of cells, wherein the composition comprises multiple enzymes listed for a given method, wherein an or each cell comprises nucleic acids encoding none, one, or multiple enzymes listed for the given method. The composition may comprise a plurality of strains carrying different nucleic acids encoding one or more listed enzymes.

Figure 10:
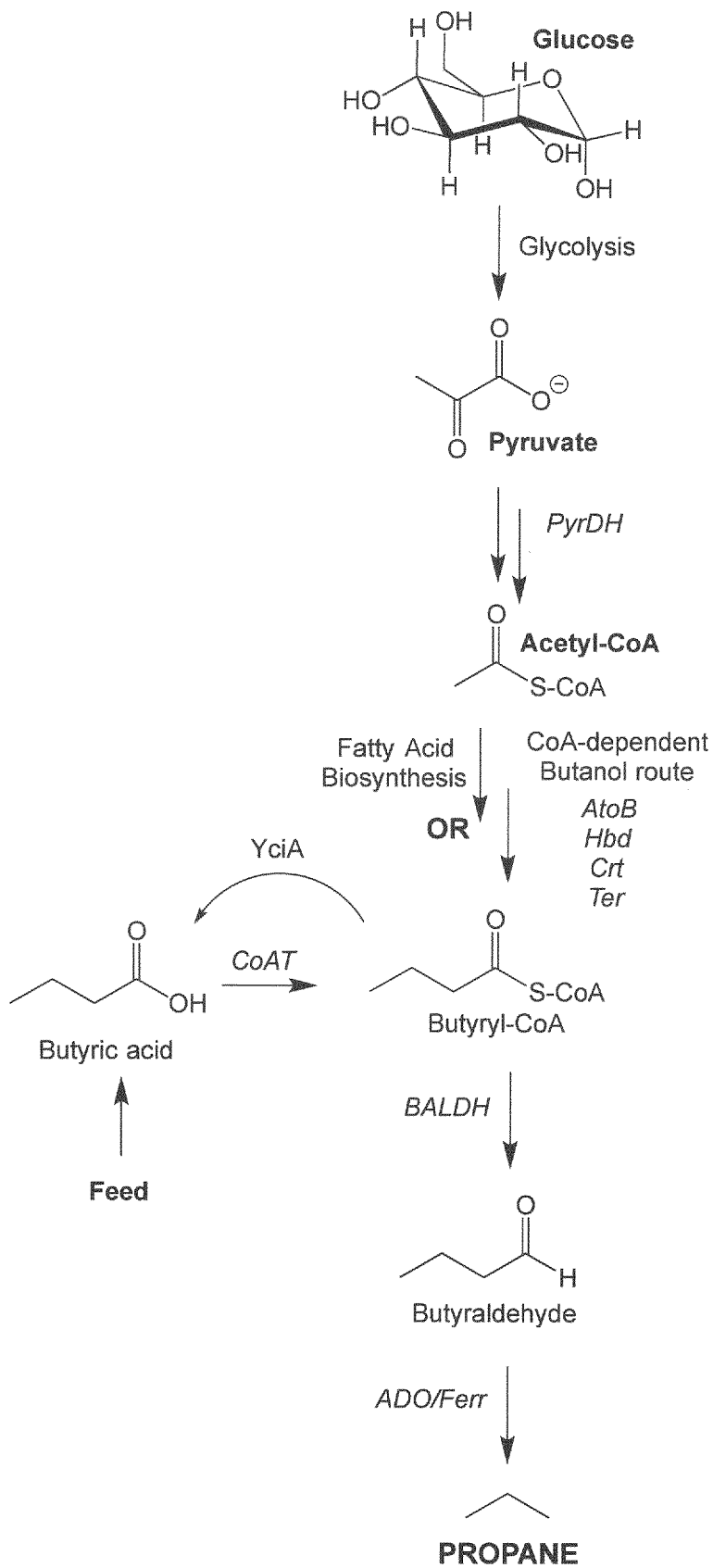
FIG. 10. Reaction pathway from glucose to propane via butyraldehyde through the action of BALDH/ADO.

The methods provided herein are applicable in the bioconversion of biomass feedstock into hydrocarbons, particularly gaseous fuels. In these methods, a bacterial cell of the invention, or a culture thereof, may be added to a biomass feedstock. The bacterial cell may individually be capable of converting glucose and/or cellulose in the feedstock into a hydrocarbon, e.g. it may be capable of carrying out an entire reaction scheme shown in FIG. 8, 9 or 10. Alternatively, the cell may only be able to process an intermediate downstream of glucose/cellulose into a hydrocarbon. The method may involve the additional step of converting the biomass feedstock into an intermediate accepted by the bacterial cell of the invention. This may be performed simultaneously or prior to the conversion of the intermediate into a hydrocarbon. The conversion may be performed by one or more additional strains of bacteria. The methods may further comprise a step of killing unwanted bacteria, e.g. through autoclaving or addition of a material toxic to unwanted bacteria but tolerated by the cells of the invention. In some embodiments, the toxic material is an antibiotic, a salt solution, a hydrogen peroxide solution, and/or an agent that alters pH.

In some embodiments the polypeptides encoding enzymes may be prepared by cell-free-protein synthesis (CFPS), e.g. using a system described in Zemella et al. ChemBioChem (2015) 16(17): 2420-2431, which is hereby incorporated by reference in its entirety.

Provided herein are methods comprising the catalysis of the conversion of a fatty acid to an alkane and/or alkene using a fatty acid decarboxylase. Preferably, the method comprises the catalysis of the conversion of a short-chain fatty acid to an alkane and/or alkene using a fatty acid decarboxylase. In some embodiments, the method comprises the catalysis of the conversion of a $C_{n+1}$ fatty acid to a $C_n$ alkane using a fatty acid decarboxylase, where n≤8, or n≤5. The fatty acid decarboxylase may be any such enzyme as described herein.

The methods may use a variety of substrates. For example, the fatty acid substrate may be butyric acid, valeric acid, or isovaleric acid, producing propane, butane and isobutane respectively. However, the method may utilise a mixture of substrates that are capable of conversion by the fatty acid decarboxylase. For example, a fatty acid decarboxylase may be provided with a mixture of butyric acid, valeric acid, and isovaleric acid, producing a mixture of propane, butane and isobutane. A fatty acid decarboxylase may be provided with a mixture of butyric acid and isovaleric acid, producing a mixture of propane and isobutane. A fatty acid decarboxylase may be provided with a mixture of butyric acid and valeric acid, producing a mixture of propane and butane. A fatty acid decarboxylase may be provided with a mixture of valeric acid and isovaleric acid, producing a mixture of butane and isobutane.

In some embodiments, the methods comprise steps prior to the conversion of a catalytic substrate into an alkene/alkane.

For example, the method may comprise the step of catalysis of the conversion of acyl-coenzyme A (acyl-CoA) to a fatty acid using acyl-CoA thioester hydrolase prior to the catalysis of the conversion of a fatty acid to an alkene/alkane using a fatty acid decarboxylase. This provides more fatty acids for conversion, resulting in increased yield of alkenes/alkanes. The acyl-coenzyme A (acyl-CoA) may, for example, be butyryl-CoA, yielding butyric acid, but may be any other acyl-CoA with a chain length of 1, 2, 3, 4 or 5 carbons. A preferred acyl-CoA thioester hydrolase is YciA (SEQ ID NO:23), or a derivative, fragment or variant thereof (e.g. a sequence comprising at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO:23). Also provided herein are methods comprising catalysis of the conversion of butyryl-CoA to butyraldehyde using an aldehyde dehydrogenase, such as a butyraldehyde dehydrogenase, followed by catalysis of the conversion of butyraldehyde to propane using an aldehyde deformylating oxygenase. The method may be a method of producing propane.

The method may utilise an aldehyde dehydrogenase from *Clostridium beijerinckii*, or a fragment, variant, or homologue thereof. The method may utilise an aldehyde dehydrogenase according to SEQ ID NO:20, or a variant, fragment or homologue thereof as described herein. The method may utilise an aldehyde deformylating oxygenase according to SEQ ID NO:21, or a variant, fragment or homologue thereof as described herein. The aldehyde deformylating oxygenase may be provided with a cofactor and electron transfer partner, such as ferredoxin and/or NADH/NADPH.

In some embodiments, the method comprises a pre-enrichment step, comprising the conversion of butyric acid into butyryl-CoA. As many suitable feed stocks are high in butyric acid, this increases overall output of this enzymatic pathway. The catalytic conversion of butyric acid to butyryl-CoA may be performed using a butyrate-acetoacetate CoA transferase. The conversion of butyryl-CoA to butyraldehyde using an aldehyde dehydrogenase then proceeds as before. Exemplary butyrate-acetoacetate CoA transferases include that provided by SEQ ID NO:22, or a variant, fragment or homologue thereof.

As the method requires multiple steps, it will be appreciated that compositions providing multiple enzymes are desirable. The disclosure therefore provides compositions comprising aldehyde dehydrogenase, aldehyde deformylating oxygenase and (optionally) butyrate-acetoacetate CoA transferase. Also provided herein are nucleic acids encoding the aldehyde dehydrogenase and an aldehyde deformylating oxygenase. These two encoded enzymes may be comprised as a single expression cassette, for example under unitary control of a promoter. Alternatively, an expression cassette may contain more than one promoter, for example up to one promoter per enzyme expressed such that a 'cassette' may contain multiple enzymes and up to the same number of promoters as enzymes. Nucleic acids may optionally further comprise the butyrate-acetoacetate CoA transferase, which may also be in the same expression cassette.

Also provided herein are a plurality of nucleic acids encoding aldehyde dehydrogenase, aldehyde deformylating oxygenase and (optionally) butyrate-acetoacetate CoA transferase. Individual nucleic acids within the plurality may comprise none, one, two, or all three enzymes.

In a preferred embodiment, the enzymes are provided in cells, such as bacterial cells. For example, cells comprising a nucleic acid encoding a heterologous aldehyde dehydrogenase may be provided. The cells may further comprise a nucleic acid encoding an aldehyde deformylating oxygenase and/or a nucleic acid encoding a butyrate-acetoacetate CoA transferase. Also provided herein is a composition comprising a plurality of cells, wherein the composition comprises at least one cell comprising a nucleic acid encoding an aldehyde dehydrogenase, at least one cell comprising a nucleic acid encoding a aldehyde deformylating oxygenase, and optionally at least one cell comprising a nucleic acid encoding a butyrate-acetoacetate CoA transferase. At least one cell may comprise nucleic acids encoding two, or three of the enzymes. Alternatively, nucleic acids encoding the enzymes may be in separate cells.

Figure 8:
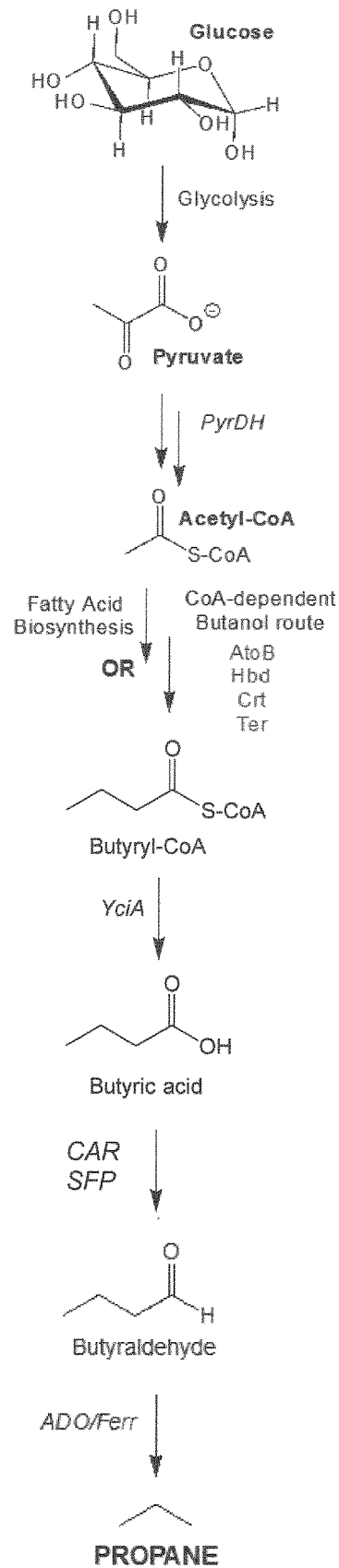
FIG. 8. Reaction pathway from glucose to propane via butyric acid and butyraldehyde through the action of YciA/CAR/SFP/ADO, from Menon et al 2015 [8].

In some embodiments, the method comprises the conversion of glucose into propane. The known pathways for this reaction proceed from butyryl-CoA to propane via butyric acid and butyraldehyde (FIG. 8). However, this reaction pathway has low yields. Furthermore, butanol is produced as a side-product by other, native enzymes acting on the enriched concentration of butyraldehyde generated by the action of CAR/SFP. The methods provided herein give higher yields of propane with lower, negligible, butanol production.

One such method proceeds via the butyric acid/fatty acid decarboxylase pathway. The reaction scheme can be seen in FIG. 9. Glucose may be converted into acetyl CoA and/or malonyl-CoA by glycolysis. The method may then comprise the following steps performed in order:

(a) catalysis of the conversion of acetyl CoA to acetylacetyl-CoA using an acetyl-CoA acetyltransferase (e.g. SEQ ID NO:28, or a fragment, homologue of variant thereof), and/or catalysis of the conversion of malonyl-CoA to acetylacetyl-CoA using acetoacetyl CoA synthase (e.g. SEQ ID NO:24, or a fragment, homologue of variant thereof), (b) catalysis of the conversion of acetylacetyl-CoA to 3-hydroxybutryryl-CoA using a clostridial 3-hydroxybutyryl-CoA dehydrogenase (e.g. SEQ ID NO:29, or a fragment, homologue of variant thereof), (c) catalysis of the conversion of 3-hydroxybutryryl-CoA to crotonyl-CoA using a 3-hydroxybutyryl-CoA dehydratase (e.g. SEQ ID NO:30, or a fragment, homologue of variant thereof), (d) catalysis of the conversion of crotonyl-CoA to butyryl-CoA using a trans-enoyl-CoA reductase (e.g. SEQ ID NO:31, or a fragment, homologue of variant thereof), (e) catalysis of the conversion of butyryl-coenzyme A (acyl-CoA) to butyric acid using acyl-CoA thioester hydrolase (e.g. SEQ ID NO:23, or a fragment, homologue of variant thereof), and (f) catalysis of the conversion of butyric acid to propane using a fatty acid carboxylase as described above to produce propane.

In some embodiments, the method of converting glucose into propane proceeds via butyraldehyde and the action of aldehyde dehydrogenase/aldehyde deformylating oxygenase. Glucose may be converted into acetyl CoA and/or malonyl-CoA by glycolysis. This reaction scheme can be seen in FIG. 10. The method may then comprise the following steps performed in order:

(a) catalysis of the conversion of acetyl CoA to acetylacetyl-CoA using an acetyl-CoA acetyltransferase (e.g. SEQ ID NO:28, or a fragment, homologue of variant thereof), and/or catalysis of the conversion of malonyl-CoA to acetylacetyl-CoA using acetoacetyl CoA synthase (e.g. SEQ ID NO:24, or a fragment, homologue of variant thereof), (b) catalysis of the conversion of acetylacetyl-CoA to 3-hydroxybutryryl-CoA using a clostridial 3-hydroxybutyryl-CoA dehydrogenase (e.g. SEQ ID NO:29, or a fragment, homologue of variant thereof), (c) catalysis of the conversion of 3-hydroxybutryryl-CoA to crotonyl-CoA using a 3-hydroxybutyryl-CoA dehydratase (e.g. SEQ ID NO:30, or a fragment, homologue of variant thereof), (d) catalysis of the conversion of crotonyl-CoA to butyryl-CoA using a trans-enoyl-CoA reductase (e.g. SEQ ID NO:31, or a fragment, homologue of variant thereof), (e) catalysis of the conversion of butyryl-CoA to butyraldehyde using an aldehyde dehydrogenase as described above, and (f) catalysis of the conversion of butyraldehyde to propane using an aldehyde deformylating oxygenase, as described above.

It will be appreciated that where the enzymes act sequentially in a metabolic pathway, the methods may comprise providing substrate for the first step and the enzymes for catalysing the subsequent conversions. The method may commence from any of steps (a)-(f), provided with the correct substrate and enzymes, before proceeding through the remaining steps in order. The steps may be performed sequentially or simultaneously. The enzymes required for the above reaction scheme may be provided in a single composition or in multiple compositions, for example within a single cell comprising a nucleic acid encoding all the enzymes specified by the method starting from any given step, or in a plurality of cells comprising a plurality of nucleic acids, each nucleic acid encoding one or more enzymes specified by the method starting from any given step.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example+/−10%.

Examples

All chemicals and solvents were purchased from commercial suppliers, and were of analytical grade or better. Propane gas standard (99.95%) was obtained from Sigma Aldrich. Media components were obtained from Formedium (Norfolk, UK). Gene sequencing and oligonucleotide synthesis were both performed by Eurofins MWG (Ebersberg, Germany). *Halomonas* strains TD01[17] and TQ10 and plasmids p321 and p341 were kindly supplied by Professor Guo-Qiang Chen (Tsinghua University, Beijing, China). The mounted Hi-Power blue LEDs and LED drivers were from Thorlabs (New Jersey, USA), with wavelengths at 455 nm (1020 mW output) and 470 nm (253 mW). The white light LED (Integral) used had a 25W power (2060 lumens).

Example 1: Initial Characterisation and Mutagenesis

The gene encoding the mature CvPAS sequence from *Chlorella variabilis* NC64A (Genbank ID: A0A248QE08; N-terminal 61 amino acid truncated)[13] was designed and synthesised by GeneArt (Germany), incorporating codon optimisation techniques of rare codon removal for optimal expression in *E. coli*. The gene was sub cloned (NcoI-XhoI) into pETM11, incorporating a 78 bp N-terminal tag containing a hexahistidine sequence for rapid protein purification. The construct ($CvPAS_{WT}$) was transformed into the *E. coli* strain BL21(DE3) (Merck) according to the manufacturer's protocol.

Figure 5:
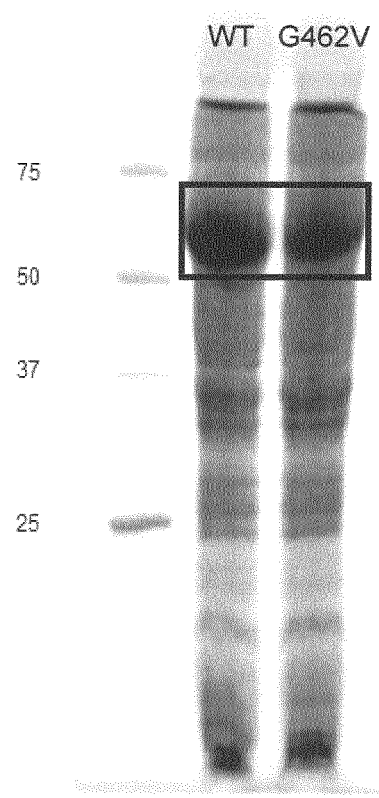
FIG. 5. SDS PAGE analysis of cell lysate of *E. coli* overexpressing wild-type and G462V variant CvPAS. The box indicates the CvPAS expression band (63 kDa).

The N-terminally truncated (mature) and Hiss-tagged version of CvPAS was highly expressed in a soluble form in *E. coli* (FIG. 5). However purification trials generated protein with a low degree of flavination, so initial characterisation studies were performed with cell-free lysate.

Variant $CvPAS_{G462V}$ was generated by site-directed mutagenesis using the Stratagene QuickChange whole plasmid synthesis protocol. PCR reactions were performed using CloneAmp HiFi PCR premix (Clontech) and the oligonucleotides 5'-GCACTGGATCCGGATGTTGTTAGCACC-TATG TG-3' and 5'-CACATAGGTGCTAACAACATCCG-GATCCAGTGC-3'. Template removal was performed by selective restriction digest (DpnI), and the PCR product was transformed into *E. coli* strain NEB5a (New England Biolabs) for plasmid recirculation and recovery. Colonies were grown on Luria broth (10 g/L tryptone, 5 g/L yeast extract and 10 g/L NaCl) containing kanamycin (15 µg/mL) overnight at 37° C., followed by plasmid extraction and purification using the NucleoSpin® plasmid kit (Macherey-Nagel). The presence of the mutation was confirmed by gene sequencing, followed by transformation into *E. coli* strain BL21(DE3) for protein expression.

Example 2: Protein Expression and Lysate Generation

Cultures of wild-type and variant CvPAS in *E. coli* strain BL21(DE3) were grown in LB medium containing kanamycin (30 µg/mL) and an overnight starter culture (1% vol) at 37° C. and 200 rpm until the $OD_{600}$ nm=0.2. The temperature was dropped to 25° C., until $OD_{600}$ nm=0.6, followed by recombinant protein expression induction by IPTG (0.5 mM). The cultures were incubated a further 17 h at 17° C., then harvested by centrifugation at 26600×g.

Cell pellet was resuspended in lysis buffer (25 mL; 50 mM Tris pH8 containing 300 mM NaCl, 10 mM imidazole, 10% glycerol, 0.25 mg/mL lysozyme, 10 µg/mL DNase I and 1×protease inhibitors) and sonicated for 20 minutes (20 s on, 60 s off; 30% amplitude). Cell-free lysate was prepared by centrifugation at 26600×g for 30 minutes at 4° C. Lysate samples were analysed for recombinant protein expression by SDS PAGE (12% Mini-PROTEAN-TGX stain-free gel; Bio-Rad), using Precision Plus unstained protein ladder (Bio-Rad) at 300 V for 20 minutes. Protein content was visualised using a Gel Doc EZ imager (Bio-Rad).

Example 3: Propane Production in Cell-Free Lysate

In vitro reactions (200 µL) for propane production were composed of cell-free lysate (180 µL) and butyric acid (0.36 to 4.5 mM) in sealed glass GC vials. The reactions were incubated at 30° C. for 24 h at 180 rpm in the presence or absence (control samples) of a blue LED (455 nm). Headspace gas was analysed for propane content using a Micro GC (100 ms injection) with an $Al_2O_3/KCl$ column.

Propane levels were determined by manual headspace injection using an Agilent 490 Micro GC, containing an $Al_2O_3/KCl$ column and a thermal conductivity detector (TCD). Headspace samples were manually injected into a heated injector (110° C.), with an injection time of 100 ms using helium as the carrier gas (10.2 psi). Compounds were separated isothermally (100° C.) over 120 s under static pressure conditions, with a sampling frequency of 100 Hz. Propane concentrations were calculated by comparing the peak areas to a standard curve generated under the same conditions.

Propane yields for wild type CvPAS were modest (1.65±0.61 mg/L lysate), but comparable to in vivo production levels using the alternative ADO decarbonylation enzyme (0.4-3.4 mg/L). Biotransformations of cell-free lysates using the variant CvPAS.G462V showed an apparent 4-fold increase in propane yield (6.45±1.4 mg/L lysate).

Figure 6:
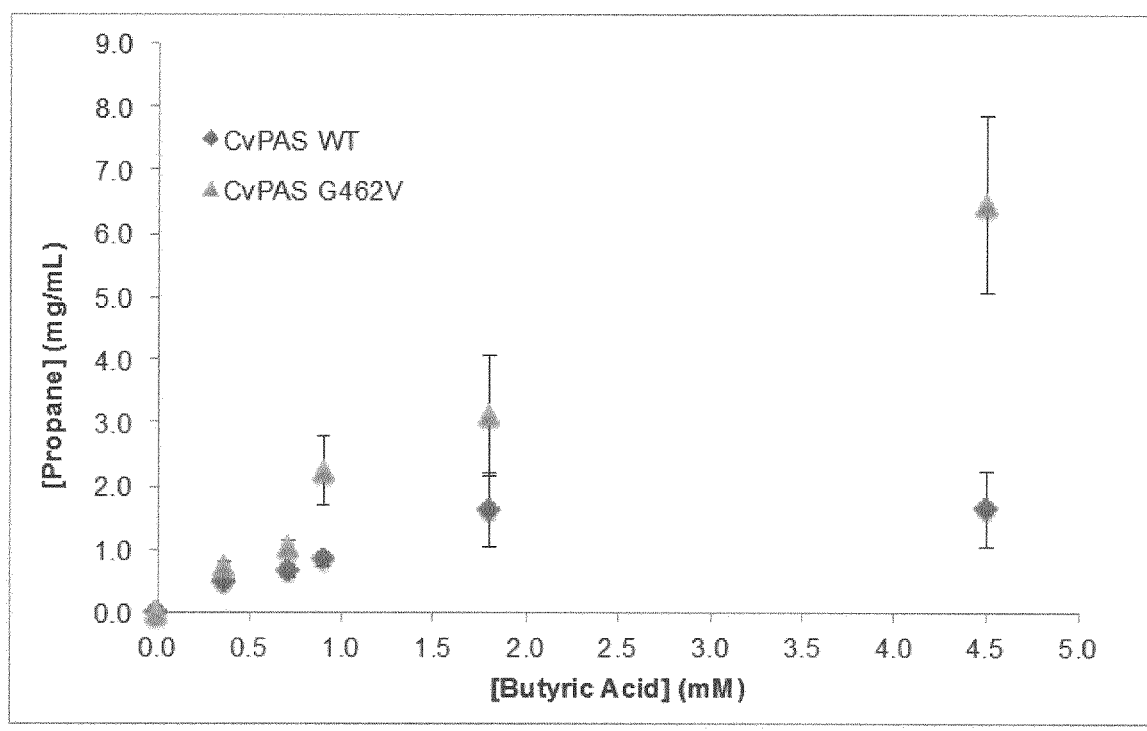
FIG. 6. Chart showing effect of butyrate concentration on wild-type and G462V variant CvPAS activity under constant light conditions. Reactions (200 µL) were composed of cell-free lysate (180 µL) and butyric acid (0.36 to 4.5 mM) in sealed glass GC vials. The reactions were incubated at 30° C. for 24 h at 180 rpm in the presence of a blue LED (455 nm). Headspace gas was analysed for propane content using a Micro GC (100 ms injection).
Figure 7:
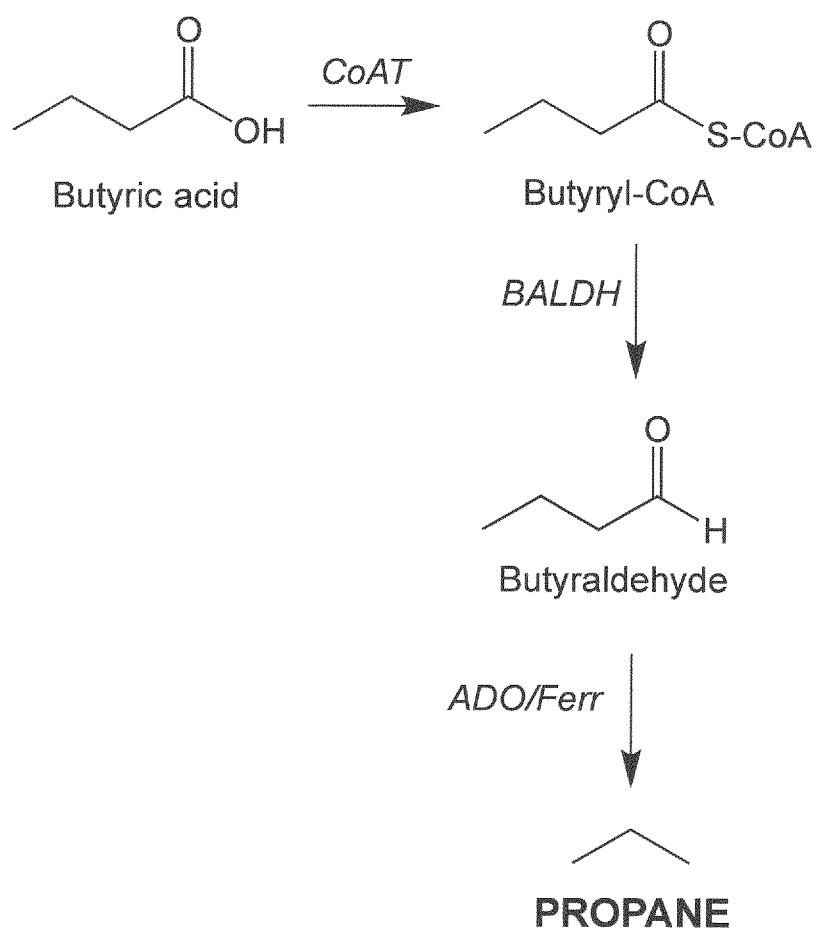
FIG. 7. Reaction pathways from butyryl-CoA to propane via the butyraldehyde intermediate through the action of aldehyde dehydrogenase (BALDH), and aldehyde deformylating oxygenase (ADO, plus electron transfer partner protein ferredoxin). The process may also begin at butyric acid through the action of using a butyrate-acetoacetate CoA transferase (CoAT).

Interestingly, preliminary concentration dependence studies suggested the mutation impacted on butyric acid binding, as seen by the lack of saturation at 4.5 mM compared to wild-type enzyme (FIG. 6). Further comparative kinetic studies are required with purified enzymes to more fully investigate the effect of the G462V mutation on activity.

Example 4: Propane Production in E. coli

Comparative biocatalytic in vivo propane production of $CvPAS_{WT}$ and variant G462V in *E. coli* was performed by the following protocol: Starter culture (5 mL) was grown overnight at 37° C. in LB containing kanamycin (50 µg/mL) at 200 rpm. Cultures (20 mL) were grown in LB containing kanamycin (50 µg/mL) and starter culture (1%) at 37° C. and 180 rpm for 6 h. IPTG (0.1 mM), butyric acid (1 mM) and ±Triton X-100 (2%) were added and 5 mL aliquots of cultures were sealed up in 20 mL tubes and incubated at 30° C. for a further 1.5 or 18 h in the presence of a blue LED (455 nm). Headspace gas was analysed for propane by Micro GC (100 ms injection) using an $Al_2O_3/KCl$ column.

The results of this experiment can be seen in Table 1. Inconsistency between the two data sets was due to different post induction times and distances from the light source, however it is clear that the variant produces markedly more propane in the headspace that the wild type. Higher concentrations of butyric acid (10 mM) showed an increase in propane production, but 100 mM concentrations lysed the cells.

TABLE 1

In vivo propane production by wild-type and variant CvPAS.

| Constructs | Post Induction time (h) | Butyric acid (mM) | Triton X-100 (2%) | Propane (nmol in hs) | Propane (mg/L culture) |
|---|---|---|---|---|---|
| Experiment Date: 8 Dec. 2017 | | | | | |
| $CvPAS_{WT}$ | 1.5 | 1 | No | 5.4 ± 1.5 | 0.05 ± 0.01 |
| $CvPAS_{G462V}$ | 1.5 | 1 | No | 30.9 ± 15.6 | 0.27 ± 0.14 |
| Experiment Date: 20 Dec. 2017 | | | | | |
| $CvPAS_{WT}$ | 18 | 1 | No | 3.3 ± 0.4 | 0.03 ± 0.01 |
| $CvPAS_{WT}$ | 18 | 1 | Yes | 3.3 ± 0.1 | 0.03 ± 0.01 |
| $CvPAS_{G462V}$ | 18 | 1 | No | 12.2 ± 0.4 | 0.11 ± 0.01 |
| $CVPAS_{G462V}$ | 18 | 1 | Yes | 22.0 ± 3.8 | 0.19 ± 0.03 |
| Experiment Date: 26 Jan. 2018 | | | | | |
| $CVPAS_{G462V}$ | 18 | 10 | No | 803.9 ± 13.5 | 7.09 ± 0.12 | hs = culture headspace.

Next, the effect of various additives on propane production was investigated.

Cultures (20-100 mL) were grown in LB medium containing kanamycin (50 µg/mL) and an overnight starter culture (1% volume; same medium) for 6 h at 37° C. and 180 rpm. Recombinant protein expression was induced with IPTG (0.1 mM) and cultures were supplemented with butyric acid (1-25 mM)±Triton X-100 (1%), sucrose (1%) and/or ethyl acetoacetate (0-30 mM). Triplicate aliquots (5 mL) of cultures were sealed into 20 mL glass vials and incubated at 30° C. for 16-18 h at 200 rpm, illuminated continuously with an LED (white or blue (455 nm or 470 nm)). Headspace gas was analysed for propane content using a Micro GC (100 ms injection) with an $Al_2O_3/KCl$ column.

Results of these experiments are show in Tables 1 and 2. Triton X-100 and sucrose additions to bacterial cultures are known to permeabilise the cells, which effectively makes them more 'leaky' [20]. This would allow an increased likelihood of CvPAS leaking out of the cell into the culture supernatant, thereby increasing its exposure to light and resulting in higher propane yields. The results show that for CvPAS variant G462V the addition of both Triton X-100 and sucrose (not metabolised by *E. coli*) led to a dramatic increase in propane production. However, this effect was not seen with the wild-type enzyme.

TABLE 2

In vivo propane production by wild-type and variant CvPAS.

| Constructs | Sucrose addition | Triton X-100 addition | Propane (nmol in hs) | Propane (mg/L culture) |
|---|---|---|---|---|
| $CvPAS_{WT}$ | No | No | 6.1 ± 0.9 | 0.05 ± 0.01 |
| | No | Yes | 3.9 ± 1.5 | 0.03 ± 0.01 |
| | Yes | No | 6.4 ± 0.2 | 0.06 ± 0.01 |
| | Yes | Yes | 4.4 ± 0.3 | 0.04 ± 0.01 |

TABLE 2-continued

In vivo propane production by wild-type and variant CvPAS.

| Constructs | Sucrose addition | Triton X-100 addition | Propane (nmol in hs) | Propane (mg/L culture) |
|---|---|---|---|---|
| CvPAS$_{G462V}$ | No | No | 8.8 ± 0.4 | 0.08 ± 0.01 |
| | No | Yes | 7.6 ± 1.8 | 0.07 ± 0.02 |
| | Yes | No | 27.0 ± 3.2 | 0.24 ± 0.03 |
| | Yes | Yes | 22.6 ± 1.1 | 0.20 ± 0.01 | hs = culture headspace.

Additional experiments were performed with the additive ethyl acetoacetate, proposed to be a stimulator of the butyrate transporter in *E. coli* [21]. In this case, the presence of 10 mM ethyl acetoacetate yielded 32.0±3.2 mg/L propane with the G462V variant of CvPAS.

Example 5: *Halomonas* Vector Construction & Conjugation

The commercial application of a process is often a balance between maximising product yields and minimising costs. For CvPAS-mediated propane production, this requires the use of in vivo biofactories rather than purified enzymes. This will impact on propane production rates, as light access will be compromised in vivo and the presence of high concentrations of butyric acid may impact on culture pH and cell viability. As such, the robust halophilic bacteria *Halomonas* was selected as a biofactory host.

The genes encoding CvPAS$_{WT}$ and variant CvPAS$_{G462V}$ were cloned into vector p321[18] for *Halomonas* conjugation using In-Fusion cloning (Clontech). Both the vector and genes were linearised by PCR amplification, incorporating overhanging bases at each end for later vector:gene annealing (oligonucleotides: p321-5'-TGCCACCGCT-GAGCAATAAAA-3' and 5'-CATC TAGTAT-TTCTCCTCTTTCTCTAGTA-3'; CvPAS-5'-GAGAAATACTAGATGGCCAGCGCA GTTGAAGATATT-3' and 5'-TGCTCAGCGGTGGCAT-TATGCTGCAACGGTTGCCG-3'). The genes were amplified without the pETM11-derived 78 bp N-terminal tag sequence. Each PCR product was DpnI digested, analysed by agarose gel electrophoresis and the correctly sized bands were extracted and purified using the Isolate II plasmid kit (Bioline), according to the manufacturer's instructions. In-Fusion cloning was performed between the linearised p321 and CvPAS variants, followed by transformation into *E. coli* strain Stellar (Clontech) for plasmid recirculation and recovery. Plasmid production, purification and sequencing were performed as above to confirm the gene insertion.

Constructs pHPAS$_{WT}$ and pHPAS$_{G462V}$ were generated by limited NcoI/XhoI double digestion of both the CvPAS plasmids and a variant form of pSEVA431 [22] containing a T7-like promoter [23] and a substitution of the chloramphenicol resistance cassette for spectinomycin resistance. The gene and vector were ligated together using the Quick Ligation kit (NEB), and the intact construct was transformed into competent *E. coli* strain S17-1 (λpir; [24]) using a kanamycin-selective agar plate. Plasmid production, purification and sequencing were performed as above to confirm the gene insertion.

The pHPAS$_{WT}$ and pHPAS$_{G462V}$ constructs in *E. coli* strain S17-1 were transformed into *Halomonas* st. TQ10 by a modified conjugation protocol. The *E. coli* donor strain and *Halomonas* st. TQ10 recipient were pre-grown on kanamycin-selective LB agar and YTN6 agar, respectively. A colony each of donor and recipient strains were mixed together on YTN2 agar (0.5% yeast extract, 1% tryptone, 2% NaCl and 1.5% agar without pH adjustment) and incubated overnight at 37° C. The mixed culture was streaked onto a YTN6 agar plate (pH 9.0) containing 10 µg/mL spectinomycin, selective for growth of *Halomonas* containing the pHPAS$_{WT}$ or pHPAS$_{G462V}$ constructs only. The plate was incubated overnight at 37° C. Uptake of the plasmid in *Halomonas* was confirmed by plasmid preparation and sequencing.

Example 6: Propane Production by CvPAS$_{G462V}$ in *Halomonas*

Propane production in *Halomonas* strains was performed by a modification of the *E. coli* general protocol as follows: Cultures were grown in YTN6 medium containing spectinomycin (50 µg/mL) with a larger inoculum (5%; OD$_{600}$=0.1-0.3) for 5 h at 37° C. and 180 rpm. Recombinant protein expression was induced with IPTG (0.1 mM) at a higher cell density than *E. coli* cultures (OD~1.6). The remainder of the in vivo propane production process was performed as above.

Results of this experiment are provided in Table 3.

TABLE 3

In vivo propane production by CvPAS wild-type and G462V variant in *Halomonas* st. XV12.

| Enzyme | Construct | Propane (nmol in hs) | Propane (mg/L culture) |
|---|---|---|---|
| CvPAS$_{WT}$ | pHPAS$_{WT}$ 1 | 0.30 ± 0.14 | 0.003 ± 0.001 |
| | pHPAS$_{WT}$ 2 | 0.17 ± 0.00 | 0.001 ± 0.00 |
| CvPAS$_{G462V}$ | PHPAS$_{G462V}$ 1 | 2.00 ± 0.03 | 0.018 ± 0.000 |
| | PHPAS$_{G462V}$ 2 | 1.13 ± 0.37 | 0.01 ± 0.003 |
| oriT-RFP | pBbE1c | ND | ND | hs = headspace. 1 and 2 refer to different colonies of *Halomonas* containing the pHPAS$_{WT}$ or pHPAS$_{G462V}$ constructs. ND = none detected.

Although the levels of propane produced are initially lower than those in *E. coli*, yields were still markedly higher for the G462V variant.

Example 7: Propane Production by CvPAS-G462V in *Halomonas* with Variable Light Intensities The effect of varying light intensity on propane yield from the variant enzyme was investigated.

Starter culture (5 mL) was grown overnight at 37° C. in YTN6 (0.5% yeast extract+1% tryptone+6% NaCl pH 9.0) containing spectinomycin (50 µg/mL) at 200 rpm. Cultures (20 mL) were grown in YTN6 containing the same antibiotics and starter culture (5%; OD$_{600}$=0.1-0.3) at 30° C. and 200 rpm for 5 h (OD~1.6). IPTG (0.1 mM) and butyric acid (1 mM) was added and aliquots (5 mL) were sealed up in 20 mL reaction vials and incubated at 30° C. for 18 hours at 200 rpm in the presence of bright white light (laid flat on the shaker) with different degrees of shielding. Headspace gas was analysed for propane by Micro GC (100 ms injection) using an Al$_2$O$_3$/KCl column.

Results of this experiment are provided in Table 4. Propane production appears to be strongly dependent on light intensity, however the levels of light used do not seem be saturating for the expression levels of the enzyme. It is expected that higher levels of light would result in even higher yields.

TABLE 4

In vivo propane production by *Halomonas* with different light intensities.

| Enzyme | Light flux (μmol) | Propane (nmol in hs) | Propane (mg/L culture) |
|---|---|---|---|
| CvPAS$_{G462V}$ | 0 | ND | ND |
| | 8 | ND | ND |
| | 18 | 0.17 ± 0.00 | 0.001 ± 0.000 |
| | 20-27 | 0.44 ± 0.14 | 0.004 ± 0.001 |
| | 34-40 | 0.87 ± 0.04 | 0.008 ± 0.000 |
| | 200-320 | 4.13 ± 0.00 | 0.036 ± 0.000 | hs = headspace. ND—none detected.

Example 8: Propane Production by CvPAS-G462V in *Halomonas* with Variable Butyrate Level The effect of varying butyrate availability on propane yield from the variant enzyme was investigated.

Starter culture (5 mL) was grown overnight at 37° C. in YTN6 (0.5% yeast extract+1% tryptone+6% NaCl pH 9.0) containing spectinomycin (50 μg/mL) at 200 rpm. Cultures (20 mL) were grown in YTN6 containing the same antibiotics and starter culture (5%; OD$_{600}$=0.1-0.3) at 30° C. and 200 rpm for 5 h (OD~1.6). IPTG (0.1 mM) and butyric acid (1 mM) was added and aliquots (5 mL) were sealed up in 20 mL reaction vials and incubated at 30° C. for 18 hours at 200 rpm in the presence of bright white light (laid flat on the shaker). Headspace gas was analysed for propane by Micro GC (100 ms injection) using an Al$_2$O$_3$/KCl column.

Results can be seen in Table 5. Propane production appears strongly dependent on butyrate concentration, with the maximum around 20 mM. Cultures grown in the presence of 1M butyric acid underwent cell lysis.

TABLE 5

In vivo propane production with different butyrate concentrations.

| Enzyme | Butyrate concentration (mM) | Propane (nmol in hs) | Propane (mg/L culture) |
|---|---|---|---|
| Experiment date: 21 Feb. 2018 | | | |
| CvPAS$_{G462V}$ | 0 | 0.2 ± 0.0 | 0.001 ± 0.000 |
| | 0.2 | 1.2 ± 0.1 | 0.011 ± 0.000 |
| | 0.5 | 3.6 ± 0.2 | 0.032 ± 0.001 |
| | 1 | 7.7 ± 0.8 | 0.068 ± 0.007 |
| | 2 | 16.7 ± 1.6 | 0.15 ± 0.01 |
| | 5 | 72.5 ± 2.8 | 0.64 ± 0.03 |
| | 10 | 318.1 ± 31.4 | 2.81 ± 0.28 |
| | 20 | 2118.3 ± 364.4 | 18.68 ± 3.21 |
| Experiment date: 23 Feb. 2018 | | | |
| CvPAS$_{G462V}$ | 0 | 0.2 ± 0.07 | 0.002 ± 0.001 |
| | 1 | 2.4 ± 0.2 | 0.021 ± 0.002 |
| | 3 | 12.9 ± 2.0 | 0.114 ± 0.018 |
| | 10 | 144.8 ± 0.1 | 1.28 ± 0.009 |
| | 30 | 13.0 ± 7.1 | 0.114 ± 0.063 |
| | 100 | 1.2 ± 1.0 | 0.010 ± 0.009 |
| | 300 | 0.33 ± 0.09 | 0.003 ± 0.001 |
| | 1000 | 0.80 ± 0.04 | 0.007 ± 0.000 |
| Experiment date: 1 Mar. 2018 | | | |
| CVPAS$_{G462V}$ | 10 | 108.9 ± 0.45 | 0.96 ± 0.00 |
| | 15 | 648.5 ± 14.0 | 5.72 ± 0.12 |
| | 20 | 1246.5 ± 41.7 | 10.99 ± 0.37 |
| | 22 | 1209.8 ± 135.2 | 10.67 ± 1.19 |
| | 24 | 884.8 ± 69.6 | 7.80 ± 0.62 |
| | 26 | 351.8 ± 207.7 | 3.10 ± 1.83 |
| | 28 | 77.4 ± 56.9 | 0.68 ± 0.50 |
| | 30 | 7.0 ± 1.2 | 0.06 ± 0.01 | hs = headspace.

Example 9: Drop-in Bio-LPG Technology Utilising Light, Seawater and Waste Feed Stocks The race to develop economically viable microbial biofuels' is a consequence of a pressing need to reduce carbon emissions, improve air quality and implement renewable and sustainable fuel strategies.[2,3] Current over reliance on fossil fuels has led to concerns over energy security and climate change. In turn this has driven new policies to restrict greenhouse gas emissions, increase the recycling of waste biomaterials and accelerate the delivery of the bio-economy.[4,5] An effective biofuel strategy would comprise scalable production of transportable and clean burning fuel derived from a microbial chassis and cultivated on existing renewable waste biomaterials. This would require minimal downstream processing and avoidance of fresh water use. Embedding this technology within existing infrastructure for localised waste processing and fuel distribution would minimise capital expenditure and facilitate conversion of biomass waste into clean burning fuels. Such 'drop-in' technology could be tailored to specific waste streams at the chosen location with concomitant societal, environmental and economic benefits. Distributed production could support localized economies and create low/medium skilled jobs, enable more effective waste management and provide energy self-sufficiency in rural communities in both advanced and developing nations of the world.

Propane is an ideal biofuel. This hydrocarbon gas is a highly efficient and clean-burning fuel with a low carbon footprint. It is currently sourced from natural gas and petroleum refining.[6] Propane is the third most widely used transportation fuel (20 million tons per annum globally). It is also used for domestic heating and cooking, non-greenhouse gas refrigerants and aerosol propellants.[6,7] Its 'drop-in' nature boosts the calorific value of current methane/biogas supplies, with lower energy requirements for liquefaction and storage.[7] Currently, the only existing commercial bio-derived route to its production is the Nesté process, an energy intensive, catalytic chemical conversion of biodiesel waste (glycerol).[8] No natural biosynthetic routes to propane are known, but engineered biological pathways have been developed based on the decarbonylation of butyraldehyde incorporating natural and engineered variants of NAD(P)H- and ferredoxin-dependent aldehyde deformylating oxygenase (ADO)[9]. These metabolic routes are based on fatty acid biosynthesis,[10] reverse β-oxidation," valine biosynthesis' and an engineered de novo pathway in *E. coli* that utilizes nine genes and is based on the fermentative clostridial butanol pathway.[7] However, the extremely low turnover numbers of ADO (~3-5 h$^{-1}$) limits the implementation of these pathways in scaled bio-propane production (bio-propane yields typically ca 30-50 mg/L).[7,10,11]

The poor catalytic properties of ADO have stimulated searches for alternative biocatalysts. A novel fatty acid photodecarboxylase (FAP) class of photoenzymes was described recently that catalyses the blue light-dependent decarboxylation of fatty acids to n-alkanes or n-alkenes.[12,13] It contains a non-covalently bound photo-excitable flavin adenine dinucleotide (FAD) cofactor with a reaction quantum yield of >80% (0.86±+0.13 s$^{-1}$) and a reported specificity for long chain fatty acids (C14-C18).[12-14] Given that long chain specific ADO catalyses the decarbonylation of butyraldehyde (C4) and that this can be improved by enzyme engineering,[10] we surmised that FAP could also be engineered to decarboxylate the C4 substrate butyric acid to form propane (and other hydrocarbon gases) at scale.

The design and implementation of a proof of concept 'in-the-field' bio-propane production technology that utilizes engineered variants of photoactive FAP is described. This technology uses biomaterial waste feed stocks and a microbial gas-producing chassis that can be propagated under non-sterile conditions in seawater. These features are desirable for localized, low cost production 'in-the-field'. We tackled enzyme redesign, chassis selection, and process development and optimization, to increase productivity, and reduce capital and operating costs for operations. Our approach was extended also to produce bio-butane and other gaseous hydrocarbons to demonstrate how complete biological routes can be engineered to bio-propane and tunable fuel blends (bio-LPGs). Bio-based fuels could ultimately replace petrochemical-derived propane, butane and liquefied petroleum gas (LPG) mixtures. This would be especially attractive in rural and/or arid communities, where localized fuel generation could displace petrochemical and refinery-sourced LPG supplies.

Light-Activated Biocatalysts for Bio-LPG Production

Recombinant E. coli strains expressing inducible, mature N-terminal Hiss-tagged FAP enzymes from Chlorella variabilis NC64A (CvFAP) and 7 other cyanobacterial homologues (Table S1) were generated.[12] Cell-free extract biotransformations showed that the highest levels of propane were detected with CvFAP$_{WT}$ (1.65±0.61 mg/L lysate; 455 nm light). The suitability of CvFAP$_{WT}$ for bio-LPG production was also explored by testing lysates for activity with valeric and isovaleric acids. These tests generated butane (1.31 mg/L) and isobutane (0.07 mg/L), respectively, as detected previously.[13] Propane was also detected in these tests (0.014 and 0.022 mg/L, respectively), attributed to the presence of butyric acid in cell-free extracts. In principle, these nascent activities indicate that production of bio-LPG blends is feasible using this enzyme. Tunable propane/butane ratios could be achieved by adjusting relative butyric/valeric acid levels. A potential limitation however is the low gas production levels of CvFAP$_{WT}$ using these volatile short chain carboxylic acid substrates.

Figure 12:
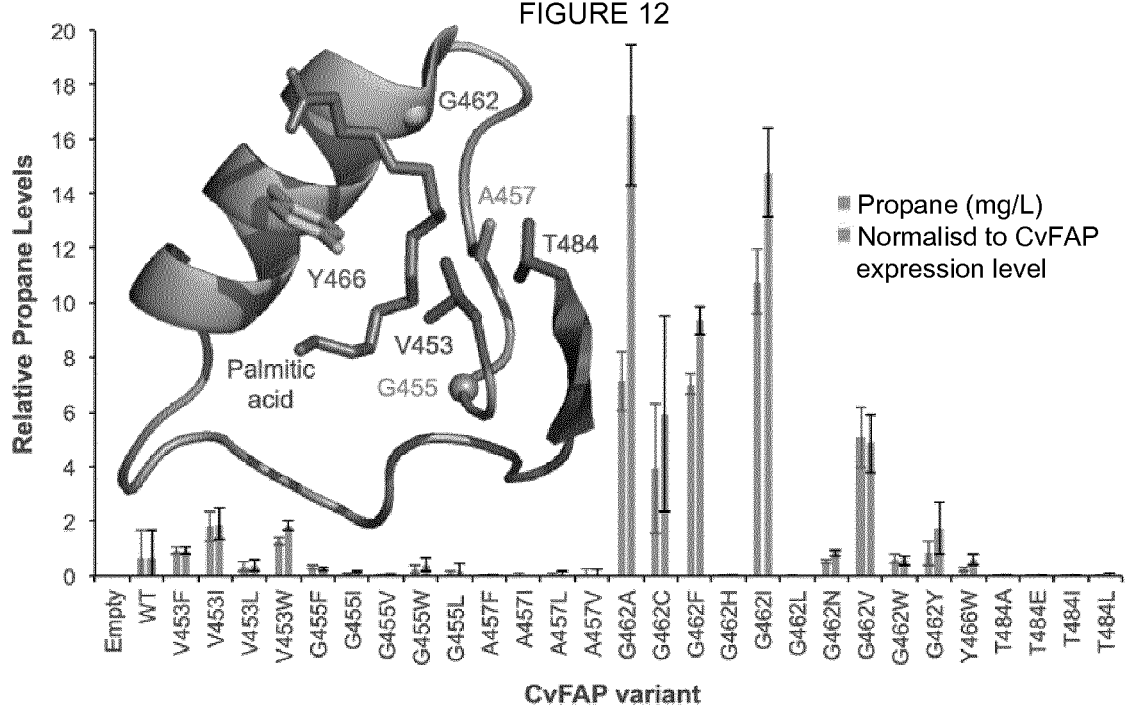
FIG. 12. Chart showing comparative in vitro propane production of variants of CvFAP. Cultures (20 mL) were grown in LB medium containing kanamycin (30 µg/mL) at 37° C. until OD600~0.6-0.8. Recombinant protein expression was induced with IPTG (0.1 mM) and cultures were supplemented with 10 mM butyric acid. Triplicate aliquots (1 mL) of cultures were sealed into 4 mL glass vials and incubated at 30° C. for 16-18 h at 200 rpm, illuminated with a blue LED panel. Headspace gas was analysed for gaseous hydrocarbon content using a Micro GC. Reactions were performed in triplicates of biological replicates. Normalised data was calculated by dividing the propane yields (mg/L lysate) by the relative protein concentration compared to the wild type (WT) enzyme (FIG. 18). Normalised activity was calculated by taking into account the relative protein concentration of each variant in the lysates compared to $CvFAP_{WT}$. Inset: Structure of the palmitic acid binding region of CvFAP (PDB: 5NCC) shown as a cartoon with secondary structure colouring. Palmitic acid and residues targeted for mutagenesis are shown as secondary structure coloured sticks.

The substrate binding channels in CvFAP[15] and ADO[15] are narrow and adopt a curved architecture. These narrow channels are ideally formed to accommodate the long aliphatic chains of C16/C18 fatty acids (CvFAP) and C16/C18 aldehydes (ADO). In all other respects the two enzymes are not related structurally. Of particular note in CvFAP$_{WT}$ are residues G462-Y484 that form part of this access channel (FIG. 12 inset). One strategy to increase the binding of butyrate is to decrease the competition for the active site by introducing a steric block to impair the binding of fatty acids of chain lengths greater than C4. This strategy is similar to that used with ADO, which resulted in enhanced ADO catalysis with shorter chain aldehydes.[15] We made a catalogue of 28 CvFAP variants, targeting residues G462, G455, Y466, V453, T484 and A457 for substitution. The side chains of each selected residue are in close proximity to the bound palmitate in the crystal structure of CvPAS$_{WT}$ (FIG. 12 inset).[12]

The initial target was residue G462, which was mutated to 10 other amino acids (V, N, W, L, C, I, F, A, H and Y). Propane production studies were performed with growing cells expressing the different variants.

Figure 18:
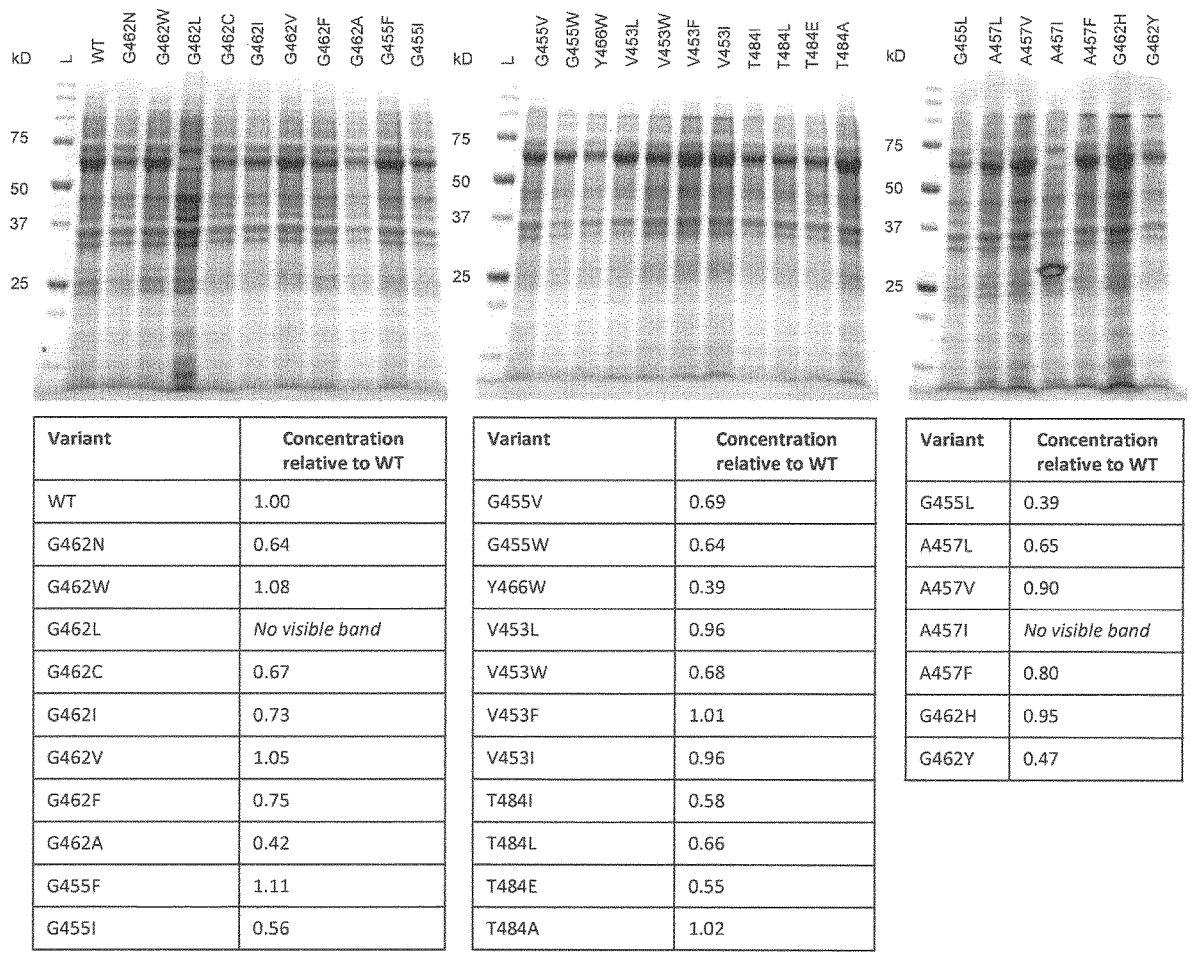
FIG. 18. Micrographs and tables showing expression of variants of CvFAP$_{WT}$ and 28 variants in E. coll. SDS PAGE analysis and relative quantitation of the soluble CvFAP$_{WT}$ band and 28 variants in E. coli. L=molecular mass ladder; WT=CvFAP$_{WT}$. Protein gels were imaged using a BioRad Gel Doc™ EZ Imager and relative protein band intensity was determined using the BioRad ImageLab™ software.

This showed a 7-fold increase in propane yield with CvFAP$_{G462V}$ (5.07±1.12 mg/L culture; FIG. 12), compared to the wild type under the same conditions. Normalised data has been corrected for the difference in relative expression levels of each variant in the extracts (FIG. 18). With (iso) valeric acids (C5), CvFAP$_{G462V}$ (iso)butane production was 2-fold greater than for CvFAP$_{WT}$ (2.52 and 1.31 mg/L culture, respectively). Further increases in propane production were achieved with variants G462I, G462F and G462A (1.9-3.5 fold greater than G462V). Overall, under the gas production conditions used, mutagenesis of residue G462 can lead to up to a 25-fold increase in propane production from butyric acid providing a range of biocatalysts for gaseous hydrocarbon production. Interestingly, all the variants of the amino acids G455, Y466, V453, T484, G455 or A457, except for G455I, produced less propane than CvFAP$_{WT}$ (FIG. 12). This suggests these residues play a role in mediating butyrate access to the active site tunnel.

Figure 13:
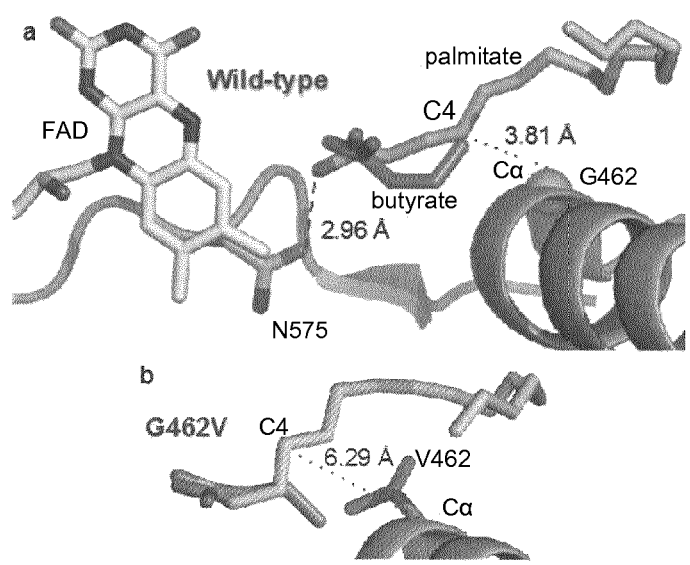
FIGS. 13A and B. Diagrammatic model of butyrate and palmitate in the active site of a) wild-type and b) G462V variant of CvFAP. The position of palmitate in the wild-type enzyme is crystallographically determined (PDB:5NCC). The positions of the remaining ligands was determined by Autodock Vina,[16] and the site directed mutagenesis (G462V) was performed using SwissPDBViewer 4.10.[48] In both panels, the protein is shown as a cartoon with secondary structure shading. The dashed line shows a hydrogen bond between palmitate and the wild-type enzyme. The dotted lines highlight the modeled ligand-GN462 residue distances.

CvPAS$_{WT}$ and variants (G462V/I/L, V453I, G455I, Y466W, T484I and A457V) were docked with long chain (palmitate) and short chain (butyrate) ligands using Autodock Vina[16] molecular docking simulations to estimate the respective binding free energy (-ΔG; kcal/mol) and the binding constants ($K_b$). This was performed see if these mutations had likely impacted on the relative binding strengths of butyrate to palmitate substrates (FIG. 13; Table S3 (FIG. 24)), as increasing the side chain size of these residues should decrease both the volume of the substrate access tunnel and the energetic favourability for the binding of palmitate. The most dramatic differences in the predicted palmitate binding constants were with variants G462I and G462V, which showed a 30-50-fold decrease from wild-type (relative -ΔG change of 1.4-1.5-fold; Table S3). A small overall increase in butyrate binding was predicted for these variants (~1.4-fold), which correlates with the significant increase in propane production during in vitro studies. Models of the variants docked with palmitate and butyrate show the distance between the Ca-atom of G462V and the C4 atom of the substrate is significantly increased (FIG. 13), due to the presence of the isopropyl group of valine instead of hydrogen. This repositioning of palmitate to a less favourable orientation relative to the wild-type complex could explain the decrease in the predicted $K_b$ for the variants. The exception is variant G455I that showed a near 2-fold increase in palmitate $K_b$. This suggests this modification may increase the enzyme affinity of CvFAP for long chain fatty acids. Therefore residue G462 appears to be a key discriminating residue, with its nature impacting on the relative affinity of short vs long chain substrates.

Ultimately, a scaled production facility will require the use of live cells under fermentation conditions, and scoping of physical parameters such as light intensity and wavelength for the biocatalyst used is important. As FAP is light activated, the wavelength and extent of light exposed to the enzyme will affect the production of gas. The impact on propane production of a variety of light sources was investigated in E. coli live cells also contained in glass vials. Light sources used included cool white (25 W; 2060 lumens) and blue LEDs (455 nm at 1020 mW or 470 nm at 253 mW). In these live cell measurements, the highest propane levels were detected at 470 nm (0.32±0.10 mg/L culture), in spite of its lower light intensity compared to the 455 nm (0.13±0.03 mg/L) and white LEDs (0.07±0.01 mg/L). This is in line with the known flavin absorbance maximum of $CvFAP_{WT}$ (blue peak absorption at 467 nm).[12] A LED array comprised of 480 individual blue LEDs was custom built to increase consistency of light exposure. This allowed comparative studies with increased reproducibility under different culturing conditions using E. coli as a laboratory test chassis harboring the G462V variant CvFAP.

In live cell cultures gas production a potential limitation is access of intracellular $CvFAP_{G462V}$ to externally supplied butyric acid. The highest propane levels were detected in cultures containing 10 mM butyric acid (7.53±0.29 mg/L culture). At butyric acid concentrations greater than 10 mM, culture pH and resultant cytotoxicity was observed (up to 25 mM, FIG. 19), attributed to lack of buffering capacity at high acid concentrations. Triton X-100 and sucrose are known to increase the permeability of E. coli cells and modest increases in propane yields were detected in the presence of (1.6-fold; Table S4 (FIG. 25)).[17] Butyrate uptake in E. coli is facilitated by the atoE transporter, which is part of the small chain fatty acid catabolism operon atoDAEB.[18,19] Acetoacetate is known to stimulate short chain fatty acids uptake by atoE.[18] Cultures supplemented with 10 mM ethyl- and methyl acetoacetate, produced near 2- and 2.8-fold (17.51±0.98 mg/L; Table S5 (FIG. 26)) and 2.8-fold (26.91±6.59 mg/L) increase in propane production, respectively. However, attempts to increase the intracellular concentrations of butyrate by generating dual constructs of $CvFAP_{G462V}$ with recombinant atoE transporter were not that effective (1.3-fold; Table S5 (FIG. 26)).[18]

An interesting aside was the observed impact of the plasmid backbone (pETM11 versus pET21b), positioning and size of a Hiss-tag on propane production in vivo. Both plasmids contain the same ColE1 origin of replication and T7 lac promoter. However, pETM11 contains a TEV protease-cleavable N-His6-tag, whereas pET21b contains a shorter C-terminal His tag. Encouragingly, there was a 6.4-fold increase in propane production by $CvFAP_{G462V}$ when contained in plasmid pET21b compared to pETM11 (48.31±2.66 vs 7.53±0.29 mg/L culture). This was increased further (97.1±10.3 mg/L) on addition of ethyl acetoacetate. This highlights the importance of exploring multiple plasmid backbones and the location/size of protein tags to determine the optimal biocatalyst expression and activity in vivo. This new construct ($CvFAP_{WT}$ and variants in pET21b) was used to scope decarboxylation activities with other volatile short chain acids for the development of a strategy to produce Bio-LPG.

Figure 14:
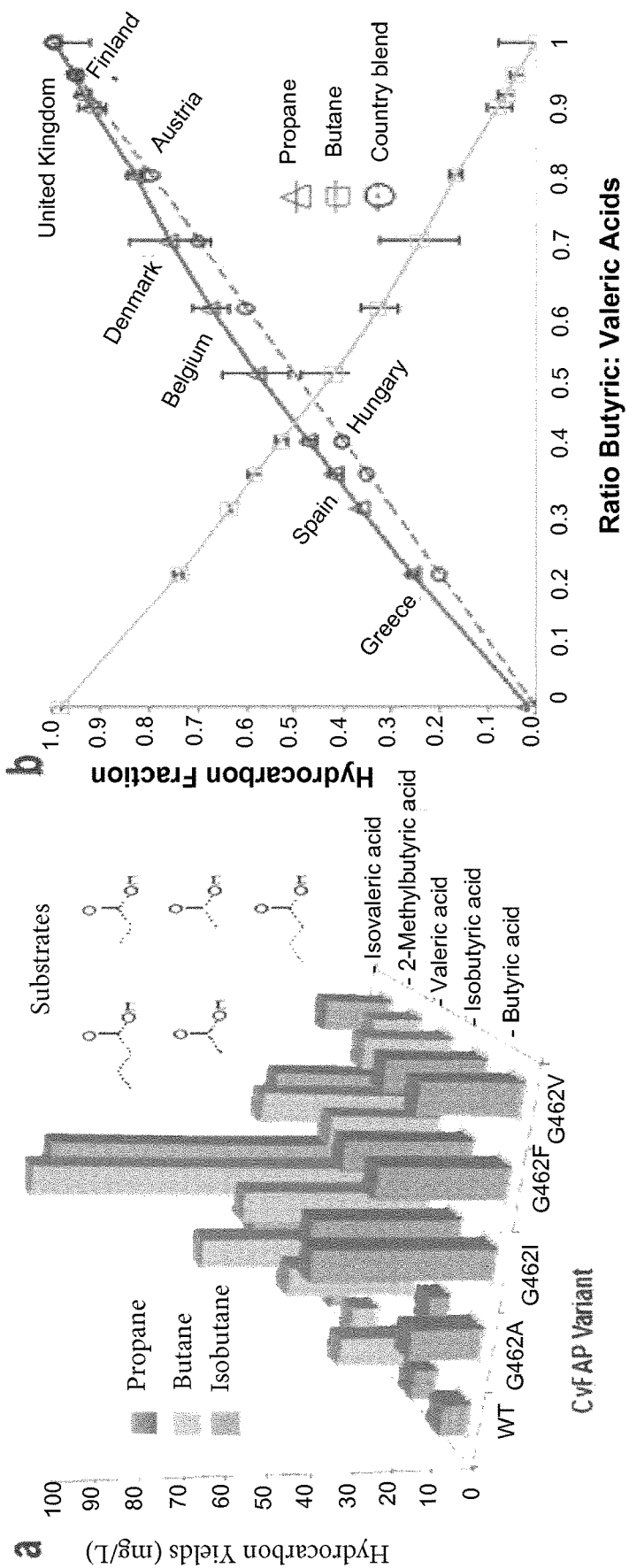
FIGS. 14A and B. Charts showing In vivo gaseous hydrocarbon production by wild type and variant CvFAP in *E. coli* st. BL21(DE3)ΔyqhD/ΔyjgB. Effect of a) CvFAP-pETM11 variants and b) butyric:valeric acid blends with $CvFAP_{G462V}$-pBbA1c on hydrocarbon production. Cultures (20 mL) were grown in LB medium containing kanamycin (50 µg/mL) at 37° C. until OD600~0.6-0.8. Recombinant protein expression was induced with IPTG (0.1 mM) followed by culture supplementation with acid substrates (10 mM total) after 1 h at 30° C. Triplicate aliquots (1 mL) of cultures were sealed into 4 mL glass vials and incubated at 30° C. for 16-18 h at 200 rpm, illuminated with a blue LED panel. Headspace gas was analysed for gaseous hydrocarbon content using a Micro GC. *a*All reactions designed to generate butane and isobutane also produced ~2% propane.

A variety of short chain fatty acids (butyric/isobutyric, valeric/2-methylbutyric and isovaleric acid) were tested with $CvFAP_{WT}$ and four variants (G462V/A/I/F) for propane, butane and/or isobutene production, respectively (FIG. 14a). Hydrocarbon levels were greater with variant G462I compared to G462V, particularly with the branched chain substrates isovaleric and 2-methylbutyric acids (5-8-fold higher; Table S6 (FIG. 27)). In comparison, propane and butane production by $FAP_{G462I}$ from the linear substrates butyric and valeric acids were less than 2-fold higher than $CvFAP_{G462V}$. Both variants G462V and G462A generated similar levels of propane and butane, while a greater variation in hydrocarbon yields were seen with the alanine substituted variant (FIG. 14a; Table S6). The G462 position is therefore important in conferring activity with a range of short chain volatile carboxylic acids required to make LPG-blends. Variant $CvFAP_{G462V}$ shows increased production of propane yields compared to $CvFAP_{WT}$ and it has similar propane and butane production levels. For this reason, it was taken forward as the most suitable biocatalyst for bio-LPG production in a more robust chassis.

Development of a Bio-LPG Strategy

The most common gases found in LPG blends are propane and n-butane, but blends may also contain isobutane, ethane, ethylene, propylene, butylene and isobutylene. The exact composition of LPG gases is country specific, and may also vary between seasons.[20] For example, in the UK LPG is 100% propane, while in Italy, the propane:butane ratio varies from 90:10 to 20:80 (FIG. 14b). Given that $CvFAP_{G462V}$ can generate both propane and butane efficiently, we investigated the possibility of in vivo production of country-specific bio-LPG blends by varying the ratio of externally supplied butyric:valeric acids. There was a remarkably close correlation between the proportions of butyric:valeric acid feed stock and the respective propane:butane concentration in the culture headspace (FIG. 14b; Table S7 (FIG. 28)).

The relative ease at which highly tunable bio-LPG blends were generated shows the potential applicability of this process, as country-specific requirements can be met by a simple manipulation of the volatile fatty acid feed ratio.

Carbon Neutral Photosynthetic Bio Propane Production

The ideal energy strategy would be the development of a sustainable carbon neutral fuel, whereby its combustion emissions ($CO_2$) would be recycled as the carbon source for the production of further biofuel. This would have multiple beneficial global environmental impacts, such as i) reduction in fossil fuel consumption leading to lower noxious and greenhouse gases emissions; ii) the ability to utilise a sustainable combustion fuel with no net $CO_2$ release (major greenhouse gas) and ill) linking of carbon capture technology to the production of a valuable commodity. Existing technologies of carbon capture and storage (CCS) have been implemented by industry to significantly reduce emissions, such as fossil fuel electricity generating plants, cement, steel and chemical companies. The International Energy Agency has estimated that CCS could potentially contribute to a 19% reduction in $CO_2$ emissions by 2050.[21]

A natural (microbial) carbon capture solution is to take advantage of the photosynthetic ability of cyanobacteria to fix $CO_2$ into organic carbon.[22] The cyanobacterium Synechcocystis PCC 6803 is an ideal target chassis as it is rapidly growing, genetically tractable,[23,24] tolerant to abiotic stress,[25] and its growth conditions are well optimsied.[26,27] Recombinant strains have been shown to produce a variety of products such as isobutyraldehyde[28] and ethanol.[29,30] We recently described the photobiological conversion of $CO_2$ into medium chain-length fatty acids' and long chain hydrocarbons' in Synechcocystis PCC 6803, the latter by the incorporation of either an ADO- or FAP-based enzymatic system. This strain was engineered to incorporate thioesterase A from E. coli (Tes4), which catalyses the direct conversion of fatty acyl-ACP to free fatty acids. In addition the native fatty acyl ACP synthase gene (Aaas) was knocked out to minimise the reverse reaction (FIG. 15a).[32] Together these changes increased the availability of free fatty acid precursors for hydrocarbon biosynthesis.[32]

To test the potential of propane production from $CO_2$, we constructed a Aaas strain of Synechcocystis expressing $CvFAP_{G462V}$+/−Tes4 under IPTG inducible (Ptrc) or constitutive (Pcoa) control (FIG. 15b). Initial testing for the presence of active $CvFAP_{G462V}$ with both promoter systems was performed by growth in photosynthetic medium supplemented with hexadecanoic acid (C16:0). The detection of pentadecane in only CvFAP$_{G462V}$ containing cultures confirmed the production of active enzyme in Synechcocystis. Strains expressing Tes4 and showed the presence of elevated levels of butyrate (concentration) compared to the wild-type Synechcocystis and Aaas strains. Testing for propane production required initial growth under standard photosynthetic conditions, followed by blue light illumination (750 µmol/s/m$^2$ or µE) in sealed glass vials to allow propane to accumulate in the headspace. In spite of an increase butyrate production in vivo, propane production was only detected with the inducible Tes4-CvFAP$_{G462V}$ construct in the presence of supplemental butyric acid (48 h; 0.012+0.001 mg/L culture; FIG. 15b). This is analogous to a previous study that showed the production of propane required the feeding of precursor molecules.[33] In addition the presence of the constitutive Pcoa showed a negative impact on culture growth (results not shown), likely due to its relatively high promoter strength.[32]

Further studies were performed in an automated flatbed photobioreactor (400 mL) to see if propane production could be obtained solely from photosynthetic derived butyric acid. Initial growth was performed under white light (30 µE) with pH maintenance, aeration (1.2 L/min air) and bicarbonate addition ($CO_2$ supply). After cell density accumulation propane production was accelerated using integral blue LEDs (460-485 nm; 750 µE).

A scaled photosynthetic-biological route to gaseous hydrocarbons will generate considerable levels of waste biomass, which in turn could be used as feedstock for biofuel (ethanol) production. However, current estimates suggest that the latter process is not economically sound as the energy return on energy invested (EROEI) is unfavourable.[34] This is because the energy requirement of running the aseptic closed loop bioreactors under ideal conditions (sunlight, fertilizer and $CO_2$ source) with additional downstream processing outweighs the energy gained from biofuel production. However the coupling of 'algal-like' biomass generation to high-value chemical or fuels production could tip the balance towards an economically viable bioprocess.[34] To make it a more sustainable process, the energy supply could be switched from fossil fuel-fuelled electricity generating plants to alternative energy sources such as hydroelectric, wind turbines or solar energy. Therefore further optimisation of photosynthetic-derived gaseous hydrocarbon production to significantly increase titres is needed to take this proof-of-concept approach forwards towards and economically and environmentally sustainable solution to clean biofuel production.

Robust Heterotrophic Chassis Development

Current prices for commercially available propane are relatively low (~$3.34/gallon USD at Jan. 1, 2018), so the success of any commercial bio-strategy is reliant on significantly increasing yields and reducing capitol and running costs. An alternative to autotrophic $CO_2$ derived bio-LPG is to harness a robust microbial chassis capable of heterotrophic growth (fermentation) of waste feedstock with cost-effective minimal bioprocessing costs. This would address another global environmental problem, namely waste bio-material accumulation. This is particularly prevalent in developing countries, where agricultural and other energy dense biological waste is often disposed of by combustion without energy capture, thereby contributing to the global increase in $CO_2$ levels. As developing countries often rely on gaseous hydrocarbon fuels for transportation, heating and cooking, the development of simplified and low cost reactors for bio-LPG production within disadvantaged communities could address energy supply concerns, generate income from waste bio-materials and even improve environmental conditions (e.g. air quality) of the local community.

The major cost-intensive factors of microorganism-derived (bio)chemicals production are capitol costs (e.g. steel-based bioreactors with complex monitoring systems), prevention of microbial contamination (sterilisation equipment and aseptic conditions) and running costs (energy-intensive aeration, mixing and downstream processing). There are also the environmental concerns over waste processing/disposal and the requirements for large quantities of clean water. To address these issues, we selected the bacterium *Halomonas* as a next generation bio-propane chassis as it is proven to grow under non-sterile conditions in the absence microbial contamination.[35] This organism is both halophilic and alkaliphilic (6-20% NaCl, pH 8-12), and continuous cultures have been grown for over a year in industrial-scale vessels with no decline in growth potentials. Seawater and recycled water can be utilised without sterilisation, thereby conserving fresh water. This enables major capital cost savings as bioreactors can be constructed with low cost materials (e.g. plastics, ceramics and cement). The industrial potential of *Halomonas* has been demonstrated by its use in the production of polyhydroxyalkanoate at >10,000 tonnes scale.[36] Given these advantages, switching from *E. coli* to *Halomonas* is estimated to reduce costs of bio-propane production by up to 65%.[37,38]

Figure 20:
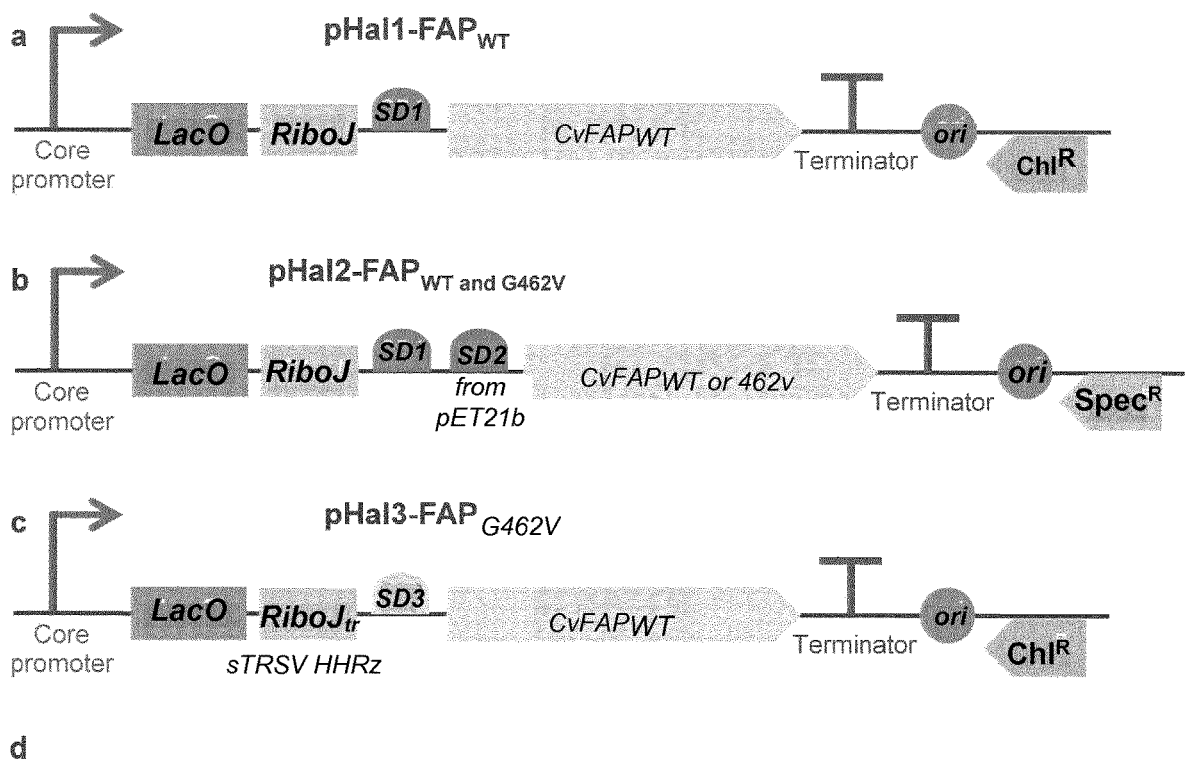
FIG. 20A to D. Chart showing schematic CvFAP Halomonas construct organisation of a) pHal1-FAP$_{WT}$, b) pHal2-FAP$_{WT/G462V}$ and c) pHal3-FAP$_{G462V}$. d) DNA sequence of the promoter region of the insert used to construct pHal3-FAP$_{G462V}$. The shading reflects which portion of the promoter region it specifies, as in part C. LacO=lac operator; SD1-3=Shine-Dalgarno sequences; ori=origin of replication; Chl$^R$ and Spec$^R$=chloramphenicol and spectinomycin resistance, respectively; RiboJ$_{tr}$=truncated RiboJ (hammerhead ribozyme from the tobacco ringspot virus satellite RNA).[1]

Halomonas-compatible constructs (pHal1-3) were generated using multiple organism specific pSEVA plasmids,[39] containing either an IPTG-inducible T7-like promoter (MmP1-lacO-RiboJ-SD; FIG. 16a)[40] or a modified medium strength T7-like promoter (FIG. 20).[41] Studies were performed in a phosphate-buffered high salt medium (6% NaCl) using *Halomonas* st. XV12, which contains a chromosomal copy of the equivalent T7-like RNA polymerase.[42] Small scale in vivo studies (1 mL) in sealed glass vials showed the CvFAP$_{G462V}$ variant construct (pHal2) in *Halomonas* generated similar propane levels seen with *E. coli* constructs under optimised conditions (78.9±14.13 mg/L culture; FIG. 16b). Encouragingly this shows that the switch in chassis from *E. coli* to *Halomonas* has not significantly diminished the propane titres when using the pHal2 construct. The equivalent wild-type construct showed a ~8-fold reduction in yields, while the presence of the lower strength promoter showed a ~5-fold reduction in propane yields (16.8±1.9 mg/L).

Surprisingly, comparative studies with cell permeabilisation or atoB transporter stimulation reagents showed no significant effect on propane yields (Table S8 (FIG. 29)), as opposed to production in *E. coli*. The former may be related to the cell wall and phospholipid adaptations for growth under halophilic conditions[43]. The lack of stimulation by ethyl acetoacetate is surprising given that putative atoE genes are present in the *Halomonas* genome.

*Halomonas* cultures displayed a relatively high tolerance to butyric acid, compared to *E. coli*, with the optimal concentrations of 80 mM (157.1±17.1 mg/L culture; FIG. 16c) in the presence of buffering salts. This is the highest reported bio-propane yield to date, with a ~9- and 5-fold increase of in vivo production levels than in *E. coli* via CvFAP$_{G462V}$ and ADO-based metabolic pathways, respectively.[7,10,11] However light access was still found to be a limiting factor, as seen by the non-saturating linear relationship between light 'intensity' (i.e. photosynthetic photon flux density (PPFD) up to 140 µE) and propane yields (FIG. 16c inset). Therefore, there is potential for dramatic increases in propane yield, once the balance between optimal intracellular light access and cell viability at high illumination rates has been achieved. Overall, this change in chassis to a *Halomonas* strain has improved the exploitation potential of bio-propane by dramatically increasing production yields with a potential major reduction in process costs.

Renewable, Sustainable Feed Stocks and Scalability

Figure 11:
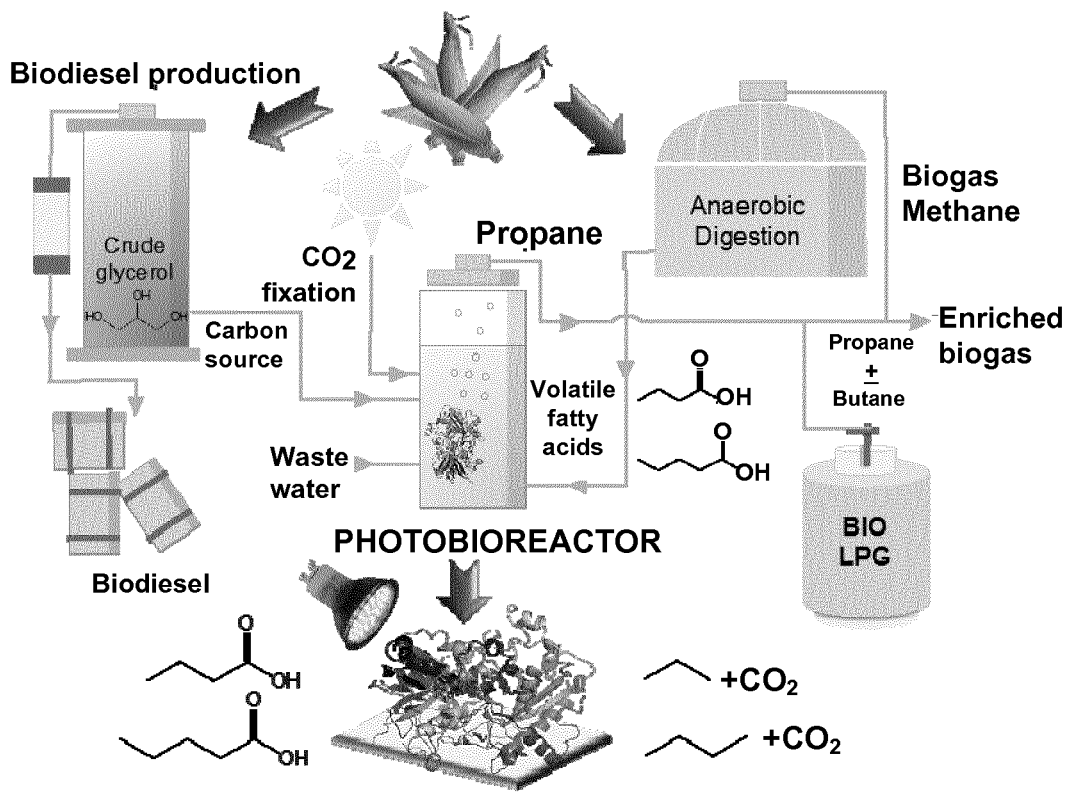
FIG. 11. Diagrammatic overview of the bio-LPG strategy, incorporating a novel photobioreactor design with existing waste feed stock, transportation and distribution infrastructures.

Key to the development of a commercially viable microbial bioprocess is the sourcing of cost effective renewable and sustainable feed stocks, and the demonstration of the scalability of the process. Propane production in *Halomonas* strains requires aerobic growth on simple carbon sources (e.g. sugars, glycerol) in high salt containing minerals, vitamins and butyric acid. Seawater is a cost effective natural mineral and salt broth (3.5%), while clarified wastewater streams provide an abundant alternative for inland sites. Further sea salt supplementation to the required salinity and mineral content at high alkalinity will effectively sanitise the medium without any requirement for sterilisation. Provision of vitamins can be achieved from autolysed spent brewery yeast, an abundant waste product. A cost-effective carbon source is raw biodiesel waste,[44] a low value product composed primarily of glycerol (60-70%), salts, methanol and residual vegetable oils (FIG. 11).[45] Butyric acid is a naturally occurring by-product from the anaerobic digestion (AD) of lignocellulosic agricultural biomass and food waste. Therefore, a plentiful supply could be obtained by tailoring AD plants to generate a waste stream enriched with butyric acid and/or other volatile fatty acids.

We developed a laboratory scaled prototype strategy with *Halomonas* expressing the highest performing pHal2-FAP$_{G462V}$ construct, utilising the cyanobacterial flatbed photobioreactor (400 mL). Comparative non-sterile aerobic fermentations were performed between 'clean' (laboratory grade reagents) and 'crude' (filtered seawater and biodiesel waste glycerin) medium in batch culture mode with online headspace monitoring for propane production.

Figure 17:
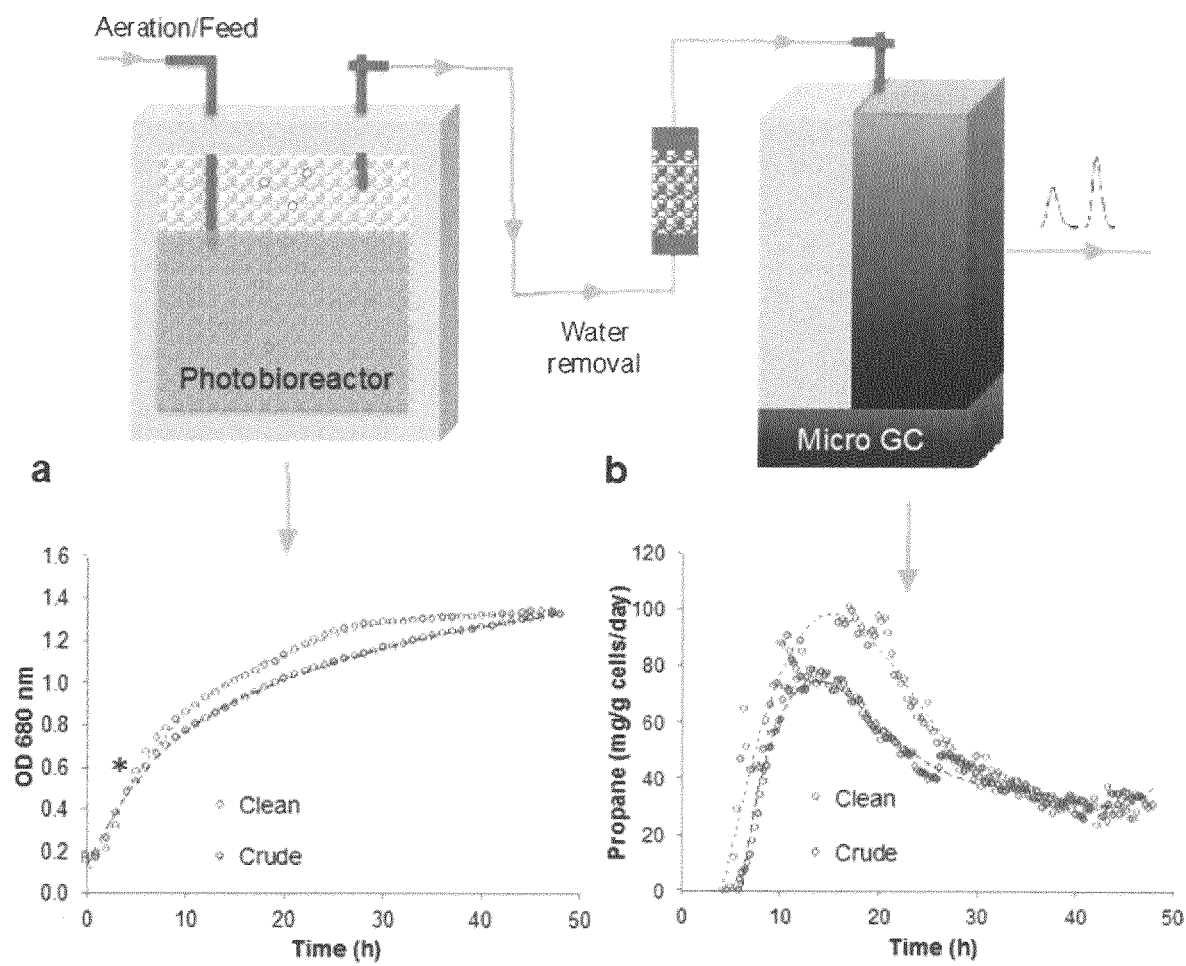
FIGS. 17A and B. Fermentation of Halomonas expressing pHal2-FAP$_{G462V}$ in a flat bed photobioreactor. a) Chart showing culture growth (OD 680 nm) and b) Chart showing propane production. Cultures (400 mL) were grown in high salt glycerol medium at pH 6.8 containing 50 µg/mL spectinomycin and 0.2 mL/L antifoam. 'Clean' fermentations included purified glycerol/NaCl, while 'Crude' ones contained biodiesel waste glycerin with sea water supplemented with additional NaCl (up to 6% total salinity). Conditions were maintained at 30° C. with maximal stirring, an airflow rate of 1.21 L/min, automated pH maintenance, culture optical density monitoring and ambient room lighting until mid log phase (4-5 hours). Recombinant protein expression was induced with IPTG (0.1 mM), followed by the addition of sodium butyrate (80-100 mM pH ~6.8) and blue light exposure (1625 pE), and maintained for ~100 h. Propane production was monitored at 15-20 minute intervals by automated headspace sampling using a Micro GC.

Encouragingly the presence of seawater and biodiesel waste impurities showed only a minor negative impact on culture growth (FIG. 17a), and by 48 h both cultures had achieved around the same cell density. There was only a small decrease in the maximal propane production rate in the crude medium (82 vs 100 mg/g cells/day; FIG. 17b), reaching peak production between 8-13 h after induction. Therefore, given there was only a small (1.2-fold) difference in propane production, we can take advantage of the cost benefits of utilising inexpensive abundant waste biomaterials and seawater when designing large scale bioreactors for renewable bio-propane production.

The robustness of a microbial chassis and/or bioprocess is also dependent on the maintenance of productivity over an extended period of time. Once proof-of-principle demonstration has been achieved with plasmid-borne inducible constructs, the commercial potential of this process will be strengthened by the development of stable, chromosomally integrated and constitutively expressed chassis capable of maintaining consistent propane production rates over prolonged fermentation times. In this study, we utilised plasmid-borne IPTG-inducible constructs, which showed the typical steady decline in propane production over time (FIG. 17b). Therefore, future application of this bio-propane/bio-LPG strategy will require genomic integration of constitutively expressed CvFAP variants, eliminating the need for both antibiotics and protein induction agents. Moreover, coupling this fermentation strategy with existing headspace extraction and propane liquefaction 'drop in' technologies and distribution infrastructure will strengthen the implementation of a potentially game-changing technology for the production of gaseous hydrocarbon fuels.

Conclusions

We have demonstrated the ability of CvFAP variants to produce a variety of bio-LPG hydrocarbons from readily available fatty acids, utilising light instead of nicotinamide cofactors. This opens up the field of gaseous biofuels production by substituting the lengthy ADO-based pathway strategy with a single light activated enzymatic step, coupled with the advantage of tight regulation of hydrocarbon yields by simply varying the light intensity. The successful transition from laboratory standard *E. coli* to the robust and cost effective *Halomonas* industrial chassis demonstrates the potential scalability of this novel bio-LPG strategy.

The 'drop-in' nature of photobioreactor strategy for gas production relies on the inherent robustness and efficient engineering capability of *Halomonas* to grow in a variety of wastewaters, with variable carbon and/or VFA sources. This will enable a tuning of the photobiocatalytic process design at any chosen locality to enable efficient volatile hydrocarbon production from the existing regionally sourced materials. This effectively brings us into the fifth generation of biofuels development, whereby localised robust non-sterile fermentations are performed utilising waste streams from existing manufacturing practices.

Additional Results and Discussion

In Vivo Propane Production

Average culture light exposure is determined by factors such as light 'intensity' (e.g. photosynthetic photon flux density in mol photons/sec/m$^2$), average distance from the light source, culture density/opaqueness, agitation rate and the shape of the reactor vessel (cylindrical vs flat bed). Initial in vivo studies showed that light access was a significant limiting factor, as replicate cultures with a distance deviation from the LED of even a few millimetres showed significant differences in propane yields, resulting in high calculation errors (e.g. 0.24+0.17 mg/L extract propane from wild type CvFAP with 1 mM butyric acid; 455 nm LED). This was confirmed by measuring the light intensity differences around each LED where the cultures are positioned (8 cm from the light source). For the 470 nm LED the highest light intensity was found to be within a narrow area (9 cm$^2$) directly below the light source (615 µmol photons/s/m$^2$). However as the cultures typically occupied a much larger area (360 cm$^2$), the average PPFD was found to be considerably lower, with an unacceptably high standard deviation (72±119 µmol photons/s/m$^2$).

To standardise culture light exposure, we assembled a custom built LED array light source composed of 480 individual blue LEDs, giving an area of 396 cm$^2$ of relatively consistent light intensity and a fixed average culture-to-LED distance (8 cm). The average PPFD (78±10 µmol photons/s/m$^2$) was similar to the average for the 470 nm LED, but importantly it showed a higher consistency of light over a wider area, and its maximal wavelength was close to the absorbance maximum of CvFAP$_{WT}$. This new light source enabled an increased reproducibility of replicate samples, allowing comparative studies to be performed.

Butyrate Accessibility

This optimisation approach to variant characterisation, unlike traditional enzyme kinetic studies, does not take into account likely differences in solubility and cofactor content of each variant protein in vivo. However this approach gives an insight into which of the different variants overall shows the best performance under fermentation conditions.

Figure 19:
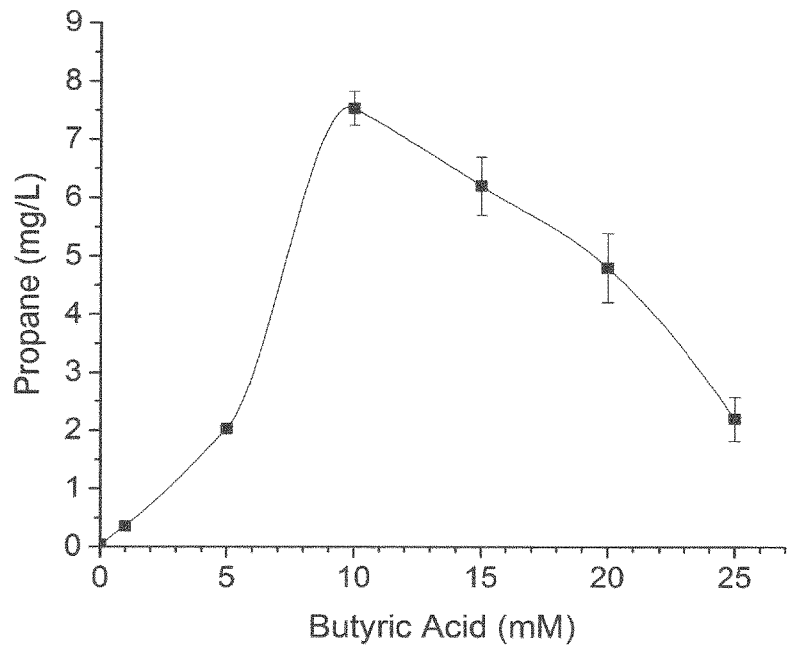
FIG. 19. Chart showing the effect of butyric acid concentration on the in vivo production of propane in E. coli in the absence of phosphate salt buffering agents. Cultures (20-100 mL) were grown in LB medium containing kanamycin (50 µg/mL) and an overnight starter culture (1% volume; same medium) for 6 h at 37° C. and 180 rpm. Recombinant protein expression was induced with IPTG (0.1 mM) and cultures were supplemented with butyric acid (1-25 mM). Triplicate aliquots (5 mL) of cultures were sealed into 20 mL glass vials and incubated at 30° C. for 16-18 h at 200 rpm, illuminated continuously with a blue LED panel. Headspace gas was analysed for propane content using a Micro GC (100 ms injection) with an Al$_2$O$_3$/KCl column.

In vivo studies with CvFAP$_{G462V}$ were performed to determine the optimal butyric acid concentration for maximal in vivo propane production (FIG. 19). Interestingly, a small level of propane (0.04±0.01 mg/L culture) was detected in cultures with no external butyric acid addition. This is a reflection of the natural intracellular levels of butyric acid and/or small quantities present in the culture medium. Careful controlling of the culture pH is needed, such as the addition of phosphate salts, to eliminate the effect of pH on propane production.

In Vivo Propane Production in *Halomonas*

Interestingly, the optimal butyrate concentration in the medium for the *Halomonas* construct was found to be around 80 mM (157.1±17.1 mg/L culture; Table S4), compared to 10 mM (17.51±0.98 mg/L) with the *E. coli* construct, in spite of the same enzyme being expressed in each construct. The apparent difference in optimal substrate concentration may be partly due to the inclusion of phosphate buffering salts in the medium, offsetting the pH change associated with butyric acid addition at induction. Comparative studies performed in the absence of phosphate salts showed the optimum to be around 40 mM, likely due to the drop in culture pH to ≤5.0 at higher concentrations of butyric acid. Additional factors that may impact are likely differences in both the butyrate tolerance (IC50) and uptake rates between the two organisms.

Methods

Materials and Equipment

All chemicals and solvents were purchased from commercial suppliers, and were of analytical grade or better. Media components were obtained from Formedium (Norfolk, UK). Gene sequencing and oligonucleotide synthesis were performed by Eurofins MWG (Ebersberg, Germany). Sequences of the oligonucleotides can be found in the Table S9 (FIG. 30). The mounted Hi-Power blue LEDs and LED drivers were from Thorlabs (New Jersey, USA), with wavelengths at 455 nm (1020 mW output) and 470 nm (253 mW). The domestically sourced white light LED (Integral) had a 25W power (2060 lumens). The photobioreactor was a thermostatic flat panel FMT 150 (400 mL; Photon Systems Instruments, Czech Republic) with integral culture monitoring (OD 680 nm), pH and feeding control and an LED blue light panel (465-470 nm; maximum PPFD=1648 pE photons).

*E. coli* strain BL21(DE3) was modified by chromosomal deletion of two aldehyde reductase genes yqhD and ahr/yjgB (BL21(DE3)ΔyqhD/ΔyjgB/Kan$^R$; GenBank: ACT44688.1 and AAA97166.1, respectively) as described previously.[46] The kanamycin selection gene was removed using the Flp-mediated excision methodology (BL21(DE3)ΔyqhD/ΔyjgB).[47] *Synechocystis* sp. PCC 6803 was modified by chromosomal deletion of the acyl-ACP synthetase (aas) encoding gene as described previously.[31,32] *Halomonas* strains TD01[36] and TQ10 and modified pSEVA plasmids were kindly supplied by Professor Guo-Qiang Chen (Tsinghua University, Beijing, China)[42]. *Halomonas* strain XV12 is a modified version of the TQ10 strain, which has been cured of an existing recombinant plasmid (unpublished results).

Gene Synthesis, Sub Cloning and Mutagenesis

Codon optimised gene synthesis of the following N-terminally truncated (ΔN) FAP enzymes was performed by GeneArt (Thermo Fisher): CvFAP$_{WT}$ from *Chlorella variabilis* NC64A[12] (Genbank: A0A248QE08; ΔN-61); CcFAP from *Chondrus crispus* (UniProt: R7Q9C0; ΔN-50 amino acids truncated), ChFAP from *Chrysochromulina* sp. (UniProt: A0A0MOJFC3), CmFAP from *Cyanidioschyzon merolae* (UniProt: M1VK13; ΔN-64), CrFAP from *Chlamydomonas reinhardtii* (UniProt: A8JHB7; ΔN-31), CsFAP from *Coccomyxa subellipsoidea* (UniProt: I0YJ13; ΔN-43), GpFAP from *Gonium pectorale* (UniProt: A0A150GC51; ΔN-38) and PtFAP from *Phaeodactylum tricornutum* (UniProt: B7FSU6)[12]. Each gene was sub cloned into pETM11 (NcoI-XhoI), incorporating a TEV protease cleavable 78 bp N-His6-tag (MKHHHHHHPMSDYDIPTTENLYFQGA, inserted before the initial methionine (residue 1)) for rapid protein purification. An additional codon optimised synthesised gene was synthesised by GeneArt, namely the short chain fatty acid transporter atoE from *E. coli* (UniProt: P76460) with its native OXB1 promoter in pET21b without a C-terminal His6-tag (www.oxfordgenetics.coma.[18,19] The gene encoding thioesterase Tes4 from *Bacteroides fragilis* (UniProt: P0ADA1) was obtained from plasmid pET-TPC4 as described previously.[10]

Variant CvFAP$_{G462V}$ was generated by site-directed mutagenesis of the wild type construct in pETM11 using the QuikChange whole plasmid synthesis protocol (Stratagene) with CloneAmp HiFi PCR premix (Clontech). The additional variants G462N/W/L/C/I/F/A/H/Y were generated using the Q5@ site directed mutagenesis kit, according to the manufacturers protocol (New England Biolabs). In each case, PCR products were analysed by agarose gel electrophoresis and gel purified using the NucleoSpin® Gel and PCR Clean-up kit (Macherey-Nagel). Constructs were transformed into *E. coli* st. NEB5☐ (Clontech) for plasmid recirculation and production. The presence of the mutations was confirmed by gene sequencing, followed by transformation into *E. coli* strains BL21(DE3) and BL21(DE3) ΔyqhD/ΔyjgB[10] for functional expression studies.

Molecular Modelling

Substrates palmitic and butyric acid docked into chain A of the crystal structure of the palmitic acid bound CvPAS structure 5NCC using Autodock vina.[16] AutoDock Tools 1.5.6 was used to assign non-polar hydrogens and prepare input files. A cubic search volume with sides of 15 Å was defined with the coordinates of C6 of palmitic acid as the centre, and an exhaustiveness of 50 was used to generate 20 conformations, out of which the lowest-energy conformation with the substrate in the correct orientation (carboxylate pointing towards the FAD) was selected. Mutations were performed in SwissPDBViewer 4.10,[48] using the exhaustive search function to identify the best rotamer for the mutated residue.

*Escherichia coli* Multi-Enzyme Constructs Generation

Dual gene construct CvFAP$_{G462V}$-atoE was generated by ligation of PCR amplified CvFAP$_{G462V}$ into the existing atoE-pET21b construct by In-Fusion cloning, with each gene controlled by its own promoter (T7 and OXB1, respectively). Additional constructs of N-His6-CvFAP$_{G462V}$ were generated in plasmids pET21b and pBbA1c[49] by PCR-mediated In-Fusion cloning. Constructs were transformed into *E. coli* st. NEB5α, BL21(DE3) and BL21(DE3)ΔyqhD/ΔyjgB[10] for functional expression studies.

Synechcocystis Constructs Generation

The generation of a *Synechocystis* specific plasmid encoding CvFAP$_{G462V}$ (pJET-FAP$_{G462V}$; codon-optimised for *E. coli*) was performed by using the previously described template pJET-FAP (CrFAP from *Chlamydomonas reinhardtii*).[32] Tes4 was sub-cloned into blunt-ended pJET1.2 plasmid to generate pJET-Tes4, under the control of a promoter.[32] Plasmids containing both Tes4 and FAP$_{G462V}$ were constructed with Ptrc or Pcoa promoters (Ptrc-Tes4-FAP$_{G462V}$ and Pcoa-Tes4-FAP$_{G462V}$ respectively) using the Biopart Assembly Standard for Idempotent Cloning (BASIC) method as described previously.[31,32,50] Plasmid assembly was validated by DNA sequencing.

Plasmids were transformed into the E. coli HB101 helper/cargo strain, containing the pRL623 mobilization plasmid. This was combined with the conjugal E. coli ED8654 strain carrying the pRL443 mobilization plasmid[51] to transform Synechocystis sp. PCC 6803 Δaas strain[32] using the tri-parental conjugation method described previously.[31,32] The conjugation mixture was grown on BG11[52] agar plates and incubated for 2 d at 30° C. with white light (60 μmol pE). Culture was recovered from the plate, re-suspended in 500 μL of BG11-Co medium,[32] and grown on BG11 agar containing 20 μg/ml erythromycin at 30° C. with white light. Colonies appeared within one week.

Halomonas Constructs Generation

In each Halomonas compatible construct, an IPTG-inducible PT7-like-promoter cassette (MmP1-lacO-RiboJ-RBS; Figure S20a-b)[42,53] replaced the existing T7 promoter. The gene encoding non-tagged CvFAP$_{WT}$ was cloned into modified pSEVA321[39] by PCR-mediated In-Fusion cloning to generate pHal1-FAP$_{WT}$. Both wild-type and G462V variant CvFAP were cloned into a second Halomonas compatible plasmid based on pSEVA441[39] (pHal2-FAP$_{WT}$ and pHal2-FAP$_{G462V}$, respectively). This plasmid contains the PT7-like-promoter, an NcoI restriction site (underlined) and a pET21b-like Shine-Delgarno sequence (SD2) upstream of the start codon (bold; TTTGTTTAACTT-TAAGAAGGAGATATA<u>CC</u>ATGG; FIG. S20b). Both the vector and pETM11 genes were double digested (NcoI and (partial) XhoI), gel purified then ligated and transformed into E. coli st. Stellar as above. An additional CvFAP$_{G462V}$ construct was generated (pHal3-FAP$_{G462V}$), based on pHal1-FAP$_{WT}$, containing an alternative engineered T7-like inducible promoter based on prior promoter engineering studies in Halomonas (FIG. S20c-d).[41] This was generated by double digestion (PacI/SmaI) and ligation of the gene and vector (pHal1-FAP$_{WT}$), the latter eliminating the existing T7-like promoter and CvFAP$_{WT}$ gene. Full-length construct was selected following transformation into E. coli st. Stellar for plasmid recircularisation, recovery and sequencing.

The insertion of E. coli derived plasmids into Halomonas st XV12 was performed using a modified conjugation protocol.[41] Halomonas constructs were transformed into E. coli strain S17-1[54], and plated onto antibiotic selective LB agar (kanamycin or chloramphenicol for pHal2 and pHal1/3 plasmids, respectively). Halomonas st. XV12 was plated onto YTN6 agar (10 g/L tryptone, 5 g/L yeast extract; 60 g/L NaCl and 15 g/L agar), and both cultures were incubated overnight at 37° C. Colonies of both E. coli S17-1 (plasmid donor) and Halomonas st. XV12 (recipient) were mixed together on YTN3 agar (10 g/L tryptone, 5 g/L yeast extract; 30 g/L NaCl and 15 g/L agar) and incubated overnight at 37° C. Individual colonies were re-plated onto antibiotic-containing YTN6 agar, which is selective for Halomonas growth only.

Protein Expression and Lysate Production

Wild type FAP-pETM11 homologues in E. coli st. BL21 (DE3) were cultured in LB Broth Miller (500 mL; Formedium) containing 30 μg/mL kanamycin at 37° C. with 180 rpm shaking until OD$_{600}$ nm=0.2. The temperature was maintained at 25° C. until OD$_{600}$ nm=0.6. Recombinant protein production was induced with 50 μM IPTG, and maintained at 17° C. overnight. Cells were harvested by centrifugation (8950×g, 4° C., 10 min), and analysed for protein content using 12% SDS-PAGE gels (Mini-PROTEAN® TGX Stain-Free™ Precast Gels, Bio-Rad). Protein gels were imaged using a BioRad Gel Doc™ EZ Imager and relative protein band intensity was determined using the BioRad ImageLab™ software.

Cell pellets were resuspended in lysis buffer (1.2-1.7 mL/g pellet; 50 mM Tris pH 8 containing 300 mM NaCl, 10 mM imidazole, 10% glycerol, 0.25 □g/mL lysozyme, 10 μg/mL DNase I and 1×protease inhibitors) and sonicated for 20 minutes (20 s on, 60 s off; 30% amplitude). Cell-free lysate was prepared by centrifugation at 48000×g for 30 minutes at 4° C. Lysate samples were analysed for recombinant protein expression by SDS PAGE (12% Mini-PROTEAN-TGX stain-free gel; Bio-Rad), using Precision Plus unstained protein ladder (Bio-Rad) at 300 V for 20 minutes. Protein content was visualised using an EZ Gel Doc (Bio-Rad).

Hydrocarbon Production

In vitro propane production reactions (200 μL) were composed of FAP-containing cell-free lysate (180 μL) and butyric acid (0.36 to 4.5 mM) in sealed glass GC vials. The reactions were incubated at 30° C. for 24 h at 180 rpm under illumination (blue LED; 455 nm). Headspace gas was analysed for propane content using a Micro GC.

In vivo propane production of pETM11- and pET21b-containing CvFAP$_{WT}$ and variants in E. coli was performed by the following general protocol: Cultures (20-100 mL) in LB medium containing kanamycin (50 μg/mL; pETM11) or ampicillin (100 μg/mL) were incubated for 4-6 h (OD$_{600}$~1) at 37° C. and 180 rpm, followed by induction with IPTG (100 μM) and butyric acid supplementation (1-1000 mM; pH 6.8). Triplicate aliquots (1-5 mL) each of 3 biological replicate cultures were sealed into glass vials (4-20 mL) and incubated at 30° C. for 16-18 h at 200 rpm, illuminated continuously with an LED (white or blue (455 nm or 470 nm)). Headspace gas was analysed for propane content using a Micro GC. Comparative in vivo studies with 10 mM butyric, isobutyric, valeric, 3-methylbutyric and isovaleric acids were performed as above, with culture induction at OD$_{600}$ of 0.6-0.8.

To test the functionality of CvFAP$_{G462V}$ in Synechocystis, cultures (8 mL) were incubated at 30° C. in BG11 medium containing hexadecanoic acid (C16:0) under 300 pE white light in an algaetron. The production of pentadecane was determined by GC. Photosynthetic in vivo butyrate and propane production studies in Synechocystis was performed in BG11 medium using a modified protocol as follows: Initial cultures in BG11 medium were incubated at 30° C. under 30 pE white light until OD 720 nm reached 1.0 (~4 days). Replicate culture aliquots (2 mL) were harvested by centrifugation and re-suspended in 1 mL BG11 medium supplemented with sodium bicarbonate (150 mM), IPTG (for Ptrc cultures only), 20 μg/ml erythromycin at 30° C.+/−butyric acid (10 mM). Cultures were sealed within 4 mL gas tight vials and incubated at 30° C. for 24-48 h under blue light (average 63 pE). Headspace gas was analysed for propane content using a Micro GC, and cell-free culture supernatant samples (10 μL) were analysed for butyric acid content by HPLC using an Agilent Hi-Plex H column.

Propane production in Halomonas strains was performed by a modification of the E. coli general protocol as follows: Cultures were grown in phosphate buffered YTN6 medium (50 mM K$_2$HPO$_4$ pH 6.6) containing spectinomycin (pHal2-FAP$_{G462V}$; 50 □g/mL) or chloramphenicol (pHal1- and pHal3 constructs; 34 μg/mL) for 5 h at 37° C. and 180 rpm. Recombinant protein expression was induced with IPTG (0.1 mM) at a higher cell density than E. coli cultures (OD~1.6). The remainder of the in vivo propane production process was performed as above, with butyric acid concentrations of 10-25 mM. The effect of cell permeabilisation was investigated by supplementing cultures with Triton X-100 (2%) and/or sucrose (1%). Butyrate transporter stimulation studies were performed in the presence of methyl and ethyl acetoacetate (0.1-30 mM). The effect of light saturation on propane production was performed by varying the distance between the cultures and the light source.

Halomonas Fermentation

The photobioreactor was set up in batch mode with high salt glycerol medium at pH 6.8 (5 g/L yeast extract, 1 g/L glycerol, 60 g/L NaCl, 50 µg/mL spectinomycin and 0.2 mL/L antifoam; 400 mL), pre-equilibrated at 30° C. with maximal stirring. An overnight starter culture (20 mL) of pHal2-FAP$_{G462V}$ was added and the culture was maintained at 30° C. with an airflow rate of 1.21 L/min, automated pH maintenance, culture optical density monitoring and ambient room lighting until mid log phase (4-5 hours). Recombinant protein expression was induced with IPTG (0.1 mM), followed by the addition of sodium butyrate (80-100 mM pH ~6.8) and blue light exposure (1625 µE), and maintained for ~100 h. During continuous flow mode, maintenance of $OD_{680nm}$ of 1.0 was achieved by automated additions of culture medium as above. Propane production was monitored at 15 min intervals by automated headspace sampling using a Micro GC, while aqueous butyrate and glycerol depletion were detected by HPLC.

Synechcocystis Fermentation

The photobioreactor (400 mL) was set up in batch mode with starter culture diluted 3:1 in fresh BG11 medium pH 8.0$^8$ in the presence/absence of supplementary 150 mM NaHCO$_3$ for pH control and CO$_2$ supply (fed and non-fed cultures, respectively). The culture was maintained at 30° C. with maximal stirring with an airflow rate of 1.21 L/min, illumination of warm white light (30 pE), automated pH maintenance (1M acetic acid) and optical density monitoring (720 nm). After reaching an optical density of ~0.5, the warm white illumination was increased to 60 µE the integral actinic blue LED light panel was activated to provide 750 µE blue light (460-480 nm). The culture was maintained at 30° C. for with manual headspace sampling and monitoring by Micro GC to quantify propane production.

Analytical Techniques

Propane levels were determined by manual headspace injection using an Agilent 490 Micro GC, containing an Al$_2$O$_3$/KCl column and a thermal conductivity detector (TCD). Headspace samples were manually introduced through a heated injector (110° C.), with an injection time of 100 ms using helium as the carrier gas (10.2 psi). During the continuous monitoring mode, fermenter exhaust gases were constantly flowing through the Micro GC cell, with periodic 100 ms sampling. Compounds were separated isothermally (100° C.) over 120 s under static pressure conditions, with a sampling frequency of 100 Hz. Propane concentrations were calculated by comparing the peak areas to a standard curve generated under the same conditions.

Aqueous culture metabolites (glycerol and butyric acid) were analysed by HPLC using an Agilent 1260 Infinity HPLC with a 1260 ALS autosampler, TCC SL column heater and a 1260 refractive index detector (RID). Cell-free culture supernatant samples (10 µL injection) were analysed isocratically on an Agilent Hi-Plex H column (300×7.7 mm; 5 mM H$_2$SO$_4$) at 60° C. with a flow rate of 0.7 mL/min for 40 minutes. Analyte concentrations were calculated by comparing the peak areas to a standard curve generated under the same HPLC conditions.

REFERENCES

A number of publications are cited above in order to more fully describe and disclose the invention and the state of the art to which the invention pertains. Full citations for these references are provided below. The entirety of each of these references is incorporated herein.

1. Bugg T D H, Resch M G. Editorial overview: Energy: Prospects for fuels and chemicals from a biomass-based biorefinery using post-genomic chemical biology tools. Curr Opin Chem Biol. 2015; 29:v-vii.
2. Chen R, Dou J. Biofuels and bio-based chemicals from lignocellulose: Metabolic engineering strategies in strain development. Biotechnol Lett. 2016; 38:213-21.
3. Cheon S, Kim H M, Gustaysson M, Lee S Y. Recent trends in metabolic engineering of microorganisms for the production of advanced biofuels. Curr Opin Chem Biol. 2016; 35:10-21.
4. de Jong E, Jungmeier G. In Industrial biorefineries & white biotechnology, eds. Pandey A, Hofer R, Larroche C, Taherzadeh M and Nampoothiri M. Place: Elsevier B.V.; 2015. pp. 3-33.
5. Toogood H S, Scrutton N S. Retooling microorganisms for the fermentative production of alcohols. Curr Opin Biotechnol. 2018; 50:1-10.
6. Sheppard M J, Kunjapur A M, Prather K U. Modular and selective biosynthesis of gasoline-range alkanes. Metab Eng. 2016; 33:28-40.
7. Zhang L, Liang Y, Wu W, Tan X, Lu X. Microbial synthesis of propane by engineering valine pathway and aldehyde-deformylating oxygenase. Biotechnol Biofuels. 2016; 9:80.
8. Menon N, Pasztor A, Menon B R, Kallio P, Fisher K, Akhtar M K, et al. A microbial platform for renewable propane synthesis based on a fermentative butanol pathway. Biotechnol Biofuels. 2015; 8:61-12.
9. Schirmer A, Rude M, Li X, Popova E, del Cardayre S. Microbial biosynthesis of alkanes. Science. 2010; 329: 559-62.
10. Khara B, Menon N, Levy C, Mansell D, Das D, Marsh E N G, et al. Production of propane and other short-chain alkanes by structure-based engineering of ligand specificity in aldehyde-deformylating oxygenase. ChemBioChem. 2013; 14:1204-8.
11. Kallio P, Pásztor A, Thiel K, Akhtar M K, Jones P R. An engineered pathway for the biosynthesis of renewable propane. Nat Commun. 2014; 5:4731.
12. Li N, Chang W C, Warui D M, Booker S J. Biochemistry. 2012; 51:7908-16.
13. Sorigué D, Légeret B, Cuiné S, Blangy S, Moulin S, Billon E, et al. An algal photoenzyme converts fatty acids to hydrocarbons. Science. 2017; 357:903-7.
14. Chen X, Yin J, Ye J, Zhang H, Che X, Ma Y, et al. Engineering Halomonas bluephagenesis TD01 for non-sterile production of poly(3-hydroxybutyrate-co-4-hydroxybutyrate). Bioresour Technol. 2017; 244:534-41.
15. Tan D, Wu Q, Chen J-C, Chen G-Q. Engineering Halomonas TD01 for the low-cost production of polyhydroxyalkanoates. Metab Eng. 2014; 26:34-47.
16. Sun C Q, O'Connor C J, Turner S J, Lewis G D, Stanley R A, Roberton A M. The effect of pH on the inhibition of bacterial growth by physiological concentrations of butyric acid: Implications for neonates fed on suckled milk. Chem Biol Interact. 1998; 113:117-31.
17. Tao W, Lv L, Chen G-Q. Engineering Halomonas species TD01 for enhanced polyhydroxyalkanoates synthesis via CRISPRi. Microb Cell Fact. 2017, DOI: 10.11861s12934-017-0655-3:1-11.
18. Zhao H, Zhang H M, Chen X, Li T, Wu Q, Ouyang Q, et al. Novel T7-like expression systems used for Halomonas. Metab Eng. 2017; 39:128-4

19. Lan et al 2013 Oxygen-tolerant coenzyme A-acylating aldehyde dehydrogenase facilitates efficient photosynthetic n-butanol biosynthesis in cyanobacteria. Energy Environ Sci. 6(9): 2672-2681
20. Hettwer, D. J. and Wang, H. Y. 1986 Protein release from chemically permeabilized *Escherichia coll*. In Separation, Recovery, and Purification in Biotechnology. ACS Symposium Series, Vol. 314 pp 2-8.
21. Jenkins, L. S. and Nunn, W. D. 1987 Genetic and molecular characterization of the genes involved in short-chain fatty acid degradation in *Escherichia coli*: the ato system. J Bacteriol. 169(1): 42-52
22. Silva-Rocha, R. et al 2013. The Standard European Vector Architecture (SEVA): a coherent platform for the analysis and deployment of complex prokaryotic phenotypes. Nucleic Acids Res. 41:D666-D675
23. Zhao, H. et al 2017. Novel T7-like expression systems used for *Halomonas*. Metab Eng. 39:128-140.
24. Simon R, Priefer U, Puhler A (1983) A broad host range mobilization system for in vivo genetic-engineering-transposon mutagenesis in gram-negative bacteria. Bio-Technol 1: 784-791.

REFERENCE LIST FOR EXAMPLE 9

1. Toogood, H. S. & Scrutton, N. S. Retooling microorganisms for the fermentative production of alcohols. *Curr Opin Biotechnol* 50, 1-10, (2018).
2 Bugg, T. D. H. & Resch, M. G. Editorial overview: Energy: Prospects for fuels and chemicals from a biomass-based biorefinery using post-genomic chemical biology tools. *Curr Opin Chem Biol* 29, v-vii, (2015).
3 Chen, R. & Dou, J. Biofuels and bio-based chemicals from lignocellulose: metabolic engineering strategies in strain development. *Biotechnol Lett* 38, 213-221, (2016).
4 Cheon, S., Kim, H. M., Gustaysson, M. & Lee, S. Y. Recent trends in metabolic engineering of microorganisms for the production of advanced biofuels. *Curr Opin Chem Biol* 35, 10-21, (2016).
5 de Jong, E. & Jungmeier, G. in *Industrial Biorefineries & White Biotechnology* (eds A. Pandey et al.) Ch. 1, 3-33 (Elsevier B.V., 2015).
6 Zhang, L., Liang, Y., Wu, W., Tan, X. & Lu, X. Microbial synthesis of propane by engineering valine pathway and aldehyde-deformylating oxygenase. *Biotechnol Biofuels* 9, 80, (2016).
7 Menon, N. et al. A microbial platform for renewable propane synthesis based on a fermentative butanol pathway. *Biotechnol Biofuels* 8, 61-12, (2015).
8 Zakaria, Z. Y., Mohamad, N. F. & Amin, N. A. S. Catalysts screening for catalytic conversion of glycerol to olefins. *J Appl Sci* 10, 1166-1170, (2010).
9 Schirmer, A., Rude, M., Li, X., Popova, E. & del Cardayre, S. Microbial biosynthesis of alkanes. *Science* 329, 559-562, (2010).
10 Kallio, P., Pásztor, A., Thiel, K., Akhtar, M. K. & Jones, P. R. An engineered pathway for the biosynthesis of renewable propane. *Nat Commun* 5, 4731, (2014).
11 Sheppard, M. J., Kunjapur, A. M. & Prather, K. L. J. Modular and selective biosynthesis of gasoline-range alkanes. *Metab Eng* 33, 28-40, (2016).
12 Sorigué, D. et al. An algal photoenzyme converts fatty acids to hydrocarbons. *Science* 357, 903-907, (2017).
13 Zhang, W. et al. Hydrocarbon synthesis via photoenzymatic decarboxylation of carboxylic acids. *J Am Chem Soc*, jacs.8b12282, (2019).
14 Huijbers, M. M. E., Zhang, W., Tonin, F. & Hollmann, F. Light-driven enzymatic decarboxylation of fatty acids. *Angew Chem Int Ed Engl* 57, 13648-13651, (2018).
15 Khara, B. et al. Production of propane and other short-chain alkanes by structure-based engineering of ligand specificity in aldehyde-deformylating oxygenase. *ChemBioChem* 14, 1204-1208, (2013).
16 Trott, O. & Olson, A. J. AutoDock Vina: Improving the speed and accuracy of docking with a new scoring function, efficient optimization and multithreading. *J. Comput. Chem.* 31, 455-461, (2010).
17 Bao, R.-M., Yang, H.-M., Yu, C.-M., Zhang, W.-F. & Tang, J.-B. An efficient protocol to enhance the extracellular production of recombinant protein from *Escherichia coli* by the synergistic effects of sucrose, glycine, and Triton X-100. *Protein Expression Purif* 126, 9-15, (2016).
18 Matta, M. K., Lioliou, E. E., Panagiotidis, C. H., Kyriakidis, D. A. & Panagiotidis, C. A. Interactions of the antizyme AtoC with regulatory elements of the *Escherichia coli* atoDAEB operon. J Bacteriol 189, 6324-6332, (2007).
19 Jenkins, L. S. & Nunn, W. D. Genetic and molecular characterization of the genes involved in short-chain fatty acid degradation in *Escherichia coli*: the ato system. *J Bacteriol* 169, 42-52, (1987).
20 Elgas. *LPG Gas Mixture of Propane & Butane: Which Gas is Present in LPG*, <https://www.elgas.com.au/blog/1972-lpg-contai ns-wh ich-gases-gases-prese nt-in-lpg-gases-used> (2019).
21 Agency, I. E. *Energy Technology Perspectives*. 48 (OECD, 2006).
22 Liberton, M. et al. Organization and flexibility of cyanobacterial thylakoid membranes examined by neutron scattering. *J. Biol. Chem.* 288, 3632-3640, (2013).
23 Kufryk, G. I., Sachet, M., Schmetterer, G. & Vermaas, W. F. J. Transformation of the Cyanobacterium *Synechocystis* Sp. PCC 6803 as a Tool for Genetic Mapping: Optimization of Efficiency. *FEMS Microbiol. Lett.* 206, 215-219, (2002).
24 Zang, X., Liu, B., Liu, S., Arunakumara, K. K. I. U. & Zhang, X. Optimum Conditions for Transformation of *Synechocystis* Sp. PCC 6803. *J. Microbiol. Seoul Korea* 45, 241-245, (2007).
25 Zavřel, T., Očenášová, P. & Červený, J. Phenotypic Characterization of *Synechocystis* Sp. PCC 6803 Substrains Reveals Differences in Sensitivity to Abiotic Stress. *PLoS One* 12, e0189130, (2017).
26 Jahn, M. et al. Growth of Cyanobacteria Is Constrained by the Abundance of Light and Carbon Assimilation Proteins. *Cell Rep.* 25, 478-486, (2018).
27 van Alphen, P., Abedini Najafabadi, H., Branco Dos Santos, F. & Hellingwerf, K. J. Increasing the Photoautotrophic Growth Rate of *Synechocystis* Sp. PCC 6803 by Identifying the Limitations of Its Cultivation. *Biotechnol. J.* 13, e1700764, (2018).
28 Atsumi, S., Higashide, W. & Liao, J. C. Direct photosynthetic recycling of carbon dioxide to isobutyraldehyde. *Nat. Biotechnol.* 27, 1177-1180, (2009).
29 Yoshikawa, K., Toya, Y. & Shimizu, H. Metabolic engineering of *Synechocystis* sp. PCC 6803 for enhanced ethanol production based on flux balance analysis. *Bioprocess Biosyst. Eng.* 40, 791-796, (2017).
30 Gao, Z., Zhao, H., Li, Z., Tan, X. & Lu, X. Photosynthetic Production of Ethanol from Carbon Dioxide in Genetically Engineered Cyanobacteria. *Energy Env. Sci.* 5, 9857-9865, (2012).

32 Yunus, I. S. & Jones, P. R. Photosynthesis-dependant biosynthesis of medium chain-length fatty acids and alcohols. *Metabolic Engineering* 44, 81-88, (2018).

32 Yunus, I. S. et al. Synthetic metabolic pathways for photobiological conversion of $CO_2$ into hydrocarbon fuel. *Metabolic Engineering* 49, 201-211, (2018).

33 Lehtinen, T., Virtanen, H., Santala, S. & Santala, V. Production of Alkanes from $CO_2$ by Engineered Bacteria. *Biotechnol. Biofuels* 11, 228, (2018).

34 Cotton, C. A. R. et al. Photosynthetic Constraints on Fuel from Microbes. *Front. Bioeng. Biotechnol.* 3, 36, (2015).

35 Tan, D., Xue, Y.-S., Aibaidula, G. & Chen, G.-Q. Unsterile and continuous production of polyhydroxybutyrate by *Halomonas* TD01. *Bioresour Technol* 102, 8130-8136, (2011).

36 Tao, W., Lv, L. & Chen, G.-Q. Engineering *Halomonas* species TD01 for enhanced polyhydroxyalkanoates synthesis via CRISPRi. *Microb Cell Fact,* 1-11, (2017).

37 Quillaguaman, J., Guzman, H., Van-Thuoc, D. & Hatti-Kaul, R. Synthesis and production of polyhydroxyalkanoates by halophiles: current potential and future prospects. *Appl Microbiol Biotechnol* 85, 1687-1696, (2009).

38 Ye, J. et al. Pilot scale-up of poly(3-hydroxybutyrate-co-4-hydroxybutyrate) production by *Halomonas bluephagenesis* via cell growth adapted optimization process. *Biotechnol J* 13, 1800074-1800010, (2018).

39 Silva-Rocha, R. et al. The Standard European Vector Architecture (SEVA): a coherent platform for the analysis and deployment of complex prokaryotic phenotypes. *Nucleic Acids Res* 41, D666-D675, (2012).

40 Tan, D., Wu, Q., Chen, J.-C. & Chen, G.-Q. Engineering *Halomonas* TD01 for the low-cost production of polyhydroxyalkanoates. *Metab Eng* 26, 34-47, (2014).

41 Li, T. et al. Engineering of core promoter regions enables the construction of constitutive and inducible promoters in *Halomonas* sp. *Biotechnol J*11, 219-227, (2016).

42 Zhao, H. et al. Novel T7-like expression systems used for *Halomonas*. *Metab Eng* 39, 128-140, (2017).

43 Vreeland, R. H., Anderson, R. & Murray, R. G. Cell wall and phospholipid composition and their contribution to the salt tolerance of *Halomonas elongata. J Bacteriol* 160, 879-883, (1984).

44 Chozhavendhan, S. et al. in *Waste to Wealth. Energy, Environment, and Sustainability* Vol. 41 (eds R Singhania, R Agarwal, R Kumar, & R Sukumaran) 65-82 (Springer Singapore, 2017).

45 Quispe, C. A. G., Coronado, C. J. R. & Carvalho Jr, J. A. Glycerol: Production, consumption, prices, characterization and new trends in combustion. Renewable Sustainable Energy Rev27, 475-493, (2013).

46 Kallio, P., Pásztor, A., Thiel, K., Akhtar, M. K. & Jones, P. R. An engineered pathway for the biosynthesis of renewable propane. *Nat. Commun.* 5, 4731, (2014).

47 Datsenko, K. A. & Wanner, B. L. One-step inactivation of chromosomal genes in *Escherichia coli* K-12 using PCR products. *Proc. Natl. Acad. Sci. U.S.A* 97, 6640-6645, (2000).

48 Guex, N. & Peitsch, M. C. SWISS-MODEL and the Swiss-PdbViewer: An environment for comparative protein modeling. *Electrophoresis* 18, 2714-2723, (1997).

49 Lee, T. S. et al. Biobrick vectors and datasheets: A synthetic biology platform for metabolic engineering. *Abstracts of Papers of the American Chemical Society* 239, (2010).

50 Storch, M. et al. BASIC: a new biopart assembly standard for idempotent cloning provides accurate, single-tier DNA assembly for synthetic biology. *ACS Synth. Biol.* 4, 781-787, (2015).

51 J., E., A., V., M., M.-P. A., E., F. & P., W. C. Reduction of conjugal transfer efficiency by three restriction activities of *Anabaena* sp. strain PCC 7120. *J. Bacteriol.* 179, 1998-2005, (1997).

52 R. Y., S., R., K., M., M. & G., C.-B. Purification and properties of unicellular blue-green algae (Order Chroococcales). *Bacteriol. Rev.* 35, 171-205, (1971).

53 Lou, C., Stanton, B., Chen, Y.-J., Munsky, B. & Voigt, C. A. Ribozyme-based insulator parts buffer synthetic circuits from genetic context. *Nat Biotechnol* 30, 1137-1142, (2012).

54 Strand, T. A., Lale, R., Degnes, K. F., Lando, M. & Valla, S. A new and improved host-independent plasmid system for RK2-based conjugal transfer. *PLoS One* 9, e90372, (2014).

For standard molecular biology techniques, see Sambrook, J., Russel, D. W. *Molecular Cloning, A Laboratory Manual.* 3 ed. 2001, Cold Spring Harbor, N.Y.: Cold Spring Harbor Laboratory Press

---

The invention claimed is:

1. A fatty acid decarboxylase comprising at least 70% sequence identity to SEQ ID NO:1 or 2, and an amino acid substitution at a position corresponding to G462 of SEQ ID NO:1, wherein the fatty acid decarboxylase has an improved butyric acid to propane decarboxylase activity compared to a fatty acid decarboxylase comprising SEQ ID NO:1.

2. The fatty acid decarboxylase according to claim 1, wherein the amino acid substitution is selected from G462V, G462F, G462A, G462Y, G462C, G462N, and G462W.

3. The fatty acid decarboxylase according to claim 1, comprising an amino acid sequence comprising a consensus sequence, wherein the consensus sequence comprises at least 70% sequence identity to SEQ ID NO:3.

4. The fatty acid decarboxylase according to claim 1, comprising an amino acid sequence comprises an active site at a position corresponding to residues 398-575 of SEQ ID NO:1,
wherein the active site comprises at least 70% identity to one or more sequences selected from SEQ ID NOs: 4 to 7.

5. The fatty acid decarboxylase according to claim 1, comprising an amino acid sequence having at least 90% sequence identity to SEQ ID NO:1 or 2.

6. The fatty acid decarboxylase according to claim 1, which accepts as a substrate a fatty acid having a chain length equal to or less than 8 carbons, preferably a chain length of 2-5 carbons.

7. The fatty acid decarboxylase according to claim 1, wherein the amino acid substitution sterically impedes fatty acids with a chain length greater than 8 carbons from binding.

8. The fatty acid decarboxylase according to claim 1, wherein the fatty acid decarboxylase gives a higher yield of a $C_n$ alkane compared to the yield of the same $C_n$ alkane obtained using a fatty acid decarboxylase lacking the substitution at a position corresponding to G462 of SEQ ID NO:1 using a $C_{n+1}$ fatty acid as a substrate, wherein n≤5.

9. The fatty acid decarboxylase according to claim 1, wherein the fatty acid decarboxylase has light-dependent decarboxylase activity, such as blue light-dependent decarboxylase activity, preferably wherein the activity is dependent of light with a wavelength of 400-520 nm.

10. The fatty acid decarboxylase according to claim 1, wherein the fatty acid decarboxylase further comprises an amino acid substitution at a position corresponding to at least one of: V453 of SEQ ID NO:1, G455 of SEQ ID NO:1, A457 of SEQ ID NO:1, Y466 of SEQ ID NO:1, or T484 of SEQ ID NO:1.

11. The fatty acid decarboxylase according to claim 10, wherein the fatty acid decarboxylase comprises an amino acid substitution selected from one or more of V453F, V453I, V453L, V453W, G455F, G455I, G455V, G455W, G455L, A457F, A457I, A457L, A457V, Y466W, T484A, T484E, T484I, T484L.

12. A cell comprising a nucleic acid encoding a fatty acid decarboxylase according to claim 1.

13. A cell according to claim 12, wherein the cell is a bacterial cell, preferably the cell of a *Halomonas* spp.

14. A method comprising catalysis of the conversion of a $C_{n+1}$ fatty acid to a $C_n$ alkane using a fatty acid decarboxylase, wherein n≤5 and the fatty acid decarboxylase is a fatty acid decarboxylase according to claim 1.

15. A method of producing a $C_n$ alkane, comprising the step of:
catalysis of the conversion of a $C_{n+1}$ fatty acid to a $C_n$ alkane using a fatty acid decarboxylase,
where n≤5,
wherein the fatty acid decarboxylase is a fatty acid decarboxylase according to claim 1.

16. The method according to claim 15, wherein the $C_{n+1}$ fatty acid is butyric acid, and the alkane is propane, or wherein the $c_{n+1}$ fatty acid is valeric acid, and the $C_n$ alkane is butane, or wherein the $C_{n+1}$ fatty acid is isovaleric acid, and the $C_n$ alkane is isobutane.

17. The method according to claim 15, comprising the step of:
   catalysis of the conversion of $C_{n+1}$ acyl-CoA to $C_{n+1}$ fatty acid using an acyl-CoA thioester hydrolase, prior to the step recited in claim 15.

18. The method according to claim 17, wherein n=3, the $C_{n+1}$ acyl is butyryl-CoA, the $C_{n+1}$ fatty acid is butyric acid, and the $C_n$ alkane is propane.

19. The method according to claim 14, wherein the $C_{n+1}$ fatty acid is butyric acid, and the $C_n$ alkane is propane, or wherein the $C_{n+1}$ fatty acid is valeric acid, and the $C_n$ alkane is butane, or wherein the $C_{n+1}$ fatty acid is isovaleric acid, and the $C_n$ alkane is isobutane.

* * * * *